United States Patent
Farand et al.

(10) Patent No.: US 11,136,290 B2
(45) Date of Patent: Oct. 5, 2021

(54) SULFINYLAMINOBENZAMIDE AND SULFONYLAMINOBENZAMIDE DERIVATIVES

(71) Applicant: The Liver Company Inc., Palo Alto, CA (US)

(72) Inventors: Julie Farand, San Mateo, CA (US); Joshua A. Kaplan, Foster City, CA (US); Gregory Notte, Redwood City, CA (US); Casey Lockwood Olen, Belmont, CA (US); Michael Sangi, San Mateo, CA (US); David Sperandio, Palo Alto, CA (US)

(73) Assignee: The Liver Company Inc., Palo Alto, CA (US)

( * ) Notice: Subject to any disclaimer, the term of this patent is extended or adjusted under 35 U.S.C. 154(b) by 0 days.

(21) Appl. No.: 16/415,787

(22) Filed: May 17, 2019

(65) Prior Publication Data
US 2019/0359565 A1    Nov. 28, 2019

Related U.S. Application Data

(60) Provisional application No. 62/674,981, filed on May 22, 2018.

(51) Int. Cl.
| | |
|---|---|
| *A61K 31/18* | (2006.01) |
| *C07C 311/08* | (2006.01) |
| *C07C 311/21* | (2006.01) |
| *C07C 311/39* | (2006.01) |
| *C07C 311/29* | (2006.01) |
| *C07C 311/46* | (2006.01) |
| *C07C 311/14* | (2006.01) |
| *C07C 311/13* | (2006.01) |
| *C07C 323/25* | (2006.01) |
| *C07C 323/30* | (2006.01) |
| *C07C 323/31* | (2006.01) |
| *C07D 205/04* | (2006.01) |
| *C07D 207/48* | (2006.01) |
| *C07D 213/89* | (2006.01) |
| *C07D 231/18* | (2006.01) |
| *C07D 235/00* | (2006.01) |
| *C07D 239/26* | (2006.01) |
| *C07D 257/04* | (2006.01) |
| *C07D 275/02* | (2006.01) |
| *C07D 277/36* | (2006.01) |
| *C07D 295/116* | (2006.01) |
| *C07D 305/08* | (2006.01) |
| *C07D 309/08* | (2006.01) |
| *C07D 335/02* | (2006.01) |
| *C07D 451/02* | (2006.01) |
| *C07D 493/08* | (2006.01) |
| *C07F 9/50* | (2006.01) |
| *C07C 313/06* | (2006.01) |

(52) U.S. Cl.
CPC ............ *C07C 323/25* (2013.01); *A61K 31/18* (2013.01); *C07C 311/08* (2013.01); *C07C 311/13* (2013.01); *C07C 311/14* (2013.01); *C07C 311/21* (2013.01); *C07C 311/29* (2013.01); *C07C 311/39* (2013.01); *C07C 311/46* (2013.01); *C07C 313/06* (2013.01); *C07C 323/30* (2013.01); *C07C 323/31* (2013.01); *C07D 205/04* (2013.01); *C07D 207/48* (2013.01); *C07D 213/89* (2013.01); *C07D 231/18* (2013.01); *C07D 235/00* (2013.01); *C07D 239/26* (2013.01); *C07D 257/04* (2013.01); *C07D 275/02* (2013.01); *C07D 277/36* (2013.01); *C07D 295/116* (2013.01); *C07D 305/08* (2013.01); *C07D 309/08* (2013.01); *C07D 335/02* (2013.01); *C07D 451/02* (2013.01); *C07D 493/08* (2013.01); *C07F 9/5022* (2013.01)

(58) Field of Classification Search
None
See application file for complete search history.

(56) References Cited

U.S. PATENT DOCUMENTS

2017/0226053 A1* 8/2017 Gauvry ................ C07D 213/84
2020/0397807 A1* 12/2020 Pranesh ................... A61P 35/00

FOREIGN PATENT DOCUMENTS

| EP | 2865664 A1 | 4/2015 |
| TW | 202003457 | 1/2020 |
| WO | WO-02/18335 A1 | 3/2002 |
| WO | WO-2016/081599 A1 | 5/2016 |
| WO | WO-2017/201313 A1 | 11/2017 |
| WO | WO-2019/226490 | 11/2019 |

OTHER PUBLICATIONS

STN file for RN 2036868-48-9, publicly available since Nov. 24, 2016 (Year: 2016).*

(Continued)

*Primary Examiner* — Amy C Bonaparte
(74) *Attorney, Agent, or Firm* — Cooley LLP

(57) ABSTRACT

Provided is a compound of Formula (I):

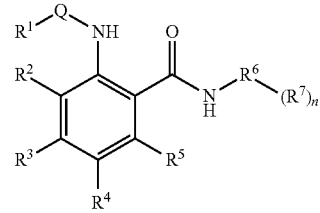

wherein the variable groups are defined herein.

43 Claims, No Drawings

(56) References Cited

OTHER PUBLICATIONS https://aurorafinechemicals.com/about.html, downloaded on Jul. 16, 2020 (Year: 2020).*
SciFinder entry for RN 2036868-48-9, downloaded on Jul. 16, 2020 (Year: 2020).*
http://online.aurorafinechemicals.com/StrSearch-new.asp?S2=&R1=&C1=&C2=&C3=ON&C4=ON&R2=V2&T1=70&T2=100&molln=&B1=Search&NDISPLAY=20&ALLFIELDS=K24.833.925, downloaded on Jul. 16, 2020 (Year: 2020).*
RN 1005134-02-0 and RN 1005178-70-0 (both publicly available in 2008) (Year: 2008).*
Childress, E.S. et al. (2018) "Small Molecule Mitochondrial Uncouplers and Their Therapeutic Potential" *J. Med. Chem.* 61:4641-4655.
Kim, J. et al. (2013) "Ruthenium-Catalyzed Direct C-H Amidation of Arenes Including Weakly Coordinating Aromatic Ketones" *Chem. Eur. J.* 19:7328-7333.
Database Registry [Online] Chemical Abstracts Service (2018) Retrieved from STN Database Accession No. 2030852-21-0:Abstract.
Database Registry [Online] Chemical Abstracts Service (2018) Retrieved from STN Database Accession No. 2196723-55-2:Abstract.
Database Registry [Online] Chemical Abstracts Service (2018) Retrieved from STN Database Accession No. 2196006-39-8:Abstract.
Database Registry [Online] Chemical Abstracts Service (2018) Retrieved from STN Database Accession No. 2192710-60-2:Abstract.
Database Registry [Online] Chemical Abstracts Service (2018) Retrieved from STN Database Accession No. 2188864-14-2:Abstract.
Database Registry [Online] Chemical Abstracts Service (2018) Retrieved from STN Database Accession No. 2177727-62-5:Abstract.
Database Registry [Online] Chemical Abstracts Service (2018) Retrieved from STN Database Accession No. 2039648-43-4:Abstract.
Intl. Search Report—Written Opinion dated Jul. 19, 2019 for PCT/US2019/032925.
Intl. Preliminary Report on Patentability dated Nov. 24, 2020 for PCT/US2019/032925.

* cited by examiner

SULFINYLAMINOBENZAMIDE AND SULFONYLAMINOBENZAMIDE DERIVATIVES

CROSS REFERENCE TO RELATED APPLICATIONS

This patent application claims the benefit of priority of U.S. Provisional Patent Application Ser. No. 62/674,981, filed May 22, 2018. The contents of this application are incorporated herein by reference.

FIELD

The present disclosure relates to novel compounds that are able to uncouple mitochondrial oxidative phosphorylation. The disclosure also relates to methods for preparing the compounds, pharmaceutical compositions comprising such compounds and methods of using the compounds or pharmaceutical compositions in therapeutic treatment.

BACKGROUND

Mitochondria are double-membrane cellular organelles that provide an efficient route for eukaryotic cells to generate ATP from energy-rich molecules. Electrons from oxidative substrates are transferred to oxygen, through a series of redox reactions, to generate water. In the process, protons are pumped from the matrix across the mitochondrial inner membrane through respiratory complexes I, III, and IV. When protons return to the mitochondrial matrix down their electrochemical gradient, ATP is synthesized by way of complex V (ATP synthase).

Mitochondrial dysfunction has been linked to neurodegenerative diseases and cancer (de Moura et al., *Environmental and Molecular Mutagenesis* 51:391-405 (2010)), insulin resistance, type 2 diabetes, hypertension and dyslipidemia (Kim et al., *Circ Res.* 2008 Feb. 29; 102(4): 401-414), alcoholic steatohepatitis, non-alcoholic fatty liver disease and non-alcoholic steatohepatitis (NASH), among other conditions.

Non-alcoholic fatty liver disease (NAFLD), a major liver disorder, was recently estimated to afflict over twenty-five percent of the global population, and one in three Americans (Younosi et al., *Hepatology,* 2016; 64:73-84; (Shulman, 2000, J. Clin. Invest. 106:171-176). Left untreated, NAFLD will often progress to NASH, and may lead to fibrosis, cirrhosis, or hepatocellular carcinoma (HCC), or any or all of the three.

One therapy proposed for treating NAFLD, NASH, and other diseases mediated, at least in part, by mitochondrial dysfunction, is the use of a mitochondrial uncoupling agent. Using a protonophore (or proton translocator) is one method proposed for "uncoupling" the electron transport mechanism of mitochondria. This uncoupling results in a processing (decomposition) of energy rich compounds, such as lipids and fatty acids. Furthermore, mitochondrial uncoupling is thought to reduce the generation of reactive oxygen species (ROS). ROS are responsible for DNA damage and alteration of proteins in vivo, and therefore may cause cellular dysfunction or programmed cell death (apoptosis). Several mitochondrial uncoupling compounds have been proposed (see for example, L. Santos et al., Small Molecule Mitochondrial Uncouplers and Their Therapeutic Potential, *J. Med. Chem.* November 2017, DOI: 10.1021/acs.jmedchem.7b01182.

There is a need to provide an uncoupler compound that does not significantly raise body temperature, but would treat mitochondria mediated diseases or conditions.

SUMMARY OF THE INVENTION

In one embodiment of this disclosure, there is provided a compound of Formula I:

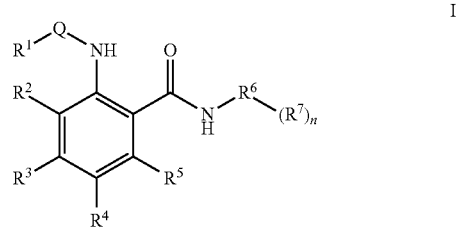

or a pharmaceutically acceptable salt, stereoisomer, mixtures of stereoisomers, tautomer, or deuterated analogs thereof, wherein:

Q is selected from the group consisting of —S(O)$_2$—, —S(O)—, —S(O)(NH)—, —S(O)(NR$^8$)—.

R$^1$ is selected from a group consisting of: C$_{1-6}$ alkyl, C$_{2-6}$ alkenyl, C$_{2-6}$ alkynyl, —NR$^{13}$R$^{13}$, 6-10 membered aryl, 5-10 membered heteroaryl, C$_{3-12}$ cycloalkyl, and 4-12 membered heterocyclyl, wherein each C$_{1-6}$ alkyl, C$_{2-6}$ alkenyl, C$_{2-6}$ alkynyl, 6-10 membered aryl, 5-10 membered heteroaryl, C$_{3-12}$ cycloalkyl, and 4-12 membered heterocyclyl are optionally further substituted with one or more R$^{11}$ groups;

R$^{11}$ is selected from a group consisting of: hydroxyl, oxo, halo, —CN, C$_{1-6}$ alkyl, C$_{2-6}$ alkenyl, C$_{2-6}$ alkynyl, C$_{1-6}$ alkoxy, C$_{1-6}$ hydroxyalkyl, C$_{1-6}$ heteroalkyl, 3-12 membered cycloalkyl, 4-12 membered heterocyclyl, 6-10 membered aryl, 5-10 membered heteroaryl, —P(O)R$^{14}$R$^{14}$, —S(O)(NH)R$^{14}$, —S(O)(NR$^8$)R$^{14}$, —S(O)(NH)NR$^{13}$R$^{13}$, —S(O)(NR$^8$)NR$^{13}$R$^{13}$, —SH, —S(O)$_{0-2}$R$^{14}$, —S(O)$_{1-2}$NR$^{13}$R$^{13}$, —SF$_5$, —NO$_2$, —NR$^{13}$R$^{13}$, —NR$^{13}$SO$_2$R$^{14}$, —OS(O)$_2$R$^{14}$, —C(O)OR$^{14}$, —C(O)R$^{14}$, —NR$^{13}$C(O)OR$^{14}$, —NR$^{13}$C(O)NR$^{13}$R$^{13}$, —NR$^{13}$S(O)$_2$NR$^{13}$R$^{13}$, and —C(O)NR$^{13}$R$^{13}$, wherein each C$_{1-6}$ alkyl, C$_{2-6}$ alkenyl, C$_{2-6}$ alkynyl, C$_{1-6}$ alkoxy, C$_{1-6}$ hydroxyalkyl, C$_{1-6}$ heteroalkyl, 3-12 membered cycloalkyl, 4-12 membered heterocyclyl, 6-10 membered aryl, and 5-10 membered heteroaryl are optionally substituted with one or more R$^9$ groups;

each R$^9$ is independently selected from the group consisting of: —H, oxo, —OH, —CN, halo, C$_{1-6}$ alkyl, C$_{1-6}$ alkoxy, C$_{1-6}$ hydroxyalkyl, C$_{1-6}$ heteroalkyl, 3-12 membered cycloalkyl, 4-12 membered heterocyclyl, 6-10 membered aryl, 5-10 membered heteroaryl, —NR$^{13}$R$^{13}$, —NR$^{13}$C(O)OR$^{14}$, —OS(O)$_2$R$^{14}$—C(O)OR$^{14}$, —S(O)(NH)R$^{14}$, —S(O)(NR$^8$)R$^{14}$, —S(O)(NH)NR$^{13}$R$^{13}$, —S(O)(NR$^8$)NR$^{13}$R$^{13}$, —S(O)$_{0-2}$R$^{14}$, —S(O)$_{1-2}$NR$^{13}$R$^{13}$, —C(O)NR$^{13}$R$^{13}$, —NR$^{13}$SO$_2$R$^{14}$, —C(O)R$^{14}$, —NR$^{13}$C(O)NR$^{13}$R$^{13}$, —NR$^{13}$S(O)$_2$NR$^{13}$R$^{13}$, SF$_5$ and —NO$_2$, wherein each of C$_{1-6}$ alkyl, C$_{1-6}$ alkoxy, C$_{1-6}$ hydroxyalkyl, C$_{1-6}$ heteroalkyl, 3-12 membered cycloalkyl, 4-12 membered heterocyclyl, 6-10 membered aryl, and 5-10 membered heteroaryl is optionally substituted with one or more R$^{16}$ groups;

each $R^{13}$ is independently selected from the group consisting of —H, $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{15}$ groups.

each $R^{14}$ is independently selected from the group consisting of: $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{15}$ groups.

each $R^{15}$ is independently selected from —H, halo, —CN, —OH, oxo, —$NO_2$, —$SF_5$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —S(O)(NH)$R^{16}$, —S(O)($NR^8$)$R^{16}$, —S(O)(NH)$NR^{16}R^{16}$, —S(O)($NR^8$)$NR^{16}R^{16}$, —S(O)$_{0-2}R^{16}$, —S(O)$_2NH_2$, —$NH_2$, —S(O)$_2NR^{16}R^{16}$, C(O)$R^{16}$, —C(O)$NR^{16}R^{16}$ and C(O)O$R^{16}$, wherein 3-6 membered cycloalkyl, 4-12 membered heterocyclyl, 6-10 membered aryl, and 5-10 membered heteroaryl are optionally substituted with one or more $R^{16}$ groups.

each $R^{16}$ is independently selected from halo, —CN, —OH, —$NH_2$, oxo, —$NO_2$, —$SF_5$, $C_{1-3}$ alkyl, $C_{1-3}$ haloalkyl, $C_{1-6}$ alkoxy, $C_{1-6}$ haloalkoxy, $C_{1-6}$ hydroxyalkyl, thiohaloalkyl, sulfonylalkyl, sulfonylhaloalkyl, sulfonylcycloalkyl, 3-6 membered cycloalkyl, —C(O)$NH_2$ and —S(O)$_2NH_2$.

$R^2$ is selected from a group consisting of: —H, —CN, —F, —Cl, $C_{1-3}$ alkyl, $C_{1-3}$ haloalkyl, $C_{1-3}$ heteroalkyl, $C_{1-3}$ alkoxy and $C_{1-3}$ haloalkoxy;

each $R^3$ and $R^4$ is independently selected from a group consisting of: —H, halo, —OH, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$SF_5$, —S(O)$_{0-2}R^{14}$, —S(O)(NH)$R^{14}$, —S(O)($NR^8$)$R^{14}$, —S(O)(NH)$NR^{13}R^{13}$, —S(O)($NR^8$)$NR^{13}R^{13}$, —SH, —$NR^{13}R^{13}$, —$NR^3SO_2R^{14}$, —$NR^{13}S(O)_2NR^{13}R^{13}$, —$NR^{13}C(O)NR^{13}R^{13}$, —$NR^{13}C(O)OR^{14}$, tri-$C_{1-4}$ alkylsilyl, —C(O)$R^{14}$, —C(O)O$R^{14}$, —C(O)$NR^{13}R^{13}$, and —$NO_2$, wherein $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl are optionally further substituted with one or more $R^9$ groups;

$R^5$ is selected from a group consisting of: —H, —CN, —F, —Cl, $C_{1-3}$ alkyl, $C_{1-3}$ haloalkyl, $C_{1-3}$ heteroalkyl, $C_{1-3}$ alkoxy and $C_{1-3}$ haloalkoxy;

wherein $R^2$ and $R^3$, or $R^3$ and $R^4$, or $R^4$ and $R^5$ can optionally join, together with the atoms to which they are attached, to form a 5-6 membered cycloalkyl, a 5-6 membered heterocyclyl, phenyl, or a 5-6 membered heteroaryl, each such cyclic groups respectively fused to the phenyl to which they are attached, and each optionally substituted with one or more $R^9$ groups;

$R^6$ is selected from the group consisting of: 5-10 membered carbobicyclic ring, 8-10 membered tricyclic ring, 6-12 membered heterobicyclic ring, and 8-12 membered polycyclic ring, wherein the 5-10 membered carbobicyclic ring, the 8-10 membered tricyclic ring, the 8-12 membered polycyclic ring, or the 6-12 membered heterobicyclic ring may be fused, bridged or spiro, and wherein the 5-10 membered carbobicyclic ring, the 8-10 membered tricyclic ring, the 6-12 membered heterobicyclic and the 8-12 membered polycyclic ring are substituted with one or more $R^7$;

$R^7$ is selected from the group consisting of: —H, halo, —CN, oxo, —OH, $C_{1-6}$ alkyl, $C_{2-6}$ alkenyl, $C_{2-6}$ alkynyl, tri-$C_{1}$-4 alkylsilyl, $C_{1-6}$ alkoxy, $C_{1-6}$ hydroxyalkyl, $C_{1-6}$ heteroalkyl, 3-12 membered cycloalkyl, —S(O)$_{0-2}R^{14}$, —S(O)(NH)$R^{14}$, —S(O)($NR^8$)$R^{14}$, —S(O)(NH)$NR^{13}R^{13}$, —S(O)($NR^8$)$NR^{13}R^{13}$, —SH, —$NR^{13}R^{13}$, —P(O)$R^{14}R^{14}$, —C(O)OH, —C(O)O$R^{14}$, —C(O)$NR^{13}R^{13}$, —S(O)$_2NR^{13}R^{13}$, —C(O)$R^{14}$, 6-10 membered aryl, 5-10 membered heteroaryl, 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, and 3-12 membered cycloalkyl are optionally substituted with one or more $R^{15}$; and n is 1, 2, or 3;

$R^8$ is $C_{1-6}$ alkyl, —C(O)$R^{14}$, 3-12 membered cycloalkyl, $C_{1-6}$ heteroalkyl, 6-10 membered aryl, 5-10 membered heteroaryl, 4-12 membered heterocyclyl, —C(O)O$R^{14}$, —C(O)$NR^{13}R^{13}$, and —SO$_2R^{14}$, wherein each of $C_{1-6}$ alkyl, —C(O)$R^{14}$, 3-12 membered cycloalkyl, $C_{1-6}$ heteroalkyl, 6-10 membered aryl, 5-10 membered heteroaryl, 4-12 membered heterocyclyl is optionally substituted with halo, —CN, oxo, hydroxyl, $C_{1-6}$ alkyl, $C_{1-6}$ alkoxy, —S(O)$_{1-2}R^{14}$, —S(O)$_2NR^{13}R^{13}$, —$NO_2$, —$SF_5$, $C_{1-6}$ haloalkyl, $C_{1-6}$ haloalkoxy, $C_{1-6}$ hydroxyalkyl, —$NR^{13}R^{13}$, —C(O)O$R^{14}$, $C_{1-6}$ heteroalkyl, 3-6 membered cycloalkyl optionally substituted with one or more $R^{16}$, 4-12 membered heterocyclyl optionally substituted with one or more $R^{16}$, 6-10 membered aryl optionally substituted with one or more $R^{16}$, 5-10 membered heteroaryl optionally substituted with one or more $R^{16}$;

subject to the provisos that:

when $R^6$ is a $C_{8-12}$ carbobicyclic ring, and both $R^3$ and $R^7$ are H, then $R^4$ is selected from the group consisting of: $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl, 7-12 membered monocyclic heterocyclyl, —$SF_5$, —$NR^{13}R^{13}$, —$NR^{13}C(O)OR^{14}$, —$NR^{13}SO_2R^{14}$, —$NR^{13}S(O)_2NR^{13}R^{13}$, —$NR^{13}C(O)NR^{13}R^{13}$, tri-$C_{14}$ alkylsilyl, —C(O)$R^{14}$, —C(O)O$R^{14}$, —C(O)$NR^{13}R^{13}$, —S(O)$_{0-2}R^{14}$, —S(O)(NH)$R^{14}$, —S(O)($NR^8$)$R^{14}$, —S(O)(NH)$NR^{13}R^{13}$, —S(O)($NR^8$)$NR^{13}R^{13}$, —SH and —$NO_2$, wherein $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl and 7-12 membered monocyclic heterocyclyl are optionally substituted with one or more $R^9$; 5-6 membered heterocyclyl is optionally substituted with $R^{17}$; and 8-10 membered bicyclic heterocyclyl is optionally substituted with one or more $R^{18}$;

when $R^6$ is an 8-10 membered heterobicyclic ring, $R^3$ is H and $R^7$ is —H, halo, cyano, oxo, —OH, $C_{1-4}$ alkoxy, $C_{1-4}$ alkyl or $C_{1-4}$ haloalkyl, then $R^4$ is selected from the group consisting of: $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl, 7-12 membered monocyclic heterocyclyl, —$SF_5$, —$NR^{13}R^{13}$, —$NR^{13}C(O)OR^{14}$, —$NR^{13}SO_2R^{14}$, —$NR^{13}S(O)_2NR^{13}R^{13}$, —$NR^{13}C(O)NR^{13}R^{13}$, tri-$C_{1-4}$ alkylsilyl, —$C(O)R^{14}$, —$C(O)OR^{14}$, —$C(O)NR^{13}R^{13}$, —$S(O)_{0-2}R^{14}$, —$S(O)(NH)R^{14}$, —$S(O)(NR^8)R^{14}$, —$S(O)(NH)NR^{13}R^{13}$, —$S(O)(NR^8)NR^{13}R^{13}$, —SH, and —$NO_2$, wherein $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl and 7-12 membered monocyclic heterocyclyl are optionally substituted with one or more $R^9$; 5-6 membered heterocyclyl is optionally substituted with $R^{17}$, and 8-10 membered bicyclic heterocyclyl is optionally substituted with one or more $R^{18}$;

when $R^6$ is a $C_6$-$C_7$ carbobicyclic ring, and $R^7$ is H or methyl, then $R^3$ is selected from the group consisting of: halo, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$SF_5$, —$S(O)_{0-2}R^{14}$, —$S(O)(NH)R^{14}$, —$S(O)(NR^8)R^{14}$, —$S(O)(NH)NR^{13}R^{13}$, —$S(O)(NR^8)NR^{13}R^{13}$, —SH, —$NR^{13}R^{13}$, —$NR^{13}SO_2R^{14}$, —$NR^{13}S(O)_2NR^{13}R^{13}$, —$NR^{13}C(O)NR^{13}R^{13}$, —$NR^{13}C(O)OR^{14}$, tri-$C_{1-4}$ alkylsilyl, —$C(O)R^{14}$, —$C(O)OR^{14}$, —$C(O)NR^{13}R^{13}$, and —$NO_2$, wherein $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl are optionally further substituted with one or more $R^9$ groups;

wherein $R^{17}$ is selected from —OH, oxo, —CN, $C_{2-6}$ alkenyl, $C_{2-6}$ alkynyl, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$S(O)_{0-2}R^{14}$, —$NR^{13}SO_2R^{14}$, —$NR^{13}S(O)_2NR^{13}R^{13}$, —$NR^{13}C(O)NR^{13}R^{13}$, —$NR^{13}C(O)OR^{14}$, —$C(O)R^{14}$, —$C(O)OR^{14}$ and —$C(O)NR^{13}R^{13}$.

and wherein $R^{18}$ is selected from $C_{2-6}$ alkenyl, $C_{2-6}$ alkynyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$S(O)_{0-2}R^{14}$, —$NR^{13}R^{13}$, —$NR^{13}SO_2R^{14}$, —$NR^{13}S(O)_2NR^{13}R^{13}$, —$NR^{13}C(O)NR^{13}R^{13}$, —$NR^{13}C(O)OR^{14}$, —$C(O)R^{14}$, —$C(O)OR^{14}$ and —$C(O)NR^{13}R^{13}$.

In another embodiment, $R^6$ is selected from the group consisting of: 5-10 membered carbobicyclic ring, 6-12 membered heterobicyclic ring, and 8-10 membered tricyclic ring, wherein the 5-10 membered carbobicyclic ring, 8-10 membered tricyclic ring, or the 6-12 membered heterobicyclic ring may be fused, bridged or spiro, and wherein the 5-10 membered carbobicyclic ring, the 6-12 membered heterobicyclic ring and the 8-10 membered tricyclic ring are substituted with one or more $R^7$.

In another embodiment, $R^6$ is selected from the group consisting of: 5-10 membered carbobicyclic ring, 8-10 membered tricyclic ring, and 6-12 membered heterobicyclic ring, wherein the 5-10 membered carbobicyclic ring, the 8-10 membered tricyclic ring, or the 6-12 membered heterobicyclic ring are bridged, and wherein the 5-10 membered carbobicyclic ring, the 8-10 membered tricyclic ring, and the 6-12 membered heterobicyclic are substituted with one or more $R^7$.

In another embodiment, $R^6$ is selected from the group consisting of: 5-10 membered carbobicyclic ring, and 6-12 membered heterobicyclic ring, wherein the 5-10 membered carbobicyclic ring, or the 6-12 membered heterobicyclic ring are bridged, and wherein the 5-10 membered carbobicyclic ring, and the 6-12 membered heterobicyclic are substituted with one $R^7$.

In some embodiments, Q is selected from the group consisting of —$S(O)_2$—, —$S(O)$—, and —$S(O)(NR^8)$—.

In some embodiments, $R^1$ is selected from a group consisting of: $C_{1-6}$ alkyl, —$NR^{13}R^{13}$, 6-10 membered aryl, 5-10 membered heteroaryl, $C_{3-12}$ cycloalkyl, and 4-12 membered heterocyclyl, wherein each $C_{1-6}$ alkyl, 6-10 membered aryl, 5-10 membered heteroaryl, $C_{3-12}$ cycloalkyl, and 4-12 membered heterocyclyl are further substituted with one or more $R^{11}$ groups.

In some embodiments, $R^2$ is selected from the group consisting of: —H, —CN, —F, methyl, methoxy and $C_1$ haloalkoxy.

In another embodiment, $R^2$ is selected from the group consisting of: —H and —F.

In some embodiments, $R^4$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, —$SF_5$, —$S(O)_{0-2}R^{14}$, —$S(O)(NH)R^{14}$, —$S(O)(NR^8)R^{14}$, —$S(O)(NH)NR^{13}R^{13}$, —$S(O)(NR^8)NR^{13}R^{13}$, —$NR^{13}R^{13}$, —$NR^3SO_2R^{14}$, —$NR^{13}S(O)_2NR^{13}R^{13}$, —$NR^{13}C(O)NR^{13}R^{13}$, —$NR^{13}C(O)OR^{14}$, —$C(O)R^{14}$, —$C(O)OR^{14}$, —$C(O)NR^{13}R^{13}$, —$NO_2$, wherein $C_{1-6}$ alkyl, $C_{1-6}$ alkoxy, $C_{1-6}$ hydroxyalkyl, and $C_{1-6}$ heteroalkyl, are further substituted with one or more $R^9$ groups.

In some embodiments, $R^4$ is selected from the group consisting of: —H, —F, —Cl, —OH, —CN, —$S(O)_{0-2}R^{14}$, —$C(O)R^{14}$, —$SF_5$, —$NO_2$, $C_{1-6}$ alkyl, and $C_{1-6}$ alkoxy, and wherein said $C_{1-6}$ alkyl or $C_{1-6}$ alkoxy is optionally substituted with one or more —F, and $R^{14}$ is selected from the group consisting of $C_{1-6}$ alkyl, $C_{3-6}$ cycloalkyl, $C_{1-6}$ hydroxyalkyl, $C_{1-6}$ heteroalkyl, wherein the $C_{1-6}$ alkyl, $C_{3-6}$ cycloalkyl, $C_{1-6}$ hydroxyalkyl, and $C_{1-6}$ heteroalkyl, are optionally substituted with one or more $R^{16}$ groups, and $R^{16}$ is independently selected from halo, —CN, —OH.

In some embodiments, $R^4$ is selected from the group consisting of: —H, —F, —Cl, —OH, —CN, —$SR^{14}$, —$SF_5$, $C_{1-6}$ alkyl, and $C_{1-6}$ alkoxy, and wherein said $C_{1-6}$ alkyl or $C_{1-6}$ alkoxy is optionally substituted with one or more —F, and $R^{14}$ is selected from the group consisting of $C_{1-3}$ haloalkyl.

In some embodiments, $R^3$ is selected from the group consisting of: —H, halo, —OH, —CN, $C_{1-6}$ alkyl, 6-10 membered aryl, 4-12 membered heterocyclyl, 5-10 membered heteroaryl, $C_{3-12}$ cycloalkyl, $C_{1-6}$ alkoxy, $C_{1-6}$ hydroxyalkyl, $C_{1-6}$ heteroalkyl, —$S(O)_{0-2}R^{14}$, —$NO_2$, and —$SF_5$, wherein said $C_{1-6}$ alkyl, 6-10 membered aryl, 4-12 membered heterocyclyl, 5-10 membered heteroaryl, $C_{3-12}$ cycloalkyl, $C_{1-6}$ alkoxy, $C_{1-6}$ hydroxyalkyl, and $C_{1-6}$ heteroalkyl are optionally further substituted with one or more $R^9$ groups.

In some embodiments, $R^3$ selected from the group consisting of: —H, —F, —Cl, —OH, —CN, $C_{1-6}$ alkyl, 4-12 membered heterocyclyl, 5-10 membered heteroaryl, $C_{3-12}$ cycloalkyl, $C_{1-6}$ alkoxy, $C_{1-6}$ hydroxyalkyl, $C_{1-6}$ heteroalkyl, —$SR^{14}$, and —$SF_5$, wherein said $C_{1-6}$ alkyl, $C_{1-6}$ alkoxy, $C_{3-12}$ cycloalkyl, 4-12 membered heterocyclyl, and 5-10 membered heteroaryl are optionally substituted with one or more $R^{16}$, and $R^{14}$ is $C_{1-3}$ haloalkyl.

In some embodiments, $R^5$ is selected from the group consisting of: —H, —F and methyl.

In another embodiment of this disclosure, there is provided a compound of Formula II:

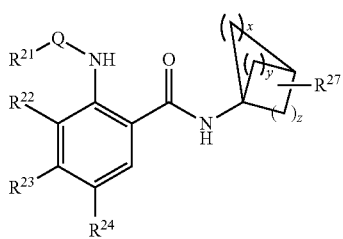

II or a pharmaceutically acceptable salt, stereoisomer, mixtures of stereoisomers, tautomer, or deuterated analogs thereof, wherein:

wherein x, y, and z are independently 1, 2, 3, or 4,

Q is selected from the group consisting of —S(O)$_2$—, —S(O)—, —S(O)(NH)—, —S(O)(NR$^{28}$)—;

$R^{21}$ is selected from a group consisting of: $C_{1-6}$ alkyl, $C_{2-6}$ alkenyl, $C_{2-6}$ alkynyl, —NR$^{33}$R$^{33}$, 6-10 membered aryl, 5-10 membered heteroaryl, $C_{3-12}$ cycloalkyl, and 4-12 membered heterocyclyl, wherein each $C_{1-6}$ alkyl, $C_{2-6}$ alkenyl, $C_{2-6}$ alkynyl, 6-10 membered aryl, 5-10 membered heteroaryl, $C_{3-12}$ cycloalkyl, and 4-12 membered heterocyclyl are optionally further substituted with one or more $R^{31}$ groups;

$R^{31}$ is selected from the group consisting of: hydroxyl, oxo, halo, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —P(O)R$^{34}$R$^{34}$, —S(O)(NH)R$^{34}$, —S(O)(NR$^{28}$)R$^{34}$, —S(O)(NH)NR$^{33}$R$^{33}$, —S(O)(NR$^{28}$)NR$^{33}$R$^{33}$, —SH, —S(O)$_{0-2}$R$^{34}$, —S(O)$_{1-2}$NR$^{33}$R$^{33}$, —SF$_5$, —NO$_2$, —NR$^{33}$R$^{33}$, —NR$^{33}$SO$_2$R$^{34}$, —OS(O)$_2$R$^{34}$, —C(O)OR$^{34}$, —C(O)R$^{34}$, —NR$^{33}$C(O)OR$^{34}$, —NR$^{33}$C(O)NR$^{33}$R$^{33}$, —NR$^{33}$S(O)$_2$NR$^{33}$R$^{33}$, and —C(O)NR$^{33}$R$^{33}$, wherein each $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl are optionally substituted with one or more $R^{29}$ groups;

each $R^{29}$ is independently selected from the group consisting of: —H, oxo, —OH, —CN, halo, $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —NR$^{33}$R$^{33}$, —NR$^{33}$C(O)OR$^{34}$, —OS(O)$_2$R$^{34}$ —C(O)OR$^{34}$, —S(O)(NH)R$^{34}$, —S(O)(NR$^8$)R$^{34}$, —S(O)(NH)NR$^{33}$R$^{33}$, —S(O)(NR$^{28}$)NR$^{33}$R$^{33}$, —S(O)$_{0-2}$R$^{34}$, —S(O)$_{1-2}$NR$^{33}$R$^{33}$, —C(O)NR$^{33}$R$^{33}$, —NR$^{33}$SO$_2$R$^{34}$, —C(O)R$^{34}$, —NR$^{33}$C(O)NR$^{33}$R$^{33}$, —NR$^{33}$S(O)$_2$NR$^{33}$R$^{33}$, —SF$_5$, —NO$_2$, wherein each of $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl is optionally substituted with one or more $R^{36}$;

each $R^{33}$ is independently selected from the group consisting of —H, $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{35}$ groups;

each $R^{34}$ is independently selected from the group consisting of: $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{35}$ groups;

each $R^{35}$ is independently selected from —H, halo, —CN, —OH, oxo, —NO$_2$, —SF$_5$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —S(O)(NH)R$^{36}$, —S(O)(NR$^{28}$)R$^{36}$, —S(O)(NH)NR$^{36}$R$^{36}$, —S(O)(NR$^{28}$)NR$^{36}$R$^{36}$, —S(O)$_{0-2}$R$^{36}$, —S(O)$_2$NH$_2$, —NH$_2$, —S(O)$_2$NR$^{36}$R$^{36}$, C(O)R$^{36}$, —C(O)NR$^{36}$R$^{36}$ and C(O)OR$^{36}$, wherein 3-6 membered cycloalkyl, 4-12 membered heterocyclyl, 6-10 membered aryl, 5-10 membered heteroaryl are optionally substituted with one or more $R^{36}$ groups;

each $R^{36}$ is independently selected from halo, —CN, —OH, —NH$_2$, oxo, —NO$_2$, —SF$_5$, $C_{1-3}$ alkyl, $C_{1-3}$ haloalkyl, $C_{1-6}$ alkoxy, $C_{1-6}$ haloalkoxy, $C_{1-6}$ hydroxyalkyl, thiohaloalkyl, sulfonylalkyl, sulfonylhaloalkyl, sulfonylcycloalkyl, 3-6 membered cycloalkyl, —C(O)NH$_2$ and —S(O)$_2$NH$_2$;

$R^{22}$ is selected from a group consisting of: —H, —CN, —F, —Cl, $C_{1-3}$ alkyl, $C_{1-3}$ haloalkyl, $C_{1-3}$ heteroalkyl, $C_{1-3}$ alkoxy and $C_{1-3}$ haloalkoxy;

each $R^{23}$ and $R^{24}$ is independently selected from a group consisting of: —H, halo, —OH, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —SF$_5$, —S(O)$_{0-2}$R$^{34}$, —S(O)(NH)R$^{34}$, —S(O)(NR$^{28}$)R$^{34}$, —S(O)(NH)NR$^{33}$R$^{33}$, —S(O)(NR$^{28}$)NR$^{33}$R$^{33}$, —SH, —NR$^{33}$R$^{33}$, —NR$^{33}$SO$_2$R$^{34}$, —NR$^{33}$S(O)$_2$NR$^{33}$R$^{33}$, —NR$^{33}$C(O)NR$^{33}$R$^{33}$, —NR$^{33}$C(O)OR$^{34}$, tri-C$_{1-4}$ alkylsilyl, —C(O)R$^{34}$, —C(O)OR$^{34}$, —C(O)NR$^{33}$R$^{33}$, —NO$_2$, wherein $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl are optionally further substituted with one or more $R^{29}$ groups;

wherein $R^{22}$ and $R^{23}$, or $R^{23}$ and $R^{24}$ can optionally join, together with the atoms to which they are attached, to form a 5-6 membered cycloalkyl, a 5-6 membered heterocyclyl, phenyl, or a 5-6 membered heteroaryl, each such cyclic groups respectively fused to the phenyl to which they are attached, and each optionally substituted with one or more $R^{29}$ groups;

$R^{27}$ is selected from the group consisting of: —H, halo, —CN, oxo, —OH, $C_{1-6}$ alkyl, $C_{2-6}$ alkenyl, $C_{2-6}$ alkynyl, tri-C$_{1}$-4 alkylsilyl, $C_{1-6}$ alkoxy, $C_{1-6}$ hydroxyalkyl, $C_{1-6}$ heteroalkyl, 3-12 membered cycloalkyl, —S(O)$_{0-2}$R$^{34}$, —S(O)(NH)R$^{34}$, —S(O)(NR$^{28}$)R$^{34}$, —S(O)(NH)

$NR^{33}R^{33}$, $-S(O)(NR^{28})NR^{33}R^{33}$, $-NR^{33}R^{33}$, $-P(O)R^{34}R^{34}$, $-C(O)OH$, $-C(O)OR^{34}$, $-C(O)NR^{33}R^{33}$, $-S(O)_2NR^{33}R^{33}$, $-C(O)R^{34}$, 6-10 membered aryl, 5-10 membered heteroaryl, 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, tri-$C_1$-4 alkylsilyl, $C_{1-6}$ alkoxy, $C_{1-6}$ hydroxyalkyl, $C_{1-6}$ heteroalkyl, and 3-12 membered cycloalkyl are optionally substituted with one or more $R^{35}$;

$R^{28}$ is $C_{1-6}$ alkyl, $-C(O)R^{34}$, 3-12 membered cycloalkyl, $C_{1-6}$ heteroalkyl, 6-10 membered aryl, 5-10 membered heteroaryl, 4-12 membered heterocyclyl, $-C(O)OR^{34}$, $-C(O)NR^{33}R^{33}$, $-SO_2R^{34}$, wherein each of $C_{1-6}$ alkyl, $C_{1-6}$ alkylcarbonyl, 3-12 membered cycloalkyl, $C_{1-6}$ heteroalkyl, 6-10 membered aryl, 5-10 membered heteroaryl, 4-12 membered heterocyclyl is optionally substituted with halo, $-CN$, oxo, hydroxyl, $C_{1-6}$ alkyl, $C_{1-6}$ alkoxy, $-S(O)_{1-2}R^{34}$, $-S(O)_2NR^{33}R^{33}$, $-NO_2$, $-SF_5$, $C_{1-6}$ haloalkyl, $C_{1-6}$ haloalkoxy, $C_{1-6}$ hydroxyalkyl, $-NR^{33}R^{33}$, $-C(O)OR^{34}$, $C_{1-6}$ heteroalkyl, 3-6 membered cycloalkyl optionally substituted with one or more $R^{36}$, 4-12 membered heterocyclyl optionally substituted with one or more $R^{36}$, 6-10 membered aryl optionally substituted with one or more $R^{36}$, 5-10 membered heteroaryl optionally substituted with one or more $R^{36}$;

subject to the provisos that:

when x+y+z is 6 to 10, and both $R^{23}$ and $R^{27}$ are H, then $R^{24}$ is selected from the group consisting of: $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl, 7-12 membered monocyclic heterocyclyl, $-SF_5$, $-NR^{33}R^{33}$, $-NR^{33}C(O)OR^{34}$, $-NR^{33}SO_2R^{34}$, $-NR^{33}S(O)_2NR^{33}R^{33}$, $-NR^{33}C(O)NR^{33}R^{33}$, tri-$C_{1-4}$ alkylsilyl, $-C(O)R^{34}$, $-C(O)OR^{34}$, $-C(O)NR^{33}R^{33}$, $-S(O)_{0-2}R^{34}$, $-S(O)(NH)R^{34}$, $-S(O)(NR^{28})R^{34}$, $-S(O)(NH)NR^{33}R^{33}$, $-S(O)(NR^{28})NR^{33}R^{33}$, $-SH$ and $-NO_2$, wherein $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl and 7-12 membered monocyclic heterocyclyl are optionally substituted with one or more $R^{29}$; 5-6 membered heterocyclyl is optionally substituted with $R^{37}$; and 8-10 membered bicyclic heterocyclyl is optionally substituted with one or more $R^{38}$; and when x+y+z is 4 or 5, and $R^{27}$ is $-H$ or methyl, $R^{23}$ is selected from the group consisting of: halo, $-CN$, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, $-SF_5$, $-S(O)_{0-2}R^{34}$, $-S(O)(NH)R^{34}$, $-S(O)(NR^{28})R^{34}$, $-S(O)(NH)NR^{33}R^{33}$, $-S(O)(NR^{28})NR^{33}R^{33}$, $-SH$, $-NR^{33}R^{33}$, $-NR^{33}SO_2R^{34}$, $-NR^{33}S(O)_2NR^{33}R^{33}$, $-NR^{33}C(O)NR^{33}R^{33}$, $-NR^{33}C(O)OR^{34}$, tri-$C_{1-4}$ alkylsilyl, $-C(O)R^{34}$, $-C(O)OR^{34}$, $-C(O)NR^{33}R^{33}$, $-NO_2$, wherein $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl are optionally further substituted with one or more $R^{29}$ groups;

wherein $R^{37}$ is selected from $-OH$, oxo, $-CN$, $C_{2-6}$ alkenyl, $C_{2-6}$ alkynyl, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, $-S(O)_{0-2}R^{34}$, $-NR^{33}SO_2R^{34}$, $-NR^{33}S(O)_2NR^{33}R^{33}$, $-NR^{33}C(O)NR^{33}R^{33}$, $-NR^{33}C(O)OR^{34}$, $-C(O)R^{34}$, $-C(O)OR^{34}$ and $-C(O)NR^{33}R^{33}$;

and wherein $R^{38}$ is selected from $C_{2-6}$ alkenyl, $C_{2-6}$ alkynyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, $-S(O)_{0-2}R^{34}$, $-NR^{33}R^{33}$, $-NR^{33}SO_2R^{34}$, $-NR^{33}S(O)_2NR^{33}R^{33}$, $-NR^{33}C(O)NR^{33}R^{33}$, $-NR^{33}C(O)OR^{34}$, $-C(O)R^{34}$, $-C(O)OR^{34}$ and $-C(O)NR^{33}R^{33}$.

In some embodiments, Q is selected from the group consisting of $-S(O)_2-$, $-S(O)-$, and $-S(O)(NR^{28})-$.

In some embodiments, $R^{21}$ is selected from a group consisting of: $C_{1-6}$ alkyl, $-NR^{33}R^{33}$, 6-10 membered aryl, 5-10 membered heteroaryl, $C_{3-12}$ cycloalkyl, and 4-12 membered heterocyclyl, wherein each $C_{1-6}$ alkyl, 6-10 membered aryl, 5-10 membered heteroaryl, $C_{3-12}$ cycloalkyl, and 4-12 membered heterocyclyl are further substituted with one or more $R^{31}$ groups.

In some embodiments, $R^{22}$ is selected from the group consisting of: $-H$, $-CN$, $-F$, methyl, $C_1$haloalkyl, $C_{1-3}$ heteroalkyl, methoxy and $C_1$ haloalkoxy.

In some embodiments, $R^{22}$ is selected from the group consisting of: $-H$, $-CN$, $-F$, -and methyl.

In some embodiments, $R^{24}$ is selected from the group consisting of: $-H$, halo, $-OH$, $-CN$, $C_{1-6}$ alkyl, $C_{1-6}$ alkoxy, $C_{1-6}$ hydroxyalkyl, $C_{1-6}$ heteroalkyl, $-SF_5$, $-S(O)_{0-2}R^{34}$, $-S(O)(NH)R^{34}$, $-S(O)(NR^{28})R^{34}$, $-S(O)(NH)NR^{33}R^{33}$, $-S(O)(NR^{28})NR^{33}R^{33}$, $-NR^{33}R^{33}$, $-NR^{33}SO_2R^{34}$, $-NR^{33}S(O)_2NR^{33}R^{33}$, $-NR^{33}C(O)NR^{33}R^{33}$, $-NR^{33}C(O)OR^{34}$, $-C(O)R^{34}$, $-C(O)OR^{34}$, $-C(O)NR^{33}R^{33}$, $-NO_2$, wherein $C_{1-6}$ alkyl, $C_{1-6}$ alkoxy, $C_{1-6}$ hydroxyalkyl, $C_{1-6}$ heteroalkyl, are further substituted with one or more $R^{29}$ groups.

In some embodiments, $R^{24}$ is selected from the group consisting of: $-H$, $-F$, $-Cl$, $-OH$, $-CN$, $S(O)_{0-2}R^{34}$, $-C(O)R^{34}$, $-NO_2$, $-SF_5$, $C_{1-6}$ alkyl, and $C_{1-6}$ alkoxy, and wherein said $C_{1-6}$ alkyl or $C_{1-6}$ alkoxy is optionally substituted with one or more $-F$, and $R^{34}$ is selected from the group consisting of $C_{1-6}$ alkyl, $C_{3-6}$ cycloalkyl, $C_{1-6}$ hydroxyalkyl, $C_{1-6}$ heteroalkyl, wherein the $C_{1-6}$ alkyl, $C_{3-6}$ cycloalkyl, $C_{1-6}$ hydroxyalkyl, and $C_{1-6}$ heteroalkyl, are optionally substituted with one or more $R^{36}$ groups, and $R^{36}$ is independently selected from halo, $-CN$ and $-OH$.

In some embodiments, $R^{24}$ is selected from the group consisting of: $-H$, $-F$, $-Cl$, $-OH$, $-CN$, $-SR^{34}$, $-SF_5$, $C_{1-6}$ alkyl, and $C_{1-6}$ alkoxy, and wherein said $C_{1-6}$ alkyl or $C_{1-6}$ alkoxy is optionally substituted with one or more $-F$, and $R^{34}$ is selected from the group consisting of $C_{1-3}$ haloalkyl.

In some embodiments, $R^{23}$ is selected from the group consisting of: $-H$, halo, $-OH$, $-CN$, $C_{1-6}$ alkyl, $C_{1-6}$ alkoxy, 6-10 membered aryl, 5-10 membered heteroaryl, 4-12 membered heterocyclyl, 3-12 membered cycloalkyl, $C_{1-6}$ hydroxyalkyl, $C_{1-6}$ heteroalkyl, $-S(O)_{0-2}R^{34}$, $-NO_2$ and $-SF_5$, wherein said $C_{1-6}$ alkyl, $C_{1-6}$ alkoxy, $C_{1-6}$ hydroxyalkyl, $C_{1-6}$ heteroalkyl, 6-10 membered aryl, 5-10 membered heteroaryl, 4-12 membered heterocyclyl, and 3-12 membered cycloalkyl are optionally further substituted with one or more $R^{36}$ groups.

In some embodiments, $R^{23}$ is selected from the group consisting of: $-H$, $-F$, $-Cl$, $-OH$, $-CN$, $C_{1-6}$ alkyl, $C_{1-6}$ alkoxy, $C_{1-6}$ hydroxyalkyl, $C_{1-6}$ heteroalkyl, —$SR^{34}$, and —$SF_5$, wherein said $C_{1-6}$ alkyl, $C_{1-6}$ alkoxy, $C_{1-6}$ hydroxyalkyl, and $C_{1-6}$ heteroalkyl are further substituted with one or more $R^{36}$ groups, and $R^{34}$ is $C_{1-3}$ haloalkyl In another embodiment of the disclosure, there is provided a compound of Formula III:

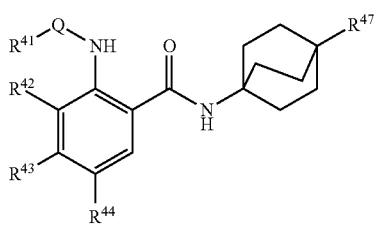

III or a pharmaceutically acceptable salt, stereoisomer, mixtures of stereoisomers, tautomer, or deuterated analogs thereof, wherein:

Q is selected from the group consisting of —$S(O)_2$—, —$S(O)$—, —$S(O)(NH)$—, —$S(O)(NR^{48})$—.

$R^{41}$ is selected from a group consisting of: $C_{1-6}$ alkyl, $C_{2-6}$ alkenyl, $C_{2-6}$ alkynyl, —$NR^{53}R^{53}$, 6-10 membered aryl, 5-10 membered heteroaryl, $C_{3-12}$ cycloalkyl, and 4-12 membered heterocyclyl, wherein each $C_{1-6}$ alkyl, $C_{2-6}$ alkenyl, $C_{2-6}$ alkynyl, 6-10 membered aryl, 5-10 membered heteroaryl, $C_{3-12}$ cycloalkyl, and 4-12 membered heterocyclyl are optionally further substituted with one or more $R^{51}$ groups;

$R^{51}$ is selected from the group consisting of: hydroxyl, oxo, halo, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$P(O)R^{54}R^{54}$, —$S(O)(NH)R^{54}$, —$S(O)(NR^{48})R^{54}$, —$S(O)(NH)NR^{53}R^{53}$, —$S(O)(NR^{48})NR^{53}R^{53}$, —$S(O)_{0-2}R^{54}$, —$S(O)_{12}NR^{53}R^{53}$, —SF, —$NO_2$, —$NR^{53}R^{53}$, —$NR^{53}SO_2R^{54}$, —$OS(O)_2R^{54}$, —$C(O)OR^{54}$, —$C(O)R^{54}$, —$NR^{53}C(O)OR^{54}$, —$NR^{53}C(O)NR^{53}R^{53}$, —$NR^{53}S(O)_2NR^{53}R^{53}$, and —$C(O)NR^{53}R^{53}$, wherein each $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl are optionally substituted with one or more $R^{49}$ groups;

each $R^{49}$ is independently selected from the group consisting of: —H, oxo, —OH, —CN, halo, $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$NR^{53}R^{53}$, —$NR^{53}C(O)OR^{54}$, —$OS(O)_2R^{54}$—$C(O)OR^{54}$, —$S(O)(NH)R^{54}$, —$S(O)(NR^{48})R^{54}$, —$S(O)(NH)NR^{53}R^{53}$, —$S(O)(NR^{48})NR^{53}R^{53}$, —$S(O)_{0-2}R^{54}$, —$S(O)_{1-2}NR^{53}R^{53}$, —$C(O)NR^{53}R^{53}$, —$NR^{53}SO_2R^{54}$, —$C(O)R^{54}$, —$NR^{53}C(O)NR^{53}R^{53}$, —$NR^{53}S(O)_2NR^{53}R^{53}$, —$SF_5$, —$NO_2$, wherein each of $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl is optionally substituted with $R^{56}$;

each $R^{53}$ is independently selected from the group consisting of —H, $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{55}$ groups;

Each $R^{54}$ is independently selected from the group consisting of: $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{55}$ groups;

each $R^{55}$ is independently selected from —H, halo, —CN, —OH, oxo, —$NO_2$, —$SF_5$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$S(O)(NH)R^{56}$, —$S(O)(NR^{48})R^{56}$, —$S(O)(NH)NR^{56}R^{56}$, —$S(O)(NR^{48})NR^{56}R^{56}$, —$S(O)_{0-2}R^{56}$, —$S(O)_2NH_2$, —$NH_2$, —$S(O)_2NR^{56}R^{56}$, $C(O)R^{56}$, —$C(O)NR^{56}R^{56}$ and $C(O)OR^{56}$, wherein 3-6 membered cycloalkyl, 4-12 membered heterocyclyl, 6-10 membered aryl, 5-10 membered heteroaryl are optionally substituted with one or more $R^6$ groups;

each $R^6$ is independently selected from halo, —CN, —OH, —$NH_2$, oxo, —$NO_2$, —$SF_5$, $C_{1-3}$ alkyl, $C_{1-3}$ haloalkyl, $C_{1-6}$ alkoxy, $C_{1-6}$ haloalkoxy, $C_{1-6}$ hydroxyalkyl, thiohaloalkyl, sulfonylalkyl, sulfonylhaloalkyl, sulfonylcycloalkyl, 3-6 membered cycloalkyl, —$C(O)NH_2$ and —$S(O)_2NH_2$;

$R^{42}$ is selected from a group consisting of: —H, —CN, —F, —Cl, $C_{1-3}$ alkyl, $C_{1-3}$ haloalkyl, $C_{1-3}$ heteroalkyl, $C_{1-3}$ alkoxy and $C_{1-3}$ haloalkoxy;

each $R^{43}$ and $R^{44}$ is independently selected from a group consisting of: —H, halo, —OH, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$SF_5$, —$S(O)_{0-2}R^{54}$, —$S(O)(NH)R^{54}$, —$S(O)(NR^{48})R^{54}$, —$S(O)(NH)NR^{53}R^{53}$, —$S(O)(NR^{48})NR^{53}R^{53}$, —SH, —$S(O)_{1-2}NR^{53}R^{53}$, —$NR^{53}R^{53}$, —$NR^{53}SO_2R^{54}$, —$NR^{53}S(O)_2NR^{53}R^{53}$, —$NR^{53}C(O)NR^{53}R^{53}$, —$NR^{53}C(O)OR^{54}$, tri-$C_{1-4}$ alkylsilyl, —$C(O)R^{54}$, —$C(O)OR^{54}$, —$C(O)NR^{53}R^{53}$, —$NO_2$, wherein $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl are optionally further substituted with one or more $R^{49}$ groups;

wherein $R^{42}$ and $R^{43}$, or $R^{43}$ and $R^{44}$ can optionally join, together with the atoms to which they are attached, to form a 5-6 membered cycloalkyl, a 5-6 membered heterocyclyl, phenyl, or a 5-6 membered heteroaryl, each such cyclic groups respectively fused to the phenyl to which they are attached, and each optionally substituted with one or more $R^{49}$ groups;

$R^{47}$ is selected from the group consisting of: —H, halo, —CN, —OH, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, 3-12 membered cycloalkyl, —$S(O)_{0-2}R^{54}$, —$S(O)(NH)R^{54}$, —$S(O)(NR^{48})R^{54}$, —$S(O)(NH)NR^{53}R^{53}$, —$S(O)(NR^{48})NR^{53}R^{53}$, —SH, —$NR^{53}R^{53}$, —$P(O)R^{54}R^{54}$, —$C(O)OH$, —$C(O)OR^{54}$, —$C(O)$ $NR^{53}R^{53}$, $-S(O)_2NR^{53}R^{53}$, $-C(O)R^{54}$, 6-10 membered aryl, 5-10 membered heteroaryl, 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, tri-$C_1$-4 alkylsilyl, $C_{1-6}$ alkoxy, $C_{1-6}$ hydroxyalkyl, $C_{1-6}$ heteroalkyl, and 3-12 membered cycloalkyl are optionally substituted with one or more $R^{55}$;

$R^{48}$ is $C_{1-6}$ alkyl, $-C(O)R^{54}$, 3-12 membered cycloalkyl, $C_{1-6}$ heteroalkyl, 6-10 membered aryl, 5-10 membered heteroaryl, 4-12 membered heterocyclyl, $C(O)OR^{54}$, $C(O)NR^{53}R^{53}$, and $SO_2R^{54}$, wherein each of $C_{1-6}$ alkyl, $C_{1-6}$ alkylcarbonyl, 3-12 membered cycloalkyl, $C_{1-6}$ heteroalkyl, 6-10 membered aryl, 5-10 membered heteroaryl, and 4-12 membered heterocyclyl is optionally substituted with halo, $-CN$, oxo, hydroxyl, $C_{1-6}$ alkyl, $C_{1-6}$ alkoxy, $-S(O)_{1-2}R^{54}$, $-S(O)_2NR^{53}R^{53}$, $-NO_2$, $-SF_5$, $C_{1-6}$ haloalkyl, $C_{1-6}$ haloalkoxy, $C_{1-6}$ hydroxyalkyl, $-NR^{53}R^{53}$, $-C(O)OR^{54}$, $C_{1-6}$ heteroalkyl, 3-6 membered cycloalkyl optionally substituted with $R^{56}$, 4-12 membered heterocyclyl optionally substituted with one or more $R^{56}$, 6-10 membered aryl optionally substituted with one or more $R^{56}$, and 5-10 membered heteroaryl optionally substituted with one or more $R^{56}$;

subject to the proviso that:

when both $R^{43}$ and $R^{47}$ are H, then $R^{44}$ is selected from the group consisting of: $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl, 7-12 membered monocyclic heterocyclyl, $-SF_5$, $-NR^{53}R^{53}$, $-NR^{53}C(O)OR^{54}$, $-NR^{53}SO_2R^{54}$, $-NR^{53}S(O)_2NR^{53}R^{53}$, $-NR^{53}C(O)NR^{53}R^{53}$, tri-$C_{1-4}$ alkylsilyl, $-C(O)R^{54}$, $-C(O)OR^{54}$, $-C(O)NR^{53}R^{53}$, $-S(O)_{0-2}R^{54}$, $-S(O)(NH)R^{54}$, $-S(O)(NR^8)R^{54}$, $-S(O)(NH)NR^{53}R^{53}$, $-S(O)(NR^8)NR^{53}R^{53}$, $-SH$ and $-NO_2$, wherein $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl and 7-12 membered monocyclic heterocyclyl are optionally substituted with one or more $R^{49}$; 5-6 membered heterocyclyl is optionally substituted with $R^{57}$; and 8-10 membered bicyclic heterocyclyl is optionally substituted with one or more $R^{58}$;

wherein $R^{57}$ is selected from $-OH$, oxo, $-CN$, $C_{2-6}$ alkenyl, $C_{2-6}$ alkynyl, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, $-S(O)_{0-2}R^{54}$, $-NR^{53}SO_2R^{54}$, $-NR^{53}S(O)_2NR^{53}R^{53}$, $-NR^{53}C(O)NR^{53}R^{53}$, $-NR^{53}C(O)OR^{54}$, $-C(O)R^{54}$, $-C(O)OR^{54}$ and $-C(O)NR^{53}R^{53}$.

and wherein $R^{58}$ is selected from $C_{2-6}$ alkenyl, $C_{2-6}$ alkynyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, $-S(O)_{0-2}R^{54}$, $-NR^{53}R^{53}$, $-NR^{53}SO_2R^{54}$, $-NR^{53}S(O)_2NR^{53}R^{53}$, $-NR^{53}C(O)NR^{53}R^{53}$, $-NR^{53}C(O)OR^{54}$, $-C(O)R^{54}$, $-C(O)OR^{54}$ and $-C(O)NR^{53}R^{53}$.

In some embodiments, $R^{47}$ is selected from the group consisting of $-H$, halo, $-CN$, $-OH$, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, $-S(O)_{0-2}R^{54}$, $-S(O)(NH)R^{54}$, $-S(O)(NR^{48})R^{54}$, $-S(O)(NH)NR^{53}R^{53}$, $-S(O)(NR^{48})NR^{53}R^{53}$, $-NR^{53}R^{53}$, $-C(O)OH$, $-C(O)OR^{54}$, $-C(O)NR^{53}R^{53}$, $-S(O)_2NR^{53}R^{53}$, $-C(O)R^{54}$, 6-10 membered aryl, 5-10 membered heteroaryl, and 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, and 3-12 membered cycloalkyl are optionally substituted with one or more $R^{55}$.

In some embodiments, $R^{47}$ is selected from the group consisting of $-H$, halo, $-CN$, $-OH$, $C_{1-6}$ alkyl, $C_{2-6}$ alkynyl, $C_{1-6}$ alkoxy, $C_{1-6}$ hydroxyalkyl, $C_{1-6}$ heteroalkyl, 3-6 membered cycloalkyl, $-S(O)_{0-2}R^{54}$, $-C(O)OH$, $-C(O)OR^{54}$, $-C(O)NR^{53}R^{53}$, $-S(O)_2NR^{53}R^{53}$, $-C(O)R^{54}$, 6-10 membered aryl, 5-10 membered heteroaryl, 4-12 membered heterocyclyl; wherein each of said 4-12 membered heterocyclyl, 6-10 membered aryl, 5-10 membered heteroaryl, $C_{1-6}$ alkyl, $C_{2-6}$ alkynyl, $C_{1-6}$ alkoxy, $C_{1-6}$ hydroxyalkyl, $C_{1-6}$ heteroalkyl, and 3-6 membered cycloalkyl are optionally substituted with one or more $R^{56}$.

In some embodiments, $R^{47}$ is selected from the group consisting of $-H$, halo, $-CN$, $-OH$, $C_{1-3}$ alkyl, $C_{1-3}$ alkoxy, $C_{1-3}$ hydroxyalkyl, $C_{1-6}$ heteroalkyl, and 6-10 membered aryl, wherein each of said 6-10 membered aryl, $C_{1-3}$ alkyl, $C_{1-3}$ alkoxy, $C_{1-3}$ hydroxyalkyl, and $C_{1-6}$ heteroalkyl are optionally substituted with one or more $R^{56}$, wherein $R^{56}$ is selected from halo, $-CN$, $-NO_2$, $-SF_5$, $C_{1-3}$ alkyl, $C_{1-3}$ haloalkyl, $C_{1-6}$ alkoxy, $C_{1-6}$ haloalkoxy, thiohaloalkyl, sulfonylalkyl, sulfonylhaloalkyl, sulfonylcycloalkyl;

In some embodiments, Q is selected from the group consisting of $-S(O)_2-$, $-S(O)-$, and $-S(O)(NR^{48})-$.

In some embodiments, $R^{41}$ is selected from the group consisting of: $C_{1-6}$ alkyl, $-NR^{53}R^{53}$, 6-10 membered aryl, 5-10 membered heteroaryl, $C_{3-12}$ cycloalkyl, and 4-12 membered heterocyclyl, wherein each $C_{1-6}$ alkyl, 6-10 membered aryl, 5-10 membered heteroaryl, $C_{3-12}$ cycloalkyl, and 4-12 membered heterocyclyl are further optionally substituted with one or more $R^{51}$ groups.

In some embodiments, $R^{51}$ is selected from the group consisting of: hydroxyl, oxo, halo, $-CN$, $C_{1-6}$ alkyl, $C_{1-6}$ alkoxy, $C_{1-6}$ hydroxyalkyl, $C_{1-6}$ heteroalkyl, 3-6 membered cycloalkyl, 4-12 membered heterocyclyl, 6-10 membered aryl, 5-10 membered heteroaryl, $-S(O)(NH)R^{54}$, $-S(O)(NR^{48})R^{54}$, $-S(O)(NH)NR^{53}R^{53}$, $-S(O)(NR^{48})NR^{53}R^{53}$, $-S(O)_{0-2}R^{54}$, $-S(O)_{1-2}NR^{53}R^{53}$, $-SF_5$, $-NO_2$, $-NR^{53}R^{53}$, $-NR^{53}SO_2R^{54}$, $-C(O)OR^{54}$, $-C(O)R^{54}$, $-NR^{53}C(O)OR^{54}$, and $-C(O)NR^{53}R^{53}$, wherein each $C_{1-6}$ alkyl, $C_{1-6}$ alkoxy, $C_{1-6}$ hydroxyalkyl, $C_{1-6}$ heteroalkyl, 3-6 membered cycloalkyl, 4-12 membered heterocyclyl, 6-10 membered aryl, and 5-10 membered heteroaryl are optionally substituted with one or more $R^{49}$ groups.

In some embodiments, each $R^{49}$ is independently selected from the group consisting of: $-H$, oxo, $-OH$, $-CN$, halo, $C_{1-3}$ alkyl, $C_{1-3}$ alkoxy, $C_{1-6}$ hydroxyalkyl, $C_{1-6}$ heteroalkyl, 3-6 membered cycloalkyl, $-NR^{53}R^{53}$, $-C(O)OR^{54}$, $-S(O)_{0-2}R^{54}$, $-S(O)_{1-2}NR^{53}R^{53}$, $-C(O)NR^{53}R^{53}$, $-NR^{53}SO_2R^{54}$, $-C(O)R^{54}$, $-SF_5$, and $-NO_2$, wherein each of $C_{1-3}$ alkyl, $C_{1-3}$ alkoxy, 3-6 membered cycloalkyl, is optionally substituted with $-CN$, one or more halo, or $C_{1-6}$ heteroalkyl.

In some embodiments, $R^{42}$ is selected from the group consisting of: $-H$, $-CN$, $-F$, methyl, $C_1$ haloalkyl, $C_{1-3}$ heteroalkyl, methoxy and $C_1$haloalkoxy.

In some embodiments, $R^{42}$ is selected from the group consisting of: $-H$ and $-F$.

In some embodiments, $R^{44}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, —$SF_5$, —$S(O)_{0-2}R^{54}$, —$S(O)(NH)R^{54}$, —$S(O)(NR^{48})R^{54}$, —$S(O)(NH)NR^{53}R^{53}$, —$S(O)(NR^{48})NR^{53}R^{53}$, —$NR^{53}R^{53}$, —$NR^{53}SO_2R^{54}$, —$NR^{53}S(O)_2NR^{53}R^{53}$, —$NR^{53}C(O)NR^{53}R^{53}$, —$NR^{53}C(O)OR^{54}$, —$C(O)R^{54}$, —$C(O)OR^{54}$, —$C(O)NR^{53}R^{53}$, —$NO_2$, wherein $C_{1-6}$ alkyl, $C_{1-6}$ alkoxy, $C_{1-6}$ hydroxyalkyl, $C_{1-6}$ heteroalkyl are further substituted with one or more $R^{49}$ groups.

In some embodiments, $R^{44}$ is selected from the group consisting of: —H, —F, —Cl, —OH, —CN, —$S(O)_{0-2}R^{54}$, —$NO_2$, —$SF_5$, $C_{1-6}$ alkyl, and $C_{1-6}$ alkoxy, and wherein said $C_{1-6}$ alkyl or $C_{1-6}$ alkoxy is optionally substituted with one or more —F, and $R^{54}$ is selected from the group consisting of $C_{1-6}$ alkyl, $C_{1-6}$ hydroxyalkyl, $C_{1-6}$ heteroalkyl, wherein the $C_{1-6}$ alkyl, $C_{1-6}$ hydroxyalkyl, and $C_{1-6}$ heteroalkyl, are optionally substituted with one or more $R^{55}$ groups, and $R^{55}$ is independently selected from halo, —CN, —OH, oxo.

In some embodiments, $R^{44}$ is selected from the group consisting of: —H, —F, —Cl, —OH, —CN, —$SR^{54}$, —$SF_5$, $C_{1-6}$ alkyl, and $C_{1-6}$ alkoxy, and wherein said $C_{1-6}$ alkyl or $C_{1-6}$ alkoxy is optionally substituted with one or more —F, and $R^{54}$ is $C_{1-3}$ haloalkyl.

In some embodiments, $R^{43}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, $C_{3-12}$ cycloalkyl, 4-12 membered heterocyclyl, 6-10 membered aryl, 5-10 membered heteroaryl, —$SF_5$, —$S(O)_{0-2}R^{54}$, —$S(O)(NH)R^{54}$, —$S(O)(NR^{48})R^{54}$, —$S(O)(NH)NR^{53}R^{53}$, —$S(O)(NR^{48})NR^{53}R^{53}$, —$NR^{53}R^{53}$, —$NR^{53}SO_2R^{54}$, —$NR^{53}S(O)_2NR^{53}R^{53}$, —$NR^{53}C(O)NR^{53}R^{53}$, —$NR^{53}C(O)OR^{54}$, —$C(O)R^{54}$, —$C(O)OR^{54}$, —$C(O)NR^{53}R^{53}$, and —$NO_2$, wherein $C_{1-6}$ alkyl, $C_{1-6}$ alkoxy, $C_{1-6}$ hydroxyalkyl, $C_{1-6}$ heteroalkyl, $C_{3-12}$ cycloalkyl, 4-12 membered heterocyclyl, 6-10 membered aryl, and 5-10 membered heteroaryl are further substituted with one or more $R^{49}$ groups.

In some embodiments, $R^{49}$ is selected from the group consisting of: —H, oxo, —OH, —CN, halo, $C_{1-3}$ alkyl, $C_{1-3}$ alkoxy, $C_{1-3}$ hydroxyalkyl, $C_{1-6}$ heteroalkyl, 3-6 membered cycloalkyl, —$NR^{53}R^{53}$, —$C(O)OR^{54}$, —$S(O)_{0-2}R^{54}$, —$S(O)_{1-2}NR^{53}R^{53}$, —$C(O)NR^{53}R^{53}$, —$C(O)R^{54}$, wherein each of $C_{1-3}$ alkyl, $C_{1-3}$ alkoxy, $C_{1-6}$ hydroxyalkyl, $C_{1-6}$ heteroalkyl, and 3-6 membered cycloalkyl is optionally substituted with —CN or one or more halo.

In some embodiments, $R^{43}$ is selected from the group consisting of: —H, halo, —CN, $C_{1-3}$ alkyl, $C_{1-3}$ alkoxy, $C_{1-3}$ hydroxyalkyl, $C_{1-6}$ heteroalkyl, $C_{3-6}$ cycloalkyl, 4-6 membered heterocyclyl, 5-10 membered heteroaryl, —$SF_5$, —$S(O)_{0-2}R^{54}$, and —$NO_2$, wherein $C_{1-3}$ alkyl, $C_{1-3}$ alkoxy, $C_{1-3}$ hydroxyalkyl, $C_{1-6}$ heteroalkyl, $C_{3-6}$ cycloalkyl, 4-6 membered heterocyclyl, and 5-10 membered heteroaryl are further substituted with one or more $R^{49}$ groups.

In some embodiments, $R^{49}$ is selected from the group consisting of: —H, oxo, —OH, —CN, halo, $C_{1-3}$ alkyl, $C_{1-3}$ alkoxy, $C_{1-3}$ hydroxyalkyl, $C_{1-6}$ heteroalkyl, 3-6 membered cycloalkyl, —$C(O)OR^{54}$, —$S(O)_{0-2}R^{54}$, —$S(O)_{1-2}NR^{53}R^{53}$, —$C(O)R^{54}$, wherein each of $C_{1-3}$ alkyl, $C_{1-3}$ alkoxy, $C_{1-3}$ hydroxyalkyl, $C_{1-6}$ heteroalkyl, and 3-6 membered cycloalkyl is optionally substituted with —CN or one or more halo.

In another embodiment of the disclosure, there is provided a compound of Formula IV:

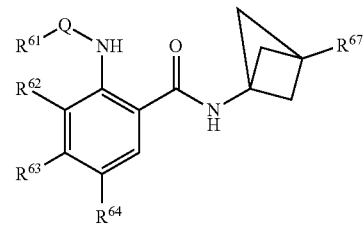

IV or a pharmaceutically acceptable salt, stereoisomer, mixtures of stereoisomers, tautomer, or deuterated analogs thereof, wherein:

Q is selected from the group consisting of —$S(O)_2$—, —$S(O)$—, —$S(O)(NH)$—, —$S(O)(NR^{68})$—;

$R^{61}$ is selected from a group consisting of: $C_{1-6}$ alkyl, $C_{2-6}$ alkenyl, $C_{2-6}$ alkynyl, —$NR^{73}R^{73}$, 6-10 membered aryl, 5-10 membered heteroaryl, $C_{3-12}$ cycloalkyl, and 4-12 membered heterocyclyl, wherein each $C_{1-6}$ alkyl, $C_{2-6}$ alkenyl, $C_{2-6}$ alkynyl, 6-10 membered aryl, 5-10 membered heteroaryl, $C_{3-12}$ cycloalkyl, and 4-12 membered heterocyclyl are optionally further substituted with one or more $R^{71}$ groups;

$R^{71}$ is selected from the group consisting of: hydroxyl, oxo, halo, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$P(O)R^{74}R^{74}$, —$S(O)(NH)R^{74}$, —$S(O)(NR^{68})R^{74}$, —$S(O)(NH)NR^{73}R^{73}$, —$S(O)(NR^{68})NR^{73}R^{73}$, —SH, —$S(O)_{0-2}R^{74}$, —$S(O)_{1-2}NR^{73}R^{73}$, —$SF_5$, —$NO_2$, —$NR^{73}R^{73}$, —$NR^{73}SO_2R^{74}$, —$OS(O)_2R^{74}$, —$C(O)OR^{74}$, —$C(O)R^{74}$, —$NR^{73}C(O)OR^{74}$, —$NR^{73}C(O)NR^{73}R^{73}$, —$NR^{73}S(O)_2NR^{73}R^{73}$, and —$C(O)NR^{73}R^{73}$, wherein each $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl are optionally substituted with one or more $R^{69}$ groups;

each $R^{69}$ is independently selected from the group consisting of: —H, oxo, —OH, —CN, halo, $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$NR^{73}R^{73}$, —$NR^{73}C(O)OR^{74}$, —$OS(O)_2R^{74}$—$C(O)OR^{74}$, —$S(O)(NH)R^{74}$, —$S(O)(NR^{68})R^{74}$, —$S(O)(NH)NR^{73}R^{73}$, —$S(O)(NR^{68})NR^{73}R^{73}$, —SH, —$S(O)_{0-2}R^{74}$, —$S(O)_{1-2}NR^{73}R^{73}$, —$C(O)NR^{73}R^{73}$, —$NR^{73}SO_2R^{74}$, —$C(O)R^{74}$, —$NR^{73}C(O)NR^{73}R^{73}$, —$NR^{73}S(O)_2NR^{73}R^{73}$, —$SF_5$, —$NO_2$, wherein each of $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl is optionally substituted with one or more $R^{76}$ groups;

each $R^{73}$ is independently selected from the group consisting of —H, $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{75}$ groups;

Each $R^{74}$ is independently selected from the group consisting of: $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{75}$ groups;

each $R^{75}$ is independently selected from —H, halo, —CN, —OH, oxo, —NO$_2$, —SF$_5$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —S(O)(NH)R$^{66}$, —S(O)(NR$^{68}$)R$^{66}$, —S(O)(NH)NR$^{66}$R$^{66}$, —S(O)(NR$^{68}$)NR$^{66}$R$^{66}$, —SH, —S(O)$_{0-2}$R$^{66}$, —S(O)$_2$NH$_2$, —NH$_2$, —S(O)$_2$NR$^{66}$R$^{66}$, C(O)R$^{66}$, —C(O)NR$^{66}$R$^{66}$ and C(O)OR$^{66}$, wherein 3-6 membered cycloalkyl, 4-12 membered heterocyclyl, 6-10 membered aryl, 5-10 membered heteroaryl are optionally substituted with one or more $R^{76}$ groups;

each $R^{76}$ is independently selected from halo, —CN, —OH, —NH$_2$, oxo, —NO$_2$, —SF$_5$, $C_{1-3}$ alkyl, $C_{1-3}$ haloalkyl, $C_{1-6}$ alkoxy, $C_{1-6}$ haloalkoxy, $C_{1-6}$ hydroxyalkyl, thioalkyl, thiohaloalkyl, thiocycloalkyl, sulfonylalkyl, sulfonylhaloalkyl, sulfonylcycloalkyl, 3-6 membered cycloalkyl, —C(O)NH$_2$ and —S(O)$_2$NH$_2$;

$R^{62}$ is selected from a group consisting of: —H, —CN, —F, —Cl, $C_{1-3}$ alkyl, $C_{1-3}$ haloalkyl, $C_{1-3}$ heteroalkyl, $C_{1-3}$ alkoxy and $C_{1-3}$ haloalkoxy;

each $R^{63}$ and $R^{64}$ is independently selected from a group consisting of: —H, halo, —OH, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —SF$_5$, —S(O)$_{0-2}$R$^{74}$, —S(O)(NH)R$^{74}$, —S(O)(NR$^{68}$)R$^{74}$, —S(O)(NH)NR$^{73}$R$^{73}$, —S(O)(NR$^{68}$)NR$^{73}$R$^{73}$, —SH, —NR$^{73}$R$^{73}$, —NR$^{73}$SO$_2$R$^{74}$, —NR$^{73}$S(O)$_2$NR$^{73}$R$^{73}$, —NR$^{73}$C(O)NR$^{73}$R$^{73}$, —NR$^{73}$C(O)OR$^{74}$, tri-$C_{1-4}$ alkylsilyl, —C(O)R$^{74}$, —C(O)OR$^{74}$, —C(O)NR$^{73}$R$^{73}$ and —NO$_2$, wherein $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl are optionally further substituted with one or more $R^{69}$ groups;

wherein $R^{62}$ and $R^{63}$, or $R^{63}$ and $R^{64}$ can optionally join, together with the atoms to which they are attached, to form a 5-6 membered cycloalkyl, a 5-6 membered heterocyclyl, phenyl, or a 5-6 membered heteroaryl, each such cyclic groups respectively fused to the phenyl to which they are attached, and each optionally substituted with one or more $R^{69}$ groups;

$R^{67}$ is selected from the group consisting of: —H, halo, —CN, —OH, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, 3-12 membered cycloalkyl, —S(O)$_{0-2}$R$^{74}$, —S(O)(NH)R$^{74}$, —S(O)(NR$^{68}$)R$^{74}$, —S(O)(NH)NR$^{73}$R$^{73}$, —S(O)(NR$^{68}$)NR$^{73}$R$^{73}$, —SH, —NR$^{73}$R$^{73}$, —P(O)R$^{74}$R$^{74}$, —C(O)OH, —C(O)OR$^{74}$, —C(O)NR$^{73}$R$^{73}$, —S(O)$_2$NR$^{73}$R$^{73}$, —C(O)R$^{74}$, 6-10 membered aryl, 5-10 membered heteroaryl and 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, and 3-12 membered cycloalkyl are optionally substituted with one or more $R^{75}$;

$R^{68}$ is $C_{1-6}$ alkyl, —C(O)R$^{74}$, 3-12 membered cycloalkyl, $C_{1-6}$ heteroalkyl, 6-10 membered aryl, 5-10 membered heteroaryl, 4-12 membered heterocyclyl, —C(O)OR$^{74}$, —C(O)NR$^{73}$R$^{73}$, —SO$_2$R$^{74}$, wherein each of $C_{1-6}$ alkyl, $C_{1-6}$ alkylcarbonyl, 3-12 membered cycloalkyl, $C_{1-6}$ heteroalkyl, 6-10 membered aryl, 5-10 membered heteroaryl, and 4-12 membered heterocyclyl is optionally substituted with halo, —CN, oxo, hydroxyl, $C_{1-6}$ alkyl, $C_{1-6}$ alkoxy, —S(O)$_{1-2}$R$^{74}$, —S(O)$_2$NR$^{73}$R$^{73}$, —NO$_2$, —SF$_5$, $C_{1-6}$ haloalkyl, $C_{1-6}$ haloalkoxy, $C_{1-6}$ hydroxyalkyl, NR$^{73}$R$^{73}$, —C(O)OR$^{74}$, $C_{1-6}$ heteroalkyl, 3-6 membered cycloalkyl optionally substituted with $R^{76}$, 4-12 membered heterocyclyl optionally substituted with one or more $R^{76}$, 6-10 membered aryl optionally substituted with one or more $R^{76}$, and 5-10 membered heteroaryl optionally substituted with one or more $R^{76}$;

In some embodiments, Q is selected from the group consisting of —S(O)$_2$—, —S(O)—, and —S(O)(NR$^{68}$)—.

In some embodiments, $R^{61}$ is selected from the group consisting of: $C_{1-6}$ alkyl, —NR$^{73}$R$^{73}$, 6-10 membered aryl, 5-10 membered heteroaryl, $C_{3-12}$ cycloalkyl, and 4-12 membered heterocyclyl, wherein each $C_{1-6}$ alkyl, 6-10 membered aryl, 5-10 membered heteroaryl, $C_{3-12}$ cycloalkyl, and 4-12 membered heterocyclyl are further substituted with one or more $R^{71}$ groups.

In some embodiments, $R^{62}$ is selected from the group consisting of: —H, —CN, —F, methyl, $C_1$ haloalkyl, $C_{1-3}$ heteroalkyl, methoxy and $C_1$ haloalkoxy.

In some embodiments, $R^{62}$ is selected from the group consisting of: —H, and —F.

In some embodiments, $R^{64}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, —SF$_5$, —S(O)$_{0-2}$R$^{74}$, —S(O)(NH)R$^{74}$, —S(O)(NR$^{68}$)R$^{74}$, —S(O)(NH)NR$^{73}$R$^{73}$, —S(O)(NR$^{68}$)NR$^{73}$R$^{73}$, —NR$^{73}$R$^{73}$, —NR$^{73}$SO$_2$R$^{74}$, —NR$^{73}$S(O)$_2$NR$^{73}$R$^{73}$, —NR$^{73}$C(O)NR$^{73}$R$^{73}$, —NR$^{73}$C(O)OR$^{74}$, —C(O)R$^{74}$, —C(O)OR$^{74}$, —C(O)NR$^{73}$R$^{73}$, —NO$_2$, wherein $C_{1-6}$ alkyl, $C_{1-6}$ alkoxy, $C_{1-6}$ hydroxyalkyl, $C_{1-6}$ heteroalkyl are further substituted with one or more $R^{69}$ groups.

In some embodiments, $R^{64}$ is selected from the group consisting of: —H, —F, —Cl, —OH, —CN, —S(O)$_{0-2}$R$^{74}$, —SF$_5$, —NO$_2$, $C_{1-6}$ alkyl, and $C_{1-6}$ alkoxy, and wherein said $C_{1-6}$ alkyl or $C_{1-6}$ alkoxy is optionally substituted with one or more —F. and $R^{74}$ is selected from the group consisting of $C_{1-6}$ alkyl, $C_{1-6}$ hydroxyalkyl, $C_{1-6}$ heteroalkyl, wherein the $C_{1-6}$ alkyl, $C_{1-6}$ hydroxyalkyl, and $C_{1-6}$ heteroalkyl, are optionally substituted with one or more $R^{75}$ groups, and $R^{75}$ is independently selected from halo, —CN, —OH, oxo.

In some embodiments, $R^{64}$ is selected from the group consisting of: —H, —F, —Cl, —OH, —CN, SR$^{74}$, —SF$_5$, $C_{1-6}$ alkyl, and $C_{1-6}$ alkoxy, and wherein said $C_{1-6}$ alkyl or $C_{1-6}$ alkoxy is optionally substituted with one or more —F, and $R^{74}$ is $C_{1-3}$ haloalkyl.

In some embodiments, $R^{63}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, $C_{3-12}$ cycloalkyl, 4-12 membered heterocyclyl, 6-10 membered aryl, 5-10 membered heteroaryl, —SF$_5$, —S(O)$_{0-2}$R$^{74}$, —S(O)(NH)R$^{74}$, —S(O)(NR$^{68}$)R$^{74}$, —S(O)(NH)NR$^{73}$R$^{73}$, —S(O)(NR$^{48}$)NR$^{73}$R$^{73}$, —NR$^{73}$R$^{73}$, —NR$^{73}$SO$_2$R$^{74}$, —NR$^{73}$S(O)$_2$NR$^{73}$R$^{73}$, —NR$^{73}$C(O)NR$^{73}$R$^{73}$, —NR$^{73}$C(O)OR$^{74}$, —C(O)R$^{74}$, —C(O)OR$^{74}$, —C(O)NR$^{73}$R$^{73}$, and —NO$_2$, wherein C$_{1-6}$ alkyl, C$_{1-6}$ alkoxy, C$_{1-6}$ hydroxyalkyl, C$_{1-6}$ heteroalkyl, C$_{3-12}$ cycloalkyl, 4-12 membered heterocyclyl, 6-10 membered aryl, and 5-10 membered heteroaryl are further substituted with one or more R$^{69}$ groups.

In some embodiments, R$^{69}$ is selected from the group consisting of: —H, oxo, —OH, —CN, halo, C$_{1-3}$ alkyl, C$_{1-3}$ alkoxy, C$_{1-6}$ hydroxyalkyl, C$_{1-6}$ heteroalkyl, 3-6 membered cycloalkyl, —NR$^{73}$R$^{73}$, —C(O)OR$^{74}$, —S(O)$_{0-2}$R$^{74}$, —S(O)$_{1-2}$NR$^{73}$R$^{73}$, —C(O)NR$^{73}$R$^{73}$, —C(O)R$^{74}$, wherein each of C$_{1-3}$ alkyl, C$_{1-3}$ alkoxy, C$_{1-6}$ hydroxyalkyl, C$_{1-6}$ heteroalkyl, and 3-6 membered cycloalkyl is optionally substituted with —CN or one or more halo.

In some embodiments, R$^{63}$ is selected from the group consisting of: —H, halo, —CN, C$_{1-3}$ alkyl, C$_{1-3}$ alkoxy, C$_{1-3}$ hydroxyalkyl, C$_{1-6}$ heteroalkyl, C$_{3-6}$ cycloalkyl, 4-6 membered heterocyclyl, 5-10 membered heteroaryl, —SF$_5$, —S(O)$_{0-2}$R$^{74}$, and —NO$_2$, wherein C$_{1-3}$ alkyl, C$_{1-3}$ alkoxy, C$_{1-3}$ hydroxyalkyl, C$_{1-6}$ heteroalkyl, C$_{3-6}$ cycloalkyl, 4-6 membered heterocyclyl, and 5-10 membered heteroaryl are further substituted with one or more R$^{69}$ groups.

In some embodiments, R$^{69}$ is selected from the group consisting of: —H, oxo, —OH, —CN, halo, C$_{1-3}$ alkyl, C$_{1-3}$ alkoxy, C$_{1-3}$ hydroxyalkyl, C$_{1-6}$ heteroalkyl, 3-6 membered cycloalkyl, —C(O)OR$^{74}$, —S(O)$_{0-2}$R$^{74}$, —S(O)$_{1-2}$NR$^{73}$R$^{73}$, —C(O)R$^{74}$, wherein each of C$_{1-3}$ alkyl, C$_{1-3}$ alkoxy, C$_{1-3}$ hydroxyalkyl, C$_{1-6}$ heteroalkyl, and 3-6 membered cycloalkyl is optionally substituted with —CN or one or more halo.

There is also provided a pharmaceutical composition comprising a compound of Formula I, Formula II, Formula III, Formula IV, or a pharmaceutically acceptable salt, stereoisomer, mixtures of stereoisomers, tautomer, or deuterated analogs thereof, together with a pharmaceutically acceptable excipient.

There is also provided a method of treating NAFLD, NASH, ASH or lipodystrophy comprising administering to a patient in need thereof, an effective amount of a composition of Formula I, Formula II, Formula III, Formula IV, or a pharmaceutically acceptable salt, stereoisomer, mixtures of stereoisomers, tautomer, or deuterated analogs thereof.

In another embodiment, there is provided a compound of Formula I, wherein R$^7$ is selected from the group consisting of —H, halo, —CN, —OH, C$_{1-6}$ alkyl, C$_{2-6}$ alkenyl, C$_{2-6}$ alkynyl, C$_{1-6}$ alkoxy, C$_{1-6}$ hydroxyalkyl, C$_{1-6}$ heteroalkyl, 3-12 membered cycloalkyl, —S(O)$_{0-2}$R$^{14}$, —S(O)(NH)R$^{14}$, —S(O)(NR$^8$)R$^{14}$, —S(O)(NH)NR$^{13}$R$^{13}$, —S(O)(NR$^8$)NR$^{13}$R$^{13}$, —NR$^{13}$R$^{13}$, —C(O)OH, —C(O)OR$^{14}$, —C(O)NR$^{13}$R$^{13}$, —S(O)$_2$NR$^{13}$R$^{13}$, —C(O)R$^{14}$, 6-10 membered aryl, 5-10 membered heteroaryl, and 4-12 membered heterocyclyl; wherein each of said 4-12 membered heterocyclyl, 6-10 membered aryl, 5-10 membered heteroaryl, C$_{1-6}$ alkyl, C$_{2-6}$ alkenyl, C$_{2-6}$ alkynyl, C$_{1-6}$ alkoxy, C$_{1-6}$ hydroxyalkyl, C$_{1-6}$ heteroalkyl, and 3-12 membered cycloalkyl are optionally substituted with one or more R$^{15}$.

In another embodiment, there is provided a compound of Formula I, wherein R$^7$ is selected from the group consisting of —H, halo, —CN, —OH, C$_{1-6}$ alkyl, C$_{2-6}$ alkynyl, C$_{1-6}$ alkoxy, C$_{1-6}$ hydroxyalkyl, C$_{1-6}$ heteroalkyl, 3-6 membered cycloalkyl, —S(O)$_{0-2}$R$^{14}$, —C(O)OH, —C(O)OR$^{14}$, —C(O)NR$^{13}$R$^{13}$, —S(O)$_2$NR$^{13}$R$^{13}$, —C(O)R$^{14}$, 6-10 membered aryl, 5-10 membered heteroaryl, 4-12 membered heterocyclyl; wherein each of said 4-12 membered heterocyclyl, 6-10 membered aryl, 5-10 membered heteroaryl, C$_{1-6}$ alkyl, C$_{2-6}$ alkynyl, C$_{1-6}$ alkoxy, C$_{1-6}$ hydroxyalkyl, C$_{1-6}$ heteroalkyl, and 3-6 membered cycloalkyl are optionally substituted with one or more R$^6$.

In another embodiment, there is provided a compound of Formula I, wherein R$^7$ is selected from the group consisting of —H, halo, —CN, —OH, C$_{1-3}$ alkyl, C$_{1-3}$ alkoxy, C$_{1-3}$ hydroxyalkyl, C$_{1-6}$ heteroalkyl, and 6-10 membered aryl, wherein each of said 6-10 membered aryl, C$_{1-3}$ alkyl, C$_{1-3}$ alkoxy, C$_{1-3}$ hydroxyalkyl, and C$_{1-6}$ heteroalkyl are optionally substituted with one or more R$^{16}$, wherein R$^{16}$ is selected from halo, —CN, —NO$_2$, —SF$_5$, C$_{1-3}$ alkyl, C$_{1-3}$ haloalkyl, C$_{1-6}$ alkoxy, C$_{1-6}$ haloalkoxy, thiohaloalkyl, sulfonylalkyl, sulfonylhaloalkyl, sulfonylcycloalkyl;

In another embodiment, there is provided a compound of Formula I, wherein R$^8$ is selected from the group consisting of C$_{1-6}$ alkyl, —C(O)R$^{14}$, 3-12 membered cycloalkyl, C$_{1-6}$ heteroalkyl, 6-10 membered aryl, 5-10 membered heteroaryl, 4-12 membered heterocyclyl, —C(O)OR$^{14}$, —C(O)NR$^{13}$R$^{13}$, and —SO$_2$R$^{14}$, wherein each of C$_{1-6}$ alkyl, 3-12 membered cycloalkyl, C$_{1-6}$ heteroalkyl, 6-10 membered aryl, 5-10 membered heteroaryl, and 4-12 membered heterocyclyl is optionally substituted with one or more R$^{16}$.

In another embodiment, there is provided a compound of Formula II, wherein R$^{27}$ is selected from the group consisting of —H, halo, —CN, —OH, C$_{1-6}$ alkyl, C$_{2-6}$ alkenyl, C$_{2-6}$ alkynyl, C$_{1-6}$ alkoxy, C$_{1-6}$ hydroxyalkyl, C$_{1-6}$ heteroalkyl, 3-12 membered cycloalkyl, —S(O)$_{0-2}$R$^{34}$, —S(O)(NH)R$^{34}$, —S(O)(NR$^{28}$)R$^{34}$, —S(O)(NH)NR$^{33}$R$^{33}$, —S(O)(NR$^{28}$)NR$^{33}$R$^{33}$, —NR$^{33}$R$^{33}$, —C(O)OH, —C(O)OR$^{34}$, —C(O)NR$^{33}$R$^{33}$, —S(O)$_2$NR$^{33}$R$^{33}$, —C(O)R$^{34}$, 6-10 membered aryl, 5-10 membered heteroaryl, and 4-12 membered heterocyclyl; wherein each of said 4-12 membered heterocyclyl, 6-10 membered aryl, 5-10 membered heteroaryl, C$_{1-6}$ alkyl, C$_{2-6}$ alkenyl, C$_{2-6}$ alkynyl, C$_{1-6}$ alkoxy, C$_{1-6}$ hydroxyalkyl, C$_{1-6}$ heteroalkyl, and 3-12 membered cycloalkyl are optionally substituted with one or more R$^{35}$;

In another embodiment, there is provided a compound of Formula II, wherein R$^{27}$ is selected from the group consisting of —H, halo, —CN, —OH, C$_{1-6}$ alkyl, C$_{2-6}$ alkynyl, C$_{1-6}$ alkoxy, C$_{1-6}$ hydroxyalkyl, C$_{1-6}$ heteroalkyl, 3-6 membered cycloalkyl, —S(O)$_{0-2}$R$^{34}$, —C(O)OH, —C(O)OR$^{34}$, —C(O)NR$^{33}$R$^{33}$, —S(O)$_2$NR$^{33}$R$^{33}$, —C(O)R$^{34}$, 6-10 membered aryl, 5-10 membered heteroaryl, 4-12 membered heterocyclyl; wherein each of said 4-12 membered heterocyclyl, 6-10 membered aryl, 5-10 membered heteroaryl, C$_{1-6}$ alkyl, C$_{2-6}$ alkynyl, C$_{1-6}$ alkoxy, C$_{1-6}$ hydroxyalkyl, C$_{1-6}$ heteroalkyl, and 3-6 membered cycloalkyl are optionally substituted with one or more R$^{36}$.

In another embodiment, there is provided a compound of Formula II, wherein R$^{27}$ is selected from the group consisting of —H, halo, —CN, —OH, C$_{1-3}$ alkyl, C$_{1-3}$ alkoxy, C$_{1-3}$ hydroxyalkyl, C$_{1-6}$ heteroalkyl, and 6-10 membered aryl, wherein each of said 6-10 membered aryl, C$_{1-3}$ alkyl, C$_1$-3 alkoxy, C$_{1-3}$ hydroxyalkyl, and C$_{1-6}$ heteroalkyl are optionally substituted with one or more R$^{36}$, wherein R$^{36}$ is selected from halo, —CN, —NO$_2$, —SF$_5$, C$_1$-3 alkyl, C$_1$-3 haloalkyl, C$_{1-6}$ alkoxy, C$_{1-6}$ haloalkoxy, thiohaloalkyl, sulfonylalkyl, sulfonylhaloalkyl, sulfonylcycloalkyl;

In another embodiment, there is provided a compound of Formula II, wherein R$^{28}$ is selected from the group consisting of C$_{1-6}$ alkyl, —C(O)R$^{34}$, 3-12 membered cycloalkyl, C$_{1-6}$ heteroalkyl, 6-10 membered aryl, 5-10 membered heteroaryl, 4-12 membered heterocyclyl, —C(O)OR$^{34}$, —C(O)NR$^{33}$R$^{33}$, and —SO$_2$R$^{34}$, wherein each of C$_{1-6}$ alkyl, 3-12 membered cycloalkyl, C$_{1-6}$ heteroalkyl, 6-10 membered aryl, 5-10 membered heteroaryl, and 4-12 membered heterocyclyl is optionally substituted with one or more $R^{36}$;

In another embodiment of the present invention, there is provided a method of treating a disease or condition mediated at least in part by mitochondrial dysfunction, in a patient in need thereof, comprising administering to the patient an effective amount of a compound of pharmaceutical composition of the disclosure, including each individual compound exemplified below.

In another embodiment of the present invention, there is provided a method of treating a disease or condition treatable through mitochondrial uncoupling, in a patient in need thereof, comprising administering to the patient an effective amount of a compound of pharmaceutical composition of the disclosure, including each individual compound exemplified below.

DETAILED DESCRIPTION OF THE INVENTION

Definitions

The following description sets forth exemplary methods, parameters and the like. It should be recognized, however, that such description is not intended as a limitation on the scope of the present disclosure but is instead provided as a description of exemplary embodiments.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Acyl" refers to a group —C(O)—

"Alkylcarbonyl" refers to the group —$C_{1-6}$C(O)—.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy. As used herein, alkoxy includes cyclic hydrocarbons attached through a non-ring member oxygen. Examples include cyclopropoxy and cyclobutoxy.

When an alkyl, alkenyl, or alkynyl group is optionally substituted, it is to be understood that the resulting divalent (or greater than divalent) group could be named alkylene, alkenylene, alkynelene. In the present specification, for simplification, the names "alkyl, alkenyl and alkynyl are preserved, whether or not the moiety is monovalent, divalent or multivalent. The same is true for all substituents herein that could have different names based upon valence.

"Haloalkoxy" refers to an alkoxy group as defined above, wherein one or more hydrogen atoms are replaced by a halogen.

"Thioalkyl" refers to the group "alkyl-S—".

"Thiohaloalkyl" means a halogenated alkyl-S—.

"Thiocycloalkyl" means the group "$C_{3-6}$ cycloalkyl-S—".

"Sulfonylalkyl" means the group "$C_{1-6}$ alkyl-S(O)$_2$—".

"Sulfonylhaloalkyl" means a halogenated $C_{1-6}$ alkyl-S(O)$_2$

"Sulfonylcycloalkyl" means the group "$C_{3-6}$ cycloalkyl-S(O)$_2$—".

"Amino" refers to the group —NR$^y$R$^y$ wherein each R$^y$ is independently selected from the group consisting of hydrogen, alkyl, alkenyl, alkynyl, aryl, heterocyclyl, cycloalkyl or heteroaryl, each of which is optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cyano" refers to the group —CN.

"Keto" or "oxo" refers to a group =O.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein $R^y$ and $R^z$ are independently selected from the group consisting of hydrogen, alkyl, aryl, haloalkyl, or heteroaryl; each of which may be optionally substituted.

"Carboxyl" refers to —C(O)OH.

"Ester" refers to both —OC(O)R and —C(O)OR, wherein R is a substituent; each of which may be optionally substituted, as defined herein.

"Cycloalkyl" refers to a saturated or partially unsaturated cyclic alkyl group having a single ring or multiple rings including fused, bridged, and spiro ring systems, also called herein "carbobicyclic" ring systems in cases of bicyclic rings containing only hydrocarbons or substituted hydrocarbons. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring-carbon atoms (i.e., $C_{3-12}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

Bicyclic hydrocarbon ring systems (or carbobicyclic ring systems) substituents include fused, bridged and spiro cycles, such as, but not limited to, octahydro-1H-indenyl, naphthalenyl, bicyclo[1.1.1]pentanyl, bicyclo[2.2.2]octanyl, bicyclo[2.1.1]hexanyl, bicycl[2.2.1]heptanyl; spiro [5.2]octanyl, spiro[4.3]octanyl, spiro[5.4]decanyl and the like.

Tricyclic groups contain three fused, bridged or spiro ring systems, and include, by way of example and non limitation, adamantanyl (IUPAC systematic name: tricyclo[3.3.1.13,7]decanyl) and the like.

Polycyclic hydrocarbon ring system substituents contain more than three ring systems, and include, for example, cubanyl (IUPAC systematic name: pentacyclo[4.2.0.0$^{2,5}$.0$^{3,8}$.0$^{4,7}$]octanyl).

The expression —S(O)(NH)— is represented by the formula:

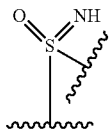

The expression —S(O)(NR$^8$)— is represented by the formula:

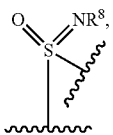

wherein $R^8$ is defined herein.

The expression —S(O)$_{0-2}$ means that the Oxygen is absent or present, and when present, there may be one or two Oxygen atoms. For example S(O)$_0$R$^{14}$ is synonamous with SR$^{14}$.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —CH$_2$OCH$_3$, —CH$_2$SCH$_3$, —CH$_2$S(O) CH$_3$, and —CH$_2$S(O)$_2$CH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from, N, NO, O, S, S(O), S(O)(NH), S(O)(NR) and S(O)$_2$. The term "heterocyclyl" includes heterocycloalkenyl groups (i.e. the heterocyclyl group having at least one double bond), bicyclic heterocyclyl groups, bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule.

As used herein, heterocyclyl has 4 to 20 ring atoms (i.e., 4-20 membered heterocyclyl), 4 to 12 ring atoms (i.e., 4-12 membered heterocyclyl), 4 to 10 ring atoms (i.e., 4-10 membered heterocyclyl), 4 to 8 ring atoms (i.e., 4-8 membered heterocyclyl), or 4 to 6 ring carbon atoms (i.e., 4-6 membered heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen, and wherein the point of attachment to another substituent may be through carbon, or, as relevant, through the heteroatom. A heterocyclyl may contain one or more oxo and/or thioxo groups. Examples of heterocyclyl groups include pyrrolidinyl, piperidinyl, piperazinyl, oxetanyl, dioxolanyl, azetidinyl, azetidinyl, morpholinyl, thiomorpholinyl, dioxothiomorpholinyl, 4-7 membered sultam, 4-7 membered cyclic carbamate, 4-7 membered cyclic carbonate, 4-7 membered cyclic sulfide,

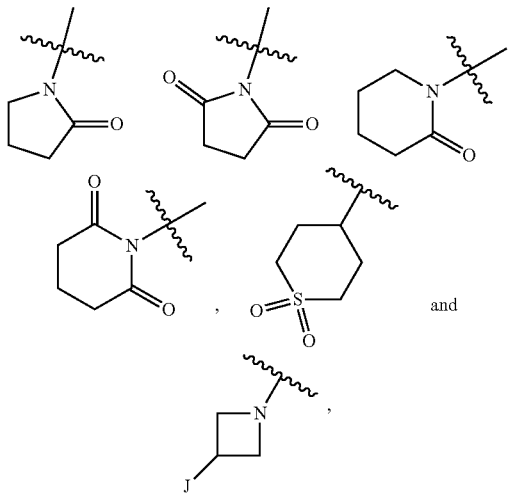

where J is an optional substituent, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Non-exclusive examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system. As used herein, a bicyclic heterocyclyl group is a heterocyclyl group attached at two points to another cyclic group, wherein the other cyclic group may itself be a heterocyclic group, or a carbocyclic group.

As used herein, the term "nitrogen or sulfur containing heterocyclyl" means a heterocyclyl moiety that contains at least one nitrogen atom or at least one sulfur atom, or both a nitrogen atom and a sulfur atom within the ring structure. It is to be understood that other heteroatoms, including oxygen, may be present in addition to the nitrogen, sulfur, or combinations thereof. Examples of nitrogen or sulfur containing heterocyclyls include morpholinyl, thiomorpholinyl, thiazolyl, isothiazolyl, oxazolidinone 1,2 dithiolyl, piperidinyl, piperazinyl, and the like.

"Hydroxy" or "hydroxyl" refers to the group —OH.

"Hydroxyalkyl" refers to an unbranched or branched alkyl group as defined above, wherein one or more hydrogen atoms are replaced by a hydroxyl.

"Nitro" refers to the group —NO$_2$.

"Sulfonyl" refers to the group —S(O)$_2$R, where R is a substituent, or a defined group.

"Alkylsulfonyl" refers to the group —S(O)$_2$R, where R is an alkyl group.

"sulfinyl" refers to the group —S(O)R, where R is a substituent, or a defined group.

"Alkylsulfinyl" refers to the group —S(O)R where R is an alkyl group

"Polycyclic" refers to ring systems that include more than three rings.

"Thiocyanate"—SCN.

"Thiol" refers to the group —SH

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl," then the general term can refer to any antecedent specifically recited term, such as (C$_{1-3}$ alkyl), (C$_{4-6}$ alkyl), —O(C$_{1-4}$ alkyl), (C$_{3-10}$ cycloalkyl), O—(C$_{3-10}$ cycloalkyl) and the like. For example, "any aryl" includes both "aryl" and "—O(aryl)" as well as examples of aryl, such as phenyl or naphthyl and the like. Also, the term "any heterocyclyl" includes both the terms "heterocyclyl" and O-(heterocyclyl)," as well as examples of heterocyclyls, such as oxetanyl, tetrahydropyranyl, morpholino, piperidinyl and the like. In the same manner, the term "any heteroaryl" includes the terms "heteroaryl" and "O-(heteroryl)," as well as specific heteroaryls, such as pyridine and the like.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted. One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Pharmaceutical Compositions

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipient, etc.) which constitutes one or more accessory ingredients. In general the formulations are prepared by uniformly and intimately bringing into association the active ingredient with liquid carriers or finely divided solid carriers or both, and then, if necessary, shaping the product.

In certain embodiments, formulations suitable for oral administration are presented as discrete units such as capsules, cachets or tablets each containing a predetermined amount of the active ingredient.

In certain embodiments, the pharmaceutical formulations include one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight). In some embodiments, the pharmaceutical compositions described herein contain about 1 to 800 mg, 1 to 600 mg, 1 to 400 mg, 1 to 200 mg, 1 to 100 mg or 1 to 50 mg of the compound of Formula I, or a pharmaceutically acceptable salt thereof. In some embodiments, the pharmaceutical compositions described herein contain not more than about 400 mg of the compound of Formula I. In some embodiments, the pharmaceutical compositions described herein contain about 100 mg of the compound of Formula I, or a pharmaceutically acceptable salt thereof.

It should be understood that in addition to the ingredients particularly mentioned above the formulations disclosed herein may include other agents conventional in the art having regard to the type of formulation in question, for example those suitable for oral administration may include flavoring agents.

Veterinary compositions comprising at least one active ingredient as above defined together with a veterinary carrier are further provided.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of Formula I (herein referred to as the active ingredients), or a pharmaceutically acceptable salt thereof, are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally. Accordingly, in one embodiment, the pharmaceutical compositions described herein are oral dosage forms. In certain embodiments, the pharmaceutical compositions described herein are oral solid dosage forms. Ultimately, it is in the discretion of a trained physician to determine the appropriate dose and route of administration that is appropriate for a particular patient with a particular disease or disorder to be treated.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

Formulation Example 2

A tablet Formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 50 mg of active ingredient, are prepared as follows:

| Ingredient | Quantity (mg/tablet) |
|---|---|
| Active Ingredient | 50.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 140 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Formulation Example 5

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 6

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Formulation Example 7

A subcutaneous formulation may be prepared as follows:

| Ingredient | Quantity |
| --- | --- |
| Active Ingredient | 5.0 mg |
| Corn Oil | 1.0 mL |

Formulation Example 8

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Formulation Example 9

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to100 |

All of the above ingredients, except water, are combined and heated to 60° C. with stirring. A sufficient quantity of water at 60° C. is then added with vigorous stirring to emulsify the ingredients and water then added q.s. 100 g.

Formulation Example 10

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

Sustained release formulations of this disclosure may be prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free acid ranging from 400-600 mg, 650-850 mg and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Formulation Example 11

A tablet Formula is prepared using the ingredients below:

| Ingredient | Quantity (mg/tablet) |
| --- | --- |
| Active Ingredient | 300.0 |
| Cellulose, microcrystalline | 100.0 |
| Colloidal silicon dioxide | 10.0 |
| Stearic acid | 5.0 |

The components are blended and compressed to form tablets.

Methods

Provided herein are methods for treating and/or preventing hyperlipidemia in a subject in need thereof, comprising administering to the subject a therapeutically effective amount of a compound of Formula (I). For example, the compounds herein may be used to treat primary (inherited) dyslipidemias such as familial hypercholesterolemia, Wolman Disease, and Cholesteryl ester storage disease, as well as secondary (acquired) dyslipidemias, such as hyperlipidemia associated with diabetes mellitus, elevated cholesterol (particularly elevated LDL cholesterol), combined hyperlipidemia/type IIb, elevated triglycerides alcohol overuse, chronic kidney disease, hypothyroidism, and primary biliary cirrhosis.

Provided herein are methods for treating and/or preventing metabolic disorders including, without limitation, diabetes, including type I and type II diabetes, metabolic syndrome, dyslipidemia, obesity, insulin resistance, hypertension, elevated serum cholesterol, and elevated triglycerides. in a subject in need thereof, comprising administering to the subject a therapeutically effective amount of a compound of Formula (I)

Also disclosed herein is a method of treating and/or preventing liver disease in a patient in need thereof, comprising administering to the patient a therapeutically effective amount of a compound of Formula (I). The presence of active liver disease can be detected by the existence of elevated enzyme levels in the blood. Specifically, blood levels of alanine aminotransferase (ALT) and aspartate aminotransferase (AST) above clinically accepted normal ranges are known to be indicative of on-going liver damage. Routine monitoring of liver disease patients for blood levels of ALT and AST is used clinically to measure progress of the liver disease while on medical treatment. Reduction of elevated ALT and AST to within the accepted normal range is taken as clinical evidence reflecting a reduction in the severity of the patient's on-going liver damage.

In certain embodiments, the liver disease is a chronic liver disease. Chronic liver diseases involve the progressive destruction and regeneration of the liver parenchyma, leading to fibrosis and cirrhosis. In general, chronic liver diseases can be caused by viruses (such as hepatitis B, hepatitis C, cytomegalovirus (CMV), or Epstein Barr Virus (EBV)), toxic agents or drugs (such as alcohol, methotrexate, or nitrofurantoin), a metabolic disease (such as non-alcoholic fatty liver disease (NAFLD), non-alcoholic steatohepatitis (NASH), haemochromatosis, or Wilson's Disease), an autoimmune disease (such as Autoimmune Chronic Hepatitis, Primary Biliary Cholangitis (formerly known as Primary Biliary Cirrhosis), or Primary Sclerosing Cholangitis), or other causes (such as right heart failure).

In one embodiment, provided herein is a method for reducing the level of cirrhosis. In one embodiment, cirrhosis is characterized pathologically by loss of the normal microscopic lobular architecture, with fibrosis and nodular regeneration. Methods for measuring the extent of cirrhosis are well known in the art. In one embodiment, the level of cirrhosis is reduced by about 5% to about 100%. In one embodiment, the level of cirrhosis is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% in the subject.

In certain embodiments, the liver disease is a metabolic liver disease. In one embodiment, the liver disease is non-alcoholic fatty liver disease (NAFLD). NAFLD is associated with insulin resistance and metabolic syndrome (obesity, combined hyperlipidemia, diabetes mellitus (type II) and high blood pressure). NAFLD is considered to cover a spectrum of disease activity, and begins as fatty accumulation in the liver (hepatic steatosis).

It has been shown that both obesity and insulin resistance probably play a strong role in the disease process of NAFLD. In addition to a poor diet, NAFLD has several other known causes. For example, NAFLD can be caused by certain medications, such as amiodarone, antiviral drugs (e.g., nucleoside analogues), aspirin (rarely as part of Reye's syndrome in children), corticosteroids, methotrexate, tamoxifen, or tetracycline. NAFLD has also been linked to the consumption of soft drinks through the presence of high fructose corn syrup which may cause increased deposition of fat in the abdomen, although the consumption of sucrose shows a similar effect (likely due to its breakdown into fructose). Genetics has also been known to play a role, as two genetic mutations for this susceptibility have been identified.

If left untreated, NAFLD can develop into non-alcoholic steatohepatitis (NASH), which is the most extreme form of NAFLD, a state in which steatosis is combined with inflammation and fibrosis. NASH is regarded as a major cause of cirrhosis of the liver. Accordingly, provided herein is a method of treating and/or preventing nonalcoholic steatohepatitis (NASH) in a patient in need thereof, comprising administering to the patient a therapeutically effective amount of a compound of Formula (I).

Also provided herein is a method of treating and/or preventing liver fibrosis in a patient in need thereof, comprising administering to the patient a therapeutically effective amount of a compound of Formula (I). Liver fibrosis is the excessive accumulation of extracellular matrix proteins including collagen that occurs in most types of chronic liver diseases. In certain embodiments, advanced liver fibrosis results in cirrhosis and liver failure. Methods for measuring liver histologies, such as changes in the extent of fibrosis, lobular hepatitis, and periportal bridging necrosis, are well known in the art. In one embodiment, treatment as described herein may improve a patient's fibrosis from baseline, for example, improving from F4 to F3, F3 to F2, or F2 to F1. In one embodiment, a patient's fibrosis score is improved by one or more following 24 weeks of daily treatment.

In one embodiment, the level of liver fibrosis, which is the formation of fibrous tissue, fibroid or fibrous degeneration, is reduced by more than about 90%. In one embodiment, the level of fibrosis, which is the formation of fibrous tissue, fibroid or fibrous degeneration, is reduced by at least about 90%, at least about 80%, at least about 70%, at least about 60%, at least about 50%, at least about 40%, at least about 30%, at least about 20%, at least about 10%, at least about 5% or at least about 2%.

In one embodiment, the compounds provided herein reduce the level of fibrogenesis in the liver. Liver fibrogenesis is the process leading to the deposition of an excess of extracellular matrix components in the liver known as fibrosis. It is observed in a number of conditions such as chronic viral hepatitis B and C, alcoholic liver disease, drug-induced liver disease, hemochromatosis, auto-immune hepatitis, Wilson disease, Primary Biliary Cholangitis (formerly known as Primary Biliary Cirrhosis), sclerosing cholangitis, liver schistosomiasis and others. In one embodiment, the level of fibrogenesis is reduced by more than about 90%. In one embodiment, the level of fibrogenesis is reduced by at least about 90%, at least about 80%, at least about 70%, at least about 60%, at least about 50%, at least about 40%, at least about 30%, at least about 20%, at least about 10%, at least about 5% or at least 2%.

In still other embodiments, provided herein is a method of treating and/or preventing primary sclerosing cholangitis (PSC) in a patient in need thereof, comprising administering to the patient a therapeutically effective amount of a compound of Formula (I).

Also disclosed herein is a method of treating or preventing cardiovascular disorder a patient in need of such treatment comprising administering a therapeutically effective amount of a compound of Formula (I). Cardiovascular diseases refer to any one or more than one of, for example, heart failure (including congestive heart failure, diastolic heart failure, systolic heart failure, heart failure with preserved ejection fraction), acute heart failure, ischemia, recurrent ischemia, myocardial infarction, arrhythmias, angina (including exercise-induced angina, variant angina, stable angina, unstable angina), acute coronary syndrome, diabetes, intermittent claudication, and idiopathic pulmonary fibrosis.

Also provided herein is a method of improving pathological consequence or outcome associated with oxidative stress in a patient in need thereof comprising administering to the patient a therapeutically effective amount of a mitochondrial uncoupling compound.

Combination Therapy

It is contemplated that the compounds of this disclosure could be used in a desirable combination product. While such a product could be in the form of compounds alone, it is sometimes preferable to co-formulate two or more compounds in a single dosage form.

Patients being treated by administration of the mitochondrial uncoupling compounds of the disclosure often exhibit diseases or conditions that may benefit from treatment with other therapeutic agents. These diseases or conditions can be of neurodegenerative nature or can be related to cancer, metabolic disorders, liver disease, gastrointestinal disorders and the like. Thus, one aspect of the disclosure is a method of treating metabolic related disease or condition, or a neurodegenerative disorder, a liver disease or condition, or cancer and the like comprising administering a compound of the in combination with one or more compounds useful for the treatment of such diseases to a subject, particularly a human subject, in need thereof.

In some embodiments, a compound of the present disclosure is co-formulated with the additional one or more active ingredients. In some embodiments, the other active ingredient is administered at approximately the same time, in a separate dosage form. In some embodiments, the other active ingredient is administered sequentially, and may be administered at different times in relation to a compound of the present disclosure.

Combinations for Liver Diseases and Conditions

In some embodiments, the therapeutic agent, or combination of therapeutic agents, are a(n) ACE inhibitor, Acetyl CoA carboxylase inhibitor, Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, intereukin-1 receptor-associated kinase 4 (IRAK4) inhibitor, Jak2 tyrosine kinase inhibitor, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21 (miR-21) inhibitor, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator, Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signalling-1 stimulator, Suppressor of cytokine signalling-3 stimulator, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, or YAP/TAZ modulator.

Non-limiting examples of therapeutic agents and targets comprise:

ACE inhibitors, such as enalapril;
Acetyl CoA carboxylase (ACC) inhibitors, such as NDI-010976 (firsocostat), DRM-01, gemcabene, PF-05175157, QLT-091382, PF-05221304;
Adenosine receptor agonists, such as CF-102 (namodenoson), CF-101, CF-502, CGS21680;
Adiponectin receptor agonists, such as ADP-355;
Amylin/calcitonin receptor agonists, such as KBP-042;
AMP activated protein kinase stimulators, such as O-304;
Angiotensin II AT-1 receptor antagonists, such as irbesartan;
Autotaxin inhibitors, such as PAT-505, PAT-048, GLPG-1690, X-165, PF-8380, AM-063;
Bioactive lipids, such as DS-102;
Cannabinoid receptor type 1 (CNR1) inhibitors, such as namacizumab, GWP-42004;
Caspase inhibitors, such as emricasan;
Pan cathepsin B inhibitors, such as VBY-376;
Pan cathepsin inhibitors, such as VBY-825;
CCR2/CCR5 chemokine antagonists, such as cenicriviroc;
CCR2 chemokine antagonists, such as propagermanium;
CCR3 chemokine antagonists, such as bertilimumab;
Chloride channel stimulators, such as cobiprostone;
Diglyceride acyltransferase 2 (DGAT2) inhibitors, such as IONIS-DGAT2Rx, PF-06865571;
Diglyceride acyltransferase 1 (DGAT1) inhibitors, such as GSK-3008356;
Dipeptidyl peptidase IV inhibitors, such as linagliptin, evogliptin;
Eotaxin ligand inhibitors, such as bertilimumab;
Extracellular matrix protein modulators, such as CNX-024;
FarnesoidXreceptor (FXR) agonists, such as AGN-242266, AKN-083, EDP-305, GNF-5120, GS-9674, LJN-452 (tropifexor), LMB-763, obeticholic acid, Px-102, Px-103, M790, M780, M450, M480, PX20606, EYP-001, INT-2228;
FarnesoidX receptor (FXR)/G-protein coupled bile acid receptor 1(TGR$^5$) agonists, such as INT-767;
Fatty acid synthase inhibitors, such as TVB-2640;
Fibroblast growth factor 19 (rhFGF19)/cytochrome P450 (CYP) 7A1 inhibitors, such as NGM-282;
Fibroblast growth factor 21 (FGF-21) ligand, such as BMS—986171, BMS—986036;
Fibroblast growth factor 21 (FGF-21)/glucagon like peptide 1 (GLP-1) agonist, such as YH-25723;
Galectin-3 inhibitors, such as GR-MD-02;
Glucagon-like peptide 1(GLP1R) agonists, such as AC-3174, liraglutide, semaglutide;
G-protein coupled bile acid receptor 1 (TGR5) agonists, such as RDX-009, INT-777;
Heat shock protein 47 (HSP47) inhibitors, such as ND-L02-s0201;
HMG CoA reductase inhibitors, such as atorvastatin, fluvastatin, pitavastatin, pravastatin, rosuvastatin, simvastatin;
IL-10 agonists, such as peg-ilodecakin;
Ileal sodium bile acid cotransporter inhibitors, such as A-4250, volixibat potassium ethanolate hydrate (SHP-262), GSK2330672;
Insulin sensitizers, such as, KBP-042, MSDC-0602K, Px-102, RG-125 (AZD4076), VVP-100X;
beta Klotho (KLB)-FGF1c agonist, such as NGM-313;
5-Lipoxygenase inhibitors, such as tipelukast (MN-001);
Lipoprotein lipase inhibitors, such as CAT-2003;
LPL gene stimulators, such as alipogene tiparvovec;
LiverX receptor (LXR) inhibitors, such as PX-L603, PX-L493, BMS—852927, T-0901317, GW-3965, SR-9238;
Lysophosphatidate-1 receptor antagonists, such as BMT-053011, UD-009. AR-479, ITMN-10534, BMS—986020, KI-16198;
Lysyl oxidase homolog 2 inhibitors, such as simtuzumab;
MEKK-5 protein kinase (ASK-1) inhibitors, such as selonsertib;
Semicarbazide-Sensitive Amine Oxidase/Vascular Adhesion Protein-1 (SSAO/VAP-1) Inhibitors, such as PXS—4728A;
Methionine aminopeptidase-2 inhibitors, such as ZGN-839;
Methyl CpG binding protein 2 modulators, such as mercaptamine;
Mineralocorticoid receptor antagonists (MCRA), such as MT-3995;
Myelin basic protein stimulators, such as olesoxime;
Myeloperoxidase inhibitors, such as PF-06667272;
NADPH oxidase ¼ inhibitors, such as GKT-831;
Nicotinic acid receptor 1 agonists, such as ARI-3037MO;
NACHT LRR PYD domain protein 3 (NLRP3) inhibitors, such as KDDF-201406-03, NBC-6;
Nuclear receptor modulators, such as DUR-928;
P2Y13 purinoceptor stimulators, such as CER-209;
PDE 3/4 inhibitors, such as tipelukast (MN-001);
PDE 5 inhibitors, such as sildenafil;
PDGF receptor beta modulators, such as BOT-191, BOT-509;
PPAR agonists, such as elafibranor (GFT-505), MBX-8025, deuterated pioglitazone R-enantiomer, pioglitazone, DRX-065, saroglitazar, IVA-337;
Protease-activated receptor-2 antagonists, such as PZ-235;
Protein kinase modulators, such as CNX-014;
Rho associated protein kinase (ROCK) inhibitors, such as KD-025;
Sodium glucose transporter-2(SGLT2) inhibitors, such as ipragliflozin, remogliflozin etabonate, ertugliflozin, dapagliflozin, sotagliflozin;
SREBP transcription factor inhibitors, such as CAT-2003, MDV-4463;
Stearoyl CoA desaturase-1 inhibitors, such as aramchol;
Thyroid hormone receptor beta agonists, such as MGL-3196, MGL-3745, VK-2809;
TLR-4 antagonists, such as JKB-121;
Tyrosine kinase receptor modulators, such as CNX-025;
GPCR modulators, such as CNX-023;
Nuclear hormone receptor modulators, such as Px-102;
In some embodiments, the therapeutic agent, or combination of therapeutic agents, are A-4250, AC-3174, acetylsalicylic acid, AK-20, alipogene tiparvovec, aramchol, ARI-3037MO, ASP-8232, bertilimumab, Betaine anhydrous, BI-1467335, BMS-986036, BMS-986171, BMT-053011, BOT-191, BTT-1023, CAT-2003, cenicriviroc, CER-209, CF-102, CGS21680, CNX-014, CNX-023, CNX-024, CNX-025, cobiprostone, colesevelam, dapagliflozin, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, GKT-831, GNF-5120, GRI-0621, GR-MD-02, selonsertib, GS-9674, hydrochlorothiazide, icosapent ethyl ester, IMM-124-E, INT-767, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452, LMB-763, MBX-8025, MDV-4463, mercaptamine, MGL-3196, MGL-3745, MSDC-0602K, namacizumab, NC-101, NDI-010976, ND-L02-s0201, NGM-282, NGM-313, NGM-386, NGM-395, norursodeoxycholic acid, 0-304, obeticholic acid, 25HC3S, olesoxime, PAT-505, PAT-048, peg-ilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), saroglitazar, semaglutide, simtuzumab, solithromycin, sotagliflozin, statins (atorvastatin, fluvastatin, pitavastatin, pravastatin, rosuvastatin, simvastatin), TCM-606F, TEV-45478, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, or ZGN-839.

Combinations for Metabolic Diseases or Conditions

Examples of metabolic disorders include, without limitation, diabetes, including type I and type II diabetes, metabolic syndrome, dyslipidemia, obesity, insulin resistance, hypertension, elevated serum cholesterol, and elevated triglycerides.

Examples of therapeutic agents used to treat metabolic disorders include antihypertensive agents and lipid lowering agents. Additional therapeutic agents used to treat metabolic disorders include insulin, sulfonylureas, biguanides, alpha-glucosidase inhibitors, and incretin mimetics. Thus, one aspect of the disclosure is a method of treating a metabolic disease comprising administering a compound of the disclosure in combination with one or more compounds useful for the treatment of metabolic diseases to a subject, particularly a human subject, in need thereof.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

LIST OF ABBREVIATIONS AND ACRONYMS

| Abbreviation | Meaning |
| --- | --- |
| ° C. | Degree Celsius |
| Ac | Acetyl |
| aq. | Aqueous |
| br | Broad |
| BSA | Bovine serum albumin |
| d | Doublet |
| DCM | Dichloromethane |
| dd | Doublet of doublets |
| ddd | Doublet of doublet of doublets |
| DMA | Dimethylacetamide |
| DMF | Dimethylformamide |
| DMSO | Dimethylsulfoxide |
| dt | Doublet-triplet |
| $EC_{50}$ | The half maximal effective concentration |
| EDCI | 1-Ethyl-3-(3-dimethylaminopropyl)-3-ethylcarbodiimide |
| EDTA | Ethylenediaminetetraacetic acid |
| Eq or equiv. | Equivalents |
| ESI | Electrospray Interface |
| Et | Ethyl |
| EtOAc | Ethyl acetate |
| EtOH | Ethanol (Ethyl alcohol) |
| FBS | Fetal bovine serum |
| g | Grams |
| HATU | 1-[Bis(dimethylamino)methylene]-1H-1,2,3-triazolo[4,5-b]pyridinium 3-oxid hexafluorophosphate |
| HEPES | 2-[4-(2-hydroxyethyl)piperazin-1-yl]ethanesulfonic acid |
| HCl | Hydrochloric acid |
| HOBT | 1-hydroxybenzotriazole |
| HPLC | High pressure liquid chromatography |
| Hrs | Hours |
| Hz | Hertz |
| i-pr | Isopropyl |
| J | Coupling constant (MHz) |
| LCMS | Liquid chromatography-mass spectrometry |
| M | Molar |
| m | multiplet |
| M+ | Mass peak |
| M + H | Mass peak plus hydrogen |
| M − H | Mass peak minus hydrogen |
| Me | Methyl |
| MeCN | Acetonitrile |
| MeOH | Methanol (Methyl alcohol) |
| Mg | Milligram |
| $MgSO_4$ | Magnesium sulfate |
| MHz | Megahertz |
| Min | Minute |
| ml/mL | Milliliter |
| mM | Millimolar |
| mmol | Millimole |
| MS | Mass spectroscopy |
| μwave | Microwave |
| n- | Normal |
| nBu/Bu | n-Butyl (normal Butyl) |
| nL | Nanoliter |
| nm | Nanometer |
| NMP | 1-methylpyrrolidin-2-one |
| NMR | Nuclear magnetic resonance |
| NP-40 | Nonyl phenoxypolyethoxylethanol |
| Ph | Phenyl |
| q | Quartet |
| q.s. | Quantity sufficient to achieve a stated function |
| RP | Reverse phase |
| Rt | Room temperature |
| s | Singlet |
| t | Triplet |
| T3P | 1-Propanephosphonic anhydride |
| TBTU | O-(benzotriazol-1-yl)-N,N,N',N'-tetramethyluronium tetrafluoroborate |
| THF | Tetrahydrofuran |

Commercial Sources

Some of the intermediates used herein are available commercially. Sources include:

J&W Pharmalab, 3930 Nebraska Ave., Levittown, Pa. 19056 USA;

TCI America, 9211 North Harborgate Street, Portland, Oreg. 97203, USA;

SpiroChem AG, Rosental area, WRO-1047-3, Mattenstrasse 24, 4058 Basel, Switzerland;

Synnovator, Inc., 104 TW Alexander Dr, Durham, N.C. 27709; and

Ark Pharma, Inc., 3860 N. Ventura Drive, Arlington Heights, Ill. 60004, USA.

General Synthesis 1

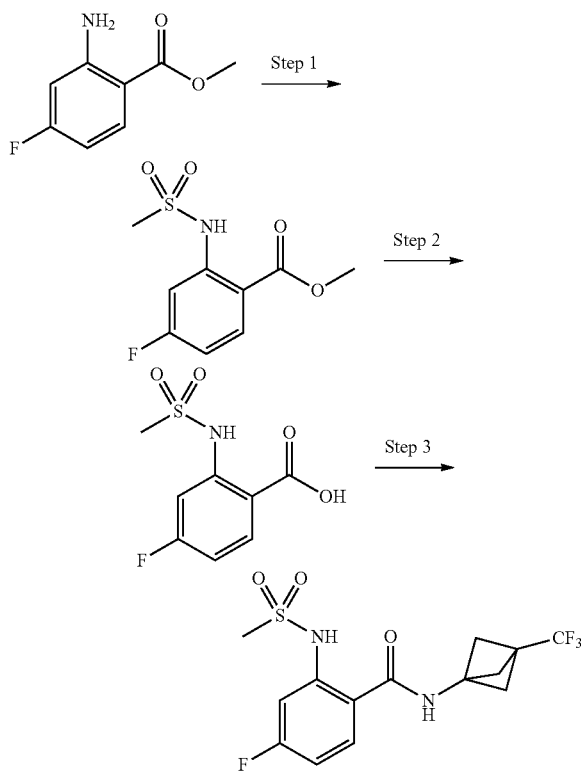

Example 1: Preparation of 4-fluoro-2-(methylsulfonamido)-N-(3-(trifluoromethyl)bicyclo[1.1.1]pentan-1-yl)benzamide Step 1

To a solution of methyl 2-amino-4-fluorobenzoate (1.64 g, 9.71 mmol) and methanesulfonyl chloride (5.28 mL, 115 mmol) in dichloromethane (100 mL) was added pyridine (7.86 mL, 97.1 mmol). The solution was stirred at room temperature for 18 hours. The reaction was quenched with 1N HCl and was stirred for 5 minutes. The mixture was extracted with DCM (3×). The combined organic layers were washed with brine, dried over anhydrous MgSO$_4$, filtered and concentrated. The crude product was purified by silica gel chromatography to afford methyl 4-fluoro-2-(methylsulfonamido)benzoate.

Step 2

To a solution of methyl 4-fluoro-2-(methylsulfonamido)benzoate (1.65 g, 6.67 mmol) in THF/MeOH/water (1:1:1, 66.0 mL) was added lithium hydroxide monohydrate (1.40 g, 33.4 mmol). The mixture was stirred at room temperature for 18 hours. The reaction was quenched with 1N HCl and concentrated. The crude product was diluted with water and was extracted with EtOAc (3×). The combined organic layers were washed with brine, dried over MgSO$_4$, filtered and concentrated to afford 4-fluoro-2-(methylsulfonamido)benzoic acid, which was used without further purification.

Step 3

A mixture of 4-fluoro-2-(methylsulfonamido)benzoic acid (650 mg, 2.79 mmol), 3-(trifluoromethyl)bicyclo[1.1.1]pentan-1-amine hydrochloride (706 mg, 3.76 mmol), EDCI (801 mg, 4.18 mmol) and HOBT (565 mg, 4.18 mmol) in DMF (30.0 mL) was stirred for 5 minutes. N,N-Diisopropylethylamine (2.43 mL, 13.9 mmol) was added and the solution was stirred at room temperature for 18 hours. The solution was concentrated, diluted with ethyl acetate and the pH was adjusted to 3 with the addition of 1N HCl. The mixture was extracted with EtOAc (3×) and the combined organic layers were washed with brine, dried over anhydrous MgSO$_4$, filtered and concentrated. The crude product was purified by silica gel chromatography, followed by crystallization, to afford 4-fluoro-2-(methylsulfonamido)-N-(3-(trifluoromethyl)bicyclo[1.1.1]pentan-1-yl)benzamide. $^1$H NMR (400 MHz, DMSO-d$_6$) δ 11.47 (s, 1H), 9.56 (s, 1H), 7.93 (dd, J=9.0, 6.3 Hz, 1H), 7.31 (dd, J=11.2, 2.6 Hz, 1H), 7.05 (td, J=8.5, 2.6 Hz, 1H), 3.23 (s, 3H), 2.35 (s, 6H). LCMS-ESI$^+$ (m/z): [M+H]$^+$ calcd 367.07; found 367.01.

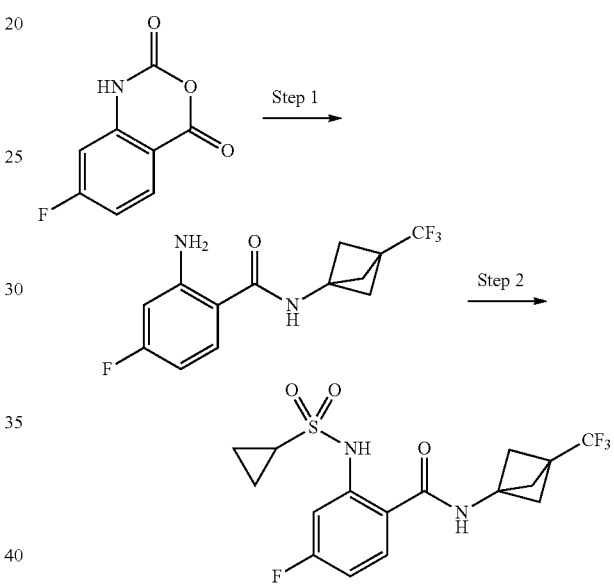

Example 2: Preparation of 2-(cyclopropanesulfonamido)-4-fluoro-N-(3-(trifluoromethyl)bicyclo[1.1.1]pentan-1-yl)benzamide Step 1

A mixture of 7-fluoro-2H-benzo[d][1,3]oxazine-2,4(1H)-dione (50.0 mg, 0.276 mmol), 3-(trifluoromethyl)bicyclo[1.1.1]pentan-1-amine hydrochloride (51.8 mg, 0.276 mmol) and sodium hydroxide (20.0 mg, 0.500 mmol) in 1,4-dioxane (3.0 mL) was heated at 105° C. for 18 hours. The mixture was filtered and the filtrate was concentrated. The crude product was purified by silica gel chromatography to afford 2-amino-4-fluoro-N-(3-(trifluoromethyl)bicyclo[1.1.1]pentan-1-yl)benzamide. LCMS-ESI$^+$ (m/z): [M+H]$^+$ calcd 289.10; found 289.48.

Step 2

A solution of 2-amino-4-fluoro-N-(3-(trifluoromethyl)bicyclo[1.1.1]pentan-1-yl)benzamide (32.0 mg, 0.111 mmol), methanesulfonyl chloride (0.113 mL, 1.11 mmol) and pyridine (0.135 mL, 1.67 mmol) in DCM (2.0 mL) was stirred at room temperature for 18 hours. The reaction was concentrated and the crude product was purified by reverse phase chromatography to afford 2-(cyclopropanesulfonamido)-4-fluoro-N-(3-(trifluoromethyl)bicyclo[1.1.1]pentan-1-yl)benzamide. ¹H NMR (400 MHz, DMSO-d₆) δ 11.42 (s, 1H), 9.59 (s, 1H), 7.92 (dd, J=8.9, 6.3 Hz, 1H), 7.35 (dd, J=11.1, 2.6 Hz, 1H), 7.08 (td, J=8.5, 2.6 Hz, 1H), 2.89 (p, J=6.4 Hz, 1H), 2.36 (s, 6H), 1.03-0.99 (m, 4H). LCMS-ESI⁺ (m/z): [M+H]⁺ calcd 393.09; found 393.75.

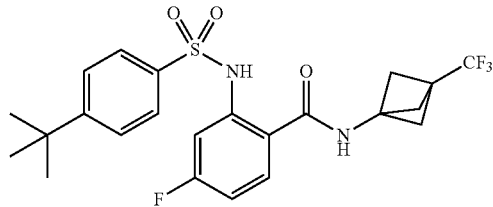 [SMILES: CC(C)(C)c1ccc(S(=O)(=O)Nc2cc(F)ccc2C(=O)NC23CC(C(F)(F)F)(C2)C3)cc1]

Example 3: Preparation of 2-((4-(tert-butyl)phenyl)sulfonamido)-4-fluoro-N-(3-(trifluoromethyl)bicyclo[1.1.1]pentan-1-yl)benzamide Following General Synthesis 1, 4-tert-butylbenzenesulfonyl chloride (1.5 equiv.) was used in Step 1 and the reaction was stirred at room temperature for 48 hours. 3-(Trifluoromethyl)bicyclo[1.1.1]pentan-1-amine hydrochloride was used in Step 3 to afford 2-((4-(tert-butyl)phenyl)sulfonamido)-4-fluoro-N-(3-(trifluoromethyl)bicyclo[1.1.1]pentan-1-yl)benzamide after purification by reverse phase chromatography. ¹H NMR (400 MHz, DMSO-d₆) δ 11.81 (s, 1H), 9.49 (s, 1H), 7.81 (dd, J=8.9, 6.2 Hz, 1H), 7.76-7.66 (m, 2H), 7.63-7.57 (m, 2H), 7.25 (dd, J=10.9, 2.6 Hz, 1H), 7.04 (td, J=8.6, 2.6 Hz, 1H), 2.32 (s, 6H), 1.26 (s, 9H). LCMS-ESI⁺ (m/z): [M+H]⁺ calcd 485.15; found 485.09.

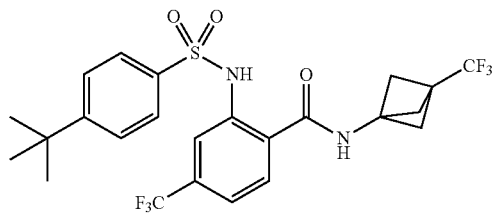 [SMILES: CC(C)(C)c1ccc(S(=O)(=O)Nc2cc(C(F)(F)F)ccc2C(=O)NC23CC(C(F)(F)F)(C2)C3)cc1]

Example 4: Preparation of 2-((4-(tert-butyl)phenyl)sulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and 4-tert-butylbenzenesulfonyl chloride (1.2 equiv.) in Step 1, then 3-(trifluoromethyl)bicyclo[1.1.1]pentan-1-amine hydrochloride in Step 3, 2-((4-(tert-butyl)phenyl)sulfonamido)-4-(trifluoromethyl)-N-(3-(trifluoromethyl)bicyclo[1.1.1]pentan-1-yl)benzamide was synthesized and purified by reverse phase chromatography. ¹H NMR (400 MHz, DMSO-d₆) δ 11.28 (s, 1H), 9.62 (s, 1H), 7.88 (d, J=8.3 Hz, 1H), 7.69-7.62 (m, 3H), 7.62-7.53 (m, 3H), 2.33 (s, 6H), 1.25 (s, 9H). LCMS-ESI⁺ (m/z): [M+H]⁺ calcd 535.15; found 535.08.

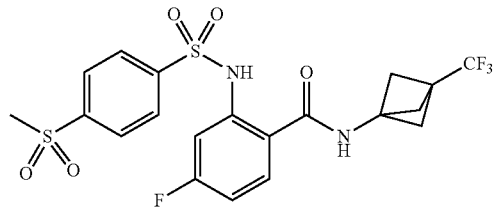 [SMILES: CS(=O)(=O)c1ccc(S(=O)(=O)Nc2cc(F)ccc2C(=O)NC23CC(C(F)(F)F)(C2)C3)cc1]

Example 5: Preparation of 4-fluoro-2-((4-(methylsulfonyl)phenyl)sulfonamido)-N-(3-(trifluoromethyl)bicyclo[1.1.1]pentan-1-yl)benzamide Following General Synthesis 1, using 4-(methylsulfonyl)benzenesulfonyl chloride (1.2 equiv.) in Step 1 and 3-(trifluoromethyl)bicyclo[1.1.1]pentan-1-amine hydrochloride in Step 3, 4-fluoro-2-((4-(methylsulfonyl)phenyl)sulfonamido)-N-(3-(trifluoromethyl)bicyclo[1.1.1]pentan-1-yl)benzamide was synthesized and purified by reverse phase chromatography. ¹H NMR (400 MHz, DMSO-d₆) δ 11.84 (s, 1H), 9.48 (s, 1H), 8.11 (d, J=8.3 Hz, 2H), 8.02 (d, J=8.5 Hz, 2H), 7.79 (dd, J=8.9, 6.2 Hz, 1H), 7.27 (d, J=10.5 Hz, 1H), 7.16-7.06 (m, 1H), 3.29 (s, 3H), 2.31 (s, 6H). LCMS-ESI⁺ (m/z): [M+H]⁺ calcd 507.07; found 507.04.

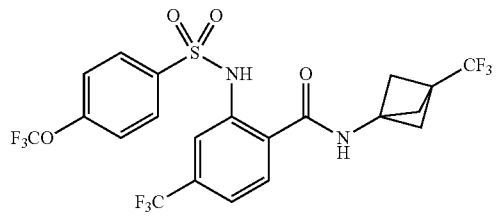 [SMILES: O=C(NC12CC(C(F)(F)F)(C1)C2)c1ccc(C(F)(F)F)cc1NS(=O)(=O)c1ccc(OC(F)(F)F)cc1]

Example 6: Preparation of 2-((4-(trifluoromethoxy)phenyl)sulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and 4-(trifluoromethoxy)benzenesulfonyl chloride (2×1.5 equiv.) over 36 hours at room temperature in Step 1, then 3-(trifluoromethyl)bicyclo[1.1.1]pentan-1-amine hydrochloride in Step 3, 2-((4-(trifluoromethoxy)phenyl) sulfonamido)-4-(trifluoromethyl)-N-(3-(trifluoromethyl)bicyclo[1.1.1]pentan-1-yl)benzamide was synthesized and purified by reverse phase chromatography. ¹H NMR (400 MHz, DMSO-d₆) δ 11.22 (s, 1H), 9.60 (s, 1H), 7.89-7.81 (m, 3H), 7.66-7.54 (m, 4H), 2.31 (s, 6H). LCMS-ESI⁺ (m/z): [M+H]⁺ calcd 563.07; found 563.05.

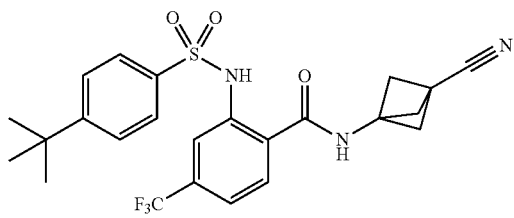 [SMILES: CC(C)(C)c1ccc(S(=O)(=O)Nc2cc(C(F)(F)F)ccc2C(=O)NC23CC(C#N)(C2)C3)cc1]

Example 7: Preparation of 2-((4-(tert-butyl)phenyl)sulfonamido)-N-(3-cyanobicyclo[1.1.1]pentan-1-yl)-4-(trifluoromethyl)benzamide Following General Synthesis 1, using methyl 2-amino-4-(trifluoromethyl)benzoate and 4-tert-butylbenzenesulfonyl chloride (1.2 equiv.) in Step 1, then 3-aminobicyclo[1.1.1]pentane-1-carbonitrile in Step 3, 2-((4-(tert-butyl)phenyl)sulfonamido)-N-(3-cyanobicyclo[1.1.1]pentan-1-yl)-4-(trifluoromethyl)benzamide was synthesized and purified by reverse phase chromatography. $^1$H NMR (400 MHz, DMSO-d$_6$) δ 11.23 (s, 1H), 9.60 (s, 1H), 7.84 (d, J=8.2 Hz, 1H), 7.68-7.62 (m, 3H), 7.62-7.53 (m, 3H), 2.58 (s, 6H), 1.26 (s, 9H). LCMS-ESI$^+$ (m/z): [M+H]$^+$ calcd 492.16; found 492.10.

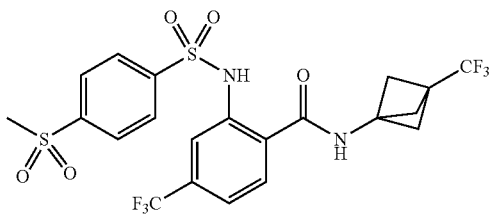 [SMILES: CS(=O)(=O)c1ccc(S(=O)(=O)Nc2cc(C(F)(F)F)ccc2C(=O)NC23CC(C(F)(F)F)(C2)C3)cc1]

Example 8: Preparation of 2-((4-(methylsulfonyl)phenyl)sulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and 4-(methylsulfonyl)benzenesulfonyl chloride (2.5 equiv.) in Step 1 for 48 hours at room temperature, then 3-(trifluoromethyl)bicyclo[1.1.1]pentan-1-amine hydrochloride in Step 3, 2-((4-(methylsulfonyl)phenyl)sulfonamido)-4-(trifluoromethyl)-N-(3-(trifluoromethyl)bicyclo[1.1.1]pentan-1-yl)benzamide was synthesized and purified by reverse phase chromatography. $^1$H NMR (400 MHz, DMSO-d$_6$) δ 11.28 (s, 1H), 9.60 (s, 1H), 8.11 (d, J=8.5 Hz, 2H), 7.95 (d, J=8.5 Hz, 2H), 7.86 (d, J=8.2 Hz, 1H), 7.71-7.60 (m, 2H), 3.28 (s, 3H), 2.30 (s, 6H). LCMS-ESI$^+$ (m/z): [M+H]$^+$ calcd 577.06; found 577.06.

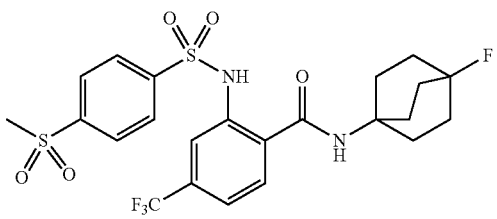 [SMILES: CS(=O)(=O)c1ccc(S(=O)(=O)Nc2cc(C(F)(F)F)ccc2C(=O)NC23CCC(F)(CC2)CC3)cc1]

Example 9: Preparation of N-(4-fluorobicyclo[2.2.2]octan-1-yl)-2-((4-(methylsulfonyl)phenyl)sulfonamido)-4-(trifluoromethyl)benzamide Following General Synthesis 1, using methyl 2-amino-4-(trifluoromethyl)benzoate and 4-(methylsulfonyl)benzenesulfonyl chloride (2.5 equiv.) in Step 1 for 48 hours at room temperature, then 4-fluorobicyclo[2.2.2]octan-1-amine hydrochloride in Step 3, N-(4-fluorobicyclo[2.2.2]octan-1-yl)-2-((4-(methylsulfonyl)phenyl)sulfonamido)-4-(trifluoromethyl)benzamide was synthesized and purified by reverse phase chromatography. $^1$H NMR (400 MHz, DMSO-d$_6$) δ 10.98 (s, 1H), 8.18 (s, 1H), 8.11 (d, J=8.5 Hz, 2H), 7.93 (d, J=8.5 Hz, 2H), 7.79 (d, J=8.1 Hz, 1H), 7.65-7.53 (m, 2H), 3.28 (s, 3H), 2.07-1.98 (m, 6H), 1.89-1.79 (m, 6H). LCMS-ESI$^+$ (m/z): [M+H]$^+$ calcd 549.11; found 549.12.

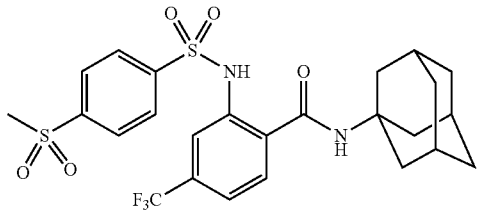 [SMILES: CS(=O)(=O)c1ccc(S(=O)(=O)Nc2cc(C(F)(F)F)ccc2C(=O)NC23CC4CC(CC(C4)C2)C3)cc1]

Example 10: Preparation of N-((3s,5s,7s)-adamantan-1-yl)-2-((4-(methylsulfonyl)phenyl)sulfonamido)-4-(trifluoromethyl)benzamide Following General Synthesis 1, using methyl 2-amino-4-(trifluoromethyl)benzoate and 4-(methylsulfonyl)benzenesulfonyl chloride (2.5 equiv.) in Step 1 for 48 hours at room temperature, then 1-adamantylamine in Step 3, N-((3s,5s,7s)-adamantan-1-yl)-2-((4-(methylsulfonyl)phenyl)sulfonamido)-4-(trifluoromethyl)benzamide was synthesized and purified by crystallization. $^1$H NMR (400 MHz, DMSO-d$_6$) δ 11.11 (s, 1H), 8.19-8.05 (m, 3H), 7.94 (d, J=8.5 Hz, 2H), 7.83 (d, J=8.1 Hz, 1H), 7.65-7.53 (m, 2H), 3.27 (s, 3H), 2.04 (bs, 3H), 1.95 (d, J=2.8 Hz, 6H), 1.64 (bs, 6H). LCMS-ESI$^+$ (m/z): [M+H]$^+$ calcd 557.14; found 557.11.

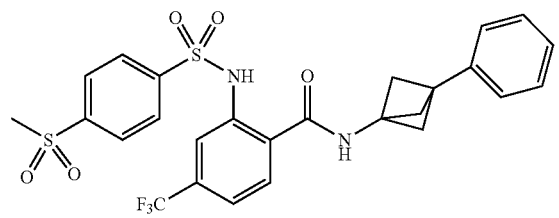 [SMILES: CS(=O)(=O)c1ccc(S(=O)(=O)Nc2cc(C(F)(F)F)ccc2C(=O)NC23CC(c4ccccc4)(C2)C3)cc1]

Example 11: Preparation of 2-((4-(methylsulfonyl)phenyl)sulfonamido)-N-(3-phenylbicyclo[1.1.1]pentan-1-yl)-4-(trifluoromethyl)benzamide Following General Synthesis 1, using methyl 2-amino-4-(trifluoromethyl)benzoate and 4-(methylsulfonyl)benzenesulfonyl chloride (2.5 equiv.) in Step 1 for 48 hours at room temperature, then 3-phenylbicyclo[1.1.1]pentan-1-amine hydrochloride in Step 3, 2-((4-(methylsulfonyl)phenyl)sulfonamido)-N-(3-phenylbicyclo[1.1.1]pentan-1-yl)-4-(trifluoromethyl)benzamide was synthesized and purified by crystallization. $^1$H NMR (400 MHz, DMSO-d$_6$) δ 11.58 (s, 1H), 9.52 (s, 1H), 8.12 (d, J=8.5 Hz, 2H), 8.00-7.94 (m, 2H), 7.91 (d, J=8.2 Hz, 1H), 7.72 (s, 1H), 7.68-7.59 (m, 1H), 7.37-7.30 (m, 2H), 7.30-7.21 (m, 3H), 3.28 (s, 3H), 2.32 (s, 6H). LCMS-ESI$^+$ (m/z): [M+H]$^+$ calcd 565.11; found 565.02.

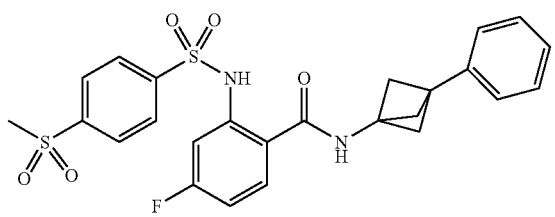 [SMILES: CS(=O)(=O)c1ccc(S(=O)(=O)Nc2cc(F)ccc2C(=O)NC23CC(c4ccccc4)(C2)C3)cc1]

Example 12: Preparation of 4-fluoro-2-((4-(methylsulfonyl)phenyl)sulfonamido)-N-(3-phenylbicyclo[1.1.1]pentan-1-yl)benzamide Following General Synthesis 1, using 4-(methylsulfonyl)benzenesulfonyl chloride (1.2 equiv.) in Step 1 and 3-phenylbicyclo[1.1.1]pentan-1-amine hydrochloride in Step 3, 4-fluoro-2-((4-(methylsulfonyl)phenyl)sulfonamido)-N-(3-phenylbicyclo[1.1.1]pentan-1-yl)benzamide was synthesized and purified by reverse phase chromatography. $^1$H NMR (400 MHz, DMSO-$d_6$) δ 12.16 (s, 1H), 9.39 (s, 1H), 8.12 (d, J=8.5 Hz, 2H), 8.04 (d, J=8.6 Hz, 2H), 7.84 (dd, J=8.9, 6.2 Hz, 1H), 7.37-7.18 (m, 6H), 7.15-7.04 (m, 1H), 3.29 (s, 3H), 2.33 (s, 6H). LCMS-ESI$^+$ (m/z): [M+H]$^+$ calcd 515.11; found 515.01.

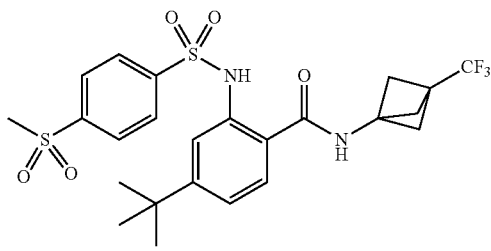 [SMILES: CC(C)(C)c1ccc(C(=O)NC23CC(C(F)(F)F)(C2)C3)c(NS(=O)(=O)c2ccc(S(C)(=O)=O)cc2)c1]

Example 13: Preparation of 4-(tert-butyl)-2-((4-(methylsulfonyl)phenyl)sulfonamido)-N-(3-(trifluoromethyl)bicyclo[1.1.1]pentan-1-yl)benzamide Following General Synthesis 1, using methyl 2-amino-4-(tert-butyl)benzoate and 4-(methylsulfonyl)benzenesulfonyl chloride (1.5 equiv.) in Step 1, then 3-(trifluoromethyl)bicyclo[1.1.1]pentan-1-amine hydrochloride in Step 3, 4-(tert-butyl)-2-((4-(methylsulfonyl)phenyl)sulfonamido)-N-(3-(trifluoromethyl)bicyclo[1.1.1]pentan-1-yl)benzamide was synthesized and purified by reverse phase chromatography. $^1$H NMR (400 MHz, DMSO-$d_6$) δ 11.54 (s, 1H), 9.37 (s, 1H), 8.09 (d, J=8.5 Hz, 2H), 7.94 (d, J=8.5 Hz, 2H), 7.61 (d, J=8.4 Hz, 1H), 7.42 (d, J=1.9 Hz, 1H), 7.22 (dd, J=8.4, 1.9 Hz, 1H), 3.27 (s, 3H), 2.31 (s, 6H), 1.22 (s, 9H). LCMS-ESI$^+$ (m/z): [M+H]$^+$ calcd 545.14; found 545.00.

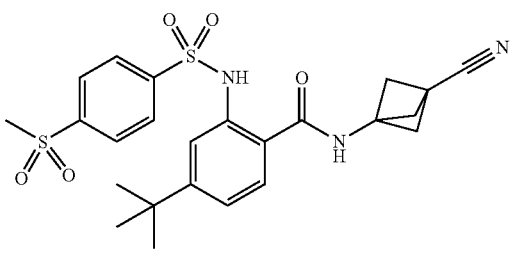 [SMILES: CC(C)(C)c1ccc(C(=O)NC23CC(C#N)(C2)C3)c(NS(=O)(=O)c2ccc(S(C)(=O)=O)cc2)c1]

Example 14: Preparation of 4-(tert-butyl)-N-(3-cyanobicyclo[1.1.1]pentan-1-yl)-2-((4-(methylsulfonyl)phenyl)sulfonamido)benzamide Following General Synthesis 1, using methyl 2-amino-4-(tert-butyl)benzoate and 4-(methylsulfonyl)benzenesulfonyl chloride (1.5 equiv.) in Step 1, then 3-aminobicyclo[1.1.1]pentane-1-carbonitrile in Step 3, 4-(tert-butyl)-N-(3-cyanobicyclo[1.1.1]pentan-1-yl)-2-((4-(methylsulfonyl)phenyl)sulfonamido)benzamide was synthesized and purified by reverse phase chromatography. $^1$H NMR (400 MHz, DMSO-$d_6$) δ 11.48 (s, 1H), 9.35 (s, 1H), 8.10 (d, J=8.5 Hz, 2H), 7.94 (d, J=8.5 Hz, 2H), 7.58 (d, J=8.4 Hz, 1H), 7.40 (d, J=1.9 Hz, 1H), 7.21 (dd, J=8.3, 1.9 Hz, 1H), 3.28 (s, 3H), 2.55 (s, 6H), 1.21 (s, 9H). LCMS-ESI$^+$ (m/z): [M+H]$^+$ calcd 502.15; found 501.99.

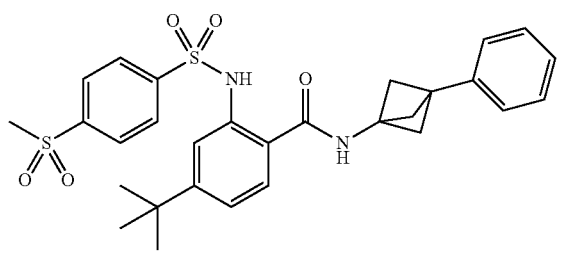 [SMILES: CC(C)(C)c1ccc(C(=O)NC23CC(c4ccccc4)(C2)C3)c(NS(=O)(=O)c2ccc(S(C)(=O)=O)cc2)c1]

Example 15: Preparation of 4-(tert-butyl)-2-((4-(methylsulfonyl)phenyl)sulfonamido)-N-(3-phenylbicyclo[1.1.1]pentan-1-yl)benzamide Following General Synthesis 1, using methyl 2-amino-4-(tert-butyl)benzoate and 4-(methylsulfonyl)benzenesulfonyl chloride (1.5 equiv.) in Step 1, then 3-phenylbicyclo[1.1.1]pentan-1-amine hydrochloride in Step 3, 4-(tert-butyl)-2-((4-(methylsulfonyl)phenyl)sulfonamido)-N-(3-phenylbicyclo[1.1.1]pentan-1-yl)benzamide was synthesized and purified by crystallization. $^1$H NMR (400 MHz, DMSO-$d_6$) δ 11.84 (s, 1H), 9.27 (s, 1H), 8.10 (d, J=8.5 Hz, 2H), 7.96 (d, J=8.5 Hz, 2H), 7.66 (d, J=8.4 Hz, 1H), 7.45 (d, J=1.9 Hz, 1H), 7.38-7.16 (m, 6H), 3.27 (s, 3H), 2.33 (s, 6H), 1.23 (s, 9H). LCMS-ESI$^+$ (m/z): [M+H]$^+$ calcd 553.18; found 553.11.

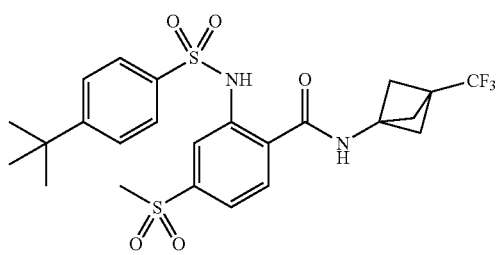 [SMILES: CC(C)(C)c1ccc(S(=O)(=O)Nc2cc(S(C)(=O)=O)ccc2C(=O)NC23CC(C(F)(F)F)(C2)C3)cc1]

Example 16: Preparation of 2-((4-(tert-butyl)phenyl)sulfonamido)-4-(methylsulfonyl)-N-(3-(trifluoromethyl)bicyclo[1.1.1]pentan-1-yl)benzamide Following General Synthesis 1, using methyl 2-amino-4-(methylsulfonyl)benzoate and 4-tert-butylbenzenesulfonyl chloride (1.5 equiv.) in Step 1, then 3-(trifluoromethyl)bicyclo[1.1.1]pentan-1-amine hydrochloride in Step 3, 2-((4-(tert-butyl)phenyl)sulfonamido)-4-(methylsulfonyl)-N-(3-(trifluoromethyl)bicyclo[1.1.1]pentan-1-yl)benzamide was synthesized and purified by crystallization. $^1$H NMR (400 MHz, DMSO-$d_6$) δ 11.25 (s, 1H), 9.63 (s, 1H), 7.95 (d, J=1.7 Hz, 1H), 7.90 (d, J=8.3 Hz, 1H), 7.73 (d, J=8.1 Hz, 1H), 7.67 (d, J=8.6 Hz, 2H), 7.59 (d, J=8.6 Hz, 2H), 3.21 (s, 3H), 2.33 (s, 6H), 1.25 (s, 9H). LCMS-ESI$^+$ (m/z): [M+H]$^+$ calcd 545.14; found 545.08.

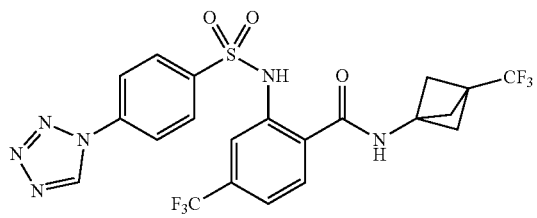 [SMILES: O=C(NC12CC(C(F)(F)F)(C1)C2)c1ccc(C(F)(F)F)cc1NS(=O)(=O)c1ccc(-n2cnnn2)cc1]

Example 17: Preparation of 2-((4-(1H-tetrazol-1-yl)phenyl)sulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and 4-(1H-tetrazol-1-yl)benzenesulfonyl chloride (1.5 equiv.) in Step 1, then 3-(trifluoromethyl)bicyclo[1.1.1]pentan-1-amine hydrochloride in Step 3, 2-((4-(1H-tetrazol-1-yl)phenyl)sulfonamido)-4-(trifluoromethyl)-N-(3-(trifluoromethyl)bicyclo[1.1.1]pentan-1-yl)benzamide was synthesized and purified by reverse phase chromatography. $^1$H NMR (400 MHz, DMSO-$d_6$) δ 11.33 (s, 1H), 10.20 (s, 1H), 9.61 (s, 1H), 8.15 (d, J=8.8 Hz, 2H), 7.99 (d, J=8.8 Hz, 2H), 7.86 (d, J=8.2 Hz, 1H), 7.73 (s, 1H), 7.65-7.58 (m, 1H), 2.32 (s, 6H). LCMS-ESI$^+$ (m/z): [M+H]$^+$ calcd 547.10; found 547.05.

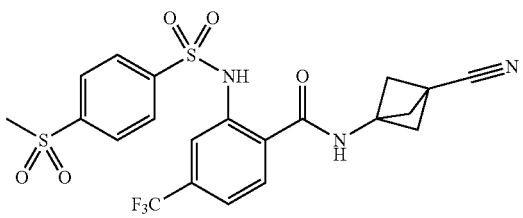 [SMILES: CS(=O)(=O)c1ccc(S(=O)(=O)Nc2cc(C(F)(F)F)ccc2C(=O)NC23CC(C#N)(C2)C3)cc1]

Example 18: Preparation of N-(3-cyanobicyclo[1.1.1]pentan-1-yl)-2-((4-(methylsulfonyl)phenyl)sulfonamido)-4-(trifluoromethyl)benzamide Following General Synthesis 1, using methyl 2-amino-4-(trifluoromethyl)benzoate and 4-(methylsulfonyl)benzenesulfonyl chloride (1.95 equiv.) in Step 1 for 48 hours at room temperature, then 3-aminobicyclo[1.1.1]pentane-1-carbonitrile in Step 3, N-(3-cyanobicyclo[1.1.1]pentan-1-yl)-2-((4-(methylsulfonyl)phenyl)sulfonamido)-4-(trifluoromethyl)benzamide was synthesized and purified by reverse phase chromatography. $^1$H NMR (400 MHz, DMSO-$d_6$) δ 11.23 (s, 1H), 9.57 (s, 1H), 8.11 (d, J=8.5 Hz, 2H), 7.95 (d, J=8.5 Hz, 2H), 7.82 (d, J=8.1 Hz, 1H), 7.69-7.57 (m, 2H), 3.29 (s, 3H), 2.54 (s, 6H). LCMS-ESI$^+$ (m/z): [M+H]$^+$ calcd 514.07; found 514.09.

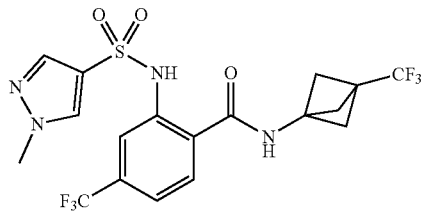 [SMILES: Cn1cc(S(=O)(=O)Nc2cc(C(F)(F)F)ccc2C(=O)NC23CC(C(F)(F)F)(C2)C3)cn1]

Example 19: Preparation of 2-((1-methyl-1H-pyrazole)-4-sulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and 1-methyl-1H-pyrazole-4-sulfonyl chloride (2.25 equiv.) in Step 1 for 72 hours at room temperature, then 3-(trifluoromethyl)bicyclo[1.1.1]pentan-1-amine hydrochloride in Step 3, 2-((1-methyl-1H-pyrazole)-4-sulfonamido)-4-(trifluoromethyl)-N-(3-(trifluoromethyl)bicyclo[1.1.1]pentan-1-yl)benzamide was synthesized and purified by crystallization. $^1$H NMR (400 MHz, DMSO-$d_6$) δ 11.16 (s, 1H), 9.69 (s, 1H), 8.33 (s, 1H), 7.92 (d, J=8.3 Hz, 1H), 7.72 (d, J=8.1 Hz, 2H), 7.59 (d, J=8.2 Hz, 1H), 3.82 (s, 3H), 2.35 (s, 6H). LCMS-ESI$^+$ (m/z): [M+H]$^+$ calcd 483.09; found 483.1.

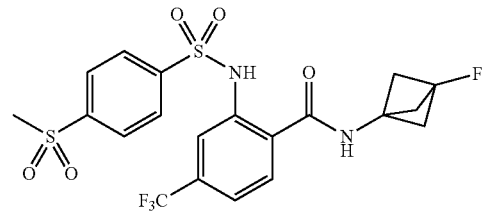 [SMILES: CS(=O)(=O)c1ccc(S(=O)(=O)Nc2cc(C(F)(F)F)ccc2C(=O)NC23CC(F)(C2)C3)cc1]

Example 20: Preparation of N-(3-fluorobicyclo[1.1.1]pentan-1-yl)-2-((4-(methylsulfonyl)phenyl)sulfonamido)-4-(trifluoromethyl)benzamide Following General Synthesis 1, using methyl 2-amino-4-(trifluoromethyl)benzoate and 4-(methylsulfonyl)benzenesulfonyl chloride (1.95 equiv.) in Step 1 for 48 hours at room temperature, then 3-fluorobicyclo[1.1.1]pentan-1-amine hydrochloride in Step 3, N-(3-fluorobicyclo[1.1.1]pentan-1-yl)-2-((4-(methylsulfonyl)phenyl)sulfonamido)-4-(trifluoromethyl)benzamide was synthesized and purified by crystallization. $^1$H NMR (400 MHz, DMSO-$d_6$) δ 11.27 (s, 1H), 9.54 (s, 1H), 8.10 (d, J=8.5 Hz, 2H), 7.94 (d, J=8.5 Hz, 2H), 7.86 (d, J=8.2 Hz, 1H), 7.70-7.58 (m, 2H), 3.28 (s, 3H), 2.38 (d, J=2.2 Hz, 6H). LCMS-ESI$^+$ (m/z): [M+H]$^+$ calcd 507.07; found 507.07.

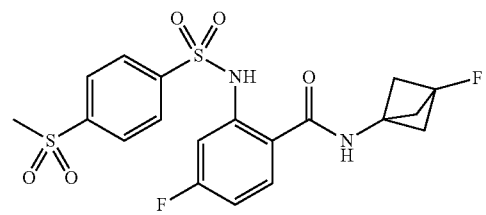 [SMILES: CS(=O)(=O)c1ccc(S(=O)(=O)Nc2cc(F)ccc2C(=O)NC23CC(F)(C2)C3)cc1]

Example 21: Preparation of 4-fluoro-N-(3-fluorobicyclo[1.1.1]pentan-1-yl)-2-((4-(methylsulfonyl)phenyl)sulfonamido)benzamide Following General Synthesis 1, using 4-(methylsulfonyl)benzenesulfonyl chloride (1.2 equiv.) in Step 1 and 3-fluorobicyclo[1.1.1]pentan-1-amine hydrochloride in Step 3, 4-fluoro-N-(3-fluorobicyclo[1.1.1]pentan-1-yl)-2-((4-(methylsulfonyl)phenyl)sulfonamido)benzamide was synthesized and purified by reverse phase chromatography. $^1$H NMR (400 MHz, DMSO-$d_6$) δ 11.84 (s, 1H), 9.42 (s, 1H), 8.10 (d, J=8.5 Hz, 2H), 8.02 (d, J=8.5 Hz, 2H), 7.80 (dd, J=8.9, 6.2 Hz, 1H), 7.26 (d, J=9.9 Hz, 1H), 7.15-7.05 (m, 1H), 3.29 (s, 3H), 2.39 (d, J=2.2 Hz, 6H). LCMS-ESI$^+$ (m/z): [M+H]$^+$ calcd 457.07; found 457.00.

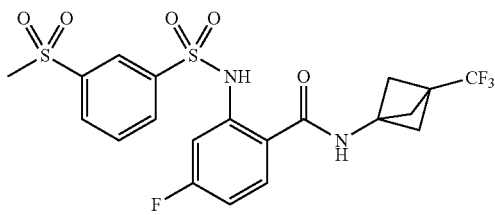 [SMILES: CS(=O)(=O)c1cccc(S(=O)(=O)Nc2cc(F)ccc2C(=O)NC23CC(C(F)(F)F)(C2)C3)c1]

Example 22: Preparation of 4-fluoro-2-((3-(methylsulfonyl)phenyl)sulfonamido)-N-(3-(trifluoromethyl)bicyclo[1.1.1]pentan-1-yl)benzamide Following General Synthesis 1, using 4-(methylsulfonyl)benzenesulfonyl chloride (1.2 equiv.) in Step 1 and 3-(trifluoromethyl)bicyclo[1.1.1]pentan-1-amine hydrochloride in Step 3, 4-fluoro-2-((3-(methylsulfonyl)phenyl)sulfonamido)-N-(3-(trifluoromethyl)bicyclo[1.1.1]pentan-1-yl)benzamide was synthesized and purified by crystallization. $^1$H NMR (400 MHz, DMSO-$d_6$) δ 11.91 (s, 1H), 9.49 (s, 1H), 8.26-8.17 (m, 2H), 8.13 (d, J=8.3 Hz, 1H), 7.87 (t, J=7.9 Hz, 1H), 7.80 (dd, J=8.9, 6.2 Hz, 1H), 7.32-7.20 (m, 1H), 7.16-7.02 (m, 1H), 3.27 (s, 3H), 2.31 (s, 6H). LCMS-ESI$^+$ (m/z): [M+H]$^+$ calcd 507.07; found 507.02.

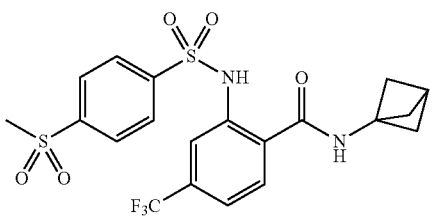

Example 23: Preparation of N-(bicyclo[1.1.1]pentan-1-yl)-2-((4-(methylsulfonyl)phenyl)sulfonamido)-4-(trifluoromethyl)benzamide Following General Synthesis 1, using methyl 2-amino-4-(trifluoromethyl)benzoate and 4-(methylsulfonyl)benzenesulfonyl chloride (1.95 equiv.) in Step 1 for 48 hours at room temperature, then bicyclo[1.1.1]pentan-1-amine hydrochloride in Step 3, N-(bicyclo[1.1.1]pentan-1-yl)-2-((4-(methylsulfonyl)phenyl)sulfonamido)-4-(trifluoromethyl)benzamide was synthesized and purified by crystallization. $^1$H NMR (400 MHz, Methanol-$d_4$) δ 8.11-8.03 (m, 2H), 7.95-7.88 (m, 3H), 7.70 (d, J=8.1 Hz, 1H), 7.47 (d, J=8.2 Hz, 1H), 3.14 (s, 3H), 2.48 (s, 1H), 2.13 (s, 6H). LCMS-ESI$^+$ (m/z): [M+H]$^+$ calcd 489.08; found 489.06.

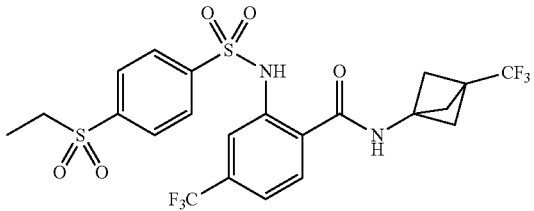 [SMILES: CCS(=O)(=O)c1ccc(S(=O)(=O)Nc2cc(C(F)(F)F)ccc2C(=O)NC23CC(C(F)(F)F)(C2)C3)cc1]

Example 24: Preparation of 2-((4-(ethylsulfonyl)phenyl)sulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and 4-(ethylsulfonyl)benzenesulfonyl chloride (1.3 equiv.) in Step 1 for 48 hours at room temperature, then 3-(trifluoromethyl)bicyclo[1.1.1]pentan-1-amine hydrochloride in Step 3, 2-((4-(ethylsulfonyl)phenyl)sulfonamido)-4-(trifluoromethyl)-N-(3-(trifluoromethyl)bicyclo[1.1.1]pentan-1-yl)benzamide was synthesized and purified by crystallization. $^1$H NMR (400 MHz, DMSO-$d_6$) δ 11.26 (s, 1H), 9.59 (s, 1H), 8.07 (d, J=8.5 Hz, 2H), 7.95 (d, J=8.5 Hz, 2H), 7.85 (d, J=8.3 Hz, 1H), 7.68-7.59 (m, 2H), 3.36 (q, J=7.3 Hz, 2H), 2.30 (s, 6H), 1.06 (t, J=7.4 Hz, 3H). LCMS-ESI$^+$ (m/z): [M+H]$^+$ calcd 571.08; found 571.14.

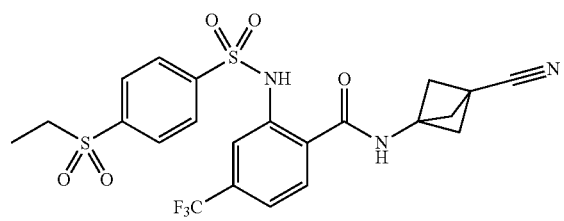 [SMILES: CCS(=O)(=O)c1ccc(S(=O)(=O)Nc2cc(C(F)(F)F)ccc2C(=O)NC23CC(C#N)(C2)C3)cc1]

Example 25: Preparation of N-(3-cyanobicyclo[1.1.1]pentan-1-yl)-2-((4-(ethylsulfonyl)phenyl)sulfonamido)-4-(trifluoromethyl)benzamide Following General Synthesis 1, using methyl 2-amino-4-(trifluoromethyl)benzoate and 4-(ethylsulfonyl)benzenesulfonyl chloride (1.3 equiv.) in Step 1 for 48 hours at room temperature, then 3-aminobicyclo[1.1.1]pentane-1-carbonitrile in Step 3, N-(3-cyanobicyclo[1.1.1]pentan-1-yl)-2-((4-(ethylsulfonyl)phenyl)sulfonamido)-4-(trifluoromethyl)benzamide was synthesized and purified by reverse phase chromatography. $^1$H NMR (400 MHz, DMSO-$d_6$) δ 11.21 (s, 1H), 9.57 (s, 1H), 8.07 (d, J=8.6 Hz, 2H), 7.95 (d, J=8.5 Hz, 2H), 7.81 (d, J=8.1 Hz, 1H), 7.67-7.59 (m, 2H), 3.37 (q, J=7.3 Hz, 2H), 2.54 (s, 6H), 1.06 (t, J=7.4 Hz, 3H). LCMS-ESI$^+$ (m/z): [M+H]$^+$ calcd 528.09; found 528.13.

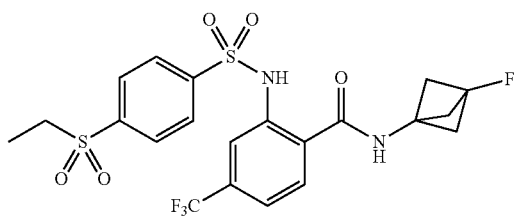 [SMILES: CCS(=O)(=O)c1ccc(S(=O)(=O)Nc2cc(C(F)(F)F)ccc2C(=O)NC23CC(F)(C2)C3)cc1]

Example 26: Preparation of 2-((4-(ethylsulfonyl)phenyl)sulfonamido)-N-(3-fluorobicyclo[1.1.1]pentan-1-yl)-4-(trifluoromethyl)benzamide Following General Synthesis 1, using methyl 2-amino-4-(trifluoromethyl)benzoate and 4-(ethylsulfonyl)benzenesulfonyl chloride (1.3 equiv.) in Step 1 for 48 hours at room temperature, then 3-fluorobicyclo[1.1.1]pentan-1-amine hydrochloride in Step 3, 2-((4-(ethylsulfonyl)phenyl)sulfonamido)-N-(3-fluorobicyclo[1.1.1]pentan-1-yl)-4-(trifluoromethyl)benzamide was synthesized and purified by reverse phase chromatography. $^1$H NMR (400 MHz, DMSO-$d_6$) δ 11.25 (s, 1H), 9.53 (s, 1H), 8.06 (d, J=8.3 Hz, 2H), 7.95 (d, J=8.5 Hz, 2H), 7.86 (d, J=8.2 Hz, 1H), 7.70-7.59 (m, 2H), 3.36 (q, J=7.3 Hz, 2H), 2.38 (d, J=2.2 Hz, 6H), 1.06 (t, J=7.4 Hz, 3H). LCMS-ESI$^+$ (m/z): [M+H]$^+$ calcd 521.08; found 521.11.

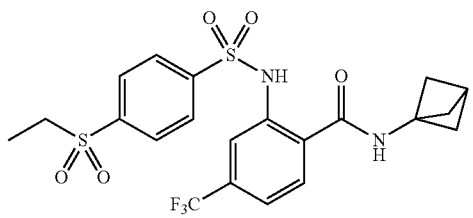 [SMILES: CCS(=O)(=O)c1ccc(S(=O)(=O)Nc2cc(C(F)(F)F)ccc2C(=O)NC23CC(C2)C3)cc1]

Example 27: Preparation of N-(bicyclo[1.1.1]pentan-1-yl)-2-((4-(ethylsulfonyl)phenyl)sulfonamido)-4-(trifluoromethyl)benzamide Following General Synthesis 1, using methyl 2-amino-4-(trifluoromethyl)benzoate and 4-(ethylsulfonyl)benzenesulfonyl chloride (1.3 equiv.) in Step 1 for 48 hours at room temperature, then bicyclo[1.1.1]pentan-1-amine hydrochloride in Step 3, N-(bicyclo[1.1.1]pentan-1-yl)-2-((4-(ethylsulfonyl)phenyl)sulfonamido)-4-(trifluoromethyl)benzamide was synthesized and purified by crystallization. $^1$H NMR (400 MHz, DMSO-$d_6$) δ 11.58 (s, 1H), 9.40 (s, 1H), 8.06 (d, J=8.5 Hz, 2H), 7.96 (d, J=8.5 Hz, 2H), 7.87 (d, J=8.2 Hz, 1H), 7.65 (s, 1H), 7.64-7.57 (m, 1H), 3.35 (q, J=7.3 Hz, 2H), 2.06 (s, 6H), 1.06 (t, J=7.3 Hz, 3H). LCMS-ESI$^+$ (m/z): [M+H]$^+$ calcd 503.09; found 503.06.

Example 28: Preparation of 2-((4-(cyclopropylsulfonyl)phenyl)sulfonamido)-4-fluoro-N-(3-(trifluoromethyl)bicyclo[1.1.1]pentan-1-yl)benzamide

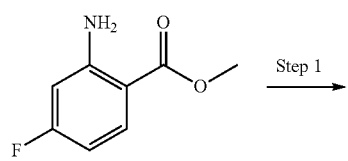

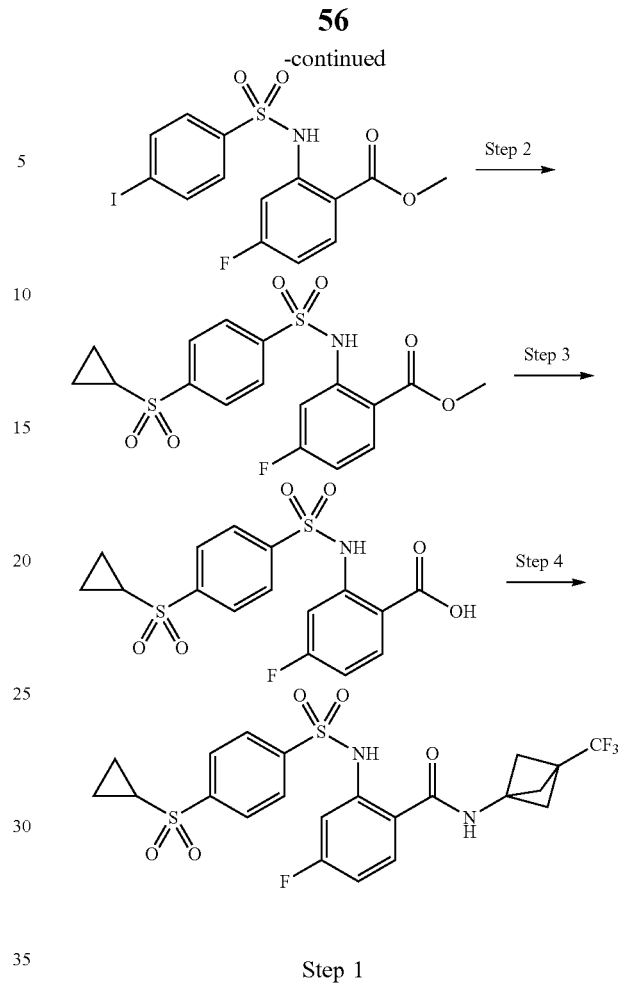

Step 1

Following Step 1 of General Synthesis 1 and using 4-iodobenzenesulfonyl chloride (1.3 equiv.) for 48 hours at room temperature, methyl 4-fluoro-2-((4-iodophenyl)sulfonamido)benzoate was synthesized and purified by silica gel chromatography. LCMS-ESI$^+$ (m/z): [(M-CH$_3$OH)+H]$^+$ calcd 403.93; found 404.04.

Step 2

A 10 mL vessel was charged with methyl 4-fluoro-2-((4-iodophenyl)sulfonamido)benzoate (100 mg, 0.230 mmol), sodium cyclopropanesulfinate (58.9 mg, 0.460 mmol), copper trifluoromethanesulfonate toluene complex (119 mg, 0.230 mmol) and DMSO (2.3 mL). The mixture was degassed with nitrogen for 10 minutes. Trans-1,2-diaminocyclohexane (55.2 µL, 0.460 mmol) was added and the solution was heated at 120° C. for 10 hours, then stirred at room temperature for 48 hours. The mixture was diluted with water and extracted with EtOAc (3×). The combined organic layers were washed with brine, dried over MgSO$_4$, filtered and concentrated. The crude mixture was purified by silica gel chromatography to afford methyl 2-((4-(cyclopropylsulfonyl)phenyl)sulfonamido)-4-fluorobenzoate. $^1$H NMR (400 MHz, Chloroform-d) δ 11.04 (s, 1H), 8.09-8.02 (m, 2H), 8.02-7.94 (m, 3H), 7.47 (dd, J=10.7, 2.5 Hz, 1H), 6.78 (ddd, J=8.9, 7.5, 2.5 Hz, 1H), 3.89 (s, 3H), 2.49-2.40 (m, 1H), 1.40-1.33 (m, 2H), 1.12-1.05 (m, 2H).

Steps 3-4

Following General Synthesis 1 and using 3-(trifluoromethyl)bicyclo[1.1.1]pentan-1-amine hydrochloride in Step 3, 2-((4-(cyclopropylsulfonyl)phenyl)sulfonamido)-4-fluoro-N-(3-(trifluoromethyl)bicyclo[1.1.1]pentan-1-yl)benzamide was synthesized and purified by reverse phase chromatography. ¹H NMR (400 MHz, DMSO-d₆) δ 11.84 (s, 1H), 9.49 (s, 1H), 8.08 (d, J=8.5 Hz, 2H), 8.02 (d, J=8.4 Hz, 2H), 7.79 (dd, J=8.9, 6.2 Hz, 1H), 7.27 (dd, J=10.5, 2.5 Hz, 1H), 7.16-7.07 (m, 1H), 3.00-2.88 (m, 1H), 2.30 (s, 6H), 1.18-1.02 (m, 4H). LCMS-ESI⁺ (m/z): [M+H]⁺ calcd 533.08; found 533.07.

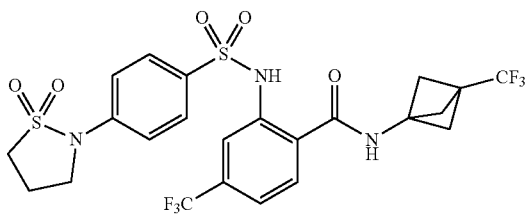 [SMILES: O=C(NC12CC(C(F)(F)F)(C1)C2)c1ccc(C(F)(F)F)cc1NS(=O)(=O)c1ccc(N2CCCS2(=O)=O)cc1]

Example 29: Preparation of 2-((4-(1,1-dioxidoisothiazolidin-2-yl)phenyl)sulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and 4-(1,1-dioxidoisothiazolidin-2-yl)benzenesulfonyl chloride (1.3 equiv.) in Step 1 for 48 hours at room temperature, then 3-(trifluoromethyl)bicyclo[1.1.1]pentan-1-amine hydrochloride in Step 3, 2-((4-(1,1-dioxidoisothiazolidin-2-yl)phenyl)sulfonamido)-4-(trifluoromethyl)-N-(3-(trifluoromethyl)bicyclo[1.1.1]pentan-1-yl)benzamide was synthesized and purified by crystallization. ¹H NMR (400 MHz, DMSO-d₆) δ 11.25 (s, 1H), 9.66 (s, 1H), 7.87 (d, J=8.3 Hz, 1H), 7.77-7.65 (m, 3H), 7.57 (d, J=8.3 Hz, 1H), 7.31-7.18 (m, 2H), 3.77 (t, J=6.5 Hz, 2H), 3.58 (t, J=7.3 Hz, 2H), 2.45-2.37 (m, 2H), 2.34 (s, 6H). LCMS-ESI⁺ (m/z): [M+H]⁺ calcd 598.09; found 598.16.

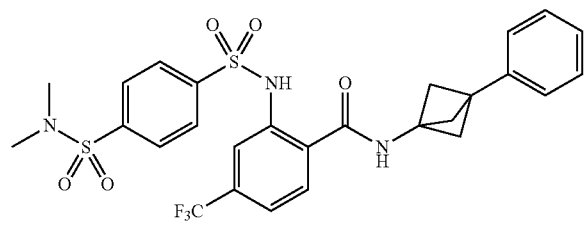 [SMILES: CN(C)S(=O)(=O)c1ccc(S(=O)(=O)Nc2cc(C(F)(F)F)ccc2C(=O)NC23CC(c4ccccc4)(C2)C3)cc1]

Example 30: Preparation of 2-((4-(N,N-dimethylsulfamoyl)phenyl)sulfonamido)-N-(3-phenylbicyclo[1.1.1]pentan-1-yl)-4-(trifluoromethyl)benzamide Following General Synthesis 1, using methyl 2-amino-4-(trifluoromethyl)benzoate and 4-(N,N-dimethylsulfamoyl)benzenesulfonyl chloride (1.3 equiv.) in Step 1 for 48 hours at reflux, then 3-phenylbicyclo[1.1.1]pentan-1-amine hydrochloride in Step 3, 2-((4-(N,N-dimethylsulfamoyl)phenyl)sulfonamido)-N-(3-phenylbicyclo[1.1.1]pentan-1-yl)-4-(trifluoromethyl)benzamide was synthesized and purified by crystallization. ¹H NMR (400 MHz, DMSO-d₆) δ 11.53 (s, 1H), 9.51 (s, 1H), 7.99-7.85 (m, 5H), 7.70-7.57 (m, 2H), 7.38-7.30 (m, 2H), 7.30-7.18 (m, 3H), 2.60 (s, 6H), 2.32 (s, 6H). LCMS-ESI⁺ (m/z): [M+H]⁺ calcd 594.13; found 594.14.

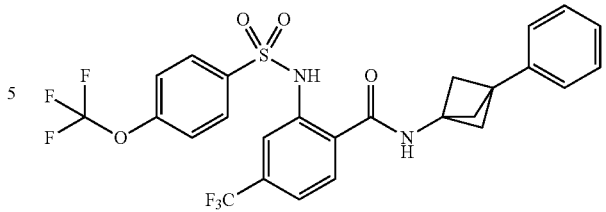

Example 31: Preparation of N-(3-phenylbicyclo[1.1.1]pentan-1-yl)-2-((4-(trifluoromethoxy)phenyl)sulfonamido)-4-(trifluoromethyl)benzamide Following General Synthesis 1, using methyl 2-amino-4-(trifluoromethyl)benzoate and 4-(trifluoromethoxy)benzenesulfonyl chloride (2.0 equiv.) in Step 1 for 7 days at room temperature, then 3-phenylbicyclo[1.1.1]pentan-1-amine hydrochloride in Step 3, N-(3-phenylbicyclo[1.1.1]pentan-1-yl)-2-((4-(trifluoromethoxy)phenyl)sulfonamido)-4-(trifluoromethyl)benzamide was synthesized and purified by silica gel chromatography. ¹H NMR (400 MHz, DMSO-d₆) δ 11.51 (s, 1H), 9.52 (s, 1H), 7.93 (bs, 1H), 7.85 (d, J=8.6 Hz, 2H), 7.71-7.43 (m, J=34.0 Hz, 4H), 7.39-7.18 (m, 5H), 2.32 (s, 6H). LCMS-ESI⁺ (m/z): [M+H]⁺ calcd 571.11; found 571.19.

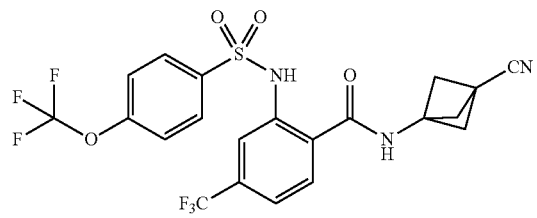 [SMILES: N#CC12CC(NC(=O)c3ccc(C(F)(F)F)cc3NS(=O)(=O)c3ccc(OC(F)(F)F)cc3)(C1)C2]

Example 32: Preparation of N-(3-cyanobicyclo[1.1.1]pentan-1-yl)-2-((4-(trifluoromethoxy)phenyl)sulfonamido)-4-(trifluoromethyl)benzamide Following General Synthesis 1, using methyl 2-amino-4-(trifluoromethyl)benzoate and 4-(trifluoromethoxy)benzenesulfonyl chloride (2.0 equiv.) in Step 1 for 7 days at room temperature, then 3-aminobicyclo[1.1.1]pentane-1-carbonitrile in Step 3, N-(3-cyanobicyclo[1.1.1]pentan-1-yl)-2-((4-(trifluoromethoxy)phenyl)sulfonamido)-4-(trifluoromethyl)benzamide was synthesized and purified by reverse phase chromatography. ¹H NMR (400 MHz, DMSO-d₆) δ 11.18 (s, 1H), 9.57 (s, 1H), 7.88-7.78 (m, 3H), 7.65-7.53 (m, 4H), 2.56 (s, 6H). LCMS-ESI⁺ (m/z): [M+H]⁺ calcd 520.08; found 520.12.

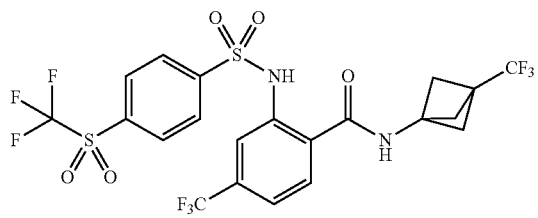 [SMILES: O=C(NC12CC(C(F)(F)F)(C1)C2)c1ccc(C(F)(F)F)cc1NS(=O)(=O)c1ccc(S(=O)(=O)C(F)(F)F)cc1]

Example 33: Preparation of 4-(trifluoromethyl)-N-(3-(trifluoromethyl)bicyclo[1.1.1]pentan-1-yl)-2-((4-((trifluoromethyl)sulfonyl)phenyl)sulfonamido)benzamide Following General Synthesis 1, using methyl 2-amino-4-(trifluoromethyl)benzoate and 4-((trifluoromethyl)sulfonyl) benzenesulfonyl chloride (2.0 equiv.) in Step 1 for 36 hours at room temperature, then 3-(trifluoromethyl)bicyclo[1.1.1]pentan-1-amine hydrochloride in Step 3, 4-(trifluoromethyl)-N-(3-(trifluoromethyl)bicyclo[1.1.1]pentan-1-yl)-2-((4-((trifluoromethyl)sulfonyl)phenyl)sulfonamido) benzamide was synthesized and purified by reverse phase chromatography. $^1$H NMR (400 MHz, DMSO-d$_6$) δ 11.22 (s, 1H), 9.54 (s, 1H), 8.34 (d, J=8.5 Hz, 2H), 8.15-8.02 (m, 2H), 7.83 (d, J=8.2 Hz, 1H), 7.65 (bs, 1H), 7.56 (s, 1H), 2.27 (s, 6H). LCMS-ESI$^+$ (m/z): [M+H]$^+$ calcd 611.04; found 611.15.

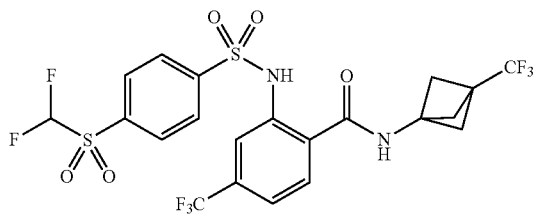 [SMILES: O=C(NC12CC(C(F)(F)F)(C1)C2)c1ccc(C(F)(F)F)cc1NS(=O)(=O)c1ccc(S(=O)(=O)C(F)F)cc1]

Example 34: Preparation of 2-((4-((difluoromethyl)sulfonyl)phenyl)sulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and 4-((difluoromethyl)sulfonyl) benzenesulfonyl chloride (2.0 equiv.) in Step 1 for 36 hours at room temperature, then 3-(trifluoromethyl)bicyclo[1.1.1]pentan-1-amine hydrochloride in Step 3, 2-((4-((difluoromethyl)sulfonyl)phenyl)sulfonamido)-4-(trifluoromethyl)-N-(3-(trifluoromethyl)bicyclo[1.1.1]pentan-1-yl)benzamide was synthesized and purified by reverse phase chromatography. $^1$H NMR (400 MHz, DMSO-d$_6$) δ 11.27 (s, 1H), 9.57 (s, 1H), 8.17 (d, J=8.5 Hz, 2H), 8.05 (d, J=8.5 Hz, 2H), 7.84 (d, J=8.2 Hz, 1H), 7.70-7.62 (m, 1H), 7.61 (s, 1H), 7.39 (t, J=51.8 Hz, 1H), 2.28 (s, 6H). LCMS-ESI$^+$ (m/z): [M+H]$^+$ calcd 593.05; found 593.16.

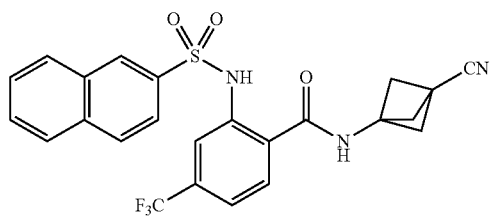 [SMILES: N#CC12CC(NC(=O)c3ccc(C(F)(F)F)cc3NS(=O)(=O)c3ccc4ccccc4c3)(C1)C2]

Example 35: Preparation of N-(3-cyanobicyclo[1.1.1]pentan-1-yl)-2-(naphthalene-2-sulfonamido)-4-(trifluoromethyl)benzamide Following General Synthesis 1, using methyl 2-amino-4-(trifluoromethyl)benzoate and naphthalene-2-sulfonyl chloride (1.2 equiv.) in Step 1 for 36 hours at room temperature, then 3-aminobicyclo[1.1.1]pentane-1-carbonitrile in Step 3, N-(3-cyanobicyclo[1.1.1]pentan-1-yl)-2-(naphthalene-2-sulfonamido)-4-(trifluoromethyl)benzamide was synthesized and purified by reverse phase chromatography. $^1$H NMR (400 MHz, DMSO-d$_6$) δ 11.31 (s, 1H), 9.56 (s, 1H), 8.47 (s, 1H), 8.13 (dd, J=16.7, 8.3 Hz, 2H), 8.03 (d, J=8.1 Hz, 1H), 7.82-7.62 (m, 5H), 7.53 (d, J=8.2 Hz, 1H), 2.51 (s, 6H). LCMS-ESI$^+$ (m/z): [M+H]$^+$ calcd 486.11; found 486.17.

Example 36: Preparation of 2-((4-(1H-imidazol-1-yl)phenyl)sulfonamido)-N-(3-phenylbicyclo[1.1.1]pentan-1-yl)benzamide

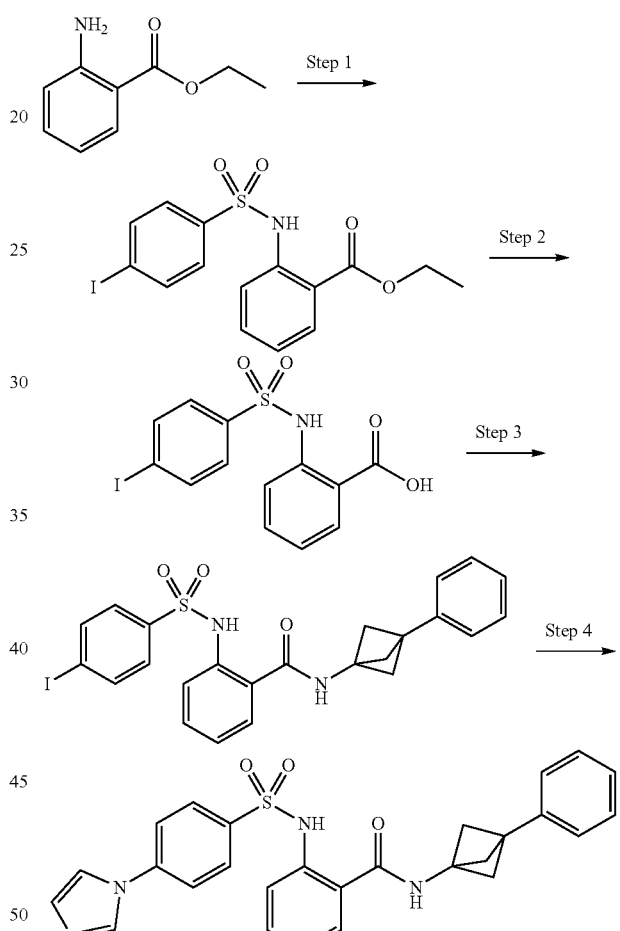

Steps 1-3

Following General Synthesis 1, using ethyl 2-aminobenzoate and 4-iodobenzenesulfonyl chloride (1.2 equiv.) in Step 1 for 48 hours at room temperature, then 3-phenylbicyclo[1.1.1]pentan-1-amine hydrochloride in Step 3, 2-((4-iodophenyl)sulfonamido)-N-(3-phenylbicyclo[1.1.1]pentan-1-yl)benzamide was synthesized and purified by silica gel chromatography. LCMS-ESI$^+$ (m/z): [M+H]$^+$ calcd 545.04; found 545.07.

Step 4

A 10 mL microwave vial was charged with 2-((4-iodophenyl)sulfonamido)-N-(3-phenylbicyclo[1.1.1]pentan-1- yl)benzamide (100 mg, 0.184 mmol), imidazole (16.3 mg, 0.239 mmol), cesium carbonate (150 mg, 0.459 mmol), copper(I) oxide (1.31 mg, 0.009 mmol), 8-hydroxyquinoline (5.33 mg, 0.037 mmol), PEG3350 (36.0 mg) and nitrogen degassed 15:1 DMA/water (2.0 mL). The mixture was subsequently degassed with nitrogen for 10 minutes, then heated at 110° C. for 18 hours with stirring. The mixture was cooled to room temperature, filtered and the solid was rinsed with EtOAc. The solution was concentrated and purified by reverse phase chromatography to afford 2-((4-(1H-imidazol-1-yl)phenyl)sulfonamido)-N-(3-phenylbicyclo[1.1.1]pentan-1-yl)benzamide. $^1$H NMR (400 MHz, DMSO-$d_6$) δ 11.74 (s, 1H), 9.34 (s, 1H), 9.13 (bs, 1H), 8.12 (s, 1H), 7.94 (s, 4H), 7.73 (d, J=7.7 Hz, 1H), 7.61-7.46 (m, 3H), 7.36-7.21 (m, 5H), 7.21-7.13 (m, 1H), 2.34 (s, 6H). LCMS-ESI$^+$ (m/z): [M+H]$^+$ calcd 485.16; found 485.38.

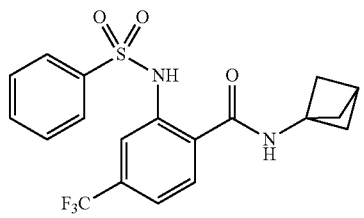 [SMILES: O=C(NC12CC(C1)C2)c1ccc(C(F)(F)F)cc1NS(=O)(=O)c1ccccc1]

Example 37: Preparation of N-(bicyclo[1.1.1]pentan-1-yl)-2-(phenylsulfonamido)-4-(trifluoromethyl)benzamide Following General Synthesis 1, using methyl 2-amino-4-(trifluoromethyl)benzoate and benzenesulfonyl chloride (1.5 equiv.) in Step 1 for 7 days at room temperature, then bicyclo[1.1.1]pentan-1-amine hydrochloride in Step 3, N-(bicyclo[1.1.1]pentan-1-yl)-2-(phenylsulfonamido)-4-(trifluoromethyl)benzamide was synthesized and purified by reverse phase chromatography. $^1$H NMR (400 MHz, DMSO-$d_6$) δ 11.55 (s, 1H), 9.44 (s, 1H), 7.86 (d, J=8.3 Hz, 1H), 7.77-7.61 (m, 4H), 7.61-7.48 (m, 3H), 2.50 (s, 1H, not visible with DMSO peak), 2.09 (s, 6H). LCMS-ESI$^+$ (m/z): [M+H]$^+$ calcd 411.10; found 411.17.

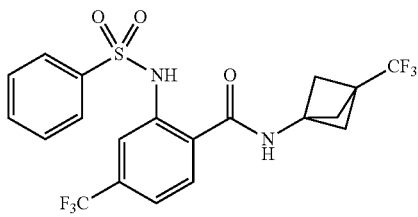 [SMILES: O=C(NC12CC(C(F)(F)F)(C1)C2)c1ccc(C(F)(F)F)cc1NS(=O)(=O)c1ccccc1]

Example 38: Preparation of 2-(phenylsulfonamido)-4-(trifluoromethyl)-N-(3-(trifluoromethyl)bicyclo[1.1.1]pentan-1-yl)benzamide Following General Synthesis 1, using methyl 2-amino-4-(trifluoromethyl)benzoate and benzenesulfonyl chloride (1.5 equiv.) in Step 1 for 7 days at room temperature, then 3-(trifluoromethyl)bicyclo[1.1.1]pentan-1-amine hydrochloride in Step 3, 2-(phenylsulfonamido)-4-(trifluoromethyl)-N-(3-(trifluoromethyl)bicyclo[1.1.1]pentan-1-yl)benzamide was synthesized and purified by crystallization. $^1$H NMR (400 MHz, DMSO-$d_6$) δ 11.29 (s, 1H), 9.64 (s, 1H), 7.86 (d, J=8.2 Hz, 1H), 7.75-7.63 (m, 4H), 7.61-7.53 (m, 3H), 2.33 (s, 6H). LCMS-ESI$^+$ (m/z): [M+H]$^+$ calcd 479.09; found 479.12.

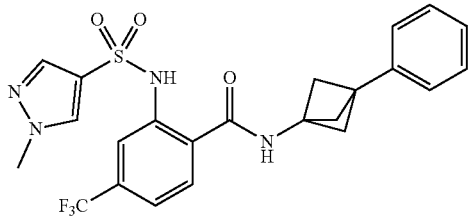 [SMILES: Cn1cc(S(=O)(=O)Nc2cc(C(F)(F)F)ccc2C(=O)NC23CC(c4ccccc4)(C2)C3)cn1]

Example 39: Preparation of 2-((1-methyl-1H-pyrazole)-4-sulfonamido)-N-(3-phenylbicyclo[1.1.1]pentan-1-yl)-4-(trifluoromethyl)benzamide Following General Synthesis 1, using methyl 2-amino-4-(trifluoromethyl)benzoate and 1-methyl-1H-pyrazole-4-sulfonyl chloride (2.25 equiv.) in Step 1 for 72 hours at room temperature, then 3-phenylbicyclo[1.1.1]pentan-1-amine hydrochloride in Step 3, 2-((1-methyl-1H-pyrazole)-4-sulfonamido)-N-(3-phenylbicyclo[1.1.1]pentan-1-yl)-4-(trifluoromethyl)benzamide was synthesized and purified by reverse phase chromatography. $^1$H NMR (400 MHz, DMSO-$d_6$) δ 11.44 (s, 1H), 9.61 (s, 1H), 8.35 (s, 1H), 7.98 (d, J=8.2 Hz, 1H), 7.75 (s, 1H), 7.71 (s, 1H), 7.58 (d, J=8.9 Hz, 1H), 7.37-7.20 (m, 5H), 3.83 (s, 3H), 2.37 (s, 6H). LCMS-ESI$^+$ (m/z): [M+H]$^+$ calcd 491.14; found 491.20.

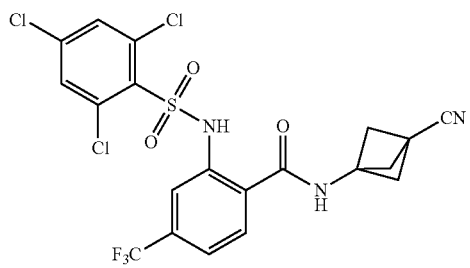 [SMILES: N#CC12CC(NC(=O)c3ccc(C(F)(F)F)cc3NS(=O)(=O)c3c(Cl)cc(Cl)cc3Cl)(C1)C2]

Example 40: Preparation of N-(3-cyanobicyclo[1.1.1]pentan-1-yl)-2-((2,4,6-trichlorophenyl)sulfonamido)-4-(trifluoromethyl)benzamide Following General Synthesis 1, using methyl 2-amino-4-(trifluoromethyl)benzoate and 2,4,6-trichlorobenzenesulfonyl chloride (2 equiv.) in Step 1 for 72 hours at room temperature, then 3-aminobicyclo[1.1.1]pentane-1-carbonitrile in Step 3, N-(3-cyanobicyclo[1.1.1]pentan-1-yl)-2-((2,4,6-trichlorophenyl)sulfonamido)-4-(trifluoromethyl)benzamide was synthesized and purified by reverse phase chromatography. $^1$H NMR (400 MHz, DMSO-$d_6$) δ 12.03 (s, 1H), 9.84 (s, 1H), 8.00-7.86 (m, 3H), 7.73 (s, 1H), 7.55 (s, 1H), 2.60 (s, 6H). LCMS-ESI$^+$ (m/z): [M+H]$^+$ calcd 537.98, found 538.02.

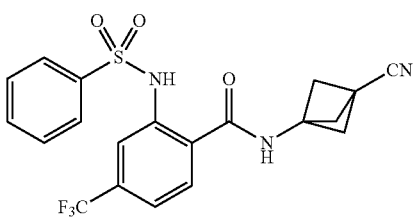 [SMILES: N#CC12CC(NC(=O)c3ccc(C(F)(F)F)cc3NS(=O)(=O)c3ccccc3)(C1)C2]

Example 41: Preparation of N-(3-cyanobicyclo[1.1.1]pentan-1-yl)-2-(phenylsulfonamido)-4-(trifluoromethyl)benzamide Following General Synthesis 1, using methyl 2-amino-4-(trifluoromethyl)benzoate and benzenesulfonyl chloride (1.5 equiv.) in Step 1 for 7 days at room temperature, then 3-aminobicyclo[1.1.1]pentane-1-carbonitrile in Step 3, N-(3-cyanobicyclo[1.1.1]pentan-1-yl)-2-(phenylsulfonamido)-4-(trifluoromethyl)benzamide was synthesized and purified by reverse phase chromatography. $^1$H NMR (400 MHz, DMSO-$d_6$) δ 11.22 (s, 1H), 9.61 (s, 1H), 7.82 (d, J=8.2 Hz, 1H), 7.76-7.62 (m, 4H), 7.62-7.53 (m, 3H), 2.57 (s, 6H). LCMS-ESI$^+$ (m/z): [M+H]$^+$ calcd 436.09; found 436.13.

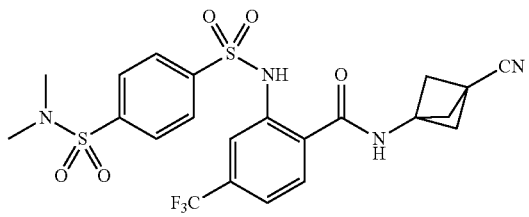 [SMILES: CN(C)S(=O)(=O)c1ccc(S(=O)(=O)Nc2cc(C(F)(F)F)ccc2C(=O)NC23CC(C#N)(C2)C3)cc1]

Example 42: Preparation of N-(3-cyanobicyclo[1.1.1]pentan-1-yl)-2-((4-(N,N-dimethylsulfamoyl)phenyl)sulfonamido)-4-(trifluoromethyl)benzamide Following General Synthesis 1, using methyl 2-amino-4-(trifluoromethyl)benzoate and 4-(N,N-dimethylsulfamoyl)benzenesulfonyl chloride (1.3 equiv.) in Step 1 for 3 days at reflux, then 3-aminobicyclo[1.1.1]pentane-1-carbonitrile in Step 3, N-(3-cyanobicyclo[1.1.1]pentan-1-yl)-2-((4-(N,N-dimethylsulfamoyl)phenyl)sulfonamido)-4-(trifluoromethyl)benzamide was synthesized and purified by reverse phase chromatography. $^1$H NMR (400 MHz, DMSO-$d_6$) δ 11.18 (s, 1H), 9.56 (s, 1H), 7.92 (s, 4H), 7.81 (d, J=8.2 Hz, 1H), 7.70-7.54 (m, 2H), 2.60 (s, 6H), 2.54 (s, 6H). LCMS-ESI$^+$ (m/z): [M+H]$^+$ calcd 543.10; found 543.17.

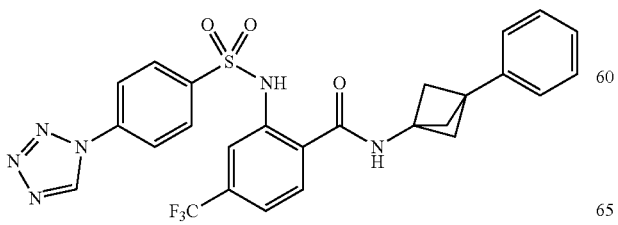

Example 43: Preparation of 2-((4-(1H-tetrazol-1-yl)phenyl)sulfonamido)-N-(3-phenylbicyclo[1.1.1]pentan-1-yl)-4-(trifluoromethyl)benzamide Following General Synthesis 1, using methyl 2-amino-4-(trifluoromethyl)benzoate and 4-(1H-tetrazol-1-yl)benzenesulfonyl chloride (1.5 equiv.) in Step 1, then 3-phenylbicyclo[1.1.1]pentan-1-amine hydrochloride in Step 3, 2-((4-(1H-tetrazol-1-yl)phenyl)sulfonamido)-N-(3-phenylbicyclo[1.1.1]pentan-1-yl)-4-(trifluoromethyl)benzamide was synthesized and purified by crystallization. $^1$H NMR (400 MHz, DMSO-$d_6$) δ 11.58 (s, 1H), 10.21 (s, 1H), 9.52 (s, 1H), 8.16 (d, J=8.4 Hz, 2H), 8.00 (d, J=8.7 Hz, 2H), 7.91 (d, J=8.3 Hz, 1H), 7.76 (s, 1H), 7.66-7.57 (m, 1H), 7.40-7.17 (m, 5H), 2.33 (s, 6H). LCMS-ESI$^+$ (m/z): [M+H]$^+$ calcd 555.14; found 555.08.

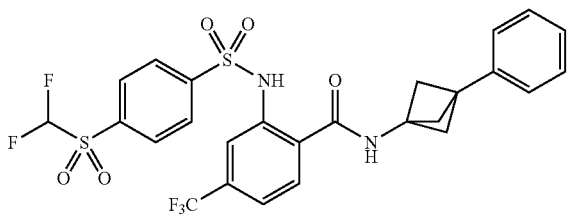 [SMILES: O=C(NC12CC(c3ccccc3)(C1)C2)c1ccc(C(F)(F)F)cc1NS(=O)(=O)c1ccc(S(=O)(=O)C(F)F)cc1]

Example 44: Preparation of 2-((4-((difluoromethyl)sulfonyl)phenyl)sulfonamido)-N-(3-phenylbicyclo[1.1.1]pentan-1-yl)-4-(trifluoromethyl)benzamide Following General Synthesis 1, using methyl 2-amino-4-(trifluoromethyl)benzoate and 4-((difluoromethyl)sulfonyl)benzenesulfonyl chloride (2.0 equiv.) in Step 1 for 36 hours at room temperature, then 3-phenylbicyclo[1.1.1]pentan-1-amine hydrochloride in Step 3, 2-((4-((difluoromethyl)sulfonyl)phenyl)sulfonamido)-N-(3-phenylbicyclo[1.1.1]pentan-1-yl)-4-(trifluoromethyl)benzamide was synthesized and purified by reverse phase chromatography. $^1$H NMR (400 MHz, DMSO-$d_6$) δ 11.57 (s, 1H), 9.49 (s, 1H), 8.18 (d, J=8.5 Hz, 2H), 8.07 (d, J=8.5 Hz, 2H), 7.91 (d, J=8.3 Hz, 1H), 7.65 (s, 2H), 7.56-7.18 (m, 6H), 2.30 (s, 6H). LCMS-ESI$^+$ (m/z): [M+H]$^+$ calcd 601.09; found 601.18.

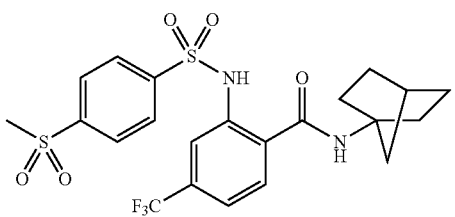 [SMILES: CS(=O)(=O)c1ccc(S(=O)(=O)Nc2cc(C(F)(F)F)ccc2C(=O)NC23CCC(CC2)C3)cc1]

Example 45: Preparation of N-(bicyclo[2.2.1]heptan-1-yl)-2-((4-(methylsulfonyl)phenyl)sulfonamido)-4-(trifluoromethyl)benzamide Following General Synthesis 1, using methyl 2-amino-4-(trifluoromethyl)benzoate and 4-(methylsulfonyl)benzenesulfonyl chloride (2.5 equiv.) in Step 1 for 48 hours at room temperature, then (1r,4r)-bicyclo[2.2.1]heptan-1-amine hydrochloride in Step 3, N-(bicyclo[2.2.1]heptan-1-yl)-2-((4-(methylsulfonyl)phenyl)sulfonamido)-4-(trifluoromethyl)benzamide was synthesized and purified by crystallization. ¹H NMR (400 MHz, DMSO-d₆) δ 11.45 (s, 1H), 8.91 (s, 1H), 8.10 (d, J=8.5 Hz, 2H), 8.00-7.85 (m, 3H), 7.69 (s, 1H), 7.61 (s, 1H), 3.26 (s, 3H), 2.13 (s, 1H), 1.76-1.57 (m, 8H), 1.41-1.29 (m, 2H). LCMS-ESI⁺ (m/z): [M+H]⁺ calcd 517.11; found 517.31.

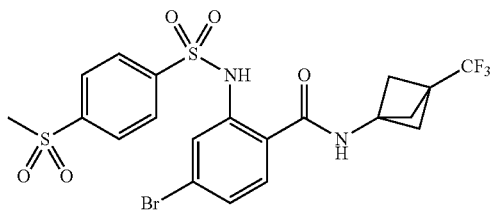 [SMILES: CS(=O)(=O)c1ccc(S(=O)(=O)Nc2cc(Br)ccc2C(=O)NC23CC(C(F)(F)F)(C2)C3)cc1]

Example 46: 4-bromo-2-((4-(methylsulfonyl)phenyl)sulfonamido)-N-(3-(trifluoromethyl)bicyclo[1.1.1]pentan-1-yl)benzamide Following General Synthesis 1, using methyl 2-amino-4-bromobenzoate and 4-(methylsulfonyl)benzenesulfonyl chloride (2.0 equiv.) in Step 1 for 24 hours at room temperature, then 3-(trifluoromethyl)bicyclo[1.1.1]pentan-1-amine hydrochloride in Step 3, 4-bromo-2-((4-(methylsulfonyl)phenyl)sulfonamido)-N-(3-(trifluoromethyl)bicyclo[1.1.1]pentan-1-yl)benzamide was synthesized and purified by silica gel chromatography. ¹H NMR (400 MHz, DMSO-d₆) δ 11.52 (s, 1H), 9.50 (s, 1H), 8.24-7.84 (m, 4H), 7.83-7.31 (m, 3H), 3.31 (s, 3H), 2.28 (s, 6H). LCMS-ESI⁺ (m/z): [M+H]⁺ calcd 566.99; found 566.99.

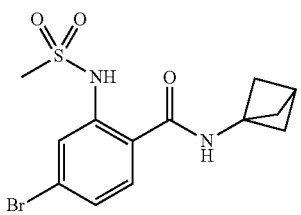 [SMILES: CS(=O)(=O)Nc1cc(Br)ccc1C(=O)NC12CC(C1)C2]

Example 47: Preparation of N-(bicyclo[1.1.1]pentan-1-yl)-4-bromo-2-(methylsulfonamido)benzamide Following General Synthesis 1, using methyl 2-amino-4-bromobenzoate and methanesulfonyl chloride (7.0 equiv.) in Step 1 for 48 hours at room temperature, then bicyclo[1.1.1]pentan-1-amine hydrochloride in Step 3, N-(bicyclo[1.1.1]pentan-1-yl)-4-bromo-2-(methylsulfonamido)benzamide was synthesized and purified by reverse phase chromatography. ¹H NMR (400 MHz, DMSO-d₆) δ 11.47 (s, 1H), 9.40 (s, 1H), 7.78 (d, J=8.5 Hz, 1H), 7.67 (d, J=2.0 Hz, 1H), 7.38 (dd, J=8.5, 2.0 Hz, 1H), 3.20 (s, 3H), 2.49 (s, 1H), 2.10 (s, 6H). LCMS-ESI⁺ (m/z): [M+H]⁺ calcd 359.01; found 359.01.

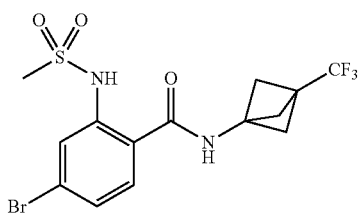 [SMILES: CS(=O)(=O)Nc1cc(Br)ccc1C(=O)NC12CC(C(F)(F)F)(C1)C2]

Example 48: Preparation of 4-bromo-2-(methylsulfonamido)-N-(3-(trifluoromethyl)bicyclo[1.1.1]pentan-1-yl)benzamide Following General Synthesis 1, using methyl 2-amino-4-bromobenzoate and methanesulfonyl chloride (7.0 equiv.) in Step 1 for 48 hours at room temperature, then 3-(trifluoromethyl)bicyclo[1.1.1]pentan-1-amine hydrochloride in Step 3, 4-bromo-2-(methylsulfonamido)-N-(3-(trifluoromethyl)bicyclo[1.1.1]pentan-1-yl)benzamide was synthesized and purified by reverse phase chromatography. ¹H NMR (400 MHz, DMSO-d₆) δ 11.23 (s, 1H), 9.61 (s, 1H), 7.77 (d, J=8.6 Hz, 1H), 7.68 (d, J=2.0 Hz, 1H), 7.41 (dd, J=8.5, 2.0 Hz, 1H), 3.21 (s, 3H), 2.35 (s, 6H). LCMS-ESI⁺ (m/z): [M+H]⁺ calcd 426.99; found 426.97.

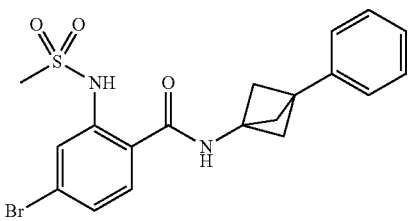 [SMILES: CS(=O)(=O)Nc1cc(Br)ccc1C(=O)NC12CC(c3ccccc3)(C1)C2]

Example 49: Preparation of 4-bromo-2-(methylsulfonamido)-N-(3-phenylbicyclo[1.1.1]pentan-1-yl)benzamide Following General Synthesis 1, using methyl 2-amino-4-bromobenzoate and methanesulfonyl chloride (7.0 equiv.) in Step 1 for 48 hours at room temperature, then 3-phenylbicyclo[1.1.1]pentan-1-amine hydrochloride in Step 3, 4-bromo-2-(methylsulfonamido)-N-(3-phenylbicyclo[1.1.1]pentan-1-yl)benzamide was synthesized and purified by crystallization. ¹H NMR (400 MHz, DMSO-d₆) δ 11.49 (s, 1H), 9.51 (s, 1H), 7.83 (d, J=8.6 Hz, 1H), 7.69 (d, J=1.9 Hz, 1H), 7.40 (dd, J=8.5, 2.0 Hz, 1H), 7.36-7.20 (m, 5H), 3.22 (s, 3H), 2.37 (s, 6H). LCMS-ESI⁺ (m/z): [M+H]⁺ calcd 435.04; found 435.08.

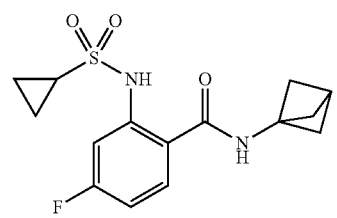 [SMILES: O=C(NC12CC(C1)C2)c1ccc(F)cc1NS(=O)(=O)C1CC1]

Example 50: Preparation of N-(bicyclo[1.1.1]pentan-1-yl)-2-(cyclopropanesulfonamido)-4-fluorobenzamide Following General Synthesis 1, using cyclopropanesulfonyl chloride (6.0 equiv.) in Step 1 for 72 hours at room temperature, then bicyclo[1.1.1]pentan-1-amine hydrochloride in Step 3, N-(bicyclo[1.1.1]pentan-1-yl)-2-(cyclopropanesulfonamido)-4-fluorobenzamide was synthesized and purified by reverse phase chromatography. $^1$H NMR (400 MHz, DMSO-d$_6$) δ 11.62 (s, 1H), 9.36 (s, 1H), 7.92 (dd, J=8.9, 6.3 Hz, 1H), 7.34 (dd, J=11.1, 2.6 Hz, 1H), 7.05 (ddd, J=8.9, 8.1, 2.6 Hz, 1H), 2.90-2.81 (m, 1H), 2.49 (s, 1H), 2.11 (s, 6H), 1.04-0.96 (m, 4H). LCMS-ESI$^+$ (m/z): [M+H]$^+$ calcd 325.10; found 325.03.

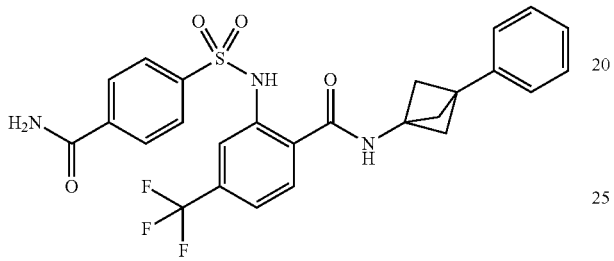

Example 51: Preparation of 2-((4-carbamoylphenyl)sulfonamido)-N-(3-phenylbicyclo[1.1.1]pentan-1-yl)-4-(trifluoromethyl)benzamide Following General Synthesis 1, using 4-carbamoylbenzenesulfonyl chloride (2.5 equiv.) in Step 1 for 72 hours at 50° C., then 3-phenylbicyclo[1.1.1]pentan-1-amine hydrochloride in Step 3, 2-((4-carbamoylphenyl)sulfonamido)-N-(3-phenylbicyclo[1.1.1]pentan-1-yl)-4-(trifluoromethyl)benzamide was synthesized and purified by crystallization. $^1$H NMR (400 MHz, DMSO-d$_6$) δ 11.52 (s, 1H), 9.53 (s, 1H), 8.15 (s, 1H), 8.01 (d, J=8.5 Hz, 2H), 7.90 (d, J=8.3 Hz, 1H), 7.79 (d, J=8.5 Hz, 2H), 7.73 (s, 1H), 7.68-7.54 (m, 2H), 7.39-7.19 (m, 5H), 2.34 (s, 6H). LCMS-ESI$^+$ (m/z): [M+H]$^+$ calcd 530.14; found 529.95.

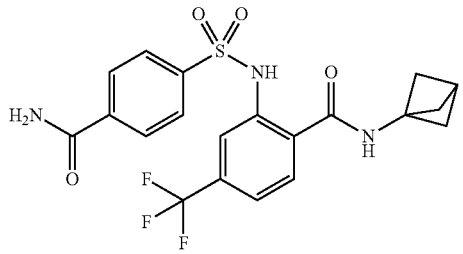 [SMILES: NC(=O)c1ccc(S(=O)(=O)Nc2cc(C(F)(F)F)ccc2C(=O)NC23CC(C2)C3)cc1]

Example 52: Preparation of N-(bicyclo[1.1.1]pentan-1-yl)-2-((4-carbamoylphenyl)sulfonamido)-4-(trifluoromethyl)benzamide Following General Synthesis 1, using 4-carbamoylbenzenesulfonyl chloride (2.5 equiv.) in Step 1 for 72 hours at 50° C., then bicyclo[1.1.1]pentan-1-amine hydrochloride in Step 3, 2-((4-carbamoylphenyl)sulfonamido)-N-(3-phenylbicyclo[1.1.1]pentan-1-yl)-4-(trifluoromethyl)benzamide was synthesized and purified by crystallization. $^1$H NMR (400 MHz, DMSO-d$_6$) δ 11.53 (s, 1H), 9.41 (s, 1H), 8.14 (s, 1H), 7.99 (d, J=8.5 Hz, 2H), 7.86 (d, J=8.3 Hz, 1H), 7.77 (d, J=8.5 Hz, 2H), 7.71 (d, J=1.7 Hz, 1H), 7.66-7.51 (m, 2H), 2.49 (s, 1H, partially visible under DMSO peak), 2.07 (s, 6H). LCMS-ESI$^+$ (m/z): [M+H]$^+$ calcd 454.10; found 454.04.

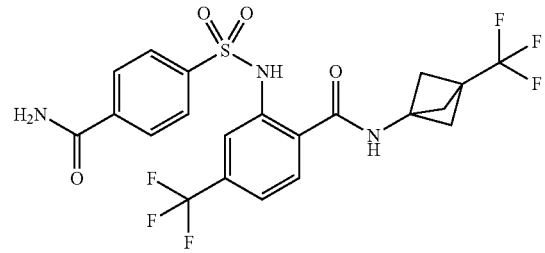 [SMILES: NC(=O)c1ccc(S(=O)(=O)Nc2cc(C(F)(F)F)ccc2C(=O)NC23CC(C(F)(F)F)(C2)C3)cc1]

Example 53: Preparation of 2-((4-carbamoylphenyl)sulfonamido)-4-(trifluoromethyl)-N-(3-(trifluoromethyl)bicyclo[1.1.1]pentan-1-yl)benzamide Following General Synthesis 1, using 4-carbamoylbenzenesulfonyl chloride (2.5 equiv.) in Step 1 for 72 hours at 50° C., then 3-(trifluoromethyl)bicyclo[1.1.1]pentan-1-amine hydrochloride in Step 3, 2-((4-carbamoylphenyl)sulfonamido)-N-(3-phenylbicyclo[1.1.1]pentan-1-yl)-4-(trifluoromethyl)benzamide was synthesized and purified by crystallization. $^1$H NMR (400 MHz, DMSO-d$_6$) δ 11.24 (s, 1H), 9.61 (s, 1H), 8.15 (s, 1H), 7.99 (d, J=8.5 Hz, 2H), 7.85 (d, J=8.3 Hz, 1H), 7.77 (d, J=8.5 Hz, 2H), 7.70 (s, 1H), 7.66-7.56 (m, 2H), 2.31 (s, 6H). LCMS-ESI$^+$ (m/z): [M+H]$^+$ calcd 522.09; found 521.95.

General Synthesis 2

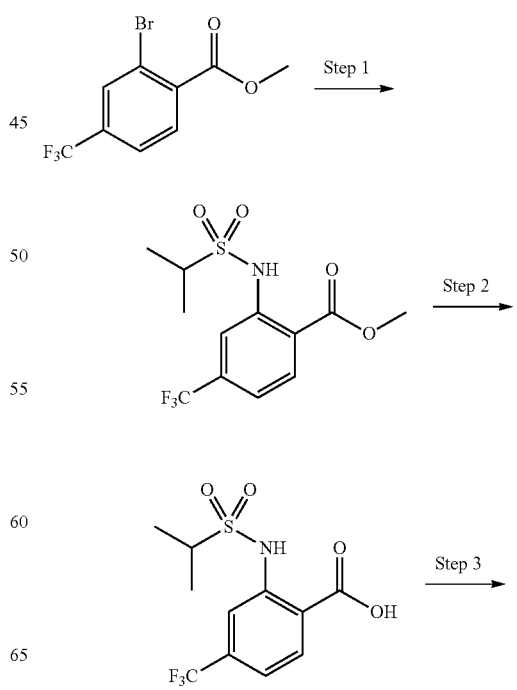

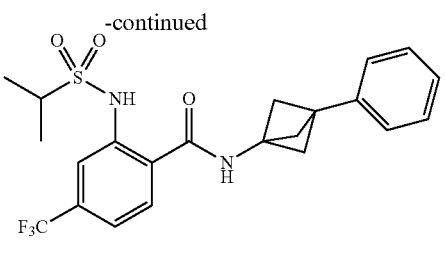

Example 54: Preparation of 2-((1-methylethyl)sulfonamido)-N-(3-phenylbicyclo[1.1.1]pentan-1-yl)-4-(trifluoromethyl)benzamide

Step 1

A 20 mL μwave vial was charged with methyl 2-bromo-4-(trifluoromethyl)benzoate (306 mg, 1.08 mmol), propane-2-sulfonamide (266 mg, 2.16 mmol), tris(dibenzylideneacetone)dipalladium (0)-chloroform adduct (112 mg, 0.108 mmol), 4,5-bis(diphenylphosphino)-9,9-dimethylxanthene (188 mg, 0.324 mmol), potassium phosphate tribasic (1.15 g, 5.41 mmol) and toluene (10.0 mL). The vial was sealed, purged with nitrogen for 5 min, and then heated at 100° C. for 18 hours. The reaction was cooled to room temperature, concentrated and diluted with water. The mixture was extracted with EtOAc (3×), washed with brine, dried over MgSO$_4$, filtered and concentrated. The crude product was purified by silica gel chromatography to afford methyl 2-((1-methylethyl)sulfonamido)-4-(trifluoromethyl)benzoate. LCMS-ESI$^+$ (m/z): [M+H]$^+$ calcd 326.07; found 326.00.

Step 2

To a solution of methyl 2-((1-methylethyl)sulfonamido)-4-(trifluoromethyl)benzoate (304 mg, 0.935 mmol) in THF/MeOH/water (1:1:1, 30.0 mL) was added lithium hydroxide monohydrate (196 mg, 4.67 mmol). The mixture was stirred at room temperature for 18 hours. The reaction was quenched with 1N HCl and concentrated. The crude product was diluted with water and was extracted with EtOAc (3×). The combined organic layers were washed with brine, dried over MgSO$_4$, filtered and concentrated to afford 2-((1-methylethyl)sulfonamido)-4-(trifluoromethyl)benzoic acid as a solid, which was used without further purification.

Step 3

A mixture of 2-((1-methylethyl)sulfonamido)-4-(trifluoromethyl)benzoic acid (45.0 mg, 0.145 mmol), 3-phenylbicyclo[1.1.1]pentan-1-amine hydrochloride (34.0 mg, 0.173 mmol), EDCI (33.7 mg, 0.217 mmol) and HOBT (29.3 mg, 0.217 mmol) in DMF (1.50 mL) was stirred for 5 minutes. N,N-Diisopropylethylamine (126 μL, 0.723 mmol) was added and the solution was stirred at room temperature for 1 hour. The solution was concentrated and the crude product was purified by crystallization to afford 2-((1-methylethyl)sulfonamido)-N-(3-phenylbicyclo[1.1.1]pentan-1-yl)-4-(trifluoromethyl)benzamide. $^1$H NMR (400 MHz, DMSO-d$_6$) δ 11.21 (s, 1H), 9.72 (s, 1H), 8.05 (d, J=8.2 Hz, 1H), 7.89 (s, 1H), 7.57 (d, J=8.1 Hz, 1H), 7.38-7.19 (m, 5H), 3.51-3.38 (m, 1H), 2.39 (s, 6H), 1.26 (d, J=6.8 Hz, 6H). LCMS-ESI$^+$ (m/z): [M+H]$^+$ calcd 453.15; found 453.00.

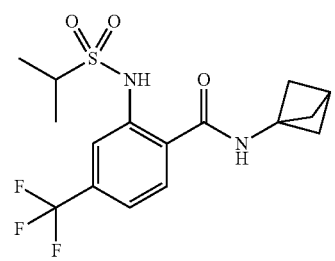 [SMILES: CC(C)S(=O)(=O)Nc1cc(C(F)(F)F)ccc1C(=O)NC12CC(C1)C2]

Example 55: Preparation of N-(bicyclo[1.1.1]pentan-1-yl)-2-((1-methylethyl)sulfonamido)-4-(trifluoromethyl)benzamide Following General Synthesis 2, using bicyclo[1.1.1]pentan-1-amine hydrochloride in Step 3, N-(bicyclo[1.1.1]pentan-1-yl)-2-((1-methylethyl)sulfonamido)-4-(trifluoromethyl)benzamide was synthesized and purified by reverse phase chromatography. $^1$H NMR (400 MHz, DMSO-d$_6$) δ 11.18 (s, 1H), 9.60 (s, 1H), 7.99 (d, J=8.3 Hz, 1H), 7.87 (s, 1H), 7.54 (dd, J=8.0, 1.7 Hz, 1H), 3.48-3.36 (m, 1H), 2.12 (s, 6H), 2.50 (s, 1H, partially visible under DMSO peak) 1.24 (d, J=6.8 Hz, 6H). LCMS-ESI$^+$ (m/z): [M+H]$^+$ calcd 377.11; found 376.94.

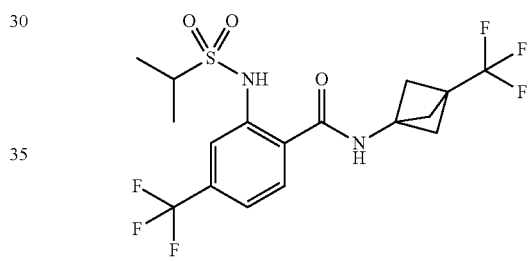

Example 56: Preparation of 2-((1-methylethyl)sulfonamido)-4-(trifluoromethyl)-N-(3-(trifluoromethyl)bicyclo[1.1.1]pentan-1-yl)benzamide Following General Synthesis 2, using 3-(trifluoromethyl)bicyclo[1.1.1]pentan-1-amine hydrochloride in Step 3, 2-((1-methylethyl)sulfonamido)-4-(trifluoromethyl)-N-(3-(trifluoromethyl)bicyclo[1.1.1]pentan-1-yl)benzamide was synthesized and purified by crystallization. $^1$H NMR (400 MHz, DMSO-d$_6$) δ 11.00 (s, 1H), 9.81 (s, 1H), 8.00 (d, J=8.3 Hz, 1H), 7.88 (s, 1H), 7.57 (d, J=9.3 Hz, 1H), 3.45 (hept, J=6.8 Hz, 1H), 2.37 (s, 6H), 1.25 (d, J=6.8 Hz, 6H). LCMS-ESI$^+$ (m/z): [M+H]$^+$ calcd 445.10; found 444.90.

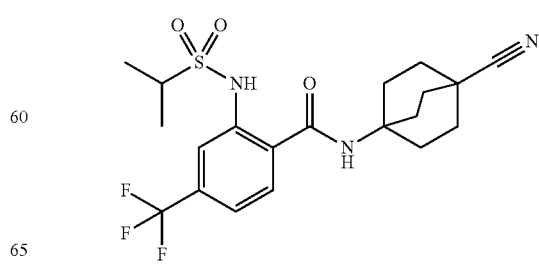

Example 57: Preparation of N-(4-cyanobicyclo[2.2.2]octan-1-yl)-2-((1-methylethyl)sulfonamido)-4-(trifluoromethyl)benzamide Following General Synthesis 2, using 4-aminobicyclo[2.2.2]octane-1-carbonitrile hydrochloride in Step 3, N-(4-cyanobicyclo[2.2.2]octan-1-yl)-2-((1-methylethyl)sulfonamido)-4-(trifluoromethyl)benzamide was synthesized and purified by crystallization. $^1$H NMR (400 MHz, DMSO-d$_6$) δ 10.49 (s, 1H), 8.40 (s, 1H), 7.90 (d, J=8.2 Hz, 1H), 7.84 (s, 1H), 7.55 (d, J=8.2 Hz, 1H), 3.46-3.34 (m, 1H), 2.00 (s, 12H), 1.24 (d, J=6.7 Hz, 6H). LCMS-ESI$^+$ (m/z): [M+H]$^+$ calcd 444.16; found 444.10.

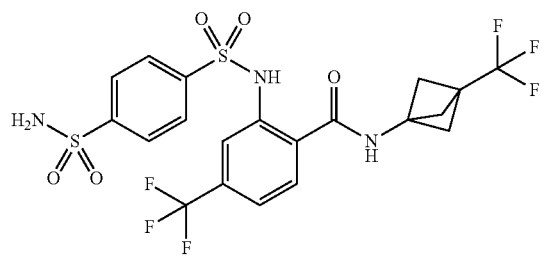 [SMILES: NS(=O)(=O)c1ccc(S(=O)(=O)Nc2cc(C(F)(F)F)ccc2C(=O)NC23CC(C(F)(F)F)(C2)C3)cc1]

Example 58: Preparation of 2-((4-sulfamoylphenyl)sulfonamido)-4-(trifluoromethyl)-N-(3-(trifluoromethyl)bicyclo[1.1.1]pentan-1-yl)benzamide Following General Synthesis 1, using 4-sulfamoylbenzenesulfonyl chloride (1.5 equiv.) in Step 1 for 24 hours at 50° C., then 3-(trifluoromethyl)bicyclo[1.1.1]pentan-1-amine hydrochloride in Step 3, 2-((4-sulfamoylphenyl)sulfonamido)-4-(trifluoromethyl)-N-(3-(trifluoromethyl)bicyclo[1.1.1]pentan-1-yl)benzamide was synthesized and purified by reverse phase chromatography. $^1$H NMR (400 MHz, DMSO-d$_6$) δ 11.37 (s, 1H), 9.64 (s, 1H), 8.02-7.83 (m, 5H), 7.69 (s, 1H), 7.66-7.57 (m, 3H), 2.32 (s, 6H). LCMS-ESI$^+$ (m/z): [M+H]$^+$ calcd 558.06; found 557.95.

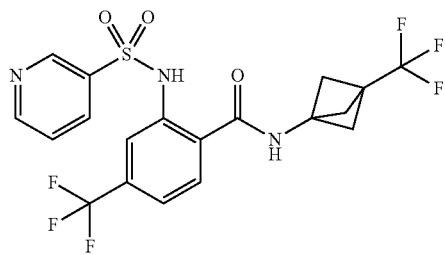 [SMILES: O=C(NC12CC(C(F)(F)F)(C1)C2)c1ccc(C(F)(F)F)cc1NS(=O)(=O)c1cccnc1]

Example 59: Preparation of 2-(pyridine-3-sulfonamido)-4-(trifluoromethyl)-N-(3-(trifluoromethyl)bicyclo[1.1.1]pentan-1-yl)benzamide Following General Synthesis 2, using pyridine-3-sulfonamide in Step 1, then 3-(trifluoromethyl)bicyclo[1.1.1]pentan-1-amine hydrochloride in Step 3, 2-(pyridine-3-sulfonamido)-4-(trifluoromethyl)-N-(3-(trifluoromethyl)bicyclo[1.1.1]pentan-1-yl)benzamide was synthesized and purified by crystallization. $^1$H NMR (400 MHz, DMSO-d$_6$) δ 11.22 (s, 1H), 9.59 (s, 1H), 8.88-8.76 (m, 2H), 8.11 (ddd, J=8.1, 2.5, 1.6 Hz, 1H), 7.85 (d, J=8.2 Hz, 1H), 7.73-7.51 (m, 3H), 2.31 (s, 6H). LCMS-ESI$^+$ (m/z): [M+H]$^+$ calcd 480.08; found 480.09.

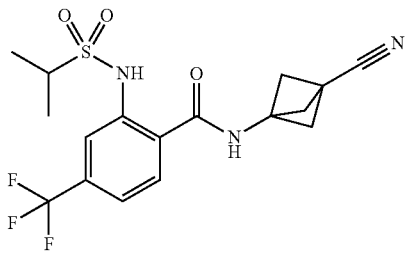 [SMILES: CC(C)S(=O)(=O)Nc1cc(C(F)(F)F)ccc1C(=O)NC12CC(C#N)(C1)C2]

Example 60: Preparation of N-(3-cyanobicyclo[1.1.1]pentan-1-yl)-2-((1-methylethyl)sulfonamido)-4-(trifluoromethyl)benzamide Following General Synthesis 2, using 3-aminobicyclo[1.1.1]pentane-1-carbonitrile in Step 3, N-(3-cyanobicyclo[1.1.1]pentan-1-yl)-2-((1-methylethyl)sulfonamido)-4-(trifluoromethyl)benzamide was synthesized and purified by reverse phase chromatography. $^1$H NMR (400 MHz, DMSO-d$_6$) δ 10.95 (s, 1H), 9.78 (s, 1H), 7.96 (d, J=8.3 Hz, 1H), 7.87 (s, 1H), 7.56 (d, J=8.0 Hz, 1H), 3.46 (hept, J=6.7 Hz, 1H), 2.61 (s, 6H), 1.24 (d, J=6.8 Hz, 6H). LCMS-ESI$^+$ (m/z): [M+H]$^+$ calcd 402.11; found 402.01.

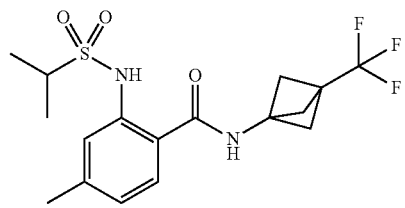 [SMILES: Cc1ccc(C(=O)NC23CC(C(F)(F)F)(C2)C3)c(NS(=O)(=O)C(C)C)c1]

Example 61: Preparation of 4-methyl-2-((1-methylethyl)sulfonamido)-N-(3-(trifluoromethyl)bicyclo[1.1.1]pentan-1-yl)benzamide Following Step 3 of General Synthesis 1, using 2-bromo-4-methylbenzoic acid and 3-(trifluoromethyl)bicyclo[1.1.1]pentan-1-amine hydrochloride, then using propane-2-sulfonamide (1.5 eq) in General Synthesis 8, 4-methyl-2-((1-methylethyl)sulfonamido)-N-(3-(trifluoromethyl)bicyclo[1.1.1]pentan-1-yl)benzamide was synthesized and purified by reverse phase chromatography. $^1$H NMR (400 MHz, DMSO-d$_6$) δ 11.19 (s, 1H), 9.52 (s, 1H), 7.73 (d, J=8.2 Hz, 1H), 7.42 (s, 1H), 6.99 (d, J=8.2 Hz, 1H), 3.46-3.30 (m, 1H), 2.37-2.32 (m, J=4.2 Hz, 9H), 1.23 (d, J=6.8 Hz, 6H). LCMS-ESI$^+$ (m/z): [M+H]$^+$ calcd 391.13; found 391.06.

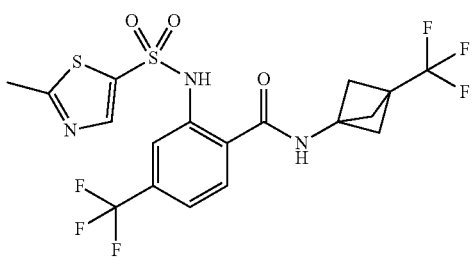 [SMILES: Cc1ncc(S(=O)(=O)Nc2cc(C(F)(F)F)ccc2C(=O)NC23CC(C(F)(F)F)(C2)C3)s1]

Example 62: Preparation of 2-((2-methylthiazole)-5-sulfonamido)-4-(trifluoromethyl)-N-(3-(trifluoromethyl)bicyclo[1.1.1]pentan-1-yl)benzamide Following General Synthesis 2, using 2-methylthiazole-5-sulfonamide in Step 1, then 3-(trifluoromethyl)bicyclo[1.1.1]pentan-1-amine hydrochloride in Step 3, 2-((2-methylthiazole)-5-sulfonamido)-4-(trifluoromethyl)-N-(3-(trifluoromethyl)bicyclo[1.1.1]pentan-1-yl)benzamide was synthesized and purified by reverse phase chromatography. $^1$H NMR (400 MHz, DMSO-d$_6$) δ 11.38 (s, 1H), 9.70 (s, 1H), 8.08 (s, 1H), 7.92 (d, J=8.2 Hz, 1H), 7.74 (s, 1H), 7.71-7.61 (m, 1H), 2.68 (s, 3H), 2.34 (s, 6H). LCMS-ESI$^+$ (m/z): [M+H]$^+$ calcd 500.05; found 500.07.

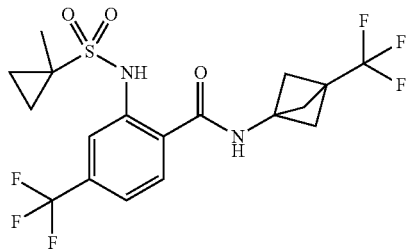 [SMILES: CC1(S(=O)(=O)Nc2cc(C(F)(F)F)ccc2C(=O)NC23CC(C(F)(F)F)(C2)C3)CC1]

Example 63: Preparation of 2-((1-methylcyclopropane)-1-sulfonamido)-4-(trifluoromethyl)-N-(3-(trifluoromethyl)bicyclo[1.1.1]pentan-1-yl)benzamide Following General Synthesis 2, using 1-methylcyclopropane-1-sulfonamide in Step 1, then 3-(trifluoromethyl)bicyclo[1.1.1]pentan-1-amine hydrochloride in Step 3, 2-((1-methylcyclopropane)-1-sulfonamido)-4-(trifluoromethyl)-N-(3-(trifluoromethyl)bicyclo[1.1.1]pentan-1-yl)benzamide was synthesized and purified by crystallization. $^1$H NMR (400 MHz, DMSO-d$_6$) δ 10.97 (s, 1H), 9.85 (s, 1H), 8.00 (d, J=8.3 Hz, 1H), 7.86 (s, 1H), 7.62 (d, J=8.2 Hz, 1H), 2.38 (s, 6H), 1.35 (s, 3H), 1.17-1.08 (m, 2H), 0.87 (t, J=3.2 Hz, 2H). LCMS-ESI$^+$ (m/z): [M+H]$^+$ calcd 457.10; found 457.07.

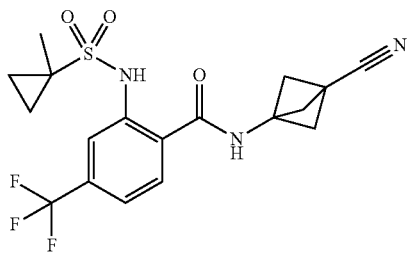 [SMILES: CC1(S(=O)(=O)Nc2cc(C(F)(F)F)ccc2C(=O)NC23CC(C#N)(C2)C3)CC1]

Example 64: Preparation of N-(3-cyanobicyclo[1.1.1]pentan-1-yl)-2-((1-methylcyclopropane)-1-sulfonamido)-4-(trifluoromethyl)benzamide Following General Synthesis 2, using 1-methylcyclopropane-1-sulfonamide in Step 1, then 3-aminobicyclo[1.1.1]pentane-1-carbonitrile in Step 3, N-(3-cyanobicyclo[1.1.1]pentan-1-yl)-2-((1-methylcyclopropane)-1-sulfonamido)-4-(trifluoromethyl)benzamide was synthesized and purified by crystallization. $^1$H NMR (400 MHz, DMSO-d$_6$) δ 10.92 (s, 1H), 9.82 (s, 1H), 7.96 (d, J=8.3 Hz, 1H), 7.84 (s, 1H), 7.61 (d, J=8.1 Hz, 1H), 2.61 (s, 6H), 1.34 (s, 3H), 1.18-1.08 (m, 2H), 0.92-0.81 (m, 2H). LCMS-ESI$^+$ (m/z): [M+H]$^+$ calcd 414.11; found 414.05.

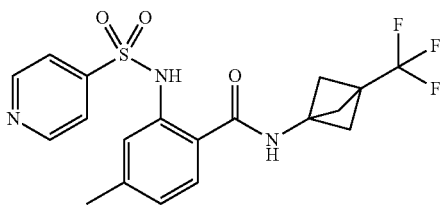 [SMILES: Cc1ccc(C(=O)NC23CC(C(F)(F)F)(C2)C3)c(NS(=O)(=O)c2ccncc2)c1]

Example 65: Preparation of 4-methyl-2-(pyridine-4-sulfonamido)-N-(3-(trifluoromethyl)bicyclo[1.1.1]pentan-1-yl)benzamide Following Step 3 of General Synthesis 1, using 2-bromo-4-methylbenzoic acid and 3-(trifluoromethyl)bicyclo[1.1.1]pentan-1-amine hydrochloride, then pyridine-4-sulfonamide (1.5 eq) in General Synthesis 8, 4-methyl-2-(pyridine-4-sulfonamido)-N-(3-(trifluoromethyl)bicyclo[1.1.1]pentan-1-yl)benzamide was synthesized and purified by reverse phase chromatography. $^1$H NMR (400 MHz, DMSO-d$_6$) δ 11.65 (s, 1H), 9.39 (s, 1H), 8.86-8.75 (m, 2H), 7.69-7.62 (m, 2H), 7.59 (d, J=8.1 Hz, 1H), 7.30 (s, 1H), 7.05-7.00 (m, 1H), 2.34-2.29 (m, 9H). LCMS-ESI$^+$ (m/z): [M+H]$^+$ calcd 426.11; found 426.11.

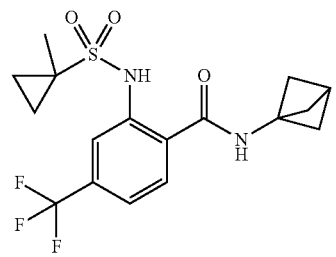 [SMILES: CC1(S(=O)(=O)Nc2cc(C(F)(F)F)ccc2C(=O)NC23CC(C2)C3)CC1]

Example 66: Preparation of N-(bicyclo[1.1.1]pentan-1-yl)-2-((1-methylcyclopropane)-1-sulfonamido)-4-(trifluoromethyl)benzamide Following General Synthesis 2, using 1-methylcyclopropane-1-sulfonamide in Step 1, then bicyclo[1.1.1]pentan-1-amine hydrochloride in Step 3, N-(bicyclo[1.1.1]pentan-1-yl)-2-((1-methylcyclopropane)-1-sulfonamido)-4-(trifluoromethyl)benzamide was synthesized and purified by crystallization. $^1$H NMR (400 MHz, DMSO-d$_6$) δ 11.13 (s, 1H), 9.64 (s, 1H), 7.99 (d, J=8.3 Hz, 1H), 7.85 (s, 1H), 7.59

(d, J=8.3 Hz, 1H), 2.13 (s, 6H), 1.34 (s, 3H), 1.19-1.04 (m, 2H), 0.92-0.77 (m, 2H). LCMS-ESI⁺ (m/z): [M+H]⁺ calcd 389.11; found 389.07.

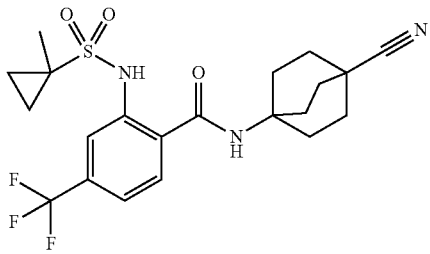 [SMILES: CC1(S(=O)(=O)Nc2cc(C(F)(F)F)ccc2C(=O)NC23CCC(C#N)(CC2)CC3)CC1]

Example 67: Preparation of N-(4-cyanobicyclo[2.2.2]octan-1-yl)-2-((1-methylcyclopropane)-1-sulfonamido)-4-(trifluoromethyl)benzamide Following General Synthesis 2, using 1-methylcyclopropane-1-sulfonamide in Step 1, then 4-aminobicyclo[2.2.2]octane-1-carbonitrile hydrochloride in Step 3, N-(4-cyanobicyclo[2.2.2]octan-1-yl)-2-((1-methylcyclopropane)-1-sulfonamido)-4-(trifluoromethyl)benzamide was synthesized and purified by reverse phase chromatography. ¹H NMR (400 MHz, DMSO-d₆) δ 10.54 (s, 1H), 8.45 (s, 1H), 7.91 (d, J=8.2 Hz, 1H), 7.82 (d, J=1.7 Hz, 1H), 7.64-7.53 (m, 1H), 2.01 (s, 12H), 1.34 (s, 3H), 1.16-1.06 (m, 2H), 0.90-0.76 (m, 2H). LCMS-ESI⁺ (m/z): [M+H]⁺ calcd 456.16; found 456.18.

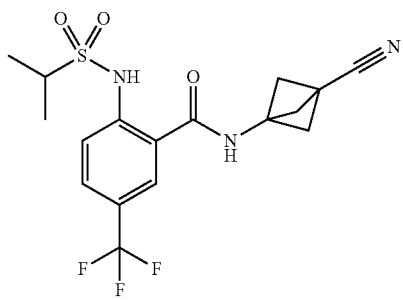 [SMILES: CC(C)S(=O)(=O)Nc1ccc(C(F)(F)F)cc1C(=O)NC12CC(C#N)(C1)C2]

Example 68: Preparation of N-(3-cyanobicyclo[1.1.1]pentan-1-yl)-2-((1-methylethyl)sulfonamido)-5-(trifluoromethyl)benzamide Following General Synthesis 2, using methyl 2-bromo-5-(trifluoromethyl)benzoate in Step 1, then 3-aminobicyclo[1.1.1]pentane-1-carbonitrile in Step 3, N-(3-cyanobicyclo[1.1.1]pentan-1-yl)-2-((1-methylethyl)sulfonamido)-5-(trifluoromethyl)benzamide was synthesized and purified by reverse phase chromatography. ¹H NMR (400 MHz, DMSO-d₆) δ 11.39 (s, 1H), 9.83 (s, 1H), 8.18 (s, 1H), 7.89 (dd, J=8.8, 1.9 Hz, 1H), 7.79 (d, J=8.8 Hz, 1H), 3.50 (hept, J=7.0 Hz, 1H), 2.62 (s, 6H), 1.26 (d, J=6.8 Hz, 6H). LCMS-ESI⁺ (m/z): [M+H]⁺ calcd 402.11; found 401.99.

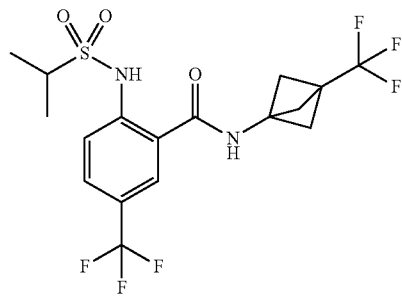 [SMILES: CC(C)S(=O)(=O)Nc1ccc(C(F)(F)F)cc1C(=O)NC12CC(C(F)(F)F)(C1)C2]

Example 69: Preparation of 2-((1-methylethyl)sulfonamido)-5-(trifluoromethyl)-N-(3-(trifluoromethyl)bicyclo[1.1.1]pentan-1-yl)benzamide Following General Synthesis 2, using methyl 2-bromo-5-(trifluoromethyl)benzoate in Step 1, then 3-(trifluoromethyl)bicyclo[1.1.1]pentan-1-amine hydrochloride in Step 3, 2-((1-methylethyl)sulfonamido)-5-(trifluoromethyl)-N-(3-(trifluoromethyl)bicyclo[1.1.1]pentan-1-yl)benzamide was synthesized and purified by crystallization. ¹H NMR (400 MHz, DMSO-d₆) δ 11.45 (s, 1H), 9.85 (s, 1H), 8.22 (s, 1H), 7.90 (dd, J=8.9, 2.0 Hz, 1H), 7.80 (d, J=8.8 Hz, 1H), 3.50 (hept, J=6.6 Hz, 1H), 2.38 (s, 6H), 1.26 (d, J=6.8 Hz, 6H). LCMS-ESI⁺ (m/z): [M+H]⁺ calcd 445.10; found 445.00.

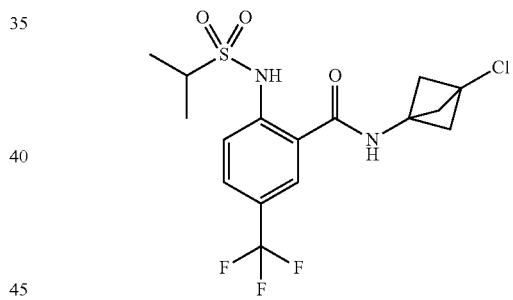

Example 70: Preparation of N-(3-chlorobicyclo[1.1.1]pentan-1-yl)-2-((1-methylethyl)sulfonamido)-5-(trifluoromethyl)benzamide Following General Synthesis 2, using methyl 2-bromo-5-(trifluoromethyl)benzoate in Step 1, then 3-chlorobicyclo[1.1.1]pentan-1-amine hydrochloride in Step 3, N-(3-chlorobicyclo[1.1.1]pentan-1-yl)-2-((1-methylethyl)sulfonamido)-5-(trifluoromethyl)benzamide was synthesized and purified by reverse phase chromatography. ¹H NMR (400 MHz, DMSO-d₆) δ 11.42 (s, 1H), 9.81 (s, 1H), 8.20 (d, J=1.0 Hz, 1H), 7.89 (dd, J=8.8, 1.4 Hz, 1H), 7.79 (d, J=8.8 Hz, 1H), 3.50 (hept, J=6.7 Hz, 1H), 2.52 (s, 6H), 1.26 (d, J=6.8 Hz, 6H). LCMS-ESI⁺ (m/z): [M+H]⁺ calcd 411.08; found 411.05.

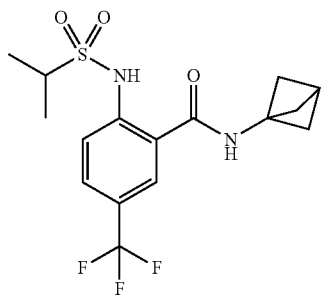 [SMILES: CC(C)S(=O)(=O)Nc1ccc(C(F)(F)F)cc1C(=O)NC12CC(C1)C2]

Example 71: Preparation of N-(bicyclo[1.1.1]pentan-1-yl)-2-((1-methylethyl)sulfonamido)-5-(trifluoromethyl)benzamide Following General Synthesis 2, using methyl 2-bromo-5-(trifluoromethyl)benzoate in Step 1, then bicyclo[1.1.1]pentan-1-amine hydrochloride in Step 3, N-(bicyclo[1.1.1]pentan-1-yl)-2-((1-methylethyl)sulfonamido)-5-(trifluoromethyl)benzamide was synthesized and purified by reverse phase chromatography. $^1$H NMR (400 MHz, DMSO-d$_6$) δ 11.65 (s, 1H), 9.65 (s, 1H), 8.21 (s, 1H), 7.87 (dd, J=8.9, 2.0 Hz, 1H), 7.79 (d, J=8.8 Hz, 1H), 3.48 (hept, J=7.0 Hz, 1H), 2.51 (beneath DMSO peak, 1H), 2.13 (s, 6H), 1.25 (d, J=6.8 Hz, 6H). LCMS-ESI$^+$ (m/z): [M+H]$^+$ calcd 377.11; found 377.04.

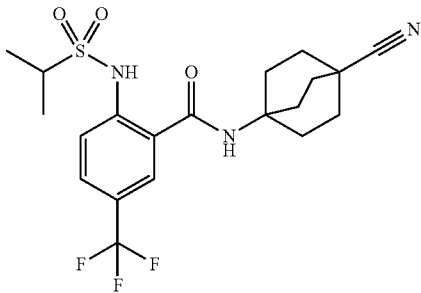 [SMILES: CC(C)S(=O)(=O)Nc1ccc(C(F)(F)F)cc1C(=O)NC12CCC(C#N)(CC1)CC2]

Example 72: Preparation of N-(4-cyanobicyclo[2.2.2]octan-1-yl)-2-((1-methylethyl)sulfonamido)-5-(trifluoromethyl)benzamide Following General Synthesis 2, using methyl 2-bromo-5-(trifluoromethyl)benzoate in Step 1, then 4-aminobicyclo[2.2.2]octane-1-carbonitrile hydrochloride in Step 3, N-(4-cyanobicyclo[2.2.2]octan-1-yl)-2-((1-methylethyl)sulfonamido)-5-(trifluoromethyl)benzamide was synthesized and purified by reverse phase chromatography. $^1$H NMR (400 MHz, DMSO-d$_6$) δ 10.92 (s, 1H), 8.47 (s, 1H), 8.07 (s, 1H), 7.85 (d, J=8.9 Hz, 1H), 7.77 (d, J=8.7 Hz, 1H), 3.50-3.39 (m, 1H), 2.01 (s, 12H), 1.24 (d, J=6.8 Hz, 6H). LCMS-ESI$^+$ (m/z): [M+H]$^+$ calcd 444.16; found 444.09.

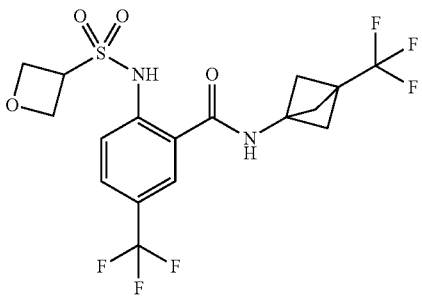 [SMILES: O=C(NC12CC(C(F)(F)F)(C1)C2)c1cc(C(F)(F)F)ccc1NS(=O)(=O)C1COC1]

Example 73: Preparation of 2-(oxetane-3-sulfonamido)-5-(trifluoromethyl)-N-(3-(trifluoromethyl)bicyclo[1.1.1]pentan-1-yl)benzamide Following General Synthesis 2, using methyl 2-bromo-5-(trifluoromethyl)benzoate and oxetane-3-sulfonamide in Step 1, then 3-(trifluoromethyl)bicyclo[1.1.1]pentan-1-amine hydrochloride in Step 3, 2-(oxetane-3-sulfonamido)-5-(trifluoromethyl)-N-(3-(trifluoromethyl)bicyclo[1.1.1]pentan-1-yl)benzamide was synthesized and purified by crystallization. $^1$H NMR (400 MHz, DMSO-d$_6$) δ 11.53 (s, 1H), 9.79 (s, 1H), 8.17 (d, J=0.9 Hz, 1H), 7.90 (d, J=8.5 Hz, 1H), 7.73 (d, J=8.7 Hz, 1H), 4.99-4.85 (m, 1H), 4.80 (t, J=7.5 Hz, 2H), 4.66 (dd, J=7.3, 5.8 Hz, 2H), 2.37 (s, 6H). LCMS-ESI$^+$ (m/z): [M+H]$^+$ calcd 459.08; found 459.19.

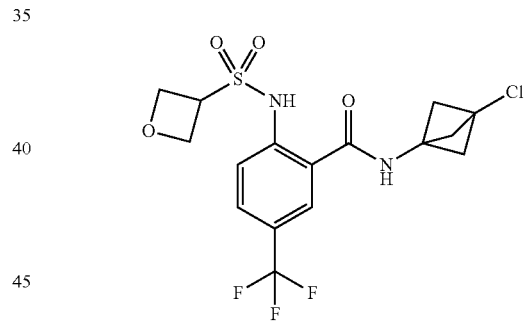

Example 74: Preparation of N-(3-chlorobicyclo[1.1.1]pentan-1-yl)-2-(oxetane-3-sulfonamido)-5-(trifluoromethyl)benzamide Following General Synthesis 2, using methyl 2-bromo-5-(trifluoromethyl)benzoate and oxetane-3-sulfonamide in Step 1, then 3-chlorobicyclo[1.1.1]pentan-1-amine hydrochloride in Step 3, N-(3-chlorobicyclo[1.1.1]pentan-1-yl)-2-(oxetane-3-sulfonamido)-5-(trifluoromethyl)benzamide was synthesized and purified by crystallization. $^1$H NMR (400 MHz, DMSO-d$_6$) δ 11.51 (s, 1H), 9.75 (s, 1H), 8.16 (d, J=1 Hz, 1H), 7.89 (d, J=8.4 Hz, 1H), 7.72 (d, J=8.7 Hz, 1H), 4.95-4.85 (m, 1H), 4.80 (t, J=7.5 Hz, 2H), 4.65 (t, J=6.5 Hz, 2H), 2.51 (s, 6H). LCMS-ESI$^+$ (m/z): [M+H]$^+$ calcd 425.05; found 425.18.

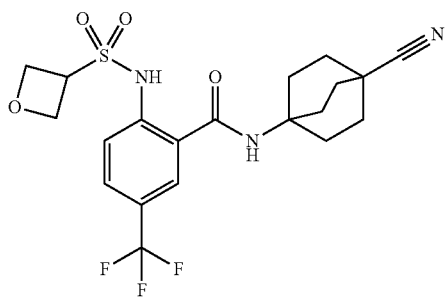 [SMILES: N#CC12CCC(NC(=O)c3cc(C(F)(F)F)ccc3NS(=O)(=O)C3COC3)(CC1)CC2]

Example 75: Preparation of N-(4-cyanobicyclo [2.2.2]octan-1-yl)-2-(oxetane-3-sulfonamido)-5-(trifluoromethyl)benzamide Following General Synthesis 2, using methyl 2-bromo-5-(trifluoromethyl)benzoate and oxetane-3-sulfonamide in Step 1, then 4-aminobicyclo[2.2.2]octane-1-carbonitrile hydrochloride in Step 3, N-(4-cyanobicyclo[2.2.2]octan-1-yl)-2-(oxetane-3-sulfonamido)-5-(trifluoromethyl)benzamide was synthesized and purified by crystallization. $^1$H NMR (400 MHz, DMSO-$d_6$) δ 11.03 (s, 1H), 8.39 (s, 1H), 8.02 (d, J=1.1 Hz, 1H), 7.85 (d, J=8.4 Hz, 1H), 7.68 (d, J=8.7 Hz, 1H), 4.89-4.72 (m, 3H), 4.68-4.57 (m, 2H), 2.00 (s, 12H). LCMS-ESI$^+$ (m/z): [M+H]$^+$ calcd 458.24; found 458.14.

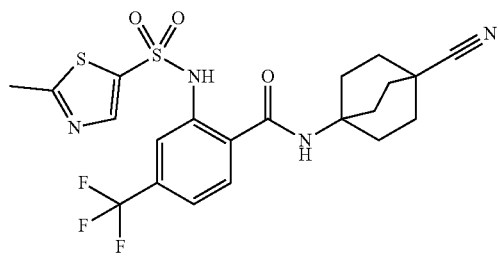 [SMILES: Cc1ncc(S(=O)(=O)Nc2cc(C(F)(F)F)ccc2C(=O)NC23CCC(C#N)(CC2)CC3)s1]

Example 76: Preparation of N-(4-cyanobicyclo [2.2.2]octan-1-yl)-2-((2-methylthiazole)-5-sulfonamido)-4-(trifluoromethyl)benzamide Following General Synthesis 2, using 2-methylthiazole-5-sulfonamide in Step 1, then 4-aminobicyclo[2.2.2]octane-1-carbonitrile hydrochloride in Step 3, N-(4-cyanobicyclo [2.2.2]octan-1-yl)-2-((2-methylthiazole)-5-sulfonamido)-4-(trifluoromethyl)benzamide was synthesized and purified by reverse phase chromatography. $^1$H NMR (400 MHz, DMSO-$d_6$) δ 11.06 (s, 1H), 8.27 (s, 1H), 8.02 (s, 1H), 7.86 (d, J=8.1 Hz, 1H), 7.71-7.51 (m, 2H), 2.68 (s, 3H), 2.06-1.86 (m, 12H). LCMS-ESI$^+$ (m/z): [M+H]$^+$ calcd 499.11; found 499.09.

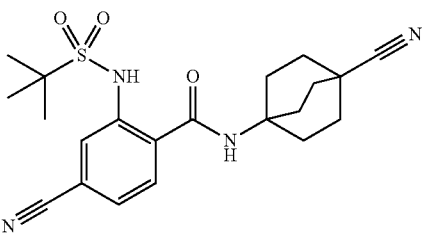 [SMILES: CC(C)(C)S(=O)(=O)Nc1cc(C#N)ccc1C(=O)NC12CCC(C#N)(CC1)CC2]

Example 77: Preparation of 4-cyano-N-(4-cyanobicyclo[2.2.2]octan-1-yl)-2-((1,1-dimethylethyl)sulfonamido)benzamide Following Step 3 of General Synthesis 1, using 2-bromo-4-cyanobenzoic acid and 4-aminobicyclo[2.2.2]octane-1-carbonitrile hydrochloride, then 2-methylpropane-2-sulfonamide (2.0 eq) in General Synthesis 8, 4-cyano-N-(4-cyanobicyclo[2.2.2]octan-1-yl)-2-((1,1-dimethylethyl) sulfonamido)benzamide was synthesized and purified by reverse phase chromatography. $^1$H NMR (400 MHz, DMSO-$d_6$) δ 10.35 (s, 1H), 8.48 (s, 1H), 7.96 (d, J=1.5 Hz, 1H), 7.83 (d, J=8.1 Hz, 1H), 7.65 (d, J=8.2 Hz, 1H), 1.99 (s, 12H), 1.28 (s, 9H). LCMS-ESI$^+$ (m/z): [M+H]$^+$ calcd 415.18; found 414.93.

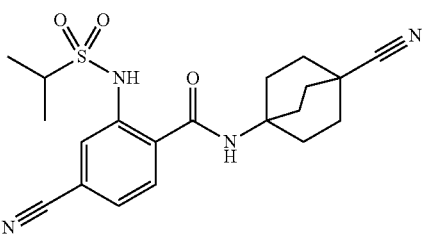 [SMILES: CC(C)S(=O)(=O)Nc1cc(C#N)ccc1C(=O)NC12CCC(C#N)(CC1)CC2]

Example 78: Preparation of 4-cyano-N-(4-cyanobicyclo[2.2.2]octan-1-yl)-2-((1-methylethyl)sulfonamido)benzamide Following Step 3 of General Synthesis 1, using 2-bromo-4-cyanobenzoic acid and 4-aminobicyclo[2.2.2]octane-1-carbonitrile hydrochloride, then propane-2-sulfonamide (2.0 eq) in General Synthesis 8, 4-cyano-N-(4-cyanobicyclo [2.2.2]octan-1-yl)-2-((1-methylethyl)sulfonamido)benzamide was synthesized and purified by reverse phase chromatography. $^1$H NMR (400 MHz, DMSO-$d_6$) δ 10.45 (s, 1H), 8.40 (s, 1H), 7.90-7.81 (m, 2H), 7.66 (dd, J=8.1, 1.6 Hz, 1H), 3.51 (m, 1H), 1.99 (s, 12H), 1.24 (d, J=6.8 Hz, 6H). LCMS-ESI$^+$ (m/z): [M+H]$^+$ calcd 401.16; found 401.09.

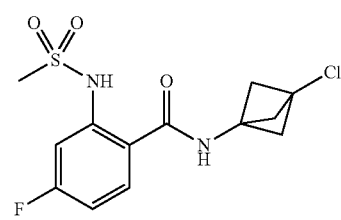 [SMILES: CS(=O)(=O)Nc1cc(F)ccc1C(=O)NC12CC(Cl)(C1)C2]

Example 79: Preparation of N-(3-chlorobicyclo [1.1.1]pentan-1-yl)-4-fluoro-2-(methylsulfonamido) benzamide Following General Synthesis 1, using 3-chlorobicyclo [1.1.1]pentan-1-amine hydrochloride in Step 3, N-(3-chlorobicyclo[1.1.1]pentan-1-yl)-4-fluoro-2-(methylsulfonamido)benzamide was synthesized and purified by crystallization. $^1$H NMR (400 MHz, DMSO-d$_6$) δ 11.45 (s, 1H), 9.51 (s, 1H), 7.91 (dd, J=9.0, 6.3 Hz, 1H), 7.31 (dd, J=11.2, 2.6 Hz, 1H), 7.04 (td, J=8.5, 2.6 Hz, 1H), 3.23 (s, 3H), 2.49 (s, 6H). LCMS-ESI$^+$ (m/z): [M+H]$^+$ calcd 333.05; found 332.91.

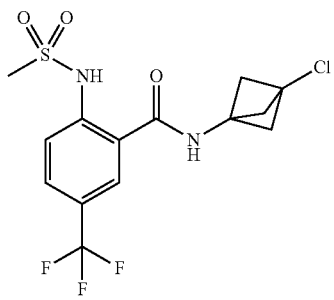 [SMILES: CS(=O)(=O)Nc1ccc(C(F)(F)F)cc1C(=O)NC12CC(Cl)(C1)C2]

Example 80: Preparation of N-(3-chlorobicyclo [1.1.1]pentan-1-yl)-2-(methylsulfonamido)-5-(trifluoromethyl)benzamide Following General Synthesis 2, using methyl 2-bromo-5-(trifluoromethyl)benzoate (1.0 eq) and methanesulfonamide (2.0 eq) in Step 1, then 3-chlorobicyclo[1.1.1]pentan-1-amine hydrochloride in Step 3, N-(3-chlorobicyclo[1.1.1]pentan-1-yl)-2-(methylsulfonamido)-5-(trifluoromethyl)benzamide was synthesized and purified by reverse phase chromatography. $^1$H NMR (400 MHz, DMSO-d$_6$) δ 11.48 (s, 1H), 9.76 (s, 1H), 8.21 (s, 1H), 7.90 (dd, J=8.8, 2.1 Hz, 1H), 7.73 (d, J=8.8 Hz, 1H), 3.26 (s, 3H), 2.52 (s, 6H). LCMS-ESI$^+$ (m/z): [M+H]$^+$ calcd 383.04; found 383.06.

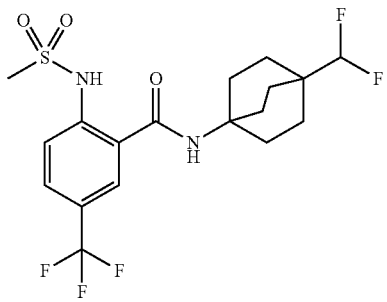 [SMILES: CS(=O)(=O)Nc1ccc(C(F)(F)F)cc1C(=O)NC12CCC(C(F)F)(CC1)CC2]

Example 81: Preparation of N-(4-(difluoromethyl) bicyclo[12.2.2]octan-1-yl)-2-(methylsulfonamido)-5-(trifluoromethyl)benzamide Following General Synthesis 2, using methyl 2-bromo-5-(trifluoromethyl)benzoate (1.0 eq) and methanesulfonamide (2.0 eq) in Step 1, then 4-(difluoromethyl)bicyclo [2.2.2]octan-1-amine hydrochloride in Step 3, N-(4-(difluoromethyl)bicyclo[2.2.2]octan-1-yl)-2-(methylsulfonamido)-5-(trifluoromethyl)benzamide was synthesized and purified by crystallization. $^1$H NMR (400 MHz, DMSO-d$_6$) δ 10.99 (s, 1H), 8.39 (s, 1H), 8.08 (d, J=2.1 Hz, 1H), 7.86 (d, J=8.7 Hz, 1H), 7.68 (d, J=8.7 Hz, 1H), 5.72 (t, J=56.8 Hz, 1H), 3.22 (s, 3H), 2.06-1.93 (m, 6H), 1.67-1.53 (m, 6H). LCMS-ESI$^+$ (m/z): [M+H]$^+$ calcd 441.13; found 441.13.

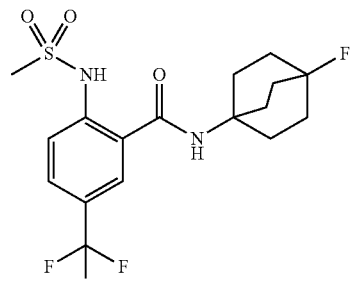

Example 82: Preparation of N-(4-fluorobicyclo [2.2.2]octan-1-yl)-2-(methylsulfonamido)-5-(trifluoromethyl)benzamide Following General Synthesis 2, using methyl 2-bromo-5-(trifluoromethyl)benzoate (1.0 eq) and methanesulfonamide (2.0 eq) in Step 1, then 4-fluorobicyclo[2.2.2]octan-1-amine hydrochloride in Step 3, N-(4-fluorobicyclo[2.2.2] octan-1-yl)-2-(methylsulfonamido)-5-(trifluoromethyl) benzamide was synthesized and purified by crystallization. $^1$H NMR (400 MHz, DMSO-d$_6$) δ 10.94 (s, 1H), 8.38 (s, 1H), 8.07 (s, 1H), 7.86 (d, J=8.8 Hz, 1H), 7.67 (d, J=8.6 Hz, 1H), 3.22 (s, 3H), 2.23-2.09 (m, 6H), 1.94-1.81 (m, 6H). LCMS-ESI$^+$ (m/z): [M+H]$^+$ calcd 409.12; found 409.09.

General Synthesis 3

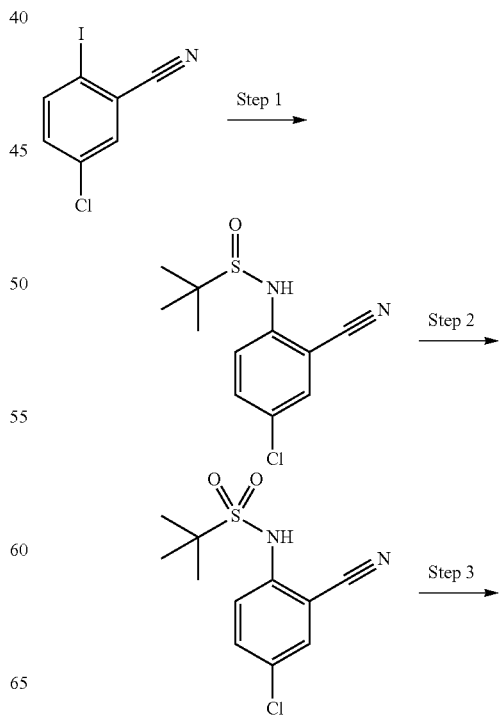

83

-continued

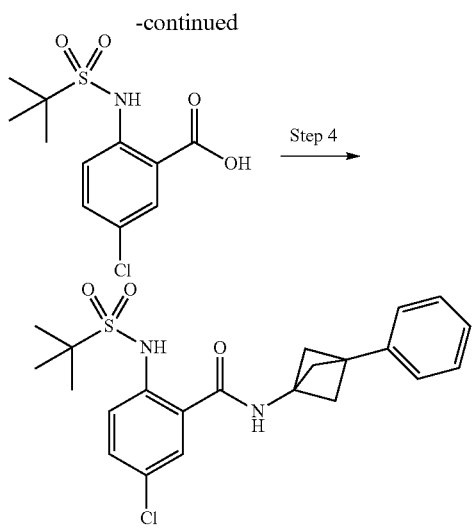

Example 83: Preparation of 5-chloro-2-((1,1-dimethylethyl)sulfonamido)-N-(3-phenylbicyclo[1.1.1]pentan-1-yl)benzamide Step 1

To a mixture of 5-chloro-2-iodobenzonitrile (0.989 g, 3.75 mmol), 2-methylpropane-2-sulfinamide (0.546 g, 4.51 mmol), (9,9-dimethyl-9H-xanthene-4,5-diyl)bis(diphenylphosphane) (0.130 g, 0.225 mmol), cesium carbonate (2.446 g, 7.508 mmol), and palladium(II) acetate (0.025 g, 0.11 mmol) was added 12 mL of 1,4-dioxane. The reaction mixture was stirred at 100° C. for 18 hours and then quenched with water. The aqueous phase was extracted 3× with ethyl acetate. The combined organic layers were washed with saturated aqueous sodium chloride solution and concentrated to a residue. The crude product was purified by silica flash chromatography to afford N-(4-chloro-2-cyanophenyl)-2-methylpropane-2-sulfinamide as a solid. LCMS-ESI$^+$ (m/z): [M+H]$^+$ calcd 257.05; found 256.78.

Step 2

N-(4-chloro-2-cyanophenyl)-2-methylpropane-2-sulfinamide (0.609 g, 2.37 mmol) was treated with a solution of 32% by weight peracetic acid in acetic acid (20.6 g, 271 mmol). The reaction mixture was stirred for 3 hours at room temperature, and then quenched with saturated aqueous sodium bicarbonate solution. The mixture was then extracted 3× with ethyl acetate. The organic phases were combined, washed with saturated aqueous sodium chloride solution, dried over anhydrous magnesium sulfate, filtered, and concentrated to a residue to afford N-(4-chloro-2-cyanophenyl)-2-methylpropane-2-sulfonamide as a solid. LCMS-ESI$^-$ (m/z): [M−H]$^-$ calcd 271.03; found 271.09.

Step 3

N-(4-chloro-2-cyanophenyl)-2-methylpropane-2-sulfonamide (0.575 g, 2.11 mmol) was dissolved in 18 mL of ethanol. 2 mL of water and sodium hydroxide pellets (1.257 g, 31.43 mmol) were added to the solution, which was stirred at 100° C. for 18 hours. The reaction mixture was then acidified with 1 M aqueous hydrochloric acid. The aqueous phase was extracted 3× with ethyl acetate. The

84 organic phases were combined, washed with saturated aqueous sodium chloride solution, dried over anhydrous magnesium sulfate, filtered, and concentrated to a residue to afford 5-chloro-2-((1,1-dimethylethyl)sulfonamido)benzoic acid as a solid. LCMS-ESI$^-$ (m/z): [M−H]$^-$ calcd 290.03; found 290.06.

Step 4

A solution of 5-chloro-2-((1,1-dimethylethyl)sulfonamido)benzoic acid (0.041 g, 0.14 mmol), 3-phenylbicyclo[1.1.1]pentan-1-amine hydrochloride (0.069 g, 0.35 mmol), 1-ethyl-3-(3-dimethylaminopropyl)carbodiimide hydrochloride (0.054 g, 0.35 mmol), and 1-hydroxybenzotriazole hydrate (0.054 g, 0.35 mmol) in 0.5 mL dimethylformamide was treated with diisopropylethylamine (0.129 g, 0.998 mmol). The mixture was stirred for 18 hours at 60° C. The crude product was purified by reverse phase HPLC, affording 5-chloro-2-((1,1-dimethylethyl)sulfonamido)-N-(3-phenylbicyclo[1.1.1]pentan-1-yl)benzamide as a solid. $^1$H NMR (400 MHz, Chloroform-d) δ 10.37 (s, 1H), 7.89 (d, J=9.0 Hz, 1H), 7.43-7.22 (m, 7H), 6.60 (s, 1H), 2.46 (s, 6H), 1.41 (s, 9H). LCMS-ESI$^-$ (m/z): [M−H]$^-$ calcd 431.12; found 431.36.

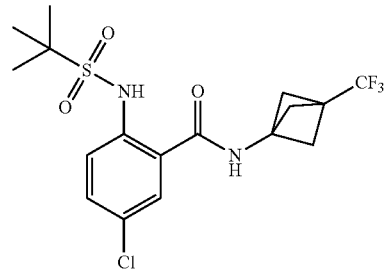

Example 84: Preparation of 5-chloro-2-((1,1-dimethylethyl)sulfonamido)-N-(3-(trifluoromethyl)bicyclo[1.1.1]pentan-1-yl)benzamide Following General Synthesis 3 using 3-(trifluoromethyl)bicyclo[1.1.1]pentan-1-amine hydrochloride (2.5 equiv.) in Step 4, 5-chloro-2-((1,1-dimethylethyl)sulfonamido)-N-(3-(trifluoromethyl)bicyclo[1.1.1]pentan-1-yl)benzamide was synthesized. $^1$H NMR (400 MHz, Chloroform-d) δ 10.27 (s, 1H), 7.89 (d, J=9.5 Hz, 1H), 7.40-7.37 (m, 2H), 6.56 (s, 1H), 2.41 (s, 6H), 1.41 (s, 9H). LCMS-ESI$^-$ (m/z): [M−H]$^-$ calcd 423.08; found 423.24.

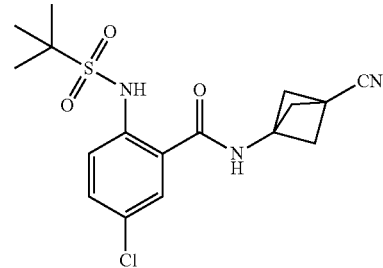 [SMILES: CC(C)(C)S(=O)(=O)Nc1ccc(Cl)cc1C(=O)NC12CC(C#N)(C1)C2]

Example 85: Preparation of 5-chloro-N-(3-cyanobicyclo[1.1.1]pentan-1-yl)-2-((1,1-dimethylethyl)sulfonamido)benzamide Following General Synthesis 3 using 3-aminobicyclo[1.1.1]pentane-1-carbonitrile (2.5 equiv.) in Step 4, 5-chloro-N-(3-cyanobicyclo[1.1.1]pentan-1-yl)-2-((1,1-dimethylethyl)sulfonamido)benzamide was synthesized. $^1$H NMR (400 MHz, Chloroform-d) δ 10.23 (s, 1H), 7.88 (d, J=9.0 Hz, 1H), 7.44-7.33 (m, 2H), 6.59 (s, 1H), 2.66 (s, 6H), 1.41 (s, 9H). LCMS-ESI$^-$ (m/z): [M–H]$^-$ calcd 380.08; found 380.23.

General Synthesis 4

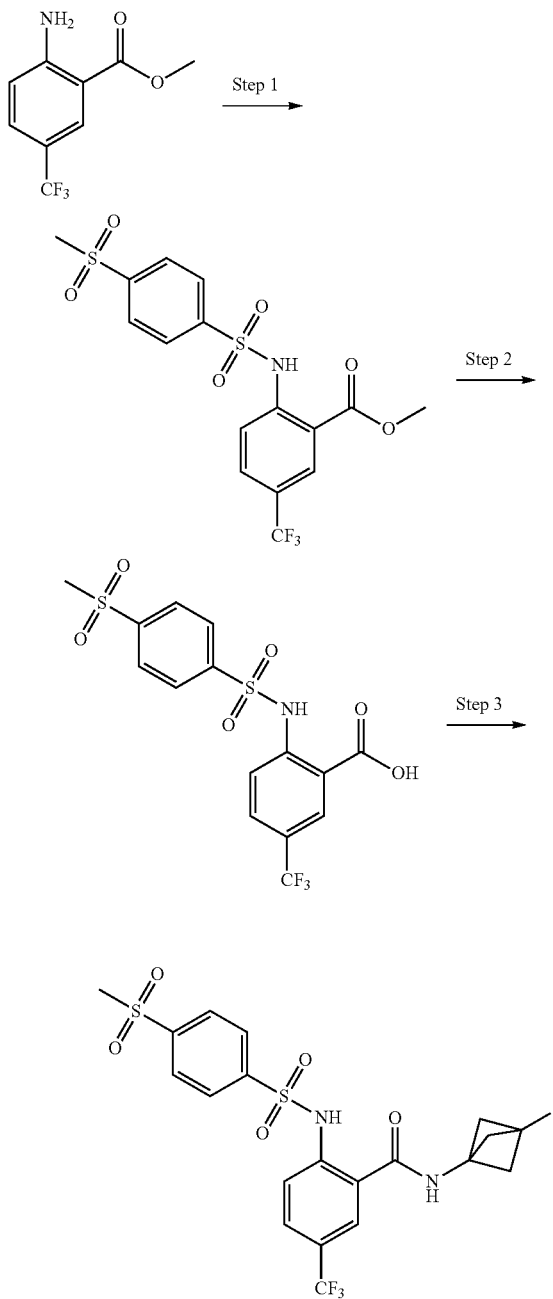

Example 86: Preparation of 2-((4-(methylsulfonyl)phenyl)sulfonamido)-5-(trifluoromethyl)-N-(3-(trifluoromethyl)bicyclo[1.1.1]pentan-1-yl)benzamide

Step 1

To a solution of methyl 2-amino-5-(trifluoromethyl)benzoate (0.261 g, 1.19 mmol) and 4-(methylsulfonyl)benzenesulfonyl chloride (0.300 g, 1.18 mmol) in 5 mL acetonitrile was added powdered indium metal (0.027 g, 0.24 mmol). The mixture was stirred at 110° C. for 18 hours. The reaction was then concentrated to a residue. The crude product was purified by silica flash chromatography to afford methyl 2-((4-(methylsulfonyl)phenyl)sulfonamido)-5-(trifluoromethyl)benzoate as a solid. LCMS-ESI$^-$ (m/z): [M–H]$^-$ calcd 436.01; found 436.18.

Step 2

Methyl 2-((4-(methylsulfonyl)phenyl)sulfonamido)-5-(trifluoromethyl)benzoate (0.083 mg, 0.19 mmol) in 3 mL ethanol was treated with sodium hydroxide pellets (0.120 g, 3.0 mmol) and 0.3 mL water. This mixture was stirred at 65° C. for 18 hours. Water was then added and the solution was acidified with 1 M aqueous hydrochloric acid. The aqueous phase was extracted 3× with ethyl acetate. The organic phases were combined, washed with saturated aqueous sodium chloride solution, dried over anhydrous magnesium sulfate, filtered, and concentrated to a residue to afford 2-((4-(methylsulfonyl)phenyl)sulfonamido)-5-(trifluoromethyl)benzoic acid as a solid. LCMS-ESI$^-$ (m/z): [M–H]$^-$ calcd 422.00; found 422.08.

Step 3

A solution of 2-((4-(methylsulfonyl)phenyl)sulfonamido)-5-(trifluoromethyl)benzoic acid (0.040 g, 0.095 mmol), 3-(trifluoromethyl)bicyclo[1.1.1]pentan-1-amine hydrochloride (0.035 g, 0.19 mmol), 1-ethyl-3-(3-dimethylaminopropyl)carbodiimide hydrochloride (0.036 g, 0.24 mmol), and 1-hydroxybenzotriazole hydrate (0.036 g, 0.24 mmol) in 0.5 mL dimethylformamide was treated with diisopropylethylamine (0.085 g, 0.66 mmol). The mixture was stirred for 18 hours at 60° C. The crude product was purified by reverse phase HPLC, affording 2-((4-(methylsulfonyl)phenyl)sulfonamido)-5-(trifluoromethyl)-N-(3-(trifluoromethyl)bicyclo[1.1.1]pentan-1-yl)benzamide as a solid. $^1$H NMR (400 MHz, DMSO-d$_6$) δ 11.94 (s, 1H), 9.75 (s, 1H), 8.10 (m, 5H), 7.87 (s, 1H), 7.65 (d, J=8.6 Hz, 1H), 3.29 (s, 3H), 2.35 (s, 6H). LCMS-ESI$^+$ (m/z): [M+H]$^+$ calcd 557.06; found 556.83.

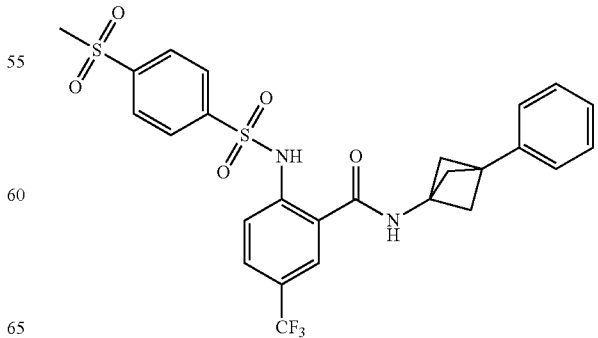

Example 87: Preparation of 2-((4-(methylsulfonyl)phenyl)sulfonamido)-N-(3-phenylbicyclo[1.1.1]pentan-1-yl)-5-(trifluoromethyl)benzamide)

Following General Synthesis 4 using 3-phenylbicyclo[1.1.1]pentan-1-amine hydrochloride (2.0 equiv.) in Step 3, 2-((4-(methylsulfonyl)phenyl)sulfonamido)-N-(3-phenylbicyclo[1.1.1]pentan-1-yl)-5-(trifluoromethyl)benzamide was synthesized. $^1$H NMR (400 MHz, DMSO-$d_6$) δ 12.26 (s, 1H), 9.68 (s, 1H), 8.20-8.07 (m, 5H), 7.88 (d, J=8.4 Hz, 1H), 7.67 (d, J=8.8 Hz, 1H), 7.39-7.21 (m, 5H), 3.29 (s, 3H), 2.37 (s, 6H). LCMS-ESI$^-$ (m/z): [M–H]$^-$ calcd 563.09; found 563.32.

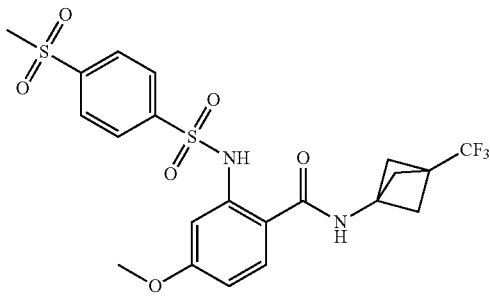 [SMILES: COc1ccc(C(=O)NC23CC(C(F)(F)F)(C2)C3)c(NS(=O)(=O)c2ccc(S(C)(=O)=O)cc2)c1]

Example 88: Preparation of 4-methoxy-2-((4-(methylsulfonyl)phenyl)sulfonamido)-N-(3-(trifluoromethyl)bicyclo[1.1.1]pentan-1-yl)benzamide Following General Synthesis 4 using methyl 2-amino-4-methoxybenzoate (1.0 equiv.) in Step 1, 4-methoxy-2-((4-(methylsulfonyl)phenyl)sulfonamido)-N-(3-(trifluoromethyl)bicyclo[1.1.1]pentan-1-yl)benzamide was synthesized. $^1$H NMR (400 MHz, DMSO-$d_6$) δ 12.09 (s, 1H), 9.32 (s, 1H), 8.10 (d, J=8.6 Hz, 2H), 8.00 (d, J=8.7 Hz, 2H), 7.70 (d, J=8.9 Hz, 1H), 6.98 (d, J=2.5 Hz, 1H), 6.76 (dd, J=9.0, 2.5 Hz, 1H), 3.79 (s, 3H), 3.28 (s, 3H), 2.31 (s, 6H). LCMS-ESI$^-$ (m/z): [M–H]$^-$ calcd 517.07; found 517.23.

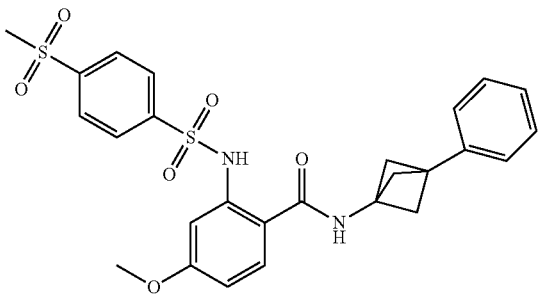 [SMILES: COc1ccc(C(=O)NC23CC(c4ccccc4)(C2)C3)c(NS(=O)(=O)c2ccc(S(C)(=O)=O)cc2)c1]

Example 89: Preparation of 4-methoxy-2-((4-(methylsulfonyl)phenyl)sulfonamido)-N-(3-phenylbicyclo[1.1.1]pentan-1-yl)benzamide Following General Synthesis 4 using methyl 2-amino-4-methoxybenzoate (1.0 equiv.) in Step 1 and 3-phenylbicyclo[1.1.1]pentan-1-amine hydrochloride (2.0 equiv.) in Step 3, 4-methoxy-2-((4-(methylsulfonyl)phenyl)sulfonamido)-N-(3-phenylbicyclo[1.1.1]pentan-1-yl)benzamide was synthesized. $^1$H NMR (400 MHz, DMSO-$d_6$) δ 12.40 (s, 1H), 9.22 (s, 1H), 8.11 (d, J=8.6 Hz, 2H), 8.02 (d, J=8.6 Hz, 2H), 7.75 (d, J=9.0 Hz, 1H), 7.37-7.19 (m, 5H), 6.99 (d, J=2.5 Hz, 1H), 6.75 (dd, J=8.9, 2.5 Hz, 1H), 3.80 (s, 3H), 3.28 (s, 3H), 2.33 (s, 6H). LCMS-ESI$^-$ (m/z): [M–H]$^-$ calcd 525.12; found 525.31.

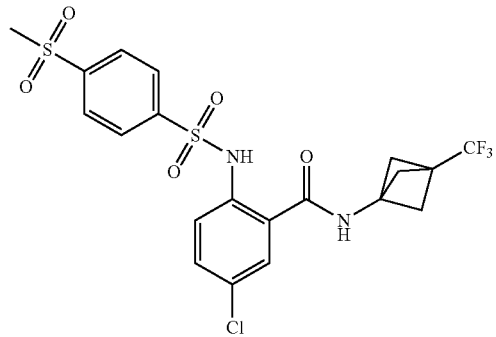 [SMILES: CS(=O)(=O)c1ccc(S(=O)(=O)Nc2ccc(Cl)cc2C(=O)NC23CC(C(F)(F)F)(C2)C3)cc1]

Example 90: Preparation of 5-chloro-2-((4-(methylsulfonyl)phenyl)sulfonamido)-N-(3-(trifluoromethyl)bicyclo[1.1.1]pentan-1-yl)benzamide Following General Synthesis 4 using methyl 2-amino-5-chlorobenzoate (1.0 equiv.) in Step 1, 5-chloro-2-((4-(methylsulfonyl)phenyl)sulfonamido)-N-(3-(trifluoromethyl)bicyclo[1.1.1]pentan-1-yl)benzamide was synthesized. $^1$H NMR (400 MHz, Chloroform-d) δ 10.72 (s, 1H), 8.02-7.92 (m, 4H), 7.67 (d, J=8.8 Hz, 1H), 7.43 (dd, J=8.9, 2.3 Hz, 1H), 7.31 (d, J=2.3 Hz, 1H), 6.47 (s, 1H), 3.08 (s, 3H), 2.36 (s, 6H). LCMS-ESI$^-$ (m/z): [M–H]$^-$ calcd 521.02; found 521.28.

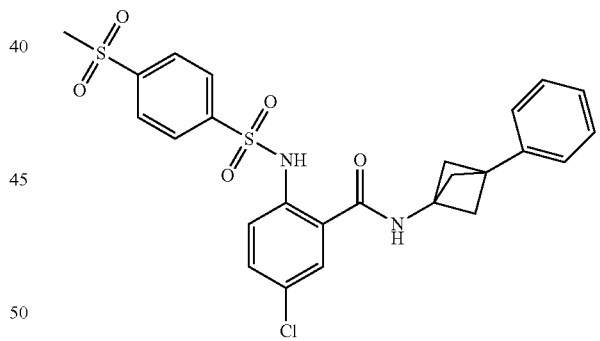

Example 91: Preparation of 5-chloro-2-((4-(methylsulfonyl)phenyl)sulfonamido)-N-(3-phenylbicyclo[1.1.1]pentan-1-yl)benzamide Following General Synthesis 4 using methyl 2-amino-5-chlorobenzoate (1.0 equiv.) in Step 1 and 3-phenylbicyclo[1.1.1]pentan-1-amine hydrochloride (2.0 equiv.) in Step 3, 5-chloro-2-((4-(methylsulfonyl)phenyl)sulfonamido)-N-(3-phenylbicyclo[1.1.1]pentan-1-yl)benzamide was synthesized. $^1$H NMR (400 MHz, Chloroform-d) δ 10.88 (s, 1H), 7.98 (dd, J=8.4, 6.1 Hz, 4H), 7.69 (d, J=8.7 Hz, 1H), 7.42 (dd, J=8.8, 2.3 Hz, 1H), 7.36-7.23 (m, 6H), 6.42 (s, 1H), 3.07 (s, 3H), 2.41 (s, 6H). LCMS-ESI$^-$ (m/z): [M–H]$^-$ calcd 529.07; found 529.33.

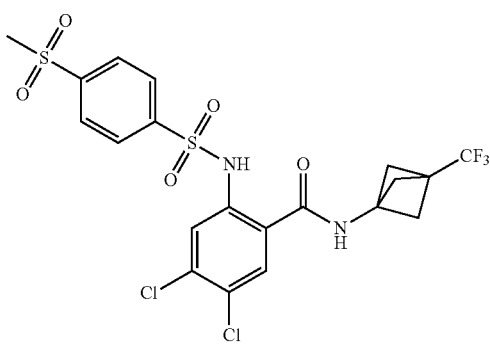 [SMILES: CS(=O)(=O)c1ccc(S(=O)(=O)Nc2cc(Cl)c(Cl)cc2C(=O)NC23CC(C(F)(F)F)(C2)C3)cc1]

Example 92: Preparation of 4,5-dichloro-2-((4-(methylsulfonyl)phenyl)sulfonamido)-N-(3-(trifluoromethyl)bicyclo[1.1.1]pentan-1-yl)benzamide Following General Synthesis 4 using methyl 2-amino-4,5-dichlorobenzoate (1.0 equiv.) in Step 1, 4,5-dichloro-2-((4-(methylsulfonyl)phenyl)sulfonamido)-N-(3-(trifluoromethyl)bicyclo[1.1.1]pentan-1-yl)benzamide was synthesized. $^1$H NMR (400 MHz, DMSO-$d_6$) δ 11.34 (s, 1H), 9.56 (s, 1H), 8.14-8.08 (m, 2H), 8.01-7.93 (m, 3H), 7.64 (s, 1H), 3.29 (s, 3H), 2.28 (s, 6H). LCMS-ESI$^-$ (m/z): [M−H]$^-$ calcd 554.98; found 555.28.

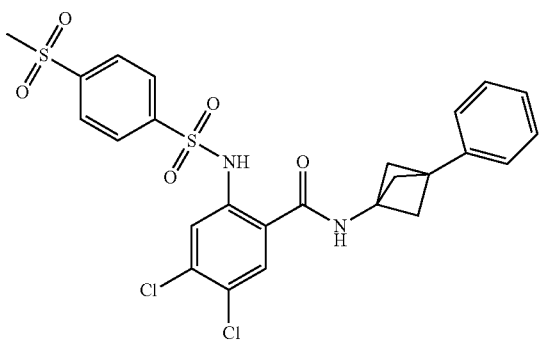 [SMILES: CS(=O)(=O)c1ccc(S(=O)(=O)Nc2cc(Cl)c(Cl)cc2C(=O)NC23CC(c4ccccc4)(C2)C3)cc1]

Example 93: Preparation of 4,5-dichloro-2-((4-(methylsulfonyl)phenyl)sulfonamido)-N-(3-phenylbicyclo[1.1.1]pentan-1-yl)benzamide Following General Synthesis 4 using methyl 2-amino-4,5-dichlorobenzoate (1.0 equiv.) in Step 1 and 3-phenylbicyclo[1.1.1]pentan-1-amine hydrochloride (2.0 equiv.) in Step 3, 4,5-dichloro-2-((4-(methylsulfonyl)phenyl)sulfonamido)-N-(3-phenylbicyclo[1.1.1]pentan-1-yl)benzamide was synthesized. $^1$H NMR (400 MHz, DMSO-$d_6$) δ 11.68 (s, 1H), 9.49 (s, 1H), 8.20-7.95 (m, 5H), 7.66 (s, 1H), 7.29 (m, 5H), 3.29 (s, 3H), 2.30 (s, 6H). LCMS-ESI$^-$ (m/z): [M−H]$^-$ calcd 563.03; found 563.36.

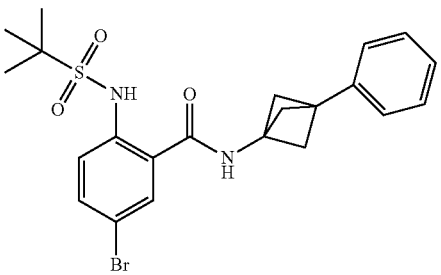 [SMILES: CC(C)(C)S(=O)(=O)Nc1ccc(Br)cc1C(=O)NC12CC(c3ccccc3)(C1)C2]

Example 94: Preparation of 5-bromo-2-((1,1-dimethylethyl)sulfonamido)-N-(3-phenylbicyclo[1.1.1]pentan-1-yl)benzamide Following General Synthesis 3 using 5-bromo-2-iodobenzonitrile in Step 1, 5-bromo-2-((1,1-dimethylethyl)sulfonamido)-N-(3-phenylbicyclo[1.1.1]pentan-1-yl)benzamide was synthesized. $^1$H NMR (400 MHz, DMSO-$d_6$) δ 11.04 (s, 1H), 9.64 (s, 1H), 8.02 (s, 1H), 7.68 (s, 2H), 7.34-7.20 (m, 5H), 2.37 (s, 6H), 1.28 (s, 9H). LCMS-ESI$^-$ (m/z): [M−H]$^-$ calcd 475.07; found 475.46.

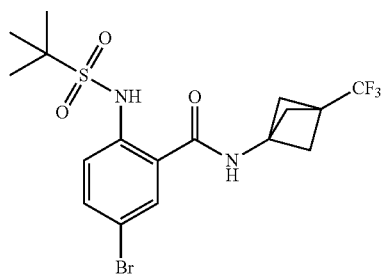 [SMILES: CC(C)(C)S(=O)(=O)Nc1ccc(Br)cc1C(=O)NC12CC(C(F)(F)F)(C1)C2]

Example 95: Preparation of 5-bromo-2-((1,1-dimethylethyl)sulfonamido)-N-(3-(trifluoromethyl)bicyclo[1.1.1]pentan-1-yl)benzamide Following General Synthesis 3 using 5-bromo-2-iodobenzonitrile in Step 1 and 3-(trifluoromethyl)bicyclo[1.1.1]pentan-1-amine hydrochloride (2.0 equiv.) in Step 4, 5-bromo-2-((1,1-dimethylethyl)sulfonamido)-N-(3-(trifluoromethyl)bicyclo[1.1.1]pentan-1-yl)benzamide was synthesized. $^1$H NMR (400 MHz, DMSO-$d_6$) δ 10.86 (s, 1H), 9.73 (s, 1H), 7.98 (d, J=1.6 Hz, 1H), 7.72-7.66 (m, 2H), 2.35 (s, 6H), 1.27 (s, 9H). LCMS-ESI$^-$ (m/z): [M−H]$^-$ calcd 467.03; found 467.38.

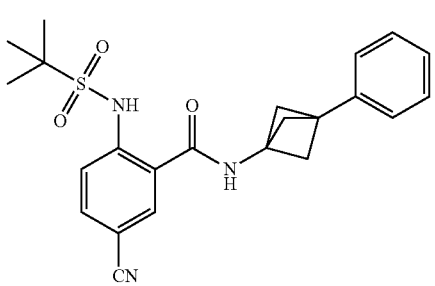 [SMILES: CC(C)(C)S(=O)(=O)Nc1ccc(C#N)cc1C(=O)NC12CC(c3ccccc3)(C1)C2]

Example 96: Preparation of 5-cyano-2-((1,1-dimethylethyl)sulfonamido)-N-(3-phenylbicyclo[1.1.1]pentan-1-yl)benzamide 5-Bromo-2-((1,1-dimethylethyl)sulfonamido)benzoic acid was synthesized following Step 1 through Step 3 of General Synthesis 3, using 5-bromo-2-iodobenzonitrile in Step 1. A solution of 5-bromo-2-((1,1-dimethylethyl)sulfonamido)benzoic acid (0.120 g, 0.357 mmol) in DMF was treated with copper(I) cyanide (0.064 g, 0.714 mmol). The mixture was stirred at 150° C. for 18 hours. The reaction was then acidified with 1 M aqueous hydrochloric acid. The aqueous phase was extracted 3× with ethyl acetate. The organic phases were combined and concentrated to a residue. The crude product was purified by silica flash chromatography to afford 5-cyano-2-((1,1-dimethylethyl)sulfonamido)benzoic acid, which was reacted according to Step 4 of General Synthesis 3 to afford 5-cyano-2-((1,1-dimethylethyl)sulfonamido)-N-(3-phenylbicyclo[1.1.1]pentan-1-yl)benzamide as a solid. $^1$H NMR (400 MHz, DMSO-d$_6$) δ 11.69 (s, 1H), 9.70 (s, 1H), 8.34 (s, 1H), 7.99-7.83 (m, 2H), 7.39-7.20 (m, 5H), 2.38 (s, 6H), 1.32 (s, 9H). LCMS-ESI$^-$ (m/z): [M−H]$^-$ calcd 422.15; found 422.29.

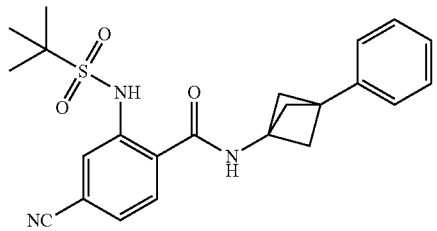

Example 98: Preparation of 4-cyano-2-((1,1-dimethylethyl)sulfonamido)-N-(3-phenylbicyclo[1.1.1]pentan-1-yl)benzamide 4-Bromobenzonitrile (1.068 g, 5.867 mmol), N-iodosuccinimide (1.452 g, 6.464 mmol), palladium(II) acetate (0.066 g, 0.29 mmol), and p-toluenesulfonic acid monohydrate (0.558 g, 2.94 mmol) were treated with 23 mL of 1,2-dichloroethane. The mixture was stirred at 70° C. for 72 hours. The reaction was then concentrated to a residue, which was purified by silica flash chromatography to afford 4-bromo-2-iodobenzonitrile. This compound was reacted following Step 1 through Step 3 of General Synthesis 3 to afford 4-bromo-2-((1,1-dimethylethyl)sulfonamido)benzoic acid. A solution of 4-bromo-2-((1,1-dimethylethyl)sulfonamido)benzoic acid (0.123 g, 0.366 mmol) in DMF was treated with copper(I) cyanide (0.098 g, 1.1 mmol). The mixture was stirred at 150° C. for 18 hours. The reaction was then acidified with 1 M aqueous hydrochloric acid. The aqueous phase was extracted 3× with ethyl acetate. The organic phases were combined and concentrated to a residue. The crude product was purified by silica flash chromatography to afford 4-cyano-2-((1,1-dimethylethyl)sulfonamido)benzoic acid, which was reacted according to Step 4 of General Synthesis 3 to afford 4-cyano-2-((1,1-dimethylethyl)sulfonamido)-N-(3-phenylbicyclo[1.1.1]pentan-1-yl)benzamide as a solid. $^1$H NMR (400 MHz, DMSO-d6) δ 11.01 (s, 1H), 9.77 (s, 1H), 8.00 (s, 1H), 7.96 (d, J=8.2 Hz, 1H), 7.67 (d, J=8.0 Hz, 1H), 7.36-7.19 (m, 5H), 2.38 (s, 6H), 1.30 (s, 9H). LCMS-ESI$^-$ (m/z): [M−H]$^-$ calcd 422.15; found 422.29.

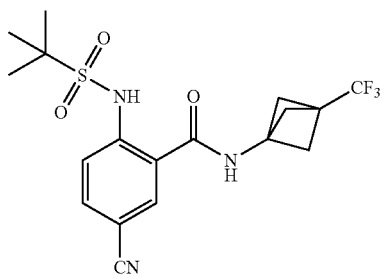 [SMILES: CC(C)(C)S(=O)(=O)Nc1ccc(C#N)cc1C(=O)NC12CC(C(F)(F)F)(C1)C2]

Example 97: Preparation of 5-cyano-2-((1,1-dimethylethyl)sulfonamido)-N-(3-(trifluoromethyl)bicyclo[1.1.1]pentan-1-yl)benzamide 5-Bromo-2-((1,1-dimethylethyl)sulfonamido)benzoic acid was synthesized following Step 1 through Step 3 of General Synthesis 3, using 5-bromo-2-iodobenzonitrile in Step 1. A solution of 5-bromo-2-((1,1-dimethylethyl)sulfonamido)benzoic acid (0.120 g, 0.357 mmol) in DMF was treated with copper(I) cyanide (0.064 g, 0.714 mmol). The mixture was stirred at 150° C. for 18 hours. The reaction was then acidified with 1 M aqueous hydrochloric acid. The aqueous phase was extracted 3× with ethyl acetate. The organic phases were combined and concentrated to a residue. The crude product was purified by silica flash chromatography to afford 5-cyano-2-((1,1-dimethylethyl)sulfonamido)benzoic acid, which was reacted according to Step 4 of General Synthesis 3 using 3-(trifluoromethyl)bicyclo[1.1.1]pentan-1-amine hydrochloride (2.0 equiv.) to afford 5-cyano-2-((1,1-dimethylethyl)sulfonamido)-N-(3-(trifluoromethyl)bicyclo[1.1.1]pentan-1-yl)benzamide. $^1$H NMR (400 MHz, DMSO-d$_6$) δ 11.48 (s, 1H), 9.79 (s, 1H), 8.30 (s, 1H), 8.00-7.80 (m, 2H), 2.37 (s, 6H), 1.32 (s, 9H). LCMS-ESI$^-$ (m/z): [M−H]-calcd 414.11; found 414.21.

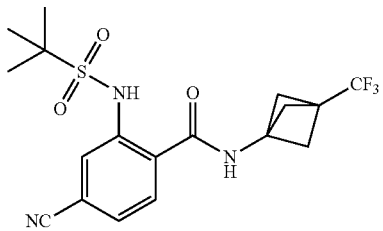 [SMILES: CC(C)(C)S(=O)(=O)Nc1cc(C#N)ccc1C(=O)NC12CC(C(F)(F)F)(C1)C2]

Example 99: Preparation of 4-cyano-2-((1,1-dimethylethyl)sulfonamido)-N-(3-(trifluoromethyl)bicyclo[1.1.1]pentan-1-yl)benzamide 4-Bromobenzonitrile (1.068 g, 5.867 mmol), N-iodosuccinimide (1.452 g, 6.464 mmol), palladium(II) acetate (0.066 g, 0.29 mmol), and p-toluenesulfonic acid monohydrate (0.558 g, 2.94 mmol) were treated with 23 mL of 1,2-dichloroethane. The mixture was stirred at 70° C. for 72 hours. The reaction was then concentrated to a residue, which was purified by silica flash chromatography to afford 4-bromo-2-iodobenzonitrile. This compound was reacted following Step 1 through Step 3 of General Synthesis 3 to afford 4-bromo-2-((1,1-dimethylethyl)sulfonamido)benzoic acid. A solution of 4-bromo-2-((1,1-dimethylethyl)sulfonamido)benzoic acid (0.123 g, 0.366 mmol) in DMF was treated with copper(I) cyanide (0.098 g, 1.1 mmol). The mixture was stirred at 150° C. for 18 hours. The reaction was then acidified with 1 M aqueous hydrochloric acid. The aqueous phase was extracted 3× with ethyl acetate. The organic phases were combined and concentrated to a residue. The crude product was purified by silica flash chromatography to afford 4-cyano-2-((1,1-dimethylethyl)sulfonamido)benzoic acid, which was reacted according to Step 4 of General Synthesis 3 using 3-(trifluoromethyl)bicyclo[1.1.1]pentan-1-amine hydrochloride (2.0 equiv.) to afford 4-cyano-2-((1,1-dimethylethyl)sulfonamido)-N-(3-(trifluoromethyl)bicyclo[1.1.1]pentan-1-yl)benzamide as a solid. $^1$H NMR (400 MHz, DMSO-d$_6$) δ 10.84 (s, 1H), 9.86 (s, 1H), 8.00 (s, 1H), 7.91 (d, J=8.1 Hz, 1H), 7.68 (d, J=8.2 Hz, 1H), 2.36 (s, 6H), 1.29 (s, 9H). LCMS-ESI$^-$ (m/z): [M−H]$^-$ calcd 414.11; found 414.21.

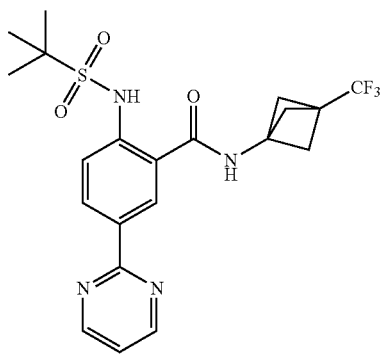 [SMILES: CC(C)(C)S(=O)(=O)Nc1ccc(-c2ncccn2)cc1C(=O)NC12CC(C(F)(F)F)(C1)C2]

Example 100: Preparation of 2-((1,1-dimethylethyl) sulfonamido)-5-(pyrimidin-2-yl)-N-(3-(trifluoromethyl)bicyclo[1.1.1]pentan-1-yl)benzamide 5-Bromo-2-((1,1-dimethylethyl)sulfonamido)-N-(3-(trifluoromethyl)bicyclo[1.1.1]pentan-1-yl)benzamide was synthesized following Example 95. To a solution of 5-bromo-2-((1,1-dimethylethyl)sulfonamido)-N-(3-(trifluoromethyl) bicyclo[1.1.1]pentan-1-yl)benzamide (0.030 g, 0.064 mmol) in 0.5 mL 1,4-dioxane was added bis(triphenylphosphine) palladium(II) dichloride (0.007 g, 0.009 mmol) and 2-tributylstannylpyrimidine (0.035 g, 0.096 mmol). The mixture was stirred at 120° C. for 3 hours. The reaction was then diluted with ethyl acetate and quenched by washing with 2 M aqueous potassium fluoride. The organic phase was concentrated to a residue, which was purified by reverse phase HPLC to afford 2-((1,1-dimethylethyl)sulfonamido)-5-(pyrimidin-2-yl)-N-(3-(trifluoromethyl)bicyclo[1.1.1]pentan-1-yl)benzamide as a solid. $^1$H NMR (400 MHz, DMSO-d$_6$) δ 11.06 (s, 1H), 9.96 (s, 1H), 8.93 (d, J=4.9 Hz, 2H), 8.78 (d, J=1.8 Hz, 1H), 8.49 (dd, J=8.9, 2.0 Hz, 1H), 7.90 (d, J=8.9 Hz, 1H), 7.47 (t, J=4.9 Hz, 1H), 2.39 (s, 6H), 1.31 (s, 9H). LCMS-ESI$^-$ (m/z): [M−H]$^-$ calcd 467.14; found 467.29.

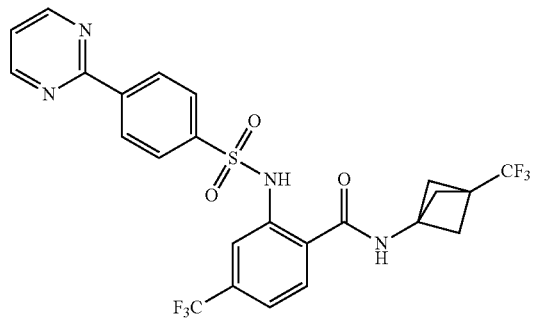 [SMILES: O=C(NC12CC(C(F)(F)F)(C1)C2)c1ccc(C(F)(F)F)cc1NS(=O)(=O)c1ccc(-c2ncccn2)cc1]

Example 101: Preparation of 2-((4-(pyrimidin-2-yl) phenyl)sulfonamido)-4-(trifluoromethyl)-N-(3-(trifluoromethyl)bicyclo[1.1.1]pentan-1-yl)benzamide 2-((4-Iodophenyl)sulfonamido)-4-(trifluoromethyl)-N-(3-(trifluoromethyl)bicyclo[1.1.1]pentan-1-yl)benzamide was synthesized following General Synthesis 4 using 4-iodobenzenesulfonyl chloride (1 equiv.) in Step 1. To a solution of 2-((4-iodophenyl)sulfonamido)-4-(trifluoromethyl)-N-(3-(trifluoromethyl)bicyclo[1.1.1]pentan-1-yl)benzamide (0.050 g, 0.083 mmol) in 0.5 mL 1,4-dioxane was added bis(triphenylphosphine) palladium(II) dichloride (0.009 g, 0.01 mmol) and 2-tributylstannylpyrimidine (0.092 g, 0.25 mmol). The mixture was stirred at 100° C. for 18 hours. The reaction was then diluted with ethyl acetate and quenched by washing with 2 M aqueous potassium fluoride. The organic phase was concentrated to a residue, which was purified by reverse phase HPLC to afford 2-((4-(pyrimidin-2-yl)phenyl) sulfonamido)-4-(trifluoromethyl)-N-(3-(trifluoromethyl)bicyclo[1.1.1]pentan-1-yl)benzamide as a solid. $^1$H NMR (400 MHz, DMSO-d$_6$) δ 11.20 (s, 1H), 9.58 (s, 1H), 8.96 (d, J=4.9 Hz, 2H), 8.52 (d, J=8.5 Hz, 2H), 7.88-7.81 (m, 3H), 7.73 (s, 1H), 7.61 (d, J=8.1 Hz, 1H), 7.54 (t, J=4.9 Hz, 1H), 2.27 (s, 6H). LCMS-ESI$^-$ (m/z): [M−H]$^-$ calcd 555.09; found 555.29.

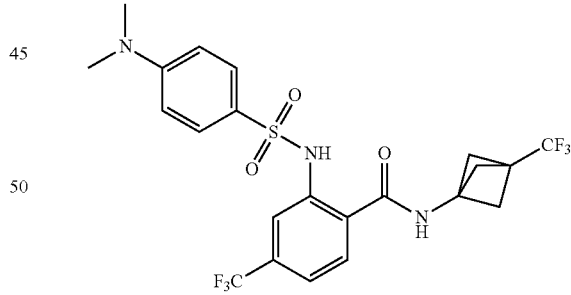

Example 102: Preparation of 2-((4-(dimethylamino) phenyl)sulfonamido)-4-(trifluoromethyl)-N-(3-(trifluoromethyl)bicyclo[1.1.1]pentan-1-yl)benzamide 2-((4-Iodophenyl)sulfonamido)-4-(trifluoromethyl)-N-(3-(trifluoromethyl)bicyclo[1.1.1]pentan-1-yl)benzamide was synthesized following General Synthesis 4 using 4-iodobenzenesulfonyl chloride (1 equiv.) in Step 1. A solution of 2-((4-iodophenyl)sulfonamido)-4-(trifluoromethyl)-N-(3-(trifluoromethyl)bicyclo[1.1.1]pentan-1-yl)benzamide (0.062 g, 0.10 mmol), copper(I) iodide (0.004 g, 0.02 mmol), 6,7-dihydroquinolin-8(5H)-one oxime (0.004 g, 0.03 mmol), and potassium hydroxide (0.029 g, 0.51 mmol) in 0.2 mL deionized water was purged with nitrogen gas. 0.2 mL of 2 M dimethylamine (0.023 g, 0.51 mmol) in tetrahydrofuran was then added. The mixture was stirred at 50° C. for 7 days. The reaction was then concentrated to a residue. The crude product was purified by reverse phase HPLC to afford 2-((4-(dimethylamino)phenyl)sulfonamido)-4-(trifluoromethyl)-N-(3-(trifluoromethyl)bicyclo[1.1.1]pentan-1-yl)benzamide as a solid. $^1$H NMR (400 MHz, DMSO-$d_6$) δ 11.10 (s, 1H), 9.65 (s, 1H), 7.87 (d, J=8.3 Hz, 1H), 7.73 (s, 1H), 7.51 (d, J=7.9 Hz, 1H), 7.47 (d, J=9.1 Hz, 2H), 6.71 (d, J=9.1 Hz, 2H), 2.96 (s, 6H), 2.34 (s, 6H). LCMS-ESI$^-$ (m/z): [M−H]$^-$ calcd 520.11; found 520.28.

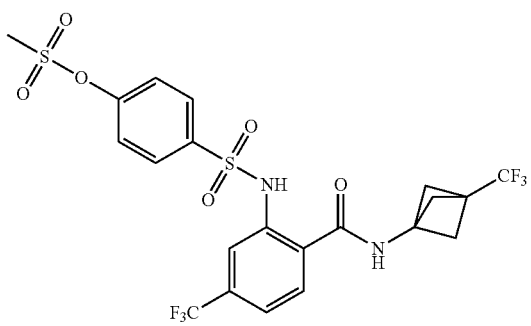 [SMILES: CS(=O)(=O)Oc1ccc(S(=O)(=O)Nc2cc(C(F)(F)F)ccc2C(=O)NC23CC(C(F)(F)F)(C2)C3)cc1]

Example 103: Preparation of 4-(N-(5-(trifluoromethyl)-2-((3-(trifluoromethyl)bicyclo[1.1.1]pentan-1-yl)carbamoyl)phenyl)sulfamoyl)phenyl methanesulfonate 2-((4-Hydroxyphenyl) sulfonamido)-4-(trifluoromethyl)-N-(3-(trifluoromethyl)bicyclo[1.1.1]pentan-1-yl)benzamide was synthesized by following Example 102. A solution of 2-((4-hydroxyphenyl)sulfonamido)-4-(trifluoromethyl)-N-(3-(trifluoromethyl)bicyclo[1.1.1]pentan-1-yl)benzamide (0.017 g, 0.034 mmol) and triethylamine (0.010 g, 0.10 mmol) in 0.15 mL dichloromethane was cooled to 0° C. Methanesulfonyl chloride (0.005 g, 0.04 mmol) was added. The mixture was stirred at 0° C. for 1 hour, and then allowed to warm to room temperature for 18 hours. The crude reaction mixture was purified by reverse phase HPLC to afford 4-(N-(5-(trifluoromethyl)-2-((3-(trifluoromethyl)bicyclo[1.1.1]pentan-1-yl)carbamoyl)phenyl)sulfamoyl)phenyl methane sulfonate as a solid. $^1$H NMR (400 MHz, DMSO-$d_6$) δ 11.27 (s, 1H), 9.62 (s, 1H), 7.93-7.77 (m, 3H), 7.72-7.48 (m, 4H), 3.45 (s, 3H), 2.33 (s, 6H). LCMS-ESI$^-$ (m/z): [M−H]$^-$ calcd 571.04; found 571.15.

General Synthesis 5

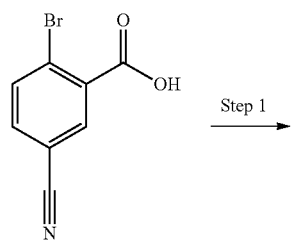
Step 1

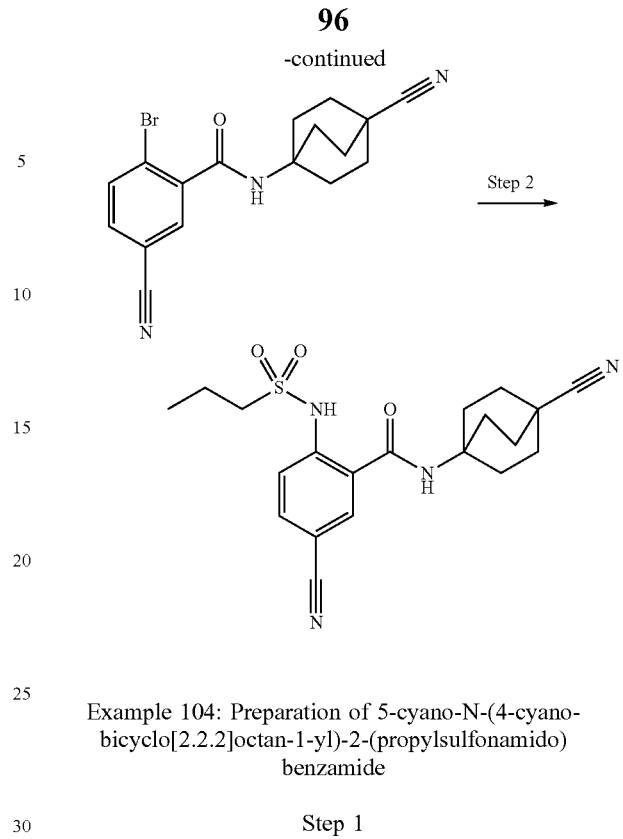

Example 104: Preparation of 5-cyano-N-(4-cyanobicyclo[2.2.2]octan-1-yl)-2-(propylsulfonamido)benzamide Step 1

A magnetically stirred mixture in dichloromethane of 2-bromo-5-cyanobenzoic acid (1.2 g, 5.4 mmol), 4-aminobicyclo[2.2.2]octane-1-carbonitrile hydrochloride (1.1 g, 5.7 mmol), and 0-(benzotriazol-1-yl)-N,N,N',N'-tetramethyluronium tetrafluoroborate (TBTU, 1.9 g, 5.9 mmol) was treated with N,N-diisopropylethylamine (2.8 mL, 16 mmol). After being allowed to stir overnight at room temperature, the mixture was partitioned between ethyl acetate and saturated aqueous sodium chloride solution. The aqueous phase was extracted three times with ethyl acetate. The combined organic phases were washed sequentially with 10% aqueous hydrochloric acid, water, and saturated aqueous sodium bicarbonate solution, then dried over anhydrous magnesium sulfate, filtered, and concentrated to a residue to afford 2-bromo-5-cyano-N-(4-cyanobicyclo[2.2.2]octan-1-yl)benzamide. LCMS-ESI$^+$ (m/z): [M+H]$^+$ calcd 358.06; found 358.15. This step can also be accomplished using the coupling reagent 1-ethyl-3-(3-dimethylaminopropyl)carbodiimide instead of TBTU; see General Synthesis 3, Step 4.

Step 2

A solution of 2-bromo-5-cyano-N-(4-cyanobicyclo[2.2.2]octan-1-yl)benzamide (50 mg, 0.14 mmol) and propane-1-sulfonamide (26 mg, 0.21 mmol) in 1 mL toluene was treated with tris(dibenzylideneacetone)dipalladium(0) (13 mg, 0.014 mmol), 9,9-dimethyl-4,5-bis(diphenylphosphino)xanthene (16 mg, 0.028 mmol), and tribasic potassium phosphate (59 mg, 0.28 mmol). The solution was heated to 110° C. and stirred for 4 hours. The mixture was then stripped of volatiles under reduced pressure, taken up in ethyl acetate, and washed with water. The aqueous phase was extracted with ethyl acetate and the organic phases combined, washed with brine, dried over anhydrous magnesium sulfate, filtered, and concentrated to a residue. Residue purified by silica flash chromatography to afford 5-cyano-N-(4-cyanobicyclo[2.2.2]octan-1-yl)-2-(propylsulfonamido)benzamide. $^1$H NMR (400 MHz, DMSO-$d_6$) δ 11.12 (s, 1H), 8.33 (s, 1H), 8.27 (d, J=1.9 Hz, 1H), 7.95 (dd, J=8.7, 1.8 Hz, 1H), 7.65 (d, J=8.7 Hz, 1H), 3.35-3.29 (m, 2H), 2.00 (s, 12H), 1.65 (h, J=7.4 Hz, 2H), 0.93 (t, J=7.4 Hz, 3H). LCMS-ESI$^-$ (m/z): [M−H]$^-$ calcd 399.15; found 399.24.

Step 2: Preparation of 2-(methylsulfonamido)-5-(trifluoromethyl)benzoic acid

A mixture containing both methyl 2-(N-(methylsulfonyl)methylsulfonamido)-5-(trifluoromethyl)benzoate and methyl 2-(methylsulfonamido)-5-(trifluoromethyl)benzoate

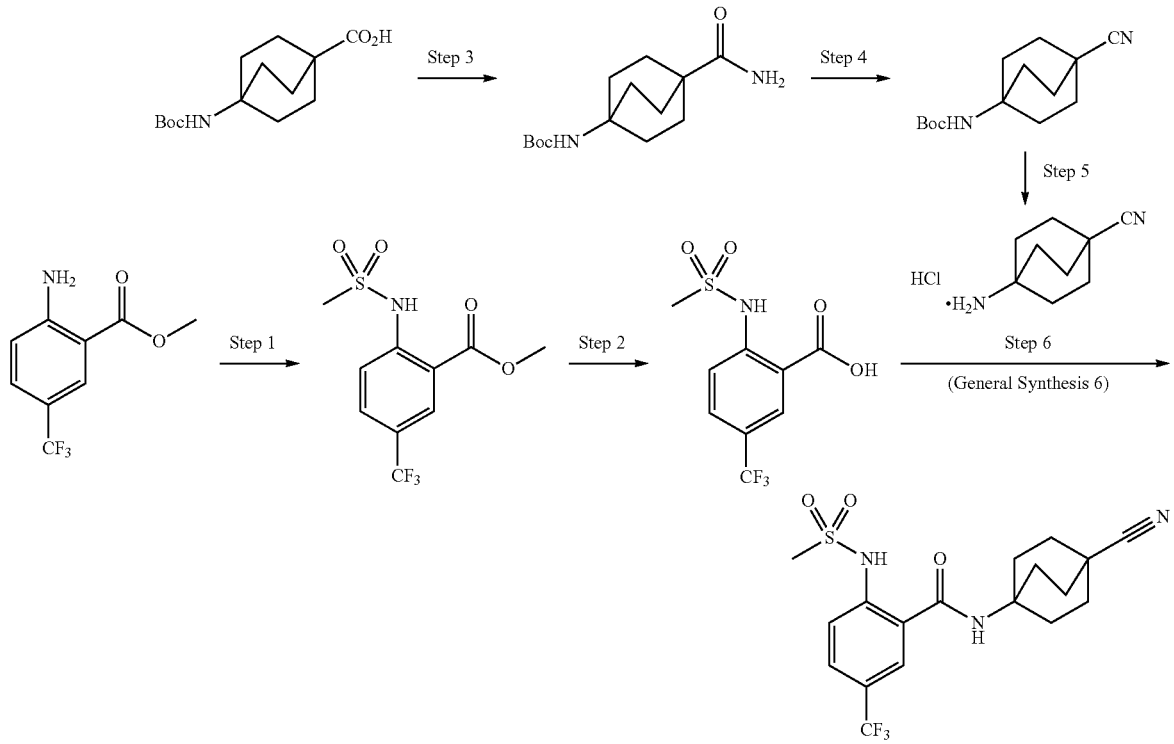

Example 105: Preparation of N-(4-cyanobicyclo[2.2.2]octan-1-yl)-2-(methylsulfonamido)-5-(trifluoromethyl)benzamide

Step 1: Preparation of methyl 2-(methylsulfonamido)-5-(trifluoromethyl)benzoate A solution of methyl 2-amino-5-(trifluoromethyl)benzoate (1.5 g, 6.9 mmol) in dichloromethane (20 mL) was treated successively with pyridine (5.6 mL, 69 mmol) and methanesulfonyl chloride (5.4 mL, 69 mmol). The mixture was alternately stirred magnetically and allowed to stand for four weeks at room temperature. The reaction mixture was treated with 10% hydrochloric acid (approximately 30 mL), stirred for 15 minutes, and then diluted with ethyl acetate. The entire mixture was filtered through a fritted pad of Celite diatomaceous earth. Next, the aqueous phase was extracted twice with ethyl acetate. The combined organic phases were washed once with saturated sodium chloride solution (admixed with some 10% hydrochloric acid), dried over anhydrous magnesium sulfate, filtered, and concentrated under reduced pressure to give a mixture of the desired intermediate and bis-sulfonylated product (methyl 2-(N-(methylsulfonyl)methylsulfonamido)-5-(trifluoromethyl)benzoate), which was carried forward to hydrolysis without further purification.

(unknown ratio, assumed 6.9 mmol combined) was taken up as a suspension in tetrahydrofuran (30 mL) and treated with water and methanol (10 mL each) and then sodium hydroxide (1.7 g, 42 mmol) was added. Mixture was allowed to stand overnight and room temperature, and then on the following day, it was heated at 65° C. with stirring. Upon completion of the hydrolysis, the mixture was acidified with 10% hydrochloric acid and extracted three times with ethyl acetate (3×30 mL). The combined organic layers were washed once with saturated aqueous sodium chloride solution, dried over anhydrous magnesium sulfate, filtered, and concentrated under reduced pressure. The desired material was crystallized from methanol/water and dried under vacuum to provide the desired intermediate. LCMS-ESI$^-$ (m/z): [M−H]$^-$ calcd 282.01; found 282.02.

Step 3: Preparation of tert-butyl (4-carbamoylbicyclo[2.2.2]octan-1-yl)carbamate To an ice-water bath cooled mixture of 4-((tert-butoxycarbonyl)amino)bicyclo[2.2.2]octane-1-carboxylic acid (6.7 g, 25 mmol) in 2-methyltetrahydrofuran (200 mL) were added successively 1-hydroxybenzotriazole hydrate (HOBT, 5.4 g, 35 mmol), 1-ethyl-3-(3-dimethylaminopropyl)carbodiimide hydrochloride (EDC, 5.4 g, 35 mmol), and N,N-diisopropylethylamine (12 mL, 70 mmol). The suspension was stirred at in the ice-water bath for thirty minutes and then at room temperature for three hours. Mixture was sonicated for about 2 minutes and then left to stir vigorously while the mixture was re-cooled in an ice-water bath. Ammonium hydroxide (28.0-30.0% NH$_3$ basis, 17 mL, 125 mmol) solution was added, the cooling bath was removed, and the mixture was stirred overnight at room temperature. Volatiles were removed under reduced pressure and the residue was partitioned between water (approximately 30 mL) and ethyl acetate (approximately 200 mL). The aqueous phase was extracted twice with ethyl acetate. The combined organics were washed successively with 10% aqueous hydrochloric acid, water, and saturated aqueous sodium hydrogen carbonate solution and then dried over anhydrous magnesium sulfate, filtered, and concentrated under reduced pressure to provide the desired intermediate. LCMS-ESI$^+$ (m/z): [M+H]$^+$ calcd 269.18; found 269.06.

Step 4: Preparation of tert-butyl (4-cyanobicyclo[2.2.2]octan-1-yl)carbamate

Phosphorus oxychloride (9.0 mL, 96 mmol) was added slowly via syringe to a cooled (ice-water bath) solution of tert-butyl (4-carbamoylbicyclo[2.2.2]octan-1-yl)carbamate (5.2 g, 19 mmol) in pyridine (80 mL) under magnetic stirring. The mixture was stirred for 30 minutes in the bath and then for 30 minutes after the bath had been removed. The mixture was added via pipette to ice-water (approximately 400 mL). The solid was collected by filtration, washed with water, and dried under vacuum to provide the desired intermediate. LCMS-ESI$^+$ (m/z): [M+H]$^+$ calcd 251.17; found 251.01.

Step 5: Preparation of 4-aminobicyclo[2.2.2]octane-1-carbonitrile hydrochloride tert-Butyl (4-cyanobicyclo[2.2.2]octan-1-yl)carbamate (0.60 g, 2.4 mmol) was taken up as a suspension in water in a sealable vessel, heated at 160° C. for 22 hours, and then allowed to cool. The mixture was treated with concentrated hydrochloric acid (0.5 mL) and concentrated to provide a mixture of the desired intermediate (LCMS-ESI$^+$ (m/z): [M+H]$^+$ calcd 151.12; found 150.95) and 4-aminobicyclo[2.2.2]octane-1-carboxamide hydrochloride (LCMS-ESI$^+$ (m/z): [M+H]$^+$ calcd 169.13; found 169.01), which was carried forward without further separation.

Step 6 (General Synthesis 6): Preparation of N-(4-cyanobicyclo[2.2.2]octan-1-yl)-2-(methylsulfonamido)-5-(trifluoromethyl)benzamide A mixture in N,N-dimethylformamide (DMF, 1 mL) of 2-(methylsulfonamido)-5-(trifluoromethyl)benzoic acid (0.12 g, 0.42 mmol) and 4-aminobicyclo[2.2.2]octane-1-carbonitrile hydrochloride (contaminated with 4-aminobicyclo[2.2.2]octane-1-carboxamide hydrochloride, 87 mg, approximately 0.47 mmol) was treated with N,N-diisopropylethylamine (0.37 mL, 2.1 mmol) and then was sonicated for about one minute. 1-Propanephosphonic anhydride solution (T3P, 50% by weight in DMF, 0.74 ml, 1.27 mmol) was then added, and the mixture was stirred overnight at 85° C. The reaction mixture was poured into ice-water (approximately 30 mL) and the resulting aqueous mixture was extracted three times with ethyl acetate. The combined extracts were washed once with saturated aqueous sodium chloride solution, dried over anhydrous magnesium sulfate, filtered, and concentrated to dryness under reduced pressure. The residue was first purified by flash chromatography (silica gel) and then by reverse-phase HPLC (acetonitrile/water/0.1% trifluoroacetic acid) to provide the desired product. $^1$H NMR (400 MHz, DMSO-d$_6$) δ 10.90 (s, 1H), 8.39 (s, 1H), 8.06 (d, J=2.2 Hz, 1H), 7.86 (d, J=8.7 Hz, 1H), 7.67 (d, J=8.7 Hz, 1H), 3.21 (s, 3H), 2.01 (s, 12H). LCMS-ESI$^+$ (m/z): [M+H]$^+$ calcd 416.12; found 416.06.

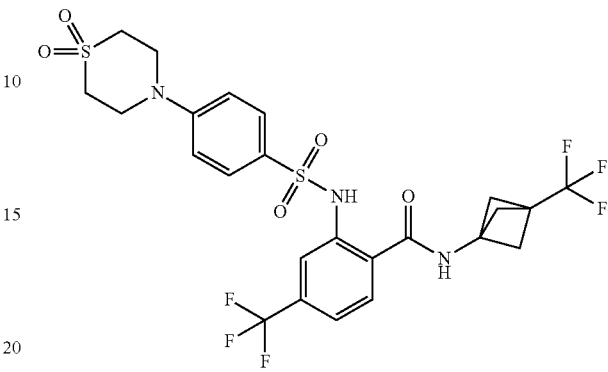

Example 106: Synthesis of 2-((4-(1,1-dioxidothiomorpholino)phenyl)sulfonamido)-4-(trifluoromethyl)-N-(3-(trifluoromethyl)bicyclo[1.1.1]pentan-1-yl)benzamide 2-((4-Iodophenyl)sulfonamido)-4-(trifluoromethyl)-N-(3-(trifluoromethyl)bicyclo[1.1.1]pentan-1-yl)benzamide was synthesized following General Synthesis 4 using 4-iodobenzenesulfonyl chloride (1 equiv.) in Step 1. 2-((4-Iodophenyl)sulfonamido)-4-(trifluoromethyl)-N-(3-(trifluoromethyl)bicyclo[1.1.1]pentan-1-yl)benzamide (39 mg, 0.065 mmol), tribasic potassium phosphate monohydrate (82 mg, 0.39 mmol), rac-2,2'-bis(diphenylphosphino)-1,1'-binaphthylene (6.0 mg, 0.0097 mmol), thiomorpholine-1,1-dioxide (26 mg, 0.19 mmol), and tris(dibenzylideneacetone)dipalladium(0) (5.2 mg, 0.0065 mmol) were dissolved in 1,4-dioxane. The mixture was purged under nitrogen and heated overnight with stirring at 100° C., then cooled, water added, and extracted with ethyl acetate three times. The combined organic layer was washed with brine, dried over magnesium sulfate, filtered and concentrated. The crude product was purified using RP-HPLC to afford 2-((4-(1,1-dioxidothiomorpholino)phenyl)sulfonamido)-4-(trifluoromethyl)-N-(3-(trifluoromethyl)bicyclo[1.1.1]pentan-1-yl)benzamide. $^1$H NMR (400 MHz, DMSO-d$_6$) δ 11.19 (s, 1H), 9.67 (s, 1H), 7.88 (d, J=8.2 Hz, 1H), 7.72 (s, 1H), 7.53 (d, J=9.1 Hz, 3H), 7.10 (d, J=9.1 Hz, 2H), 3.93-3.84 (m, 4H), 3.14-3.04 (m, 4H), 2.35 (s, 6H). LCMS-ESI$^-$ (m/z): [M–H]$^-$ calcd 610.09; found 610.30.

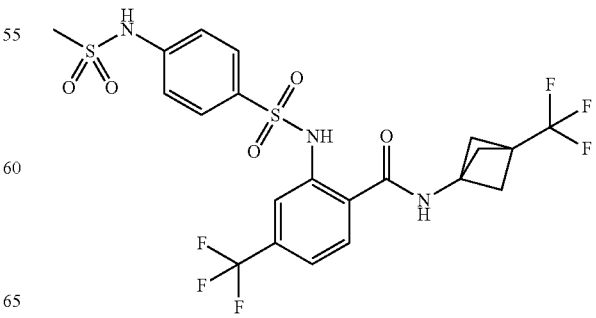

Example 107: Synthesis of 2-((4-(methylsulfonamido)phenyl)sulfonamido)-4-(trifluoromethyl)-N-(3-(trifluoromethyl)bicyclo[1.1.1]pentan-1-yl)benzamide 2-((4-Iodophenyl)sulfonamido)-4-(trifluoromethyl)-N-(3-(trifluoromethyl)bicyclo[1.1.1]pentan-1-yl)benzamide was synthesized following General Synthesis 4 using 4-iodobenzenesulfonyl chloride (1 equiv.) in Step 1. 2-((4-Iodophenyl)sulfonamido)-4-(trifluoromethyl)-N-(3-(trifluoromethyl)bicyclo[1.1.1]pentan-1-yl)benzamide (31 mg, 0.051 mmol), methanesulfonamide (24 mg, 0.26 mmol), copper(I) oxide (2.5 mg, 0.017 mmol), and cesium carbonate (50 mg, 0.15 mmol) were taken up in water and reacted with stirring at 150° C. for 5 hours. The mixture was acidified with acetic acid and purified by RP-HPLC to afford 2-((4-(methylsulfonamido)phenyl)sulfonamido)-4-(trifluoromethyl)-N-(3-(trifluoromethyl)bicyclo[1.1.1]pentan-1-yl)benzamide. $^1$H NMR (400 MHz, DMSO-$d_6$) δ 11.12 (s, 1H), 10.47 (s, 1H), 9.63 (s, 1H), 7.85 (d, J=7.8 Hz, 1H), 7.69 (s, 1H), 7.65 (d, J=8.8 Hz, 2H), 7.59 (d, J=7.6 Hz, 1H), 7.27 (d, J=9.0 Hz, 2H), 3.10 (s, 3H), 2.33 (s, 6H). LCMS-ESI (m/z): [M−H]$^-$ calcd 570.06; found 570.13.

General Syntheses 7 and 8

Example 108: Preparation of 2-((1-cyanocyclopropane)-1-sulfonamido)-5-(trifluoromethyl)-N-(3-(trifluoromethyl)bicyclo[1.1.1]pentan-1-yl)benzamide Step 1 (General Synthesis 7): Preparation of 2-iodo-5-(trifluoromethyl)-N-(3-(trifluoromethyl)bicyclo[1.1.1]pentan-1-yl)benzamide A mixture of 2-iodo-5-(trifluoromethyl)benzoic acid (0.79 g, 2.5 mmol), 3-(trifluoromethyl)bicyclo[1.1.1]pentan-1-amine hydrochloride (0.52 g, 2.8 mmol), and O-(benzotriazol-1-yl)-N,N,N',N'-tetramethyluronium tetrafluoroborate (TBTU, 0.88 g, 2.75 mmol) in dichloromethane (15 mL) was treated with N,N-diisopropylethylamine (1.3 mL, 7.5 mmol). The mixture was allowed to stir at room temperature overnight. The mixture was partitioned between ethyl acetate and saturated aqueous sodium hydrogen carbonate solution. The latter was extracted three times with ethyl acetate. The combined organic extracts were washed successively with 10% aqueous hydrochloric acid and saturated aqueous sodium chloride solution, dried over anhydrous magnesium sulfate, filtered, and concentrated to dryness under reduced pressure to provide the desired intermediate. LCMS-ESI (m/z): [M−H]$^-$ calcd 447.97; found 448.03.

Step 2: Preparation of 1-cyanocyclopropane-1-sulfonamide

A solution of tert-butyl ((1-cyanocyclopropyl)sulfonyl)carbamate (Enamine, 0.30 g, 1.2 mmol) was cooled in an ice-water bath while trifluoroacetic acid (0.93 mL, 12 mmol) was added dropwise. The mixture allowed to gradually

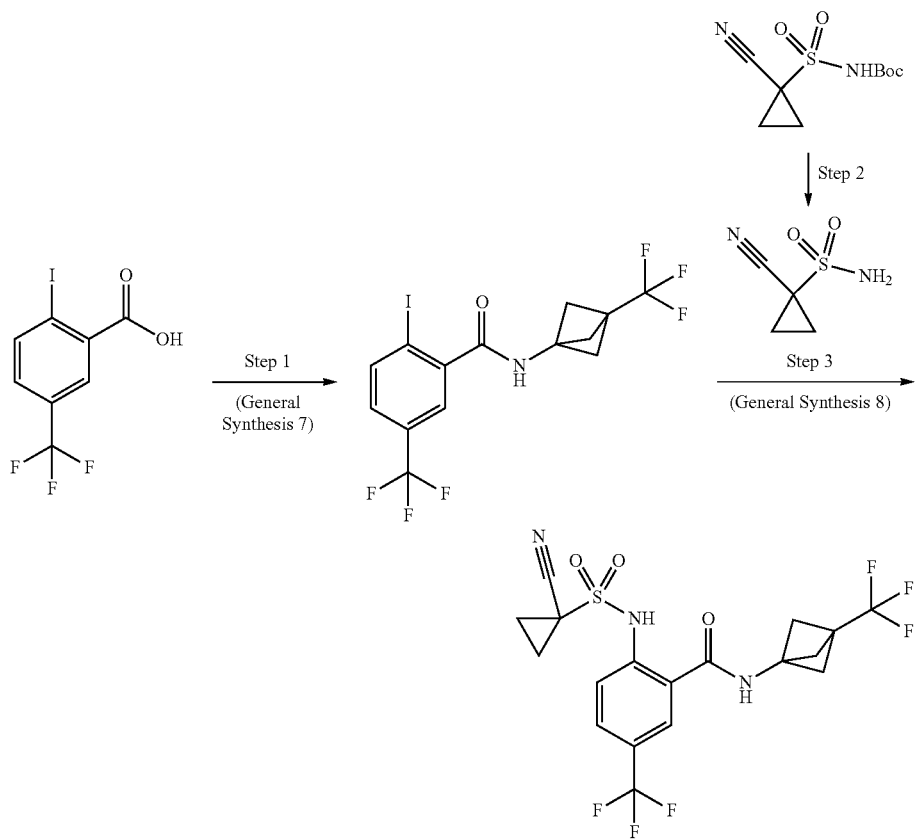

warm to room temperature as the bath was extinguished. When LC/MS analysis deemed the transformation to be complete, the mixture was concentrated under reduced pressure. The residue was co-evaporated once from diethyl ether and then carried forward without further purification. LCMS-ESI⁻ (m/z): [M−H]⁻ calcd 145.01; found 144.92.

Step 3 (General Synthesis 8): Preparation of 2-((1-cyanocyclopropane)-1-sulfonamido)-5-(trifluoromethyl)-N-(3-(trifluoromethyl)bicyclo[1.1.1]pentan-1-yl)benzamide A mixture of 1-cyanocyclopropane-1-sulfonamide (0.18 g, 1.2 mmol), 2-iodo-5-(trifluoromethyl)-N-(3-(trifluoromethyl)bicyclo[1.1.1]pentan-1-yl)benzamide (0.19 g, 0.41 mmol), copper(I) iodide (16 mg, 0.08 mmol), sarcosine (9 mg, 0.1 mmol), and potassium carbonate (~325 mesh, 170 mg, 1.2 mmol) or preferably tribasic potassium phosphate (0.25 g, 1.2 mmol) in N,N-dimethylformamide (3 mL) was heated in at 100° C. block for approximately three days. After cooling, the mixture was partitioned between ethyl acetate and 10% hydrochloric acid. The aqueous phase was extracted three times with ethyl acetate. The combined extracts were washed once each with water and saturated aqueous sodium chloride solution, dried over anhydrous magnesium sulfate, filtered, and concentrated under reduced pressure. The residue was purified by reverse phase high performance liquid chromatography (RP-HPLC, acetonitrile/water/0.1% trifluoroacetic acid) to provide the desired product. ¹H NMR (400 MHz, DMSO-d₆) δ 12.12 (bs, 1H), 10.01 (bs, 1H), 8.23 (d, J=2.1 Hz, 1H), 8.04-7.84 (m, 1H), 7.78 (d, J=8.7 Hz, 1H), 2.38 (s, 6H), 1.88 (m, 2H), 1.67 (m, 2H). LCMS-ESI⁻ (m/z): [M−H]⁻ calcd 466.07; found 466.22.

1H), 7.77 (dd, J=8.8, 5.0 Hz, 2H), 7.67 (s, 1H), 7.60 (d, J=6.8 Hz, 1H), 7.42 (t, J=8.7 Hz, 2H), 2.33 (s, 6H). LCMS-ESI⁻ (m/z): [M−H]⁻ calcd 495.06; found 495.19.

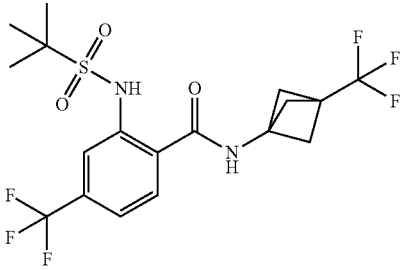

Example 110: Synthesis of 2-((1,1-dimethylethyl)sulfonamido)-4-(trifluoromethyl)-N-(3-(trifluoromethyl)bicyclo[1.1.1]pentan-1-yl)benzamide 2-Bromo-4-(trifluoromethyl)-N-(3-(trifluoromethyl)bicyclo[1.1.1]pentan-1-yl)benzamide was synthesized by subjecting 2-bromo-4-(trifluoromethyl)benzonitrile to Step 3 and Step 4 of General Synthesis 3, using 3-(trifluoromethyl)bicyclo[1.1.1]pentan-1-amine hydrochloride (1.5 equiv.) in Step 4. 2-((1,1-dimethylethyl)sulfonamido)-4-(trifluoromethyl)-N-(3-(trifluoromethyl)bicyclo[1.1.1]pentan-1-yl)benzamide was prepared with General Synthesis 8 using 2-bromo-4-(trifluoromethyl)-N-(3-(trifluoromethyl)bicyclo[1.1.1]pentan-1-yl)benzamide (1 equiv.) and 2-methylpropane-2-sulfonamide (3 equiv.). ¹H NMR (400 MHz, DMSO-d₆) δ 10.94 (s, 1H), 9.86 (s, 1H), 8.02 (s, 1H), 7.97 (d, J=8.2 Hz, 1H), 7.56 (d, J=8.2 Hz, 1H), 2.37 (s, 6H), 1.29 (s, 9H). LCMS-ESI⁻ (m/z): [M−H]⁻ calcd 457.10; found 457.24.

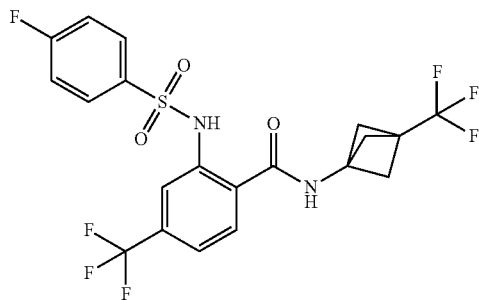 [SMILES: O=C(NC12CC(C(F)(F)F)(C1)C2)c1ccc(C(F)(F)F)cc1NS(=O)(=O)c1ccc(F)cc1]

Example 109: Synthesis of 2-((4-(methylsulfonamido)phenyl)sulfonamido)-4-(trifluoromethyl)-N-(3-(trifluoromethyl)bicyclo[1.1.1]pentan-1-yl)benzamide 2-Bromo-4-(trifluoromethyl)-N-(3-(trifluoromethyl)bicyclo[1.1.1]pentan-1-yl)benzamide was synthesized by subjecting 2-bromo-4-(trifluoromethyl)benzonitrile to Step 3 and Step 4 of General Synthesis 3, using 3-(trifluoromethyl)bicyclo[1.1.1]pentan-1-amine hydrochloride (1.5 equiv.) in Step 4. 2-((4-(methylsulfonamido)phenyl)sulfonamido)-4-(trifluoromethyl)-N-(3-(trifluoromethyl)bicyclo[1.1.1]pentan-1-yl)benzamide was prepared with General Synthesis 8 using 2-bromo-4-(trifluoromethyl)-N-(3-(trifluoromethyl)bicyclo[1.1.1]pentan-1-yl)benzamide (1 equiv.) and 4-fluorobenzenesulfonamide (3 equiv.). ¹H NMR (400 MHz, DMSO-d₆) δ 11.19 (s, 1H), 9.62 (s, 1H), 7.86 (d, J=8.0 Hz,

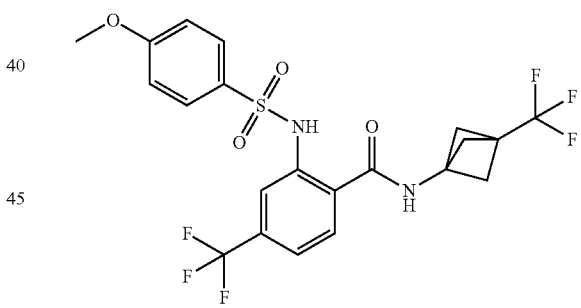

Example 111: Synthesis of 2-((4-methoxyphenyl)sulfonamido)-4-(trifluoromethyl)-N-(3-(trifluoromethyl)bicyclo[1.1.1]pentan-1-yl)benzamide 2-Bromo-4-(trifluoromethyl)-N-(3-(trifluoromethyl)bicyclo[1.1.1]pentan-1-yl)benzamide was synthesized by subjecting 2-bromo-4-(trifluoromethyl)benzonitrile to Step 3 and Step 4 of General Synthesis 3, using 3-(trifluoromethyl)bicyclo[1.1.1]pentan-1-amine hydrochloride (1.5 equiv.) in Step 4. 2-((4-Methoxyphenyl)sulfonamido)-4-(trifluoromethyl)-N-(3-(trifluoromethyl)bicyclo[1.1.1]pentan-1-yl)benzamide was prepared with General Synthesis 8 using 2-bromo-4-(trifluoromethyl)-N-(3-(trifluoromethyl)bicyclo[1.1.1]pentan-1-yl)benzamide (1 equiv.) and 4-methoxybenzenesulfonamide (3 equiv.). ¹H NMR (400 MHz, DMSO-d₆) δ 11.17 (s, 1H), 9.64 (s, 1H), 7.86 (d, J=8.1 Hz, 1H), 7.70

(s, 1H), 7.65 (d, J=8.9 Hz, 2H), 7.56 (d, J=8.5 Hz, 1H), 7.07 (d, J=9.0 Hz, 2H), 3.80 (s, 3H), 2.34 (s, 6H). LCMS-ESI⁻ (m/z): [M–H]⁻ calcd 507.08; found 507.24.

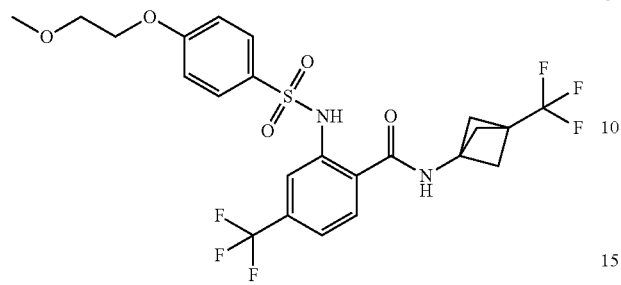

Example 112: Synthesis of 2-((4-(2-methoxy-ethoxy)phenyl)sulfonamido)-4-(trifluoromethyl)-N-(3-(trifluoromethyl)bicyclo[1.1.1]pentan-1-yl)benzamide 2-Bromo-4-(trifluoromethyl)-N-(3-(trifluoromethyl)bicyclo[1.1.1]pentan-1-yl)benzamide was synthesized by subjecting 2-bromo-4-(trifluoromethyl)benzonitrile to Step 3 and Step 4 of General Synthesis 3, using 3-(trifluoromethyl)bicyclo[1.1.1]pentan-1-amine hydrochloride (1.5 equiv.) in Step 4. 4-(2-Methoxyethoxy)benzenesulfonamide was prepared by treating 4-fluorobenzenesulfonamide (100 mg, 0.57 mmol) with sodium hydroxide (110 mg, 2.9 mmol) in 0.33 mL of 2-methoxyethanol (7.4 mmol), heating the mixture at 110° C. with stirring overnight, and purifying the product by silica flash chromatography. 2-((4-(2-Methoxyethoxy)phenyl)sulfonamido)-4-(trifluoromethyl)-N-(3-(trifluoromethyl)bicyclo[1.1.1]pentan-1-yl)benzamide was prepared with General Synthesis 8 using 2-bromo-4-(trifluoromethyl)-N-(3-(trifluoromethyl)bicyclo[1.1.1]pentan-1-yl)benzamide (1 equiv.) and 4-(2-methoxyethoxy)benzenesulfonamide (3 equiv.). ¹H NMR (400 MHz, DMSO-d₆) δ 11.13 (s, 1H), 9.64 (s, 1H), 7.86 (d, J=8.2 Hz, 1H), 7.70 (s, 1H), 7.62 (d, J=9.0 Hz, 2H), 7.57 (d, J=8.3 Hz, 1H), 7.08 (d, J=9.0 Hz, 2H), 4.20-4.05 (m, 2H), 3.70-3.58 (m, 2H), 3.28 (s, 3H), 2.34 (s, 6H). LCMS-ESI⁻ (m/z): [M–H]⁻ calcd 551.11; found 551.23.

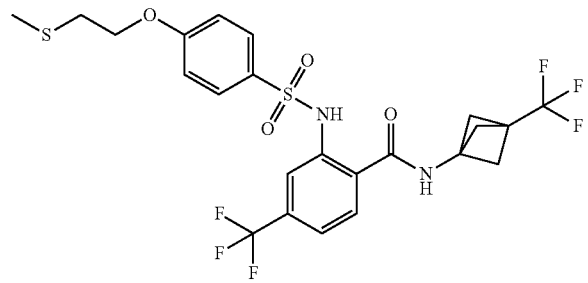 [SMILES: CSCCOc1ccc(S(=O)(=O)Nc2cc(C(F)(F)F)ccc2C(=O)NC23CC(C(F)(F)F)(C2)C3)cc1]

Example 113: Synthesis of 2-((4-(2-(methylthio)ethoxy)phenyl)sulfonamido)-4-(trifluoromethyl)-N-(3-(trifluoromethyl)bicyclo[1.1.1]pentan-1-yl)benzamide 2-Bromo-4-(trifluoromethyl)-N-(3-(trifluoromethyl)bicyclo[1.1.1]pentan-1-yl)benzamide was synthesized by subjecting 2-bromo-4-(trifluoromethyl)benzonitrile to Step 3 and Step 4 of General Synthesis 3, using 3-(trifluoromethyl)bicyclo[1.1.1]pentan-1-amine hydrochloride (1.5 equiv.) in Step 4. 4-(2-(Methylthio)ethoxy)benzenesulfonamide was prepared by treating 4-fluorobenzenesulfonamide (100 mg, 0.57 mmol) with sodium hydroxide (110 mg, 2.9 mmol) in 0.5 mL of 2-(methylthio)ethanol (6.0 mmol), heating the mixture at 110° C. with stirring overnight, and purifying the product by silica flash chromatography. 2-((4-(2-(methylthio)ethoxy)phenyl)sulfonamido)-4-(trifluoromethyl)-N-(3-(trifluoromethyl)bicyclo[1.1.1]pentan-1-yl)benzamide was prepared with General Synthesis 8 using 2-bromo-4-(trifluoromethyl)-N-(3-(trifluoromethyl)bicyclo[1.1.1]pentan-1-yl)benzamide (1 equiv.) and 4-(2-(methylthio)ethoxy)benzenesulfonamide (3 equiv.). ¹H NMR (400 MHz, DMSO-d₆) δ 11.16 (s, 1H), 9.66 (s, 1H), 7.86 (d, J=8.1 Hz, 1H), 7.70 (s, 1H), 7.63 (d, J=8.9 Hz, 2H), 7.58 (d, J=7.8 Hz, 1H), 7.09 (d, J=9.0 Hz, 2H), 4.19 (t, J=6.5 Hz, 2H), 2.83 (t, J=6.5 Hz, 2H), 2.33 (s, 6H), 2.12 (s, 3H). LCMS-ESI⁺ (m/z): [M+H]⁺ calcd 569.10; found 568.87.

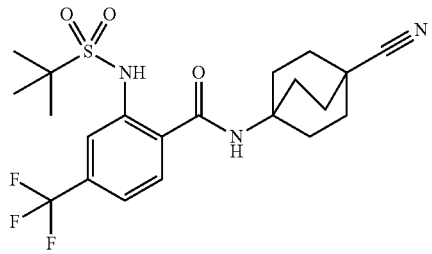 [SMILES: CC(C)(C)S(=O)(=O)Nc1cc(C(F)(F)F)ccc1C(=O)NC12CCC(C#N)(CC1)CC2]

Example 114: Synthesis of N-(4-cyanobicyclo[2.2.2]octan-1-yl)-2-((1,1-dimethylethyl)sulfonamido)-4-(trifluoromethyl)benzamide N-(4-cyanobicyclo[2.2.2]octan-1-yl)-2-((1,1-dimethylethyl)sulfonamido)-4-(trifluoromethyl)benzamide was synthesized by following General Synthesis 3, using 2-bromo-4-(trifluoromethyl)benzonitrile (1 equiv.) in Step 1, and 4-aminobicyclo[2.2.2]octane-1-carbonitrile hydrochloride (1.8 equiv.) in Step 4. ¹H NMR (400 MHz, DMSO-d₆) δ 10.42 (s, 1H), 8.49 (s, 1H), 7.96 (s, 1H), 7.87 (d, J=8.1 Hz, 1H), 7.53 (d, J=8.2 Hz, 1H), 2.00 (s, 12H), 1.27 (s, 9H). LCMS-ESI⁻ (m/z): [M–H]⁻ calcd 456.16; found 456.32.

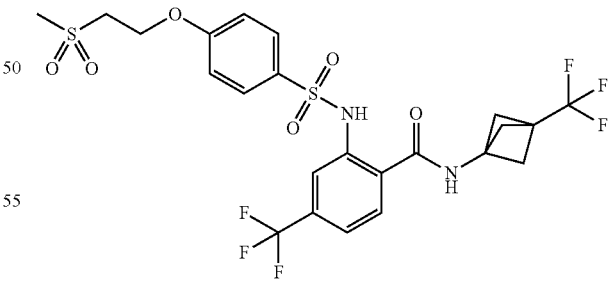

Example 115: Synthesis of 2-((4-(2-(methylsulfonyl)ethoxy)phenyl)sulfonamido)-4-(trifluoromethyl)-N-(3-(trifluoromethyl)bicyclo[1.1.1]pentan-1-yl)benzamide 2-((4-(2-(Methylthio)ethoxy)phenyl)sulfonamido)-4-(trifluoromethyl)-N-(3-(trifluoromethyl)bicyclo[1.1.1]pentan- 1-yl)benzamide, prepared following the procedure described in Example 113, was treated with a solution of 32% peracetic acid by weight in acetic acid. After stirring for 5 hours at room temperature, the reaction was diluted with water. The aqueous phase was extracted three times with ethyl acetate and concentrated to a residue. Crude product purified by RP-HPLC to afford 2-((4-(2-(methylsulfonyl)ethoxy)phenyl)sulfonamido)-4-(trifluoromethyl)-N-(3-(trifluoromethyl)bicyclo[1.1.1]pentan-1-yl)benzamide. $^1$H NMR (400 MHz, DMSO-$d_6$) δ 11.20 (s, 1H), 9.67 (s, 1H), 7.87 (d, J=8.2 Hz, 1H), 7.71 (s, 1H), 7.66 (d, J=8.9 Hz, 2H), 7.57 (d, J=8.0 Hz, 1H), 7.14 (d, J=8.9 Hz, 2H), 4.39 (t, J=5.6 Hz, 2H), 3.64 (t, J=5.5 Hz, 2H), 3.05 (s, 3H), 2.34 (s, 6H). LCMS-ESI$^-$ (m/z): [M–H]$^-$ calcd 599.07; found 599.29.

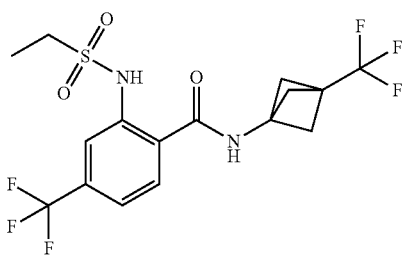 [SMILES: CCS(=O)(=O)Nc1cc(C(F)(F)F)ccc1C(=O)NC12CC(C(F)(F)F)(C1)C2]

Example 116: Synthesis of 2-(ethylsulfonamido)-4-(trifluoromethyl)-N-(3-(trifluoromethyl)bicyclo[1.1.1]pentan-1-yl)benzamide 2-Bromo-4-(trifluoromethyl)-N-(3-(trifluoromethyl)bicyclo[1.1.1]pentan-1-yl)benzamide was synthesized by subjecting 2-bromo-4-(trifluoromethyl)benzonitrile to Step 3 and Step 4 of General Synthesis 3, using 3-(trifluoromethyl)bicyclo[1.1.1]pentan-1-amine hydrochloride (1.5 equiv.) in Step 4. 2-(Ethylsulfonamido)-4-(trifluoromethyl)-N-(3-(trifluoromethyl)bicyclo[1.1.1]pentan-1-yl)benzamide was prepared with procedure General Synthesis 8 using 2-bromo-4-(trifluoromethyl)-N-(3-(trifluoromethyl)bicyclo[1.1.1]pentan-1-yl)benzamide (1 equiv.) and ethanesulfonamide (3 equiv.). $^1$H NMR (400 MHz, DMSO-$d_6$) δ 11.03 (s, 1H), 9.80 (s, 1H), 8.00 (d, J=8.2 Hz, 1H), 7.82 (s, 1H), 7.59 (d, J=8.3 Hz, 1H), 3.30 (q, J=7.3 Hz, 2H), 2.37 (s, 6H), 1.19 (t, J=7.3 Hz, 3H). LCMS-ESI$^-$ (m/z): [M–H]$^-$ calcd 429.07; found 429.15.

General Synthesis 9

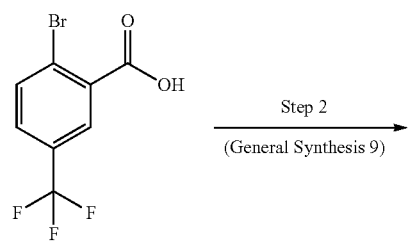

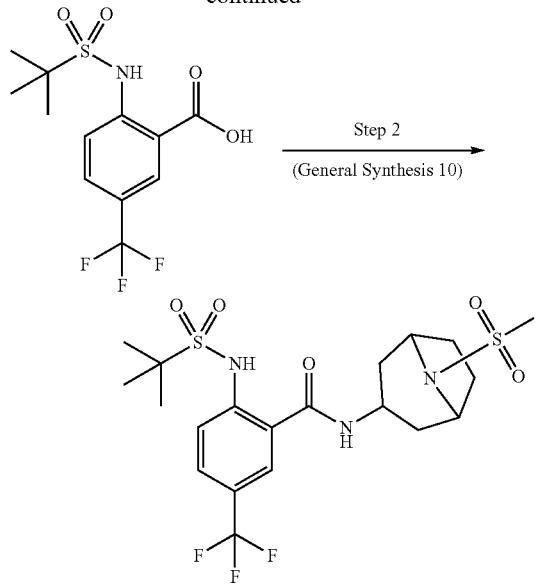

Step 1 (General Synthesis 9,): Preparation of 2-((1,1-dimethylethyl)sulfonamido)-5-(trifluoromethyl)benzoic acid A mixture of 2-bromo-5-(trifluoromethyl)benzoic acid (6.5 g, 24 mmol), 2-methylpropane-2-sulfonamide (4.6 g, 34 mmol), copper(I) iodide (0.92 g, 4.8 mmol), and potassium carbonate (8.4 g, 61 mmol) in N,N-dimethylformamide (DMF, 60 mL) was heated at 100° C. overnight. Upon cooling, the mixture was diluted with water and was acidified with hydrochloric acid. The mixture was extracted three times with ethyl acetate. The combined extracts were washed with saturated aqueous sodium chloride solution, dried over anhydrous magnesium sulfate, filtered, and concentrated under reduced pressure. The residue was purified by flash chromatography (silica gel) to provide the desired intermediate. LCMS-ESI$^-$ (m/z): [M–H]$^-$ calcd 324.06; found 324.05.

Step 2: Preparation of 2-((1,1-dimethylethyl)sulfonamido)-N-(8-(methylsulfonyl)-8-azabicyclo[3.2.1]octan-3-yl)-5-(trifluoromethyl)benzamide The titled compound, as a mixture of diastereomers, was prepared from 2-((1,1-dimethylethyl)sulfonamido)-5-(trifluoromethyl)benzoic acid (115 mg, 0.35 mmol) and 8-(methylsulfonyl)-8-azabicyclo[3.2.1]octan-3-amine (79 mg, 0.39 mmol) according to General Synthesis 10. $^1$H NMR (400 MHz, DMSO-$d_6$) δ 11.56 (s, 1H, diastereomer 1), 11.02 (s, 1H, diastereomer 2), 9.01 (d, J=7.9 Hz, 1H, diastereomer 1), 8.75 (m, 1H, diastereomer 2), 8.18 (d, J=2.0 Hz, 1H, diastereomer 1), 7.96 (d, J=2.0 Hz, 1H, diastereomer 2), 7.93 (d, J=3.0 Hz, 1H, diastereomer 1), 7.91 (d, J=3.0 Hz, 1H, diastereomer 2), 7.86 (m, 2H, diastereomers 1 and 2), 4.34 (tt, J=11.6, 6.0 Hz, 1H, diastereomer 1), 4.20 (m, 2H, diastereomer 1), 4.15 (s, 2H, diastereomer 2), 4.09-3.98 (m, 1H, diastereomer 2), 2.96 (s, 3H, diastereomer 1), 2.96 (s, 3H, diastereomer 2), 2.13 (m, 2H), 2.09-1.95 (m, 8H), 1.92 (dd, J=5.9, 3.0 Hz, 1H, diastereomer 1), 1.89 (dd, J=6.2, 2.8 Hz, 1H, diastereomer 2), 1.84-1.71 (m, 4H), 1.31 (s, 18H, diastereomers 1 and 2). LCMS-ESI$^-$ (m/z): [M–H]$^-$ calcd 510.14; found 510.31.

General Synthesis 10

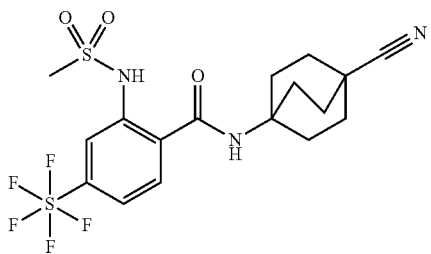 [SMILES: CS(=O)(=O)Nc1cc(S(F)(F)(F)(F)F)ccc1C(=O)NC12CCC(C#N)(CC1)CC2]

Example 117: Preparation of N-(4-cyanobicyclo [2.2.2]octan-1-yl)-2-(methylsulfonamido)-4-(pentafluoro-$\lambda^6$-sulfanyl)benzamide A magnetically stirred mixture in dichloromethane of 2-(methylsulfonamido)-4-(pentafluoro-$\lambda^6$-sulfanyl)benzoic acid (as described, in Example 146, 0.15 g, 0.44 mmol), 4-aminobicyclo[2.2.2]octane-1-carbonitrile hydrochloride (86 mg, 0.46 mmol), and O-(benzotriazol-1-yl)-N,N,N',N'-tetramethyluronium tetrafluoroborate (TBTU, 0.15 g, 0.48 mmol) was treated with N,N-diisopropylethylamine (0.23 mL, 1.3 mmol). After being allowed to stir overnight at room temperature, the mixture was purified by RP-HPLC (acetonitrile/water/0.1% trifluoroacetic acid) to provide the desired product. $^1$H NMR (400 MHz, DMSO-$d_6$) δ 10.22 (s, 1H), 8.29 (s, 1H), 7.85 (d, J=2.2 Hz, 1H), 7.83 (d, J=8.7 Hz, 1H), 7.77 (dd, J=8.7, 2.2 Hz, 1H), 3.12 (s, 3H), 1.99 (s, 12H). LCMS-ESI$^-$ (m/z): [M–H]$^-$ calcd 472.09; found 472.22.

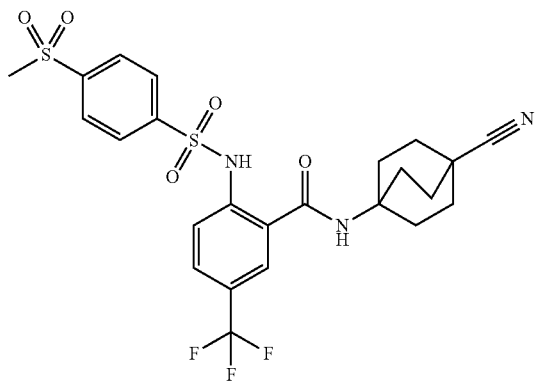 [SMILES: CS(=O)(=O)c1ccc(S(=O)(=O)Nc2ccc(C(F)(F)F)cc2C(=O)NC23CCC(C#N)(CC2)CC3)cc1]

Example 118: Synthesis of N-(4-cyanobicyclo [2.2.2]octan-1-yl)-2-((4-(methylsulfonyl)phenyl) sulfonamido)-5-(trifluoromethyl)benzamide 4-(Methylsulfonyl)benzenesulfonamide was prepared by treating 4-(methylsulfonyl)benzenesulfonyl chloride (500 mg, 2.0 mmol) with 28% by weight aqueous ammonium hydroxide solution (0.55 mL, 4.0 mmol) in methanol at 0° C. After warming to room temperature with stirring over 3 hours, the solid 4-(methylsulfonyl)benzenesulfonamide was collected by filtration, washed with water, and dried under reduced atmosphere. 2-((4-(Methylsulfonyl)phenyl)sulfonamido)-5-(trifluoromethyl)benzoic acid was prepared with General Synthesis 9, using 4-(methylsulfonyl)benzenesulfonamide (1.2 equiv.). 2-((4-(methylsulfonyl)phenyl)sulfonamido)-5-(trifluoromethyl)benzoic acid was subjected to General Synthesis 10 to afford N-(4-cyanobicyclo[2.2.2]octan-1-yl)-2-((4-(methylsulfonyl)phenyl)sulfonamido)-5-(trifluoromethyl)benzamide. $^1$H NMR (400 MHz, DMSO-$d_6$) δ 11.51 (s, 1H), 8.38 (s, 1H), 8.12 (d, J=8.6 Hz, 2H), 8.04 (d, J=8.6 Hz, 2H), 7.97 (s, 1H), 7.83 (d, J=8.7 Hz, 1H), 7.61 (d, J=8.6 Hz, 1H), 3.30 (s, 3H), 2.02-1.89 (m, 12H). LCMS-ESI$^-$ (m/z): [M–H]$^-$ calcd 554.10; found 554.34.

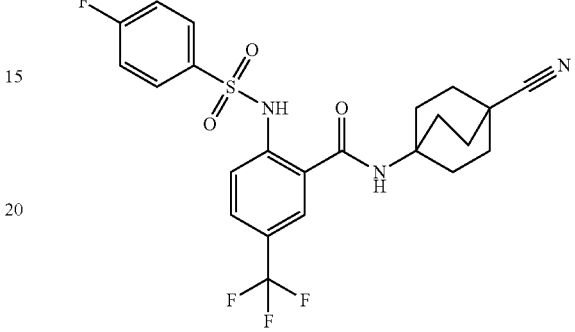

Example 119: Synthesis of N-(4-cyanobicyclo [2.2.2]octan-1-yl)-2-((4-fluorophenyl)sulfonamido)-5-(trifluoromethyl)benzamide 2-((4-Fluorophenyl)sulfonamido)-5-(trifluoromethyl) benzoic acid was prepared with General Synthesis 9, using 4-fluorobenzenesulfonamide (1.2 equiv.). 2-((4-Fluorophenyl)sulfonamido)-5-(trifluoromethyl)benzoic acid was subjected to General Synthesis 10 to afford N-(4-cyanobicyclo [2.2.2]octan-1-yl)-2-((4-fluorophenyl)sulfonamido)-5-(trifluoromethyl)benzamide. $^1$H NMR (400 MHz, DMSO-$d_6$) δ 11.39 (s, 1H), 8.38 (s, 1H), 7.96 (s, 1H), 7.89-7.83 (m, 2H), 7.82 (d, J=8.2 Hz, 1H), 7.61 (d, J=8.6 Hz, 1H), 7.43 (t, J=8.8 Hz, 2H), 1.99 (s, 12H). LCMS-ESI$^-$ (m/z): [M–H]$^-$ calcd 494.12; found 494.33.

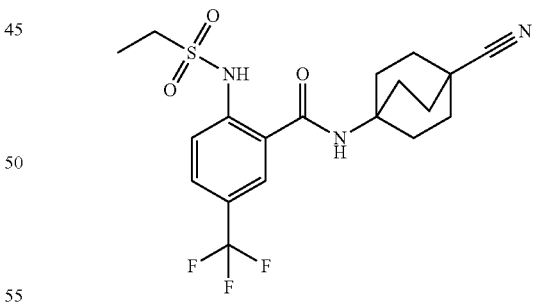

Example 120: Synthesis of N-(4-cyanobicyclo [2.2.2]octan-1-yl)-2-(ethylsulfonamido)-5-(trifluoromethyl)benzamide 2-(Ethylsulfonamido)-5-(trifluoromethyl)benzoic acid was prepared using General Synthesis 9, using ethanesulfonamide (1.5 equiv.). 2-(Ethylsulfonamido)-5-(trifluoromethyl)benzoic acid was subjected to General Synthesis 10 to afford N-(4-cyanobicyclo[2.2.2]octan-1-yl)-2-(ethylsulfonamido)-5-(trifluoromethyl)benzamide. $^1$H NMR (400

MHz, DMSO-d$_6$) δ 10.94 (s, 1H), 8.46 (s, 1H), 8.07 (s, 1H), 7.86 (d, J=8.7 Hz, 1H), 7.71 (d, J=8.7 Hz, 1H), 3.32-3.26 (m, 2H), 2.00 (s, 12H), 1.17 (t, J=7.3 Hz, 3H). LCMS-ESI$^-$ (m/z): [M−H]$^-$ calcd 428.13; found 428.29.

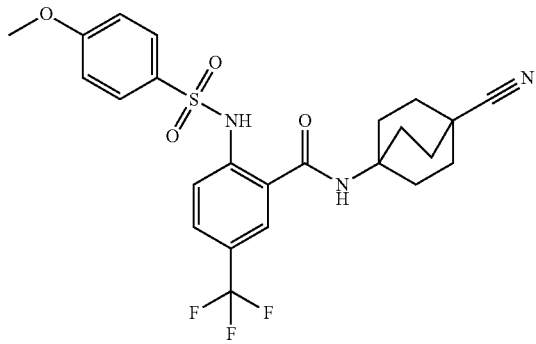 [SMILES: COc1ccc(S(=O)(=O)Nc2ccc(C(F)(F)F)cc2C(=O)NC23CCC(C#N)(CC2)CC3)cc1]

Example 121: Synthesis of N-(4-cyanobicyclo[2.2.2]octan-1-yl)-2-((4-methoxyphenyl)sulfonamido)-5-(trifluoromethyl)benzamide 2-((4-Methoxyphenyl)sulfonamido)-5-(trifluoromethyl)benzoic acid was prepared using General Synthesis 9, using 4-methoxybenzenesulfonamide (1.3 equiv.). 2-((4-Methoxyphenyl)sulfonamido)-5-(trifluoromethyl)benzoic acid was subjected to General Synthesis 10 to afford N-(4-cyanobicyclo[2.2.2]octan-1-yl)-2-((4-methoxyphenyl)sulfonamido)-5-(trifluoromethyl)benzamide. $^1$H NMR (400 MHz, DMSO-d$_6$) δ 11.30 (s, 1H), 8.37 (s, 1H), 7.95 (s, 1H), 7.80 (d, J=8.7 Hz, 1H), 7.76-7.67 (m, 2H), 7.63 (d, J=8.6 Hz, 1H), 7.20-6.94 (m, 2H), 3.80 (s, 3H), 1.99 (s, 12H). LCMS-ESI$^-$ (m/z): [M−H]$^-$ calcd 506.14; found 506.31.

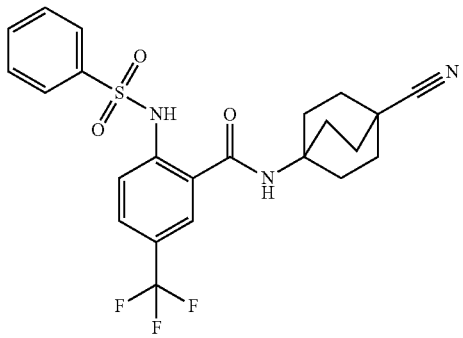 [SMILES: N#CC12CCC(NC(=O)c3cc(C(F)(F)F)ccc3NS(=O)(=O)c3ccccc3)(CC1)CC2]

Example 122: Synthesis of N-(4-cyanobicyclo[2.2.2]octan-1-yl)-2-(phenylsulfonamido)-5-(trifluoromethyl)benzamide 2-(Phenylsulfonamido)-5-(trifluoromethyl)benzoic acid was prepared with General Synthesis 9, using benzenesulfonamide (1.3 equiv.). 2-(Phenylsulfonamido)-5-(trifluoromethyl)benzoic acid was subjected to General Synthesis 10 to afford N-(4-cyanobicyclo[2.2.2]octan-1-yl)-2-(phenylsulfonamido)-5-(trifluoromethyl)benzamide. $^1$H NMR (400

MHz, DMSO-d$_6$) δ 11.42 (s, 1H), 8.36 (s, 1H), 7.96 (s, 1H), 7.85-7.75 (m, 3H), 7.65 (m, 2H), 7.58 (m, 2H), 1.99 (s, 12H). LCMS-ESI$^-$ (m/z): [M−H]$^-$ calcd 476.13; found 476.34.

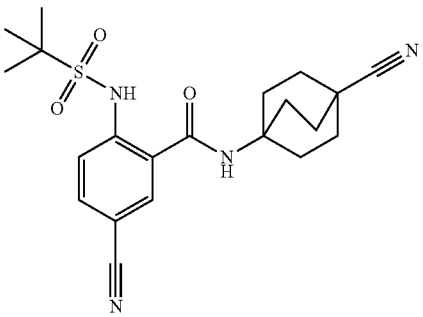 [SMILES: CC(C)(C)S(=O)(=O)Nc1ccc(C#N)cc1C(=O)NC12CCC(C#N)(CC1)CC2]

Example 123: Synthesis of 5-cyano-N-(4-cyanobicyclo[2.2.2]octan-1-yl)-2-((1,1-dimethylethyl)sulfonamido)benzamide 5-Cyano-2-((1,1-dimethylethyl)sulfonamido)benzoic acid was prepared with General Synthesis 9, using 2-methylpropane-2-sulfonamide (1.3 equiv.) and 2-bromo-5-cyanobenzoic acid (1.0 equiv.). 5-Cyano-2-((1,1-dimethylethyl)sulfonamido)benzoic acid was subjected to General Synthesis 10 to afford 5-cyano-N-(4-cyanobicyclo[2.2.2]octan-1-yl)-2-((1,1-dimethylethyl)sulfonamido)benzamide. $^1$H NMR (400 MHz, DMSO-d$_6$) δ 11.04 (s, 1H), 8.41 (s, 1H), 8.24 (d, J=1.8 Hz, 1H), 7.92 (dd, J=8.8, 1.5 Hz, 1H), 7.83 (d, J=8.8 Hz, 1H), 2.00 (s, 12H), 1.29 (s, 9H). LCMS-ESI$^+$ (m/z): [M+H]$^+$ calcd 415.18; found 414.81.

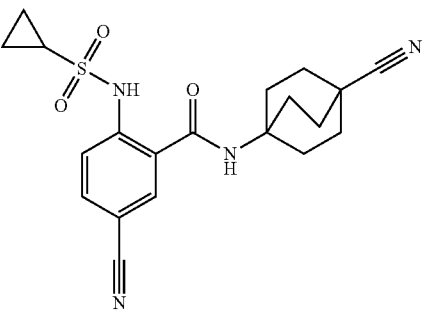 [SMILES: N#Cc1ccc(NS(=O)(=O)C2CC2)c(C(=O)NC23CCC(C#N)(CC2)CC3)c1]

Example 124: Synthesis of 5-cyano-N-(4-cyanobicyclo[2.2.2]octan-1-yl)-2-(cyclopropanesulfonamido)benzamide 5-Cyano-N-(4-cyanobicyclo[2.2.2]octan-1-yl)-2-(cyclopropanesulfonamido)benzamide was prepared by following General Synthesis 5, using cyclopropane-1-sulfonamide (1.5 equiv.) in Step 2. $^1$H NMR (400 MHz, DMSO-d$_6$) δ 11.15 (s, 1H), 8.33 (s, 1H), 8.31-8.22 (m, 1H), 7.95 (d, J=8.6 Hz, 1H), 7.69 (d, J=8.7 Hz, 1H), 2.94-2.84 (m, 1H), 2.00 (s, 12H), 1.03 (d, J=6.3 Hz, 4H). LCMS-ESI$^-$ (m/z): [M−H]$^-$ calcd 397.13; found 397.29.

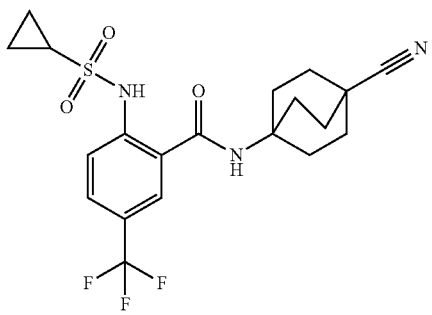 [SMILES: N#CC12CCC(NC(=O)c3cc(C(F)(F)F)ccc3NS(=O)(=O)C3CC3)(CC1)CC2]

Example 125: Synthesis of N-(4-cyanobicyclo[2.2.2]octan-1-yl)-2-(cyclopropanesulfonamido)-5-(trifluoromethyl)benzamide N-(4-cyanobicyclo[2.2.2]octan-1-yl)-2-(cyclopropanesulfonamido)-5-(trifluoromethyl)benzamide was prepared by following General Synthesis 5, using 2-bromo-5-(trifluoromethyl)benzoic acid (1.0 equiv.) in Step 1, and cyclopropane-1-sulfonamide (1.5 equiv.) in Step 2. $^1$H NMR (400 MHz, DMSO-$d_6$) δ 10.92 (s, 1H), 8.44 (s, 1H), 8.07 (s, 1H), 7.87 (d, J=8.8 Hz, 1H), 7.75 (d, J=8.7 Hz, 1H), 2.82 (p, J=6.4 Hz, 1H), 2.01 (s, 12H), 1.00 (d, J=5.7 Hz, 4H). LCMS-ESI$^-$ (m/z): [M−H]$^-$ calcd 440.13; found 440.30.

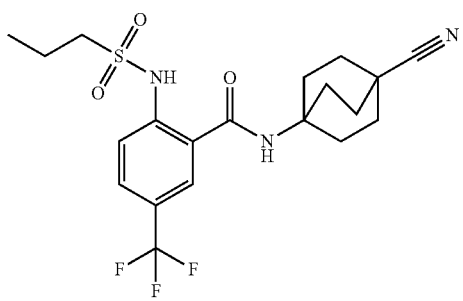 [SMILES: CCCS(=O)(=O)Nc1ccc(C(F)(F)F)cc1C(=O)NC12CCC(C#N)(CC1)CC2]

Example 126: Synthesis of N-(4-cyanobicyclo[2.2.2]octan-1-yl)-2-(propylsulfonamido)-5-(trifluoromethyl)benzamide N-(4-cyanobicyclo[2.2.2]octan-1-yl)-2-(propylsulfonamido)-5-(trifluoromethyl)benzamide was prepared by following General Synthesis 5, using 2-bromo-5-(trifluoromethyl)benzoic acid (1.0 equiv.) in Step 1, and propane-1-sulfonamide (1.7 equiv.) in Step 2. $^1$H NMR (400 MHz, DMSO-$d_6$) δ 10.93 (s, 1H), 8.46 (s, 1H), 8.06 (s, 1H), 7.86 (d, J=8.7 Hz, 1H), 7.71 (d, J=8.7 Hz, 1H), 3.35-3.21 (m, 2H), 2.01 (s, 12H), 1.65 (h, J=7.4 Hz, 2H), 0.93 (t, J=7.4 Hz, 3H). LCMS-ESI$^-$ (m/z): [M−H]$^-$ calcd 442.14; found 442.27.

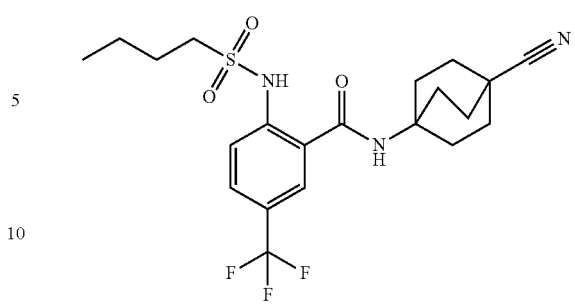

Example 127: Synthesis of 2-(butylsulfonamido)-N-(4-cyanobicyclo[2.2.2]octan-1-yl)-5-(trifluoromethyl)benzamide 2-(Butylsulfonamido)-N-(4-cyanobicyclo[2.2.2]octan-1-yl)-5-(trifluoromethyl)benzamide was prepared by following General Synthesis 5, using 2-bromo-5-(trifluoromethyl)benzoic acid (1.0 equiv.) in Step 1, and butane-1-sulfonamide (1.7 equiv.) in Step 2. $^1$H NMR (400 MHz, DMSO-$d_6$) δ 10.96 (s, 1H), 8.46 (s, 1H), 8.07 (s, 1H), 7.87 (d, J=8.7 Hz, 1H), 7.71 (d, J=8.7 Hz, 1H), 3.32-3.27 (m, 2H), 2.01 (s, 12H), 1.60 (p, J=7.5 Hz, 2H), 1.33 (h, J=7.4 Hz, 2H), 0.82 (t, J=7.3 Hz, 3H). LCMS-ESI$^+$ (m/z): [M+H]$^+$ calcd 458.17; found 458.00.

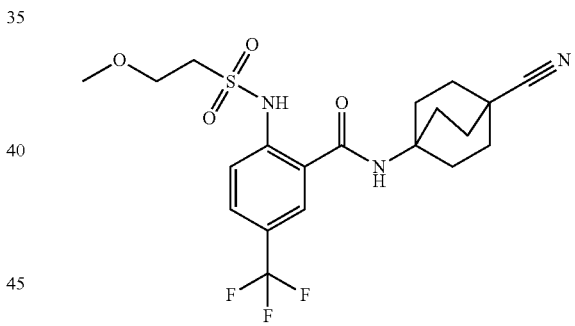

Example 128: Synthesis of N-(4-cyanobicyclo[2.2.2]octan-1-yl)-2-((2-methoxyethyl)sulfonamido)-5-(trifluoromethyl)benzamide N-(4-Cyanobicyclo[2.2.2]octan-1-yl)-2-((2-methoxyethyl)sulfonamido)-5-(trifluoromethyl)benzamide was prepared by following General Synthesis 5, using 2-bromo-5-(trifluoromethyl)benzoic acid (1.0 equiv.) in Step 1, and 2-methoxyethane-1-sulfonamide (1.5 eq.) in Step 2. $^1$H NMR (400 MHz, DMSO-$d_6$) δ 11.09 (s, 1H), 8.41 (s, 1H), 8.07 (s, 1H), 7.85 (d, J=8.7 Hz, 1H), 7.72 (d, J=8.7 Hz, 1H), 3.64 (t, J=5.1 Hz, 2H), 3.60-3.56 (m, 2H), 3.10 (s, 3H), 2.01 (s, 12H). LCMS-ESI$^+$ (m/z): [M+H]$^+$ calcd 460.15; found 460.00.

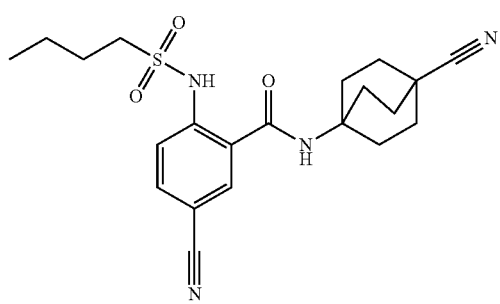 [SMILES: CCCCS(=O)(=O)Nc1ccc(C#N)cc1C(=O)NC12CCC(C#N)(CC1)CC2]

Example 129: Synthesis of 2-(butylsulfonamido)-5-cyano-N-(4-cyanobicyclo[2.2.2]octan-1-yl)benzamide 2-(Butylsulfonamido)-5-cyano-N-(4-cyanobicyclo[2.2.2]octan-1-yl)benzamide was prepared by following General Synthesis 5, using butane-1-sulfonamide (1.5 eq.) in Step 2. $^1$H NMR (400 MHz, DMSO-d$_6$) δ 11.14 (s, 1H), 8.34 (s, 1H), 8.27 (d, J=1.9 Hz, 1H), 7.95 (dd, J=8.7, 1.9 Hz, 1H), 7.66 (d, J=8.7 Hz, 1H), 3.39-3.29 (m, 2H), 2.00 (s, 12H), 1.60 (p, J=7.5 Hz, 2H), 1.33 (h, J=7.4 Hz, 2H), 0.82 (t, J=7.3 Hz, 3H). LCMS-ESI$^-$ (m/z): [M–H]$^-$ calcd 413.16; found 413.26.

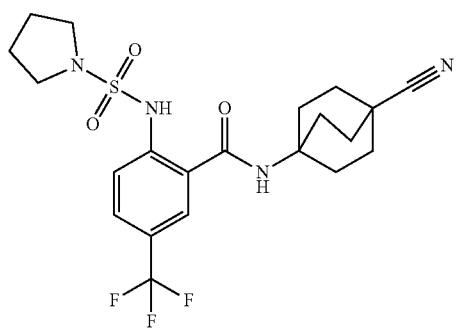 [SMILES: N#CC12CCC(NC(=O)c3cc(C(F)(F)F)ccc3NS(=O)(=O)N3CCCC3)(CC1)CC2]

Example 130: Synthesis of N-(4-cyanobicyclo[2.2.2]octan-1-yl)-2-(pyrrolidine-1-sulfonamido)-5-(trifluoromethyl)benzamide N-(4-cyanobicyclo[2.2.2]octan-1-yl)-2-(pyrrolidine-1-sulfonamido)-5-(trifluoromethyl)benzamide was prepared by following General Synthesis 5, using 2-bromo-5-(trifluoromethyl)benzoic acid (1.0 equiv.) in Step 1, and pyrrolidine-1-sulfonamide (1.5 eq.) in Step 2. $^1$H NMR (400 MHz, DMSO-d$_6$) δ 10.92 (s, 1H), 8.47 (s, 1H), 8.04 (s, 1H), 7.86 (d, J=8.7 Hz, 1H), 7.70 (d, J=8.7 Hz, 1H), 3.18 (t, J=6.7 Hz, 4H), 2.01 (s, 12H), 1.79-1.71 (m, 4H). LCMS-ESI$^-$ (m/z): [M–H]$^-$ calcd 469.15; found 469.32.

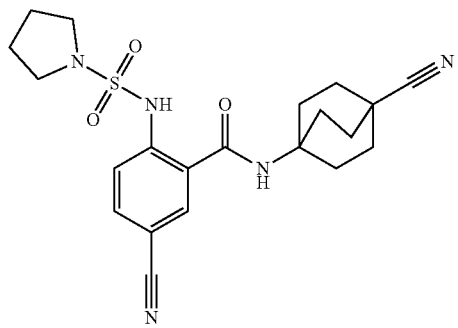 [SMILES: N#Cc1ccc(NS(=O)(=O)N2CCCC2)c(C(=O)NC23CCC(C#N)(CC2)CC3)c1]

Example 131: Synthesis of 5-cyano-N-(4-cyanobicyclo[2.2.2]octan-1-yl)-2-(pyrrolidine-1-sulfonamido)benzamide 5-Cyano-N-(4-cyanobicyclo[2.2.2]octan-1-yl)-2-(pyrrolidine-1-sulfonamido)benzamide was prepared by following General Synthesis 5, using pyrrolidine-1-sulfonamide (1.5 eq.) in Step 2. $^1$H NMR (400 MHz, DMSO-d$_6$) δ 11.12 (s, 1H), 8.35 (s, 1H), 8.25 (s, 1H), 7.94 (d, J=8.7 Hz, 1H), 7.63 (d, J=8.7 Hz, 1H), 3.19 (t, J=6.6 Hz, 4H), 2.00 (s, 12H), 1.79-1.72 (m, 4H). LCMS-ESI$^-$ (m/z): [M–H]$^-$ calcd 426.16; found 426.30.

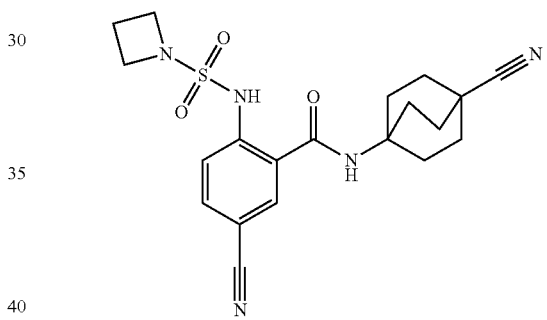

Example 132: Synthesis of 2-(azetidine-1-sulfonamido)-5-cyano-N-(4-cyanobicyclo[2.2.2]octan-1-yl)benzamide 2-(Azetidine-1-sulfonamido)-5-cyano-N-(4-cyanobicyclo[2.2.2]octan-1-yl)benzamide was prepared by following General Synthesis 5, using azetidine-1-sulfonamide (1.5 eq.) in Step 2. $^1$H NMR (400 MHz, DMSO-d$_6$) δ 11.25 (s, 1H), 8.35 (s, 1H), 8.28 (s, 1H), 7.96 (d, J=8.1 Hz, 1H), 7.64 (d, J=8.6 Hz, 1H), 3.82 (t, J=7.6 Hz, 4H), 2.14 (p, J=7.4 Hz, 2H), 2.00 (s, 12H). LCMS-ESI$^-$ (m/z): [M–H]$^-$ calcd 412.14; found 412.30.

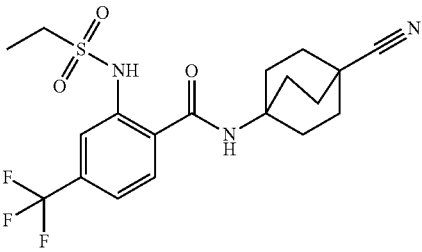 [SMILES: CCS(=O)(=O)Nc1cc(C(F)(F)F)ccc1C(=O)NC12CCC(C#N)(CC1)CC2]

Example 133: Synthesis of N-(4-cyanobicyclo[2.2.2]octan-1-yl)-2-(ethylsulfonamido)-4-(trifluoromethyl)benzamide 2-Bromo-N-(4-cyanobicyclo[2.2.2]octan-1-yl)-4-(trifluoromethyl)benzamide was prepared by following General Synthesis 3 Step 4 using 2-bromo-4-(trifluoromethyl)benzoic acid (1.0 equiv.) and 4-aminobicyclo[2.2.2]octane-1-carbonitrile hydrochloride (1.2 equiv.). N-(4-cyanobicyclo[2.2.2]octan-1-yl)-2-(ethylsulfonamido)-4-(trifluoromethyl)benzamide was prepared by following General Synthesis 8, using 2-bromo-N-(4-cyanobicyclo[2.2.2]octan-1-yl)-4-(trifluoromethyl)benzamide (1.0 equiv.) and ethanesulfonamide (3.0 equiv.). $^1$H NMR (400 MHz, DMSO-d$_6$) δ 10.47 (s, 1H), 8.37 (s, 1H), 7.89 (d, J=8.1 Hz, 1H), 7.77 (s, 1H), 7.56 (d, J=7.9 Hz, 1H), 3.24 (q, J=7.3 Hz, 2H), 2.00 (s, 12H), 1.18 (t, J=7.3 Hz, 3H). LCMS-ESI$^-$ (m/z): [M−H]$^-$ calcd 428.13; found 428.24.

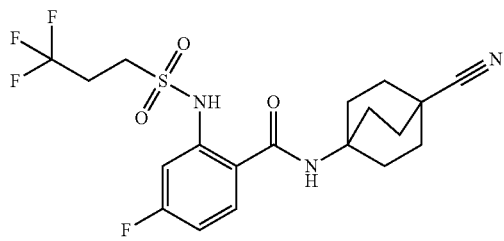 [SMILES: N#CC12CCC(NC(=O)c3ccc(F)cc3NS(=O)(=O)CCC(F)(F)F)(CC1)CC2]

Example 134: Synthesis of N-(4-cyanobicyclo[2.2.2]octan-1-yl)-4-fluoro-2-((3,3,3-trifluoropropyl)sulfonamido)benzamide 4-Fluoro-2-((3,3,3-trifluoropropyl)sulfonamido)benzoic acid was prepared by following General Synthesis 9, using 2-bromo-4-fluorobenzoic acid (1.0 equiv.) and 3,3,3-trifluoropropane-1-sulfonamide (1.2 equiv.). 4-Fluoro-2-((3,3,3-trifluoropropyl)sulfonamido)benzoic acid was subjected to General Synthesis 10 to afford N-(4-cyanobicyclo[2.2.2]octan-1-yl)-4-fluoro-2-((3,3,3-trifluoropropyl)sulfonamido)benzamide. $^1$H NMR (400 MHz, DMSO-d$_6$) δ 11.18 (s, 1H), 8.18 (s, 1H), 7.83 (dd, J=8.8, 6.4 Hz, 1H), 7.31 (dd, J=10.9, 2.5 Hz, 1H), 7.07 (td, J=8.5, 2.3 Hz, 1H), 3.63-3.53 (m, 2H), 2.81-2.62 (m, 2H), 1.98 (s, 12H). LCMS-ESI$^-$ (m/z): [M−H]$^-$ calcd 446.12; found 446.22.

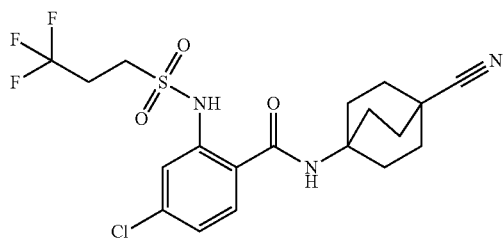 [SMILES: N#CC12CCC(NC(=O)c3ccc(Cl)cc3NS(=O)(=O)CCC(F)(F)F)(CC1)CC2]

Example 135: Synthesis of 4-chloro-N-(4-cyanobicyclo[2.2.2]octan-1-yl)-2-((3,3,3-trifluoropropyl)sulfonamido)benzamide 4-Chloro-2-((3,3,3-trifluoropropyl)sulfonamido)benzoic acid was prepared by following General Synthesis 9, using 2-bromo-4-chlorobenzoic acid (1.0 equiv.) and 3,3,3-trifluoropropane-1-sulfonamide (1.2 equiv.). 4-Chloro-2-((3,3,3-trifluoropropyl)sulfonamido)benzoic acid was subjected to General Synthesis 10 to afford 4-chloro-N-(4-cyanobicyclo[2.2.2]octan-1-yl)-2-((3,3,3-trifluoropropyl)sulfonamido)benzamide. $^1$H NMR (400 MHz, DMSO-d$_6$) δ 10.92 (s, 1H), 8.22 (s, 1H), 7.74 (d, J=8.5 Hz, 1H), 7.52 (d, J=2.0 Hz, 1H), 7.30 (dd, J=8.4, 1.8 Hz, 1H), 3.62-3.51 (m, 2H), 2.80-2.64 (m, 2H), 1.98 (s, 12H). LCMS-ESI$^-$ (m/z): [M−H]$^-$ calcd 462.09; found 462.27.

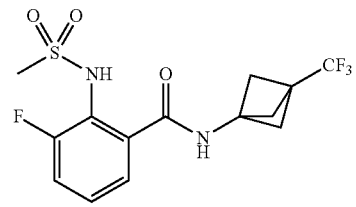

Example 136: Preparation of 3-fluoro-2-(methylsulfonamido)-N-(3-(trifluoromethyl)bicyclo[1.1.1]pentan-1-yl)benzamide

Step 1: Preparation of 3-fluoro-2-(methylsulfonamido)benzoic acid

The titled intermediate was prepared from 2-amino-3-fluorobenzoic acid in the manner analogous to that which furnished 2-(methylsulfonamido)-5-(trifluoromethyl)benzoic acid from 2-amino-5-(trifluoromethyl)benzoic acid. $^1$H NMR (400 MHz, DMSO-d$_6$) δ 13.67 (bs, 1H), 9.60 (bs, 1H), 7.70 (dt, J=7.8, 1.2 Hz, 1H), 7.55 (ddd, J=10.8, 8.3, 1.5 Hz, 1H), 7.35 (td, J=8.1, 5.1 Hz, 1H), 3.15 (s, 3H).

Step 2: Preparation of 3-fluoro-2-(methylsulfonamido)-N-(3-(trifluoromethyl)bicyclo[1.1.1]pentan-1-yl)benzamide The titled compound was prepared via the coupling of 3-fluoro-2-(methylsulfonamido)benzoic acid (0.13 g, 0.54 mmol) and 3-(trifluoromethyl)bicyclo[1.1.1]pentan-1-amine hydrochloride (0.11 g, 0.57 mmol) according to step 3 of General Synthesis 4. $^1$H NMR (400 MHz, DMSO-d$_6$) δ 9.57 (s, 1H), 9.29 (s, 1H), 7.45 (ddd, J=10.1, 7.2, 2.6 Hz, 1H), 7.38 (m, 2H), 3.09 (s, 3H), 2.32 (s, 6H). LCMS-ESI$^+$ (m/z): [M+H]$^+$ calcd 367.1; found 367.0.

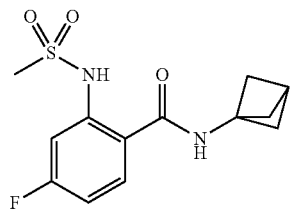 [SMILES: CS(=O)(=O)Nc1cc(F)ccc1C(=O)NC12CC(C1)C2]

Example 137: Preparation of N-(bicyclo[1.1.1]pentan-1-yl)-4-fluoro-2-(methylsulfonamido)benzamide A mixture of 4-fluoro-2-(methylsulfonamido)benzoic acid (0.12 g, 0.52 mmol) and 1-bicyclo[1.1.1]pentan-1-amine hydrochloride (65 mg, 0.54 mmol, 1.05 eq) in N,N- dimethylformamide (DMF, 2.5 mL) was treated with N,N-diisopropylethylamine (DIEA, 0.27 mL, 1.5 mmol). After a brief sonication, the mixture was treated with 1-[bis(dimethylamino)methylene]-1H-1,2,3-triazolo[4,5-b]pyridinium 3-oxide hexafluorophosphate (henceforth "HATU," 0.24 g, 0.64 mmol). After the coupling reaction was deemed to be complete, the mixture was concentrated under reduced pressure and purified by reverse-phase HPLC (acetonitrile/water/0.1% trifluoroacetic acid) to provide the desired product. $^1$H NMR (400 MHz, DMSO-$d_6$) δ 11.70 (s, 1H), 9.34 (s, 1H), 7.93 (dd, J=8.9, 6.3 Hz, 1H), 7.30 (dd, J=11.2, 2.6 Hz, 1H), 7.01 (ddd, J=8.9, 8.1, 2.6 Hz, 1H), 3.22 (s, 3H), 2.49 (s, 1H), 2.10 (s, 6H). LCMS-ESI$^+$ (m/z): [M+H]$^+$ calcd 299.1; found 299.0.

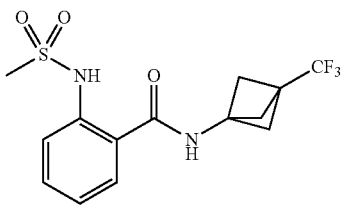 [SMILES: CS(=O)(=O)Nc1ccccc1C(=O)NC12CC(C(F)(F)F)(C1)C2]

Example 138: Preparation of 2-(methylsulfonamido)-N-(3-(trifluoromethyl)bicyclo[1.1.1]pentan-1-yl)benzamide A mixture of 2-(methylsulfonamido)benzoic acid (76 mg, 0.35 mmol) in N,N-dimethylformamide/pyridine (5:1, 3 mL) and THF (0.50 mL) was sonicated and then treated with 1-[bis(dimethylamino)methylene]-1H-1,2,3-triazolo[4,5-b]pyridinium 3-oxid hexafluorophosphate (HATU, 0.17 g, 0.44 mmol). After 90 minutes, the mixture was treated successively with N,N-diisopropylethylamine (DIEA, 75 μL, 0.42 mmol) and 3-(trifluoromethyl)bicyclo[1.1.1]pentan-1-amine hydrochloride (73 mg, 0.39 mmol). The reaction mixture was sonicated for one minute and then after 20 minutes, it was concentrated and purified by reverse-phase high performance liquid chromatography (acetonitrile/water/0.1% trifluoroacetic acid) to provide the titled product. $^1$H NMR (400 MHz, DMSO-$d_6$) δ 11.08 (s, 1H), 9.55 (s, 1H), 7.83 (dd, J=7.8, 1.3 Hz, 1H), 7.64-7.48 (m, 2H), 7.18 (ddd, J=8.3, 6.3, 2.2 Hz, 1H), 3.15 (s, 3H), 2.35 (s, 6H). LCMS-ESI$^+$ (m/z): [M+H]$^+$ calcd 349.08; found 349.01.

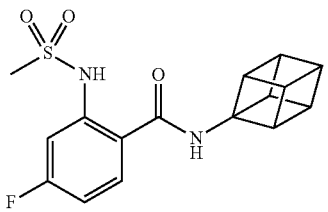 [SMILES: CS(=O)(=O)Nc1cc(F)ccc1C(=O)NC12C3C4C5C3C1C5C42]

Example 139: Preparation of N-(cuban-1-yl)-4-fluoro-2-(methylsulfonamido)benzamide Analogously to step 3 of General Synthesis 4, 4-fluoro-2-(methylsulfonamido)benzoic acid (80 mg, 0.34 mmol) was coupled to cuban-1-amine hydrochloride (PharmaBlock, 1.05 eq) to provide the desired product. $^1$H NMR (400 MHz, DMSO-$d_6$) δ 11.76 (s, 1H), 9.51 (s, 1H), 8.02 (dd, J=9.0, 6.3 Hz, 1H), 7.31 (dd, J=11.2, 2.6 Hz, 1H), 7.05 (ddd, J=8.9, 8.1, 2.6 Hz, 1H), 4.20 (m, 3H), 3.94 (m, 4H), 3.22 (s, 3H). LCMS-ESI$^+$ (m/z): [M+H]$^+$ calcd 335.1; found: 335.0.

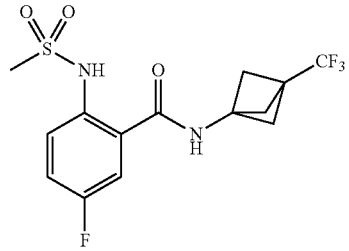 [SMILES: CS(=O)(=O)Nc1ccc(F)cc1C(=O)NC12CC(C(F)(F)F)(C1)C2]

Example 140: Preparation of 5-fluoro-2-(methylsulfonamido)-N-(3-(trifluoromethyl)bicyclo[1.1.1]pentan-1-yl)benzamide Analogously to step 3 of General Synthesis 4, 5-fluoro-2-(methylsulfonamido)benzoic acid (Enamine, 0.10 g, 0.43 mmol) was coupled to 3-(trifluoromethyl)bicyclo[1.1.1]pentan-1-amine hydrochloride (1.1 eq) to provide the desired product. $^1$H NMR (400 MHz, DMSO-$d_6$) δ 10.68 (s, 1H), 9.55 (s, 1H), 7.68 (dd, J=9.7, 3.0 Hz, 1H), 7.55 (dd, J=9.1, 5.0 Hz, 1H), 7.44 (ddd, J=9.1, 8.0, 2.9 Hz, 1H), 3.10 (s, 3H), 2.35 (s, 6H). LCMS-ESI$^+$ (m/z): [M+H]$^+$ calcd 367.1; found 367.0.

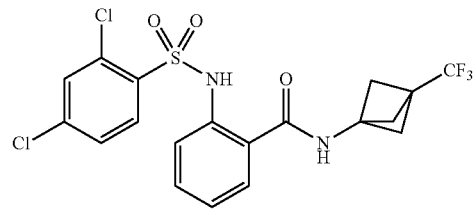 [SMILES: O=C(NC12CC(C(F)(F)F)(C1)C2)c1ccccc1NS(=O)(=O)c1ccc(Cl)cc1Cl]

Example 141: Preparation of 2-((2,4-dichlorophenyl)sulfonamido)-N-(3-(trifluoromethyl)bicyclo[1.1.1]pentan-1-yl)benzamide Step 1: Preparation of 2-((2,4-dichlorophenyl)sulfonamido)benzoic acid A mixture of anthranilic acid (1.4 g, 10 mmol) in water (100 mL) was treated with sodium hydroxide (0.57 g, 14 mmol). After the mixture was sonicated for two minutes, 2,4-dichlorobenzenesulfonyl chloride (2.5 g, 10 mmol) was added in a single portion. The mixture was sonicated for approximately 20 minutes before being left to stir magnetically overnight. On the following day, the mixture was heated at 75° C. for one hour. After cooling, the mixture was treated with dichloromethane, and the resulting biphasic mixture was acidified to approximately pH 1 with hydrochloric acid. The aqueous phase was extracted three times with dichloromethane. The combined organic extracts were dried over anhydrous magnesium sulfate, filtered, and concentrated under reduced pressure. The residue was purified by reverse-phase HPLC (acetonitrile/water/0.1% trifluoroacetic acid) to provide the desired intermediate. $^1$H NMR (400 MHz, DMSO-$d_6$) δ 11.77 (s, 1H), 8.19 (d, J=8.6 Hz, 1H), 7.95 (dd, J=8.0, 1.6 Hz, 1H), 7.88 (d, J=2.1 Hz, 1H), 7.68 (dd, J=8.6, 2.1 Hz, 1H), 7.50 (ddd, J=8.4, 7.3, 1.7 Hz, 1H), 7.38 (dd, J=8.5, 1.1 Hz, 1H), 7.16-7.07 (m, 1H).

Step 2: Preparation of 2-((2,4-dichlorophenyl)sulfonamido)-N-(3-(trifluoromethyl)bicyclo[1.1.1]pentan-1-yl)benzamide Analogously to step 3 of General Synthesis 4, 2-((2,4-dichlorophenyl)sulfonamido)benzoic acid (0.13 g, 0.36 mmol) was coupled to 3-(trifluoromethyl)bicyclo[1.1.1]pentan-1-amine hydrochloride (1.05 eq) to provide the desired product. $^1$H NMR (400 MHz, DMSO-$d_6$) δ 11.86 (s, 1H), 9.57 (s, 1H), 8.09 (d, J=8.6 Hz, 1H), 7.89 (d, J=2.1 Hz, 1H), 7.72 (dd, J=8.0, 1.4 Hz, 1H), 7.64 (dd, J=8.6, 2.1 Hz, 1H), 7.42 (m, 2H), 7.13 (td, J=7.5, 1.5 Hz, 1H), 2.36 (s, 6H). LCMS-ESI$^+$ (m/z): [M+H]$^+$ calcd 479.0; found 478.9.

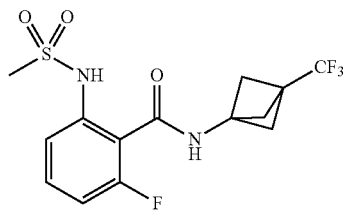 [SMILES: CS(=O)(=O)Nc1cccc(F)c1C(=O)NC12CC(C(F)(F)F)(C1)C2]

Example 142: Preparation of 2-fluoro-6-(methylsulfonamido)-N-(3-(trifluoromethyl)bicyclo[1.1.1]pentan-1-yl)benzamide Step 1: Preparation of 2-fluoro-6-(methylsulfonamido)benzoic acid A mixture of 2-amino-6-fluorobenzoic acid (2.1 g, 14 mmol) and saturated aqueous sodium hydrogen carbonate solution (21 mL) was sonicated, and then to the magnetically stirred mixture was added methanesulfonyl chloride (1.3 mL, 16 mmol). 1,4-dioxane (12 mL) was added and stirring was continued. The mixture was acidified to approximately pH 1 with hydrochloric acid. No evolution of gas was observed. The mixture was partitioned with dichloromethane. The aqueous phase was extracted three times with dichloromethane. The combined organic extracts were dried over anhydrous magnesium sulfate, filtered, and concentrated. The residue was purified by reverse-phase HPLC (acetonitrile/water/0.1% trifluoroacetic acid) to provide the desired intermediate. $^1$H NMR (400 MHz, DMSO-$d_6$) δ 10.58 (s, 1H), 10.50 (s, 1H), 7.97 (dd, J=8.8, 6.3 Hz, 1H), 7.80-7.68 (m, 2H), 7.50-7.40 (m, 2H), 7.35 (dd, J=11.1, 2.6 Hz, 1H), 7.14 (td, J=8.5, 2.5 Hz, 1H), 3.21 (s, 3H).

Step 2: Preparation of 2-fluoro-6-(methylsulfonamido)-N-(3-(trifluoromethyl)bicyclo[1.1.1]pentan-1-yl)benzamide Analogously to step 3 of General Synthesis 4, 2-fluoro-6-(methylsulfonamido)benzoic acid (88 mg, 0.38 mmol) was coupled to 3-(trifluoromethyl)bicyclo[1.1.1]pentan-1-amine hydrochloride (1.05 eq) to provide the desired product. $^1$H NMR (400 MHz, DMSO-$d_6$) δ 9.51 (s, 1H), 9.33 (s, 1H), 7.48 (td, J=8.3, 6.4 Hz, 1H), 7.33-7.23 (m, 1H), 7.13 (ddd, J=9.5, 8.4, 1.0 Hz, 1H), 3.08 (s, 3H), 2.33 (s, 6H). LCMS-ESI$^+$ (m/z): [M+H]$^+$ calcd 367.1; found 367.0.

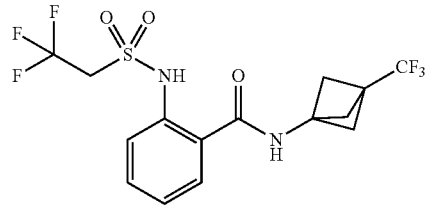 [SMILES: O=C(NC12CC(C(F)(F)F)(C1)C2)c1ccccc1NS(=O)(=O)CC(F)(F)F]

Example 143: Preparation of 2-((2,2,2-trifluoroethyl)sulfonamido)-N-(3-(trifluoromethyl)bicyclo[1.1.1]pentan-1-yl)benzamide Step 1: Preparation of 2-((2,2,2-trifluoroethyl)sulfonamido)benzoic acid A mixture of 2-aminobenzoic acid (0.75 g, 5.5 mmol) and pyridine (0.67 mL, 8.2 mmol) in dichloromethane (15 mL) was cooled in a wet ice/acetone bath and treated dropwise with a solution of 2,2,2-trifluoroethylsulfonyl chloride (1.0 g, 5.5 mmol) in dichloromethane (2 mL). The stirred mixture was allowed to gradually warm to room temperature as the bath extinguished overnight. Aqueous hydrochloric acid (10%, approximately 20 mL) was added. The resulting biphasic suspension was stirred for 3 days. The solid was collected by filtration, washed with dichloromethane, and dried to provide the desired intermediate. $^1$H NMR (400 MHz, DMSO-$d_6$) δ 11.26 (s, 1H), 8.02 (ddd, J=7.9, 1.5, 0.6 Hz, 1H), 7.70-7.60 (m, 2H), 7.24 (ddd, J=7.9, 6.7, 1.8 Hz, 1H), 4.83 (q, J=9.8 Hz, 2H).

Step 2: 2-((2,2,2-trifluoroethyl)sulfonamido)-N-(3-(trifluoromethyl)bicyclo[0.1.1]pentan-1-yl)benzamide Analogously to Step 3 of General Synthesis 4, 2-((2,2,2-trifluoroethyl)sulfonamido)benzoic acid (0.10 g, 0.35 mmol) was coupled to 3-(trifluoromethyl)bicyclo[1.1.1]pentan-1-amine hydrochloride (1.05 eq) to provide the desired product. $^1$H NMR (400 MHz, DMSO-$d_6$) δ 11.62 (s, 1H), 9.59 (s, 1H), 7.86-7.78 (m, 1H), 7.60-7.54 (m, 2H), 7.23 (ddd, J=8.3, 5.1, 3.4 Hz, 1H), 4.77 (q, J=9.8 Hz, 2H), 2.35 (s, 6H). LCMS-ESI$^+$ (m/z): [M+H]$^+$ calcd 417.1; found 417.0.

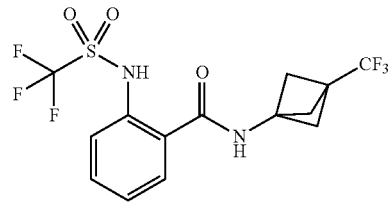 [SMILES: O=C(NC12CC(C(F)(F)F)(C1)C2)c1ccccc1NS(=O)(=O)C(F)(F)F]

Example 144: Preparation of N-(3-(trifluoromethyl)bicyclo[1.1.1]pentan-1-yl)-2-((trifluoromethyl)sulfonamido)benzamide A sealed mixture of 2-((trifluoromethyl)sulfonamido)benzoic acid (0.10 g, 0.37 mmol) and thionyl chloride (0.46 mL, 6.3 mmol) was heated overnight at 85° C. The mixture was concentrated under reduced pressure and co-evaporated once from toluene. The putative acid chloride was taken up in dichloromethane (1 mL) and added dropwise to a suspension of 3-(trifluoromethyl)bicyclo[1.1.1]pentan-1-amine hydrochloride (70 mg, 0.37 mmol) and sodium hydrogen carbonate (0.16 g, 1.9 mmol) in dichloromethane (3 mL). The mixture was stirred for approximately 10 days at room temperature. The mixture was then partitioned between ethyl acetate and 1% aqueous hydrochloric acid. The aqueous phase was extracted twice with ethyl acetate. The combined organic extracts were washed once with saturated aqueous sodium chloride solution, dried over anhydrous magnesium sulfate, filtered, and concentrated to dryness under reduced pressure. The residue was purified by reverse-phase HPLC (acetonitrile/water/0.1% trifluoroacetic acid) to provide the desired product. $^1$H NMR (400 MHz, DMSO-$d_6$) δ 9.93 (s, 1H), 7.75 (dd, J=7.8, 1.6 Hz, 1H), 7.48 (td, J=7.7, 7.2, 1.6 Hz, 1H), 7.41 (dd, J=8.2, 1.2 Hz, 1H), 7.26 (t, J=7.6 Hz, 1H), 2.32 (s, 6H). LCMS-ESI$^+$ (m/z): [M+H]$^+$ calcd 403.1; found 403.1.

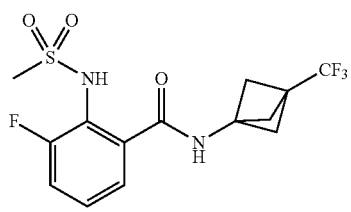 [SMILES: CS(=O)(=O)Nc1c(F)cccc1C(=O)NC12CC(C(F)(F)F)(C1)C2]

Example 145: Preparation of 3-fluoro-2-(methylsulfonamido)-N-(3-(trifluoromethyl)bicyclo[1.1.1]pentan-1-yl)benzamide Analogously to Step 3 of General Synthesis 4, 3-fluoro-2-(methylsulfonamido)benzoic acid (Enamine, 0.13 g, 0.54 mmol) was coupled to 3-(trifluoromethyl)bicyclo[1.1.1]pentan-1-amine hydrochloride (1.05 eq) to provide the desired product. $^1$H NMR (400 MHz, DMSO-$d_6$) δ 9.57 (s, 1H), 9.29 (s, 1H), 7.45 (ddd, J=10.1, 7.2, 2.6 Hz, 1H), 7.38 (m, 2H), 3.09 (s, 3H), 2.32 (s, 6H). LCMS-ESI$^+$ (m/z): [M+H]$^+$ calcd 367.1; found 367.0.

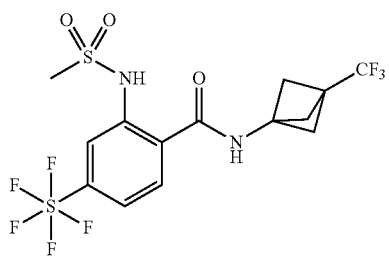 [SMILES: CS(=O)(=O)Nc1cc(S(F)(F)(F)(F)F)ccc1C(=O)NC12CC(C(F)(F)F)(C1)C2]

Example 146: Preparation of 2-(methylsulfonamido)-4-(pentafluoro-$\lambda^6$-sulfanyl)-N-(3-(trifluoromethyl)bicyclo[1.1.1]pentan-1-yl)benzamide Step 1: Preparation of 2-nitro-4-(pentafluoro-$\lambda^6$-sulfanyl)benzoic acid In a pressure vessel, 4-(pentafluoro-$\lambda^6$-sulfanyl)benzoic acid) (10 g, 41 mmol)) was taken up as a suspension in nitric acid (fuming, 98%, 80 mL) and sonicated to give a homogeneous suspension. Sulfuric acid (oleum, 5 ml) was added. The vessel was sealed and the suspension was stirred at 100° C. for two days. After cooling to room temperature, the suspension was poured onto ice (approximately 800 g) and swirled vigorously. The solid was collected by filtration to provide the desired material. Additional material was obtained via an extractive workup of the filtrate. LCMS-ESI$^-$ (m/z): [M−H]$^-$ calcd 291.98; found 291.77.

Step 2: Preparation of 2-amino-4-(pentafluoro-$\lambda^6$-sulfanyl)benzoic acid

An aqueous slurry of Raney Nickel (approximately 2 mL) was added to a solution of 2-nitro-4-(pentafluoro-$\lambda^6$-sulfanyl)benzoic acid (2.9, 9.8 mmol) in methanol (100 mL). The resulting suspension was stirred for three hours under an atmosphere of hydrogen and then was filtered through a pad of Celite diatomaceous earth. The filtrate was concentrated under reduced pressure to provide the desired material. LCMS-ESI$^+$ (m/z): [M+H]$^+$ calcd 264.00; found 263.96.

Step 3: Preparation of methyl 2-amino-4-(pentafluoro-$\lambda^6$-sulfanyl)benzoate To a cooled (ice water bath) mixture of 2-amino-4-(pentafluoro-$\lambda^6$-sulfanyl)benzoic acid (2.45 mmol) in 2-methyltetrahydrofuran (50 mL) and methanol (10 mL) was added a 2.0 M solution of trimethylsilyldiazomethane in hexane (1.8 mL, 3.7 mmol) via syringe over 5 minutes. After stirring overnight at room temperature, the mixture was cooled in an ice-water bath and quenched with the addition of acetic acid (3 mL). The mixture was concentrated under reduced pressure, and the resulting residue was purified by flash chromatography (silica gel) to provide the desired material. LCMS-ESI$^+$ (m/z): [M+H]$^+$ calcd 278.02; found 277.94.

Step 4: Preparation of 2-(methylsulfonamido)-4-(pentafluoro-$\lambda^6$-sulfanyl)benzoic acid The titled intermediate was prepared from methyl 2-amino-4-(pentafluoro-$\lambda^6$-sulfanyl)benzoate in a manner analogous to that which furnished 4-fluoro-2-(methylsulfonamido)benzoic acid from methyl 2-amino-4-fluorobenzoate (General Synthesis 1, steps 1 and 2). LCMS-ESI$^+$ (m/z): [M+H]$^+$ calcd 339.98; found 340.16.

Step 5: Preparation of 2-(methylsulfonamido)-4-(pentafluoro-$\lambda^6$-sulfanyl)-N-(3-(trifluoromethyl)bicyclo[1.1.1]pentan-1-yl)benzamide Analogously to Step 3 of General Synthesis 4, 2-(methylsulfonamido)-4-(pentafluoro-$\lambda^6$-sulfanyl)benzoic acid (98 mg, 0.29 mmol) was coupled to 3-(trifluoromethyl)bicyclo[1.1.1]pentan-1-amine hydrochloride (1.2 eq) to provide the desired product. $^1$H NMR (400 MHz, DMSO-$d_6$) δ 10.88 (s, 1H), 9.72 (s, 1H), 7.97 (d, J=8.8 Hz, 1H), 7.94 (d, J=2.3 Hz, 1H), 7.78 (dd, J=8.8, 2.3 Hz, 1H), 3.18 (s, 3H), 2.37 (s, 6H). LCMS-ESI$^-$ (m/z): [M−H]$^-$ calcd 473.0; found 473.3.

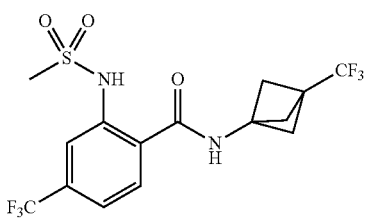 [SMILES: CS(=O)(=O)Nc1cc(C(F)(F)F)ccc1C(=O)NC12CC(C(F)(F)F)(C1)C2]

Example 147: Preparation of 2-(methylsulfonamido)-4-(trifluoromethyl)-N-(3-(trifluoromethyl) bicyclo[1.1.1]pentan-1-yl)benzamide Analogously to Step 3 of General Synthesis 4, 2-(methylsulfonamido)-4-(trifluoromethyl)benzoic acid (0.13 g, 0.45 mmol) was coupled to 3-(trifluoromethyl)bicyclo [1.1.1]pentan-1-amine hydrochloride (1.05 eq) to provide the desired product. $^1$H NMR (400 MHz, DMSO-$d_6$) δ 11.01 (s, 1H), 9.73 (s, 1H), 8.00 (d, J=8.2 Hz, 1H), 7.79 (d, J=1.7 Hz, 1H), 7.58 (dd, J=8.4, 1.8 Hz, 1H), 3.21 (s, 3H), 2.37 (s, 6H). LCMS-ESI⁻ (m/z): [M−H]⁻ calcd 415.1; found 415.4.

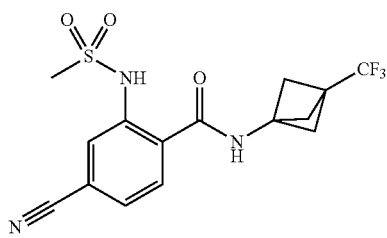 [SMILES: CS(=O)(=O)Nc1cc(C#N)ccc1C(=O)NC12CC(C(F)(F)F)(C1)C2]

Example 148: Preparation of 4-cyano-2-(methylsulfonamido)-N-(3-(trifluoromethyl)bicyclo[1.1.1] pentan-1-yl)benzamide

Step 1: Preparation of 4-iodo-2-(methylsulfonamido)benzoic acid

The titled intermediate was prepared from methyl 2-amino-4-iodobenzoate in a manner analogous to that which furnished 2-(methylsulfonamido)-5-(trifluoromethyl) benzoic acid. LCMS-ESI⁻ (m/z): [M−H]⁻ calcd 339.92; found 340.04.

Step 2: Preparation of 4-cyano-2-(methylsulfonamido)benzoic acid

A mixture of 4-iodo-2-(methylsulfonamido)benzoic acid (0.95 g, 2.8 mmol) and cuprous cyanide (0.32 g, 3.6 mmol) in N,N-dimethylformamide (DMF, 5 mL) was stirred overnight at 140° C. The mixture was filtered through a pad of Celite diatomaceous earth, and the filtrate was concentrated under reduced pressure. The residue was taken up in water (approximately 25 mL), treated with N,N-ethylenediamine (approximately 5 mL), and then acidified with 10% aqueous hydrochloric acid. The aqueous mixture was extracted three times with ethyl acetate. The combined extracts were washed once each with water, 10% aqueous hydrochloric acid, and saturated aqueous sodium chloride solution. The combined organic layers were dried over anhydrous magnesium sulfate, filtered, and concentrated under reduced pressure to provide the desired intermediate. LCMS-ESI⁻ (m/z): [M−H]⁻ calcd 239.02; found 239.03.

Step 3: Preparation of 4-cyano-2-(methylsulfonamido)-N-(3-(trifluoromethyl)bicyclo[1.1.1]pentan-1-yl)benzamide Analogously to Step 3 of General Synthesis 4, 4-cyano-2-(methylsulfonamido)benzoic acid (0.12 g, 0.50 mmol) was coupled to 3-(trifluoromethyl)bicyclo[1.1.1]pentan-1-amine hydrochloride (1.05 eq) to provide the desired product. $^1$H NMR (400 MHz, DMSO-$d_6$) δ 10.95 (s, 1H), 9.73 (s, 1H), 7.93 (d, J=8.2 Hz, 1H), 7.86 (d, J=1.5 Hz, 1H), 7.67 (dd, J=8.2, 1.6 Hz, 1H), 3.28 (s, 3H), 2.36 (s, 6H). LCMS-ESI⁻ (m/z): [M−H]⁻ calcd 372.1; found 372.3.

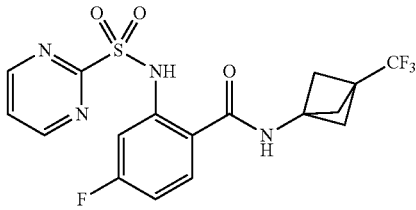 [SMILES: O=C(NC12CC(C(F)(F)F)(C1)C2)c1ccc(F)cc1NS(=O)(=O)c1ncccn1]

Example 149: Preparation of 4-fluoro-2-(pyrimidine-2-sulfonamido)-N-(3-(trifluoromethyl)bicyclo [1.1.1]pentan-1-yl)benzamide

Step 1: Preparation of methyl 4-fluoro-2-(N-(pyrimidin-2-ylsulfonyl)pyrimidine-2-sulfonamido) benzoate A suspension of 2-mercaptopyrimidine (1.1 g, 10 mmol, 1.0 equiv) in a mixture of dichloromethane (50 mL) and a 1 M solution of hydrochloric acid having 25 wt % of calcium chloride (50 mL) was sonicated to a homogeneity and then was cooled to an internal temperature of −30 to −25° C. Calcium chloride hexahydrate (38 g) was dissolved in sodium hypochlorite (8.25% solution, 1 M, 33 mL, 33 mmol, 3.3 equiv), and the resulting clear solution was added dropwise to the stirred solution of 2-mercaptopyrimidine while maintaining the internal temperature at −30 to −25° C. The resulting slurry was stirred for 15 min at −30 to −25° C. (internal temperature) before it was diluted with of ice/water (50 mL) and poured into a separatory funnel (pre-cooled with ice water). The organic phase was rapidly separated and collected in a flask cooled in a Dry Ice-acetone bath. Methyl 2-amino-4-fluorobenzoate (3.4 g, 20 mmol, 2.0 eq) was added with stirring. The flask was moved to an ice-water bath and the mixture was stirred for 60 min at 0° C. To the resulting suspension was added anhydrous magnesium sulfate. The slurry was filtered and concentrated under reduced pressure. The residue was taken up in warm toluene, giving a suspension, which after filtration recovered unreacted methyl 2-amino-4-fluorobenzoate. The concentrated filtrate was purified by flash chromatography (silica gel) to furnish the desired intermediate. $^1$H NMR (400 MHz, DMSO-$d_6$) δ 10.96 (s, 1H), 9.03 (d, J=4.9 Hz, 2H), 8.71 (d, J=4.8 Hz, 2H), 7.99 (dd, J=8.9, 6.5 Hz, 1H), 7.81 (t, J=4.9 Hz, 1H), 7.47-7.31 (m, 2H), 7.08 (td, J=8.5, 2.5 Hz, 1H), 3.85 (s, 3H).

Step 2: Preparation of 4-fluoro-2-(pyrimidine-2-sulfonamido)benzoic acid

A solution of methyl 4-fluoro-2-(N-(pyrimidin-2-ylsulfonyl)pyrimidine-2-sulfonamido)benzoate (0.92 g, 2.0 mmol) in tetrahydrofuran (15 mL) was treated with a solution of aqueous sodium hydroxide (4M, 2.0 mL, 8.1 mmol). Water was added to the resulting suspension to give a homogeneous mixture was stirred for four hours at room temperature and was then refrigerated overnight. An additional volume of sodium hydroxide solution (0.5 mL) was added. At the completion of the reaction, the mixture was acidified to approximately pH 1 by the addition of 10% aqueous hydrochloric acid. The aqueous phase was extracted three times with ethyl acetate. The combined extracts were washed once with saturated aqueous sodium chloride solution, dried over anhydrous magnesium sulfate, filtered, and concentrated to dryness under reduced pressure. The residue was triturated with hot isopropanol. After cooling, the solid was collected by filtration, washed with cold isopropanol, and dried to provide the desired intermediate. LCMS-ESI⁻ (m/z): [M−H]⁻ calcd 296.02; found 296.17.

Step 3: Preparation of 4-fluoro-2-(pyrimidine-2-sulfonamido)-N-(3-(trifluoromethyl)bicyclo[1.1.1]pentan-1-yl)benzamide Following General Synthesis 4, 4-fluoro-2-(pyrimidine-2-sulfonamido)benzoic acid (86 mg, 0.29 mmol) was coupled to 3-(trifluoromethyl)bicyclo[1.1.1]pentan-1-amine hydrochloride (0.32 mmol, 1.1 eq) in Step 3 to provide the desired product. ¹H NMR (400 MHz, DMSO-d₆) δ 12.14 (s, 1H), 9.62 (s, 1H), 9.02 (d, J=4.9 Hz, 2H), 7.87 (dd, J=8.9, 6.2 Hz, 1H), 7.81 (t, J=4.9 Hz, 1H), 7.33 (dd, J=11.0, 2.6 Hz, 1H), 7.15-6.94 (m, 1H), 2.36 (s, 6H). LCMS-ESI⁺ (m/z): [M+H]⁺ calcd 431.07; found 431.06.

Example 150: Preparation of 5-(methylsulfonyl)-2-((4-(pentafluoro-λ⁶-sulfanyl)phenyl)sulfonamido)-N-(3-(trifluoromethyl)bicyclo[1.1.1]pentan-1-yl)benzamide Preparation of 5-(methylsulfonyl)-2-((4-(pentafluoro-λ⁶-sulfanyl)phenyl)sulfonamido)-N-(3-(trifluoromethyl)bicyclo[1.1.1]pentan-1-yl)benzamide Following General Synthesis 4 using methyl 2-amino-5-(methylsulfonyl)benzoate (described elsewhere in this document, 0.40 g, 1.7 mmol) and 4-(pentafluorosulfanyl)benzene sulfonyl chloride (1.0 eq) in Step 1 and 3-(trifluoromethyl)bicyclo[1.1.1]pentan-1-amine hydrochloride (0.27 mmol, 1.1 eq) in Step 3, the desired product was synthesized. ¹H NMR (400 MHz, DMSO-d₆) δ 12.01 (bs, 1H), 9.88 (s, 1H), 8.27 (d, J=2.1 Hz, 1H), 8.16 (m, 2H), 8.09 (m, 2H), 8.00 (m, 1H), 7.65 (d, J=8.7 Hz, 1H), 3.19 (s, 3H), 2.34 (s, 6H). LCMS-ESI⁺ (m/z): [M+H]⁺ calcd 615.0; found 614.9.

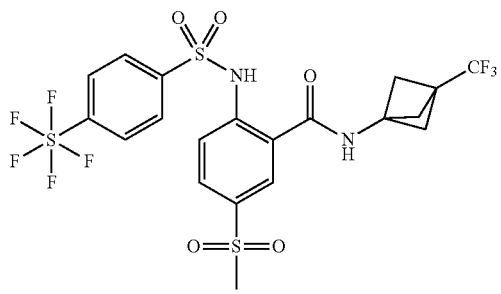 [SMILES: CS(=O)(=O)c1ccc(NS(=O)(=O)c2ccc(S(F)(F)(F)(F)F)cc2)c(C(=O)NC23CC(C(F)(F)F)(C2)C3)c1]

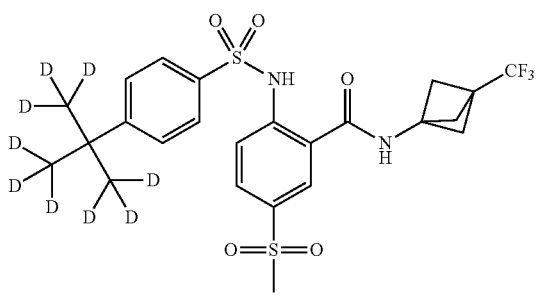 [SMILES: [2H]C([2H])([2H])C(c1ccc(S(=O)(=O)Nc2ccc(S(C)(=O)=O)cc2C(=O)NC23CC(C(F)(F)F)(C2)C3)cc1)(C([2H])([2H])[2H])C([2H])([2H])[2H]]

Example 151: Preparation of 2-((4-(2-(methyl-d₃)propan-2-yl-1,1,1,3,3,3-d₆)phenyl)sulfonamido)-5-(methylsulfonyl)-N-(3-(trifluoromethyl)bicyclo[1.1.1]pentan-1-yl)benzamide Step 1: Preparation of methyl 2-amino-5-(methylsulfonyl)benzoate To a cooled (ice water bath) mixture of 2-amino-5-(methylsulfonyl)benzoic acid (1.7 g, 7.8 mmol) in tetrahydrofuran (30 mL) and methanol (5 mL) was added a 2.0 M solution of trimethylsilyldiazomethane in hexane (5.8 mL, 12 mmol) via syringe. The mixture was allowed to stir in the cooling bath for 10 minutes before it was removed. After stirring at room temperature for 20 minutes, the mixture was quenched by the addition of acetic acid (approximately 1 mL). The mixture was concentrated under reduced pressure, and the resulting residue was co-evaporated once from toluene to provide the desired material. LCMS-ESI⁺ (m/z): [M+H]⁺ calcd 230.04; found 229.92.

Step 2: Preparation of 2-((4-(2-(methyl-d₃)propan-2-yl-1,1,1,3,3,3-d₆)phenyl)sulfonamido)-5-(methylsulfonyl)-N-(3-(trifluoromethyl)bicyclo[1.1.1]pentan-1-yl)benzamide Following General Synthesis 4, using 4-(2-(methyl-d₃)propan-2-yl-1,1,1,3,3,3-d₆)benzenesulfonyl chloride (2.1 mmol) and methyl 2-amino-5-(methylsulfonyl)benzoate (1.7 mmol) in Step 1 and 3-(trifluoromethyl)bicyclo[1.1.1]pentan-1-amine hydrochloride (0.32 mmol, 1.2 equiv) in Step 3, the title compound was synthesized. ¹H NMR (400 MHz, DMSO-d₆) δ 11.95 (s, 1H), 9.85 (s, 1H), 8.28 (d, J=2.1 Hz, 1H), 8.00 (d, J=8.8 Hz, 1H), 7.82 (d, J=8.6 Hz, 2H), 7.69 (d, J=8.8 Hz, 1H), 7.62 (d, J=8.5 Hz, 2H), 3.18 (s, 3H), 2.37 (s, 6H). LCMS-ESI⁺ (m/z): [M+H]⁺ calcd 554.2; found 554.1.

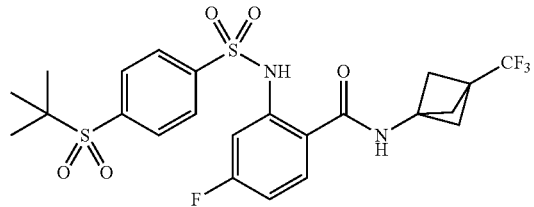 [SMILES: CC(C)(C)S(=O)(=O)c1ccc(S(=O)(=O)Nc2cc(F)ccc2C(=O)NC23CC(C(F)(F)F)(C2)C3)cc1]

Example 152: Preparation of 2-((4-(tert-butylsulfonyl)phenyl)sulfonamido)-4-fluoro-N-(3-(trifluoromethyl)bicyclo[1.1.1]pentan-1-yl)benzamide Following General Synthesis 4, 2-((4-(tert-butylsulfonyl)phenyl)sulfonamido)-4-fluorobenzoic acid (0.15 g, 0.31 mmol) and 3-(trifluoromethyl)bicyclo[1.1.1]pentan-1-amine hydrochloride (1.1 eq) were coupled in Step 3 to provide the desired product. ¹H NMR (400 MHz, DMSO-d₆) δ 11.76 (s, 1H), 9.46 (s, 1H), 7.99 (s, 4H), 7.77 (dd, J=8.9, 6.2 Hz, 1H), 7.25 (dd, J=10.5, 2.6 Hz, 1H), 7.12 (m, 1H), 2.29 (s, 6H), 1.21 (s, 9H). LCMS-ESI⁺ (m/z): [M+H]⁺ calcd 549.11; found 548.95.

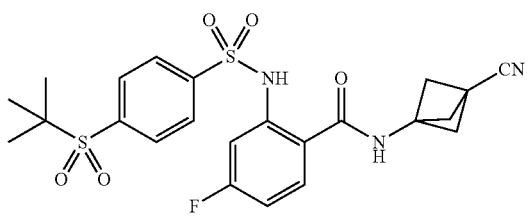 [SMILES: CC(C)(C)S(=O)(=O)c1ccc(S(=O)(=O)Nc2cc(F)ccc2C(=O)NC23CC(C#N)(C2)C3)cc1]

Example 153: Preparation of 2-((4-(tert-butylsulfonyl)phenyl)sulfonamido)-N-(3-cyanobicyclo[1.1.1]pentan-1-yl)-4-fluorobenzamide Step 1: Preparation of methyl 4-fluoro-2-((4-iodophenyl)sulfonamido)benzoate The titled intermediate was prepared from methyl 2-amino-4-fluorobenzoate (1.0 g, 5.9 mmol) and 4-iodobenzenesulfonyl chloride, according to General Synthesis 4. LCMS-ESI+ (m/z): [M+H]+ calcd 435.94; found 435.80.

Step 2: Preparation of tributyl(tert-butylthio)stannane

To a solution of 2-methyl-2-propanethiol (1.3 g, 15 mmol) and triethylamine (2.5 mL, 18 mmol) in dry carbon tetrachloride (100 mL) under Argon was added tributyltin chloride (4.1 mL, 15 mmol) dropwise over 20 minutes, with vigorous magnetic stirring. The suspension was stirred for 2 days at room temperature and was allowed to stand overnight for one more day. The suspension was filtered through a pad of Celite diatomaceous earth. The filtrate was washed successively with 5% aqueous acetic acid (100 mL) and water (100 mL). The organic layer was dried over anhydrous magnesium sulfate, filtered, and concentrated to give the putative desired intermediate, which was carried forward without further purification.

Step 3: Preparation of methyl 2-((4-(tert-butylthio)phenyl)sulfonamido)-4-fluorobenzoate A mixture in N,N-dimethylformamide (DMF, 10 mL) of methyl 4-fluoro-2-((4-iodophenyl)sulfonamido)benzoate (0.90 g, 2.1 mmol), tributyl(tert-butylthio)stannane (1.6 g, 4.2 mmol), and tetrakis(triphenylphosphine)palladium(0) (0.18 g, 0.16 mmol, 7.5 mol %) was heated in a microwave reactor for 30 minutes at 130° C. After cooling, the mixture was concentrated under reduced pressure. The residue was diluted with diethyl ether and was washed three times with 10% aqueous potassium fluoride solution. The organic phase was dried over anhydrous magnesium sulfate, filtered, and concentrated under reduced pressure to give the crude desired intermediate, which was carried forward without further purification. LCMS-ESI+ (m/z): [M+H]+ calcd 398.08; found 397.89.

Step 4: Preparation of methyl 2-((4-(tert-butylsulfonyl)phenyl)sulfonamido)-4-fluorobenzoate A solution of crude methyl 2-((4-(tert-butylthio)phenyl)sulfonamido)-4-fluorobenzoate (2.1 mmol assumed) in dichlormethane (50 mL) was cooled in an ice-water bath while stirring while 3-chloroperoxybenzoic acid (mCPBA, ≤77%, 1.4 g, 6.2 mmol) was added in a single portion. The mixture was removed from the cooling bath after 10 minutes. After stirring for approximately 2.5 hours, an additional portion of 3-chloroperoxybenzoic acid (mCPBA, ≤77%, 0.60 g, 2.7 mmol) was added. After being stirring overnight at room temperature, the reaction mixture was diluted with ethyl acetate, washed twice with saturated aqueous sodium hydrogen carbonate solution, once with saturated aqueous sodium chloride solution, dried over anhydrous magnesium sulfate, filtered, and concentrated under reduced pressure. The residue was purified by flash chromatography (silica gel) to furnish the desired intermediate. LCMS-ESI− (m/z): [M−H]− calcd 428.07; found 428.18.

Step 5: Preparation of 2-((4-(tert-butylsulfonyl)phenyl)sulfonamido)-4-fluorobenzoic acid A mixture of chromatographed methyl 2-((4-(tert-butylsulfonyl)phenyl)sulfonamido)-4-fluorobenzoate (0.66 g, 1.5 mmol) in tetrahydrofuran/methanol/water (2:2:1, 15 mL) was treated with sodium hydroxide (0.37 g, 9.2 mmol) and then sonicated for 10 minutes before being heated gently to promote homogeneity. After 90 minutes of standing at room temperature, the mixture was acidified with 10% aqueous hydrochloric acid. The acidic aqueous mixture was extracted three times with ethyl acetate. The combined extracts were washed once with saturated aqueous sodium chloride solution, dried over anhydrous magnesium sulfate, filtered, and concentrated to provide the desired intermediate. LCMS-ESI− (m/z): [M−H]− calcd 414.06; found 414.13.

Step 6: Preparation of 2-((4-(tert-butylsulfonyl)phenyl)sulfonamido)-N-(3-cyanobicyclo[1.1.1]pentan-1-yl)-4-fluorobenzamide Following General Synthesis 4, 2-((4-(tert-butylsulfonyl)phenyl)sulfonamido)-4-fluorobenzoic acid (0.15 g, 0.31 mmol) and 3-aminobicyclo[1.1.1]pentane-1-carbonitrile (1.1 eq) were coupled in Step 3 to provide the desired product. 1H NMR (400 MHz, DMSO-d6) δ 11.72 (s, 1H), 9.45 (s, 1H), 7.99 (s, 4H), 7.74 (dd, J=9.0, 6.2 Hz, 1H), 7.24 (dd, J=10.5, 2.6 Hz, 1H), 7.11 (td, J=8.5, 2.6 Hz, 1H), 2.53 (s, 6H), 1.22 (s, 9H). LCMS-ESI+ (m/z): [M+H]+ calcd 506.11; found 505.95.

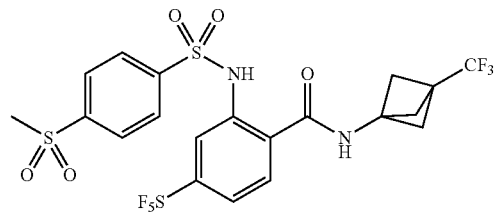

Example 154: Preparation of 2-((4-(methylsulfonyl)phenyl)sulfonamido)-4-(pentafluoro-λ6-sulfanyl)-N-(3-(trifluoromethyl)bicyclo[1.1.1]pentan-1-yl)benzamide Following General Synthesis 4, 2-((4-(methylsulfonyl)phenyl)sulfonamido)-4-(pentafluoro-λ6-sulfanyl)benzoic acid (0.15 g, 0.31 mmol) and 3-(trifluoromethyl)bicyclo[1.1.1]pentan-1-amine hydrochloride (1.1 eq) were coupled in Step 3 to provide the desired product. 1H NMR (400 MHz, DMSO-d6) δ 11.22 (bs, 1H), 9.62 (bs, 1H), 8.13 (m, 2H), 7.95 (m, 2H), 7.83 (m, 2H), 7.76 (m, 1H), 3.28 (s, 3H), 2.30 (s, 6H). LCMS-ESI⁺ (m/z): [M+H]⁺ calcd 615.03; found 614.92.

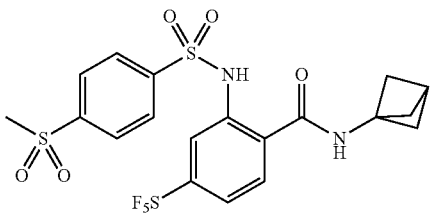

Example 155: Preparation of N-(bicyclo[1.1.1]pentan-1-yl)-2-((4-(methylsulfonyl)phenyl)sulfonamido)-4-(pentafluoro-λ⁶-sulfanyl)benzamide Following General Synthesis 4 using methyl 2-amino-4-(pentafluoro-λ⁶-sulfanyl)benzoate (described elsewhere in this document, 1.0 g, 3.6 mmol) and 4-(methylsulfonyl) benzenesulfonyl chloride (1.0 eq) in Step 1 and bicyclo [1.1.1]pentan-1-amine hydrochloride (0.31 mmol, 1.1 eq) in Step 3, the desired product was synthesized. ¹H NMR (400 MHz, DMSO-d₆) δ 11.51 (s, 1H), 9.42 (s, 1H), 8.12 (d, J=8.5 Hz, 2H), 7.96 (d, J=8.5 Hz, 2H), 7.86 (d, J=8.6 Hz, 1H), 7.81-7.73 (m, 2H), 3.27 (s, 3H), 2.48 (s, 1H), 2.06 (s, 6H). LCMS-ESI⁺ (m/z): [M+H]⁺ calcd 547.04; found 546.95.

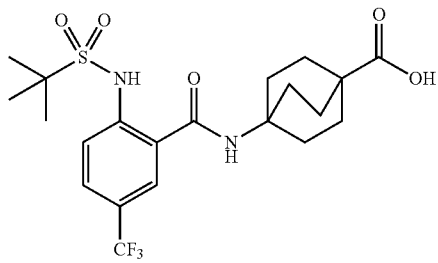 [SMILES: CC(C)(C)S(=O)(=O)Nc1ccc(C(F)(F)F)cc1C(=O)NC12CCC(C(=O)O)(CC1)CC2]

Example 156: Preparation of 4-(2-((1,1-dimethylethyl)sulfonamido)-5-(trifluoromethyl)benzamido) bicyclo[2.2.2]octane-1-carboxylic acid Step 1: Preparation of methyl 4-(2-((1,1-dimethylethyl)sulfonamido)-5-(trifluoromethyl)benzamido) bicyclo[2.2.2]octane-1-carboxylate Following General Synthesis 4, 2-((1,1-dimethylethyl) sulfonamido)-5-(trifluoromethyl)benzoic acid (0.22 g, 0.67 mmol) was coupled to methyl 4-aminobicyclo[2.2.2]octane-1-carboxylate hydrochloride (1.1 eq) in Step 3, providing, after flash chromatography, the desired product. LCMS-ESI⁺ (m/z): [M+H]⁺ calcd 491.17; found 490.91.

Step 2: Preparation of 4-(2-((1,1-dimethylethyl) sulfonamido)-5-(trifluoromethyl)benzamido)bicyclo [2.2.2]octane-1-carboxylic acid A mixture of methyl 4-(2-((1,1-dimethylethyl)sulfonamido)-5-(trifluoromethyl)benzamido)bicyclo[2.2.2]octane-1-carboxylate (0.12 g, 0.25 mmol) in tetrahydrofuran/methanol/water (2:2:1, 15 mL) was treated with sodium hydroxide (60 mg, 1.5 mmol) and heated at 65° C. for one hour. The mixture was acidified with 10% hydrochloric acid and concentrated under reduced pressure. The residue was purified by reverse-phase HPLC (acetonitrile/water/0.1% trifluoroacetic acid) to provide the desired product. ¹H NMR (400 MHz, DMSO-d₆) δ 10.90 (s, 1H), 8.50 (s, 1H), 8.02 (d, J=2.1 Hz, 1H), 7.89 (d, J=8.8 Hz, 1H), 7.83 (dd, J=9.0, 2.1 Hz, 1H), 2.04-1.94 (m, 6H), 1.85-1.74 (m, 6H), 1.29 (s, 9H). LCMS-ESI⁻ (m/z): [M−H]⁻ calcd 475.16; found 475.32.

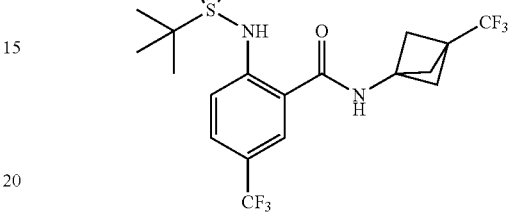

Example 157: Preparation of 2-((1,1-dimethylethyl) sulfonamido)-5-(trifluoromethyl)-N-(3-(trifluoromethyl)bicyclo[1.1.1]pentan-1-yl)benzamide Step 1: Preparation of methyl 2-iodo-5-(trifluoromethyl)benzoate To a cooled (ice water bath) mixture of 2-iodo-5-(trifluoromethyl)benzoic acid (2.5 g, 7.9 mmol) in tetrahydrofuran (50 mL) and methanol (10 mL) was added dropwise a 0.6 M solution of trimethylsilyldiazomethane in hexane (TCI America, 16 mL, 9.9 mmol) via syringe. After LC/MS analysis confirmed the consumption of the starting acid, acetic acid (approximately 3 mL) was added. The mixture was concentrated under reduced pressure, and the putative desired intermediate was carried forward without further purification.

Step 2: Preparation of methyl 2-((tert-butylsulfinyl) amino)-5-(trifluoromethyl)benzoate Following Step 3 of General Synthesis 3, methyl 2-iodo-5-(trifluoromethyl)benzoate (2.6 g, 7.9 mmol) was coupled to 2-methylpropane-2-sulfinamide (1.2 eq). After an aqueous work-up, the crude residue was purified by flash chromatography (silica gel) to provide the desired intermediate. LCMS-ESI⁺ (m/z): [M+H]⁺ calcd 324.08; found 323.79.

Step 3: Preparation of methyl 2-((1,1-dimethylethyl)sulfonamido)-5-(trifluoromethyl)benzoate To a solution of methyl 2-((tert-butylsulfinyl)amino)-5-(trifluoromethyl)benzoate (1.4 g, 4.4 mmol) in dichloromethane (20 mL) was added 3-chloroperbenzoic acid (mCPBA, ≤77%, 1.5 g, 6.6 mmol). The homogeneous mixture was stirred overnight at room temperature before being diluted with ethyl acetate (approximately 100 mL) and washed with saturated aqueous sodium hydrogen carbonate solution (3×50 mL). The organic layer was dried over anhydrous magnesium sulfate, filtered, and concentrated under reduced pressure to give the desired intermediate. LCMS-ESI⁻ (m/z): [M−H]⁻ calcd 338.08; found 338.14.

Step 4: Preparation of 2-((1,1-dimethylethyl)sulfonamido)-5-(trifluoromethyl)benzoic acid A mixture of methyl 2-((1,1-dimethylethyl)sulfonamido)-5-(trifluoromethyl)benzoate (1.5 g, 4.4 mmol) in tetrahydrofuran/methanol/water (2:2:1, 30 mL) was treated with sodium hydroxide (1.1 g, 26 mmol).

After being gently warmed to promote homogeneity, the mixture was left to stir overnight at room temperature. Upon completion, the mixture was acidified with 10% aqueous hydrochloric acid. The aqueous mixture was extracted three times with ethyl acetate. The combined extracts were washed once with saturated aqueous sodium chloride solution, dried over anhydrous magnesium sulfate, filtered, and concentrated to provide the desired intermediate. LCMS-ESI⁻ (m/z): [M−H]⁻ calcd 324.06; found 324.08.

Step 5: Preparation of 2-((1,1-dimethylethyl)sulfonamido)-5-(trifluoromethyl)-N-(3-(trifluoromethyl)bicyclo[1.1.1]pentan-1-yl)benzamide Following General Synthesis 4, 2-((1,1-dimethylethyl)sulfonamido)-5-(trifluoromethyl)benzoic acid (0.13 g, 0.40 mmol) was coupled to 3-(trifluoromethyl)bicyclo[1.1.1]pentan-1-amine hydrochloride (1.1 eq) in Step 3, providing the desired product. ¹H NMR (400 MHz, DMSO-d₆) δ 11.41 (s, 1H), 9.89 (s, 1H), 8.18 (d, J=2.1 Hz, 1H), 7.94 (d, J=8.9 Hz, 1H), 7.88 (dd, J=9.0, 2.0 Hz, 1H), 2.38 (s, 6H), 1.31 (s, 9H). LCMS-ESI⁺ (m/z): [M+H]⁺ calcd 459.11; found 458.75.

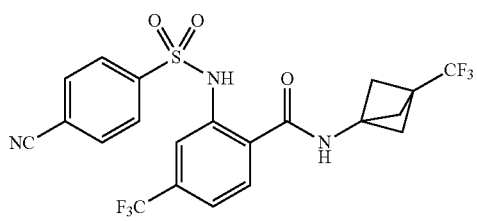 [SMILES: N#Cc1ccc(S(=O)(=O)Nc2cc(C(F)(F)F)ccc2C(=O)NC23CC(C(F)(F)F)(C2)C3)cc1]

Example 158: Preparation of 2-((4-cyanophenyl)sulfonamido)-4-(trifluoromethyl)-N-(3-(trifluoromethyl)bicyclo[1.1.1]pentan-1-yl)benzamide 2-((4-cyanophenyl)sulfonamido)-4-(trifluoromethyl)benzoyl chloride (0.15 g, 0.39 mmol) was taken up in 2-methyltetrahydrofuran (3 mL) and added dropwise to a mixture of 3-trifluoromethylbicyclo[1.1.1]pentan-1-amine hydrochloride (80 mg, 0.42 mmol) and N,N-diisopropylethylamine (0.40 mL, 2.3 mmol) in N,N-dimethylformamide (1 mL). The reaction mixture was stirred at 55° C. overnight, concentrated, and purified by flash chromatography (silica gel). The residue was recrystallized from acetonitrile/water, filtered, washed with water, and dried under vacuum to provide the desired product. ¹H NMR (400 MHz, DMSO-d₆) δ 11.22 (s, 1H), 9.59 (s, 1H), 8.06 (d, J=8.5 Hz, 2H), 7.89-7.80 (m, 3H), 7.65 (s, 1H), 7.63 (s, 1H), 2.32 (s, 6H). LCMS-ESI⁺ (m/z): [M+H]⁺ calcd 504.07; found 504.03.

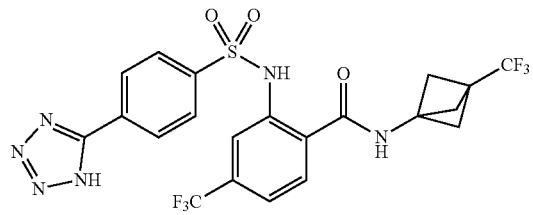 [SMILES: O=C(NC12CC(C(F)(F)F)(C1)C2)c1ccc(C(F)(F)F)cc1NS(=O)(=O)c1ccc(-c2nnn[nH]2)cc1]

Example 159: Preparation of 2-((4-(1H-tetrazol-5-yl)phenyl)sulfonamido)-4-(trifluoromethyl)-N-(3-(trifluoromethyl)bicyclo[1.1.1]pentan-1-yl)benzamide A mixture in N,N-dimethylformamide (2 mL) of 2-((4-cyanophenyl)sulfonamido)-4-(trifluoromethyl)-N-(3-(trifluoromethyl)bicyclo[1.1.1]pentan-1-yl)benzamide (0.27 g, 0.53 mmol), sodium azide (0.10 g, 1.6 mmol), and triethylamine hydrochloride (0.22 g, 1.6 mmol) was heated at 130° C. in a microwave reactor for 2 hours. The reaction mixture was diluted with ethyl acetate, 10% hydrochloric acid, and ice. The aqueous phase was extracted three times with ethyl acetate. The combined extracts were washed once with saturated aqueous sodium chloride solution, dried over anhydrous magnesium sulfate, filtered, and concentrated under reduced pressure. The residue was purified by reverse-phase HPLC (acetonitrile/water/0.1% trifluoroacetic acid) to provide the desired product. ¹H NMR (400 MHz, DMSO-d₆) δ 9.59 (s, 1H), 8.19 (d, J=8.6 Hz, 2H), 7.90 (d, J=8.5 Hz, 2H), 7.82 (d, J=8.2 Hz, 1H), 7.69 (d, J=1.8 Hz, 1H), 7.59 (dd, J=8.2, 1.8 Hz, 1H), 2.28 (s, 6H). LCMS-ESI⁺ (m/z): [M+H]⁺ calcd 547.09; found 547.06.

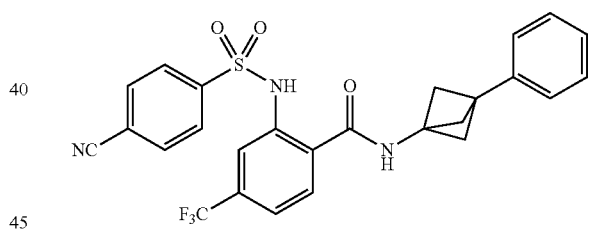

Example 160: Preparation of 2-((4-cyanophenyl)sulfonamido)-N-(3-phenylbicyclo[1.1.1]pentan-1-yl)-4-(trifluoromethyl)benzamide

Step 1: Preparation of methyl 2-((4-cyanophenyl)sulfonamido)-4-(trifluoromethyl)benzoate Following General Synthesis 4, using 4-cyanobenzenesulfonyl chloride (2.0 g, 10 mmol, 1.1 eq) and methyl 2-amino-4-(trifluoromethyl)benzoate (2.0 g, 9.1 mmol, 1.0 eq) in Step 1, the crude title intermediate was synthesized. LCMS-ESI⁻ (m/z): [M−H]⁻ calcd 383.04; found 383.21.

Step 2: Preparation of 2-((4-cyanophenyl)sulfonamido)-4-(trifluoromethyl)benzoic acid A solution of crude methyl 2-((4-cyanophenyl)sulfonamido)-4-(trifluoromethyl)benzoate in 2-methyltetrahydrofuran (50 mL) was treated successively with water (10 mL) and lithium hydroxide monohydrate (0.90 g, 22 mmol, 3.0 eq). The mixture was stirred overnight at room temperature and then was acidified with 10% aqueous hydrochloric acid and extracted three times with ethyl acetate. The combined organic layers were washed with saturated aqueous sodium chloride solution, dried over anhydrous magnesium sulfate, filtered, and concentrated under reduced pressure to give the desired intermediate. LCMS-ESI⁻ (m/z): [M−H]⁻ calcd 369.02; found 369.07.

Step 3: Preparation of 2-((4-cyanophenyl)sulfonamido)-4-(trifluoromethyl)benzoyl chloride A mixture of 2-((4-cyanophenyl)sulfonamido)-4-(trifluoromethyl)benzoic acid (0.57 g, 1.5 mmol) in chlorobenzene (8 mL) was treated with thionyl chloride (2.2 mL, 31 mmol) and then heated for approximately 30 minutes at 150° C. The mixture was then concentrated under reduced pressure, co-evaporated once with toluene, and carried forward without further purification.

Step 4: Preparation of 2-((4-cyanophenyl)sulfonamido)-N-(3-phenylbicyclo[1.1.1]pentan-1-yl)-4-(trifluoromethyl)benzamide 2-((4-Cyanophenyl)sulfonamido)-4-(trifluoromethyl)benzoyl chloride (0.15 g, 0.39 mmol) was taken up in 2-methyltetrahydrofuran (3 mL) and added dropwise to a mixture of 3-phenylbicyclo[1.1.1]pentan-1-amine hydrochloride (83 mg, 0.42 mmol) and N,N-diisopropylethylamine (0.40 mL, 2.3 mmol) in N,N-dimethylformamide (1 mL). The reaction mixture was stirred at 55° C. overnight, concentrated, and purified by flash chromatography (silica gel) to provide the desired product. ¹H NMR (400 MHz, DMSO-d₆) δ 11.46 (s, 1H), 9.49 (s, 1H), 8.07 (d, J=8.5 Hz, 2H), 7.89 (d, J=8.2 Hz, 1H), 7.86 (d, J=8.5 Hz, 2H), 7.69 (d, J=1.7 Hz, 1H), 7.63 (d, J=8.2 Hz, 1H), 7.39-7.31 (m, 2H), 7.31-7.20 (m, 3H), 2.33 (s, 6H). LCMS-ESI⁺ (m/z): [M+H]⁺ calcd 512.12; found 512.02.

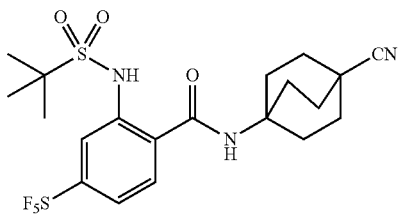

Example 161: Preparation of N-(4-cyanobicyclo[2.2.2]octan-1-yl)-2-((1,1-dimethylethyl)sulfonamido)-4-(pentafluoro-λ⁶-sulfanyl)benzamide Following General Synthesis 6, 2-((1,1-dimethylethyl)sulfonamido)-4-(pentafluoro-λ⁶-sulfanyl)benzoic acid (0.15 g, 0.39 mmol) was coupled to 4-aminobicyclo[2.2.2]octane-1-carbonitrile hydrochloride (contaminated with 4-aminobicyclo[2.2.2]octane-1-carboxamide hydrochloride, 85 mg, approximately 0.46 mmol) to provide, after flash chromatography (silica gel), the desired product. ¹H NMR (400 MHz, DMSO-d₆) δ 10.37 (s, 1H), 8.48 (s, 1H), 8.14 (s, 1H), 7.86 (d, J=8.8 Hz, 1H), 7.71 (d, J=8.7 Hz, 1H), 1.99 (s, 12H), 1.28 (s, 9H). LCMS-ESI⁺ (m/z): [M+H]⁺ calcd 516.13; found 515.80.

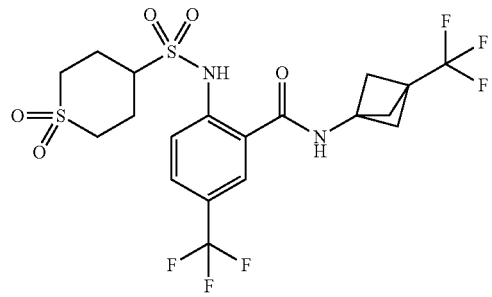 [SMILES: O=C(NC12CC(C(F)(F)F)(C1)C2)c1cc(C(F)(F)F)ccc1NS(=O)(=O)C1CCS(=O)(=O)CC1]

Example 162: Preparation of 2-((1,1-dioxidotetrahydro-2H-thiopyran)-4-sulfonamido)-5-(trifluoromethyl)-N-(3-(trifluoromethyl)bicyclo[1.1.1]pentan-1-yl)benzamide

Step 1: Preparation of tetrahydro-2H-thiopyran-4-sulfonamide 1,1-dioxide

A mixture of 1,1-dioxo-1λ⁶-thiane-4-sulfonyl chloride (0.21 g, 0.90 mmol) in 2-methyltetrahydrofuran (1 mL) was added to an ice-bath cooled solution of ammonium hydroxide (1.2 mL, 9.0 mmol). The vial that contained the sulfonyl chloride was rinsed with a 1:1 mixture of ammonium hydroxide solution/p-dioxane (2 mL), which was also added. The mixture was left to stir overnight and to gradually warm to room temperature. The mixture was concentrated under reduced pressure, removing most of the volatiles. The solid was collected by filtration, washed with water, and dried to give the desired intermediate. LCMS-ESI⁻ (m/z): [M−H]⁻ calcd 212.01; found 212.01.

Step 2: Preparation of 2-((1,1-dioxidotetrahydro-2H-thiopyran)-4-sulfonamido)-5-(trifluoromethyl)-N-(3-(trifluoromethyl)bicyclo[1.1.1]pentan-1-yl)benzamide According to General Synthesis 8, tetrahydro-2H-thiopyran-4-sulfonamide 1,1-dioxide (0.12 g, 0.55 mmol) was coupled to 2-iodo-5-(trifluoromethyl)-N-(3-(trifluoromethyl)bicyclo[1.1.1]pentan-1-yl)benzamide (0.22 g, 0.48 mmol) to furnish the desired product. ¹H NMR (400 MHz, DMSO-d₆) δ 11.73 (s, 1H), 9.89 (s, 1H), 8.24 (m, 1H), 7.94 (d, J=8.6 Hz, 1H), 7.78 (d, J=8.8 Hz, 1H), 3.78 (m, 1H), 3.29-3.09 (m, 4H), 2.45-2.35 (m, 2H), 2.38 (s, 6H), 2.18-1.95 (m, 2H). LCMS-ESI⁻ (m/z): [M−H]⁻ calcd 533.07; found 533.24.

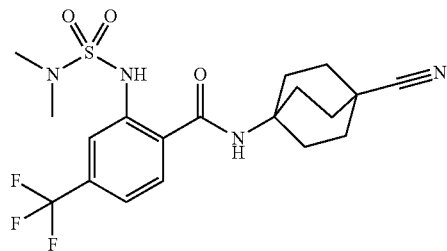 [SMILES: CN(C)S(=O)(=O)Nc1cc(C(F)(F)F)ccc1C(=O)NC12CCC(C#N)(CC1)CC2]

Example 163: Preparation of N-(4-cyanobicyclo [2.2.2]octan-1-yl)-2-((N,N-dimethylsulfamoyl) amino)-4-(trifluoromethyl)benzamide

Step 1: Preparation of 2-((N,N-dimethylsulfamoyl) amino)-4-(trifluoromethyl)benzoic acid 2-Amino-4-(trifluoromethyl)benzoic acid (5.2 g, 25 mmol) was added to an aqueous solution of sodium hydroxide (1M, 51 mL, 51 mmol). The suspension was sonicated for about 10 minutes and then was transferred to a stirring plate. N,N-dimethylsulfamoyl chloride (8.2 mL, 76 mmol) was added a solution in toluene (125 mL) via pipette to the rapidly stirred mixture. The reaction vessel was equipped with a reflux condenser and heated overnight at 100° C. After cooling to room temperature, the reaction mixture was allowed to cool to room temperature. The organic phase was washed once with 1M sodium hydroxide solution and then with water. The combined extracts were acidified with hydrochloric acid, giving a precipitate, which was collected by filtration, washed with water, and dried. The contents of the filter cake were purified by RP-HPLC (acetonitrile/water/0.1% trifluoroacetic acid) to provide the desired intermediate. LCMS-ESI⁻ (m/z): [M−H]⁻ calcd 311.04; found 311.02.

Step 2: Preparation of N-(4-cyanobicyclo[2.2.2] octan-1-yl)-2-((N,N-dimethylsulfamoyl)amino)-4-(trifluoromethyl)benzamide The titled compound was prepared from 2-((N,N-dimethylsulfamoyl)amino)-4-(trifluoromethyl)benzoic acid (0.18 g, 0.57 mmol) and 4-aminobicyclo[2.2.2]octane-1-carbonitrile hydrochloride (0.11 g, 0.60 mmol) according to General Synthesis 10. ¹H NMR (400 MHz, DMSO-d₆) δ 10.55 (s, 1H), 8.40 (s, 1H), 7.90 (d, J=8.2 Hz, 1H), 7.74 (d, J=1.7 Hz, 1H), 7.54 (d, J=8.0 Hz, 1H), 2.71 (s, 6H), 2.00 (s, 12H). LCMS-ESI⁻ (m/z): [M−H]⁻ calcd 443.14; found 443.28.

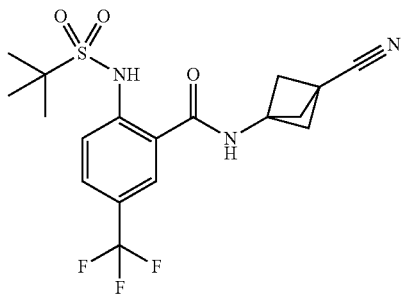 [SMILES: CC(C)(C)S(=O)(=O)Nc1ccc(C(F)(F)F)cc1C(=O)NC12CC(C#N)(C1)C2]

Example 164: Preparation of N-(3-cyanobicyclo [1.1.1]pentan-1-yl)-2-((1,1-dimethylethyl)sulfonamido)-5-(trifluoromethyl)benzamide The titled compound was prepared from 2-((1,1-dimethylethyl)sulfonamido)-5-(trifluoromethyl)benzoic acid (0.12 g, 0.38 mmol) and 3-aminobicyclo[1.1.1]pentane-1-carbonitrile hydrochloride (60 mg, 0.41 mmol) according to General Synthesis 10. ¹H NMR (400 MHz, DMSO-d₆) δ 11.37 (s, 1H), 9.86 (s, 1H), 8.15 (m, 1H), 7.92 (d, J=8.9 Hz, 1H), 7.87 (dd, J=9.0, 2.0 Hz, 1H), 2.62 (s, 6H), 1.31 (s, 9H). LCMS-ESI⁻ (m/z): [M−H]⁻ calcd 414.12; found 414.21.

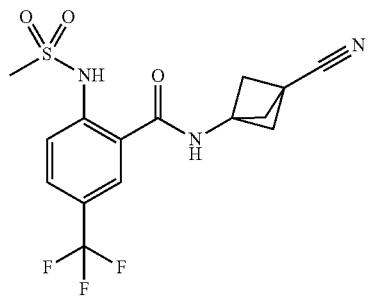 [SMILES: CS(=O)(=O)Nc1ccc(C(F)(F)F)cc1C(=O)NC12CC(C#N)(C1)C2]

Example 165: Preparation of N-(3-cyanobicyclo [1.1.1]pentan-1-yl)-2-(methylsulfonamido)-5 (trifluoromethyl)benzamide The titled compound was prepared from 2-(methylsulfonamido)-5-(trifluoromethyl)benzoic acid (98 mg, 0.35 mmol) and 3-aminobicyclo[1.1.1]pentane-1-carbonitrile hydrochloride (55 mg, 0.38 mmol) according to General Synthesis 10. ¹H NMR (400 MHz, DMSO-d₆) δ 11.46 (s, 1H), 9.79 (s, 1H), 8.18 (m, 1H), 7.91 (dd, J=8.8, 2.1 Hz, 1H), 7.73 (d, J=8.7 Hz, 1H), 3.26 (s, 3H), 2.62 (s, 6H). LCMS-ESI⁻ (m/z): [M−H]⁻ calcd 372.07; found 372.12.

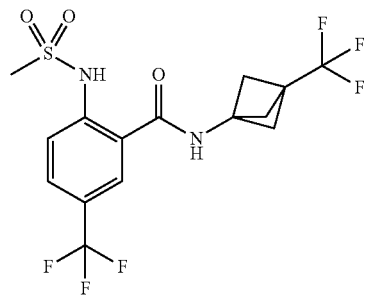 [SMILES: CS(=O)(=O)Nc1ccc(C(F)(F)F)cc1C(=O)NC12CC(C(F)(F)F)(C1)C2]

Example 166: Preparation of 2-(methylsulfonamido)-5-(trifluoromethyl)-N-(3-(trifluoromethyl) bicyclo[1.1.1]pentan-1-yl)benzamide The titled compound was prepared from 2-(methylsulfonamido)-5-(trifluoromethyl)benzoic acid (87 mg, 0.31 mmol) and 3-(trifluoromethyl)bicyclo[1.1.1]pentane-1-amine hydrochloride (63 mg, 0.34 mmol) according to General Synthesis 10. ¹H NMR (400 MHz, DMSO-d₆) δ 11.51 (s, 1H), 9.82 (s, 1H), 8.23 (d, J=2.6 Hz, 1H), 7.91 (dd, J=8.8, 2.1 Hz, 1H), 7.73 (d, J=8.7 Hz, 1H), 3.27 (s, 3H), 2.38 (s, 6H). LCMS-ESI⁻ (m/z): [M−H]⁻ calcd 415.06; found 415.15.

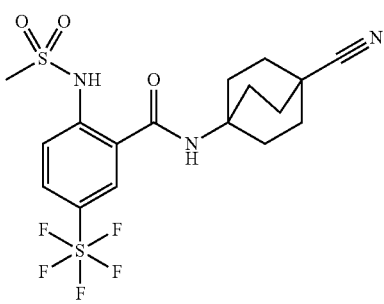 [SMILES: CS(=O)(=O)Nc1ccc(S(F)(F)(F)(F)F)cc1C(=O)NC12CCC(C#N)(CC1)CC2]

Example 167: Preparation of N-(4-cyanobicyclo [2.2.2]octan-1-yl)-2-(methylsulfonamido)-5-(pentafluoro-λ⁶-sulfanyl)benzamide The titled compound was prepared from 2-(methylsulfonamido)-5-(pentafluoro-λ⁶-sulfanyl)benzoic acid (0.17 g, 0.49 mmol) and 4-aminobicyclo[2.2.2]octane-1-carbonitrile hydrochloride (0.10 g, 0.54 mmol) according to General Synthesis 10. $^1$H NMR (400 MHz, DMSO-$d_6$) δ 10.80 (s, 1H), 8.47 (s, 1H), 8.14 (d, J=2.6 Hz, 1H), 8.03 (dd, J=9.2, 2.7 Hz, 1H), 7.65 (d, J=9.1 Hz, 1H), 3.23 (s, 3H), 2.00 (s, 12H). LCMS-ESI⁻ (m/z): [M–H]⁻ calcd 472.09; found 472.23.

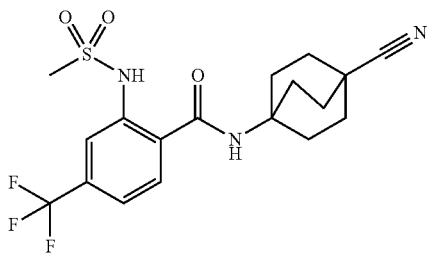 [SMILES: CS(=O)(=O)Nc1cc(C(F)(F)F)ccc1C(=O)NC12CCC(C#N)(CC1)CC2]

Example 168: Preparation of N-(4-cyanobicyclo [2.2.2]octan-1-yl)-2-(methylsulfonamido)-4-(trifluoromethyl)benzamide The titled compound was prepared from 2-(methylsulfonamido)-4-(trifluoromethyl)benzoic acid (0.15 g, 0.52 mmol) and 4-aminobicyclo[2.2.2]octane-1-carbonitrile hydrochloride (0.10 g, 0.55 mmol) according to General Synthesis 10. $^1$H NMR (400 MHz, DMSO-$d_6$) δ 10.35 (s, 1H), 8.30 (s, 1H), 7.87 (d, J=8.1 Hz, 1H), 7.71 (d, J=1.7 Hz, 1H), 7.57 (d, J=8.0 Hz, 1H), 3.14 (s, 3H), 1.99 (s, 12H). LCMS-ESI⁻ (m/z): [M–H]⁻ calcd 414.12; found 414.22.

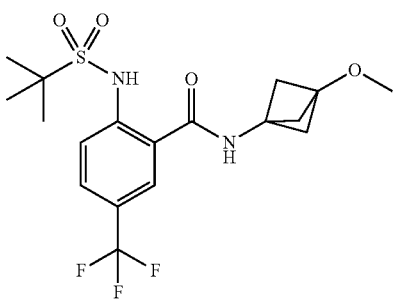 [SMILES: COC12CC(NC(=O)c3cc(C(F)(F)F)ccc3NS(=O)(=O)C(C)(C)C)(C1)C2]

Example 169: Preparation of 2-((1,1-dimethylethyl)sulfonamido)-N-(3-methoxybicyclo[1.1.1]pentan-1-yl)-5-(trifluoromethyl)benzamide The titled compound was prepared from 2-((1,1-dimethylethyl)sulfonamido)-5-(trifluoromethyl)benzoic acid (0.12 g, 0.38 mmol) and 3-methoxybicyclo[1.1.1]pentane-1-amine hydrochloride (62 mg, 0.41 mmol) according to General Synthesis 10. $^1$H NMR (400 MHz, DMSO-$d_6$) δ 11.50 (s, 1H), 9.76 (s, 1H), 8.19 (m, 1H), 7.92 (d, J=8.9 Hz, 1H), 7.86 (dd, J=8.9, 2.0 Hz, 1H), 3.24 (s, 3H), 2.21 (s, 6H), 1.30 (s, 9H). LCMS-ESI⁻ (m/z): [M–H]⁻ calcd 419.13; found 419.22.

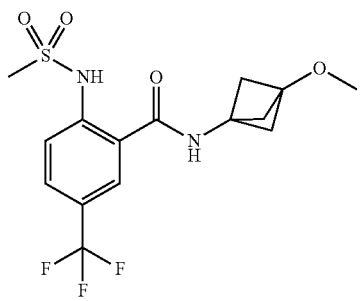

Example 170: Preparation of N-(3-methoxybicyclo [1.1.1]pentan-1-yl)-2-(methylsulfonamido)-5-(trifluoromethyl)benzamide The titled compound was prepared from 2-(methylsulfonamido)-5-(trifluoromethyl)benzoic acid (98 mg, 0.35 mmol) and 3-methoxybicyclo[1.1.1]pentane-1-amine hydrochloride (57 mg, 0.38 mmol) according to General Synthesis 10. $^1$H NMR (400 MHz, DMSO-$d_6$) δ 11.66 (s, 1H), 9.69 (s, 1H), 8.25 (d, J=2.1 Hz, 1H), 7.90 (dd, J=8.8, 2.0 Hz, 1H), 7.72 (d, J=8.6 Hz, 1H), 3.26 (s, 3H), 3.24 (s, 3H), 2.21 (s, 6H). LCMS-ESI⁻ (m/z): [M–H]⁻ calcd 377.09; found 377.13.

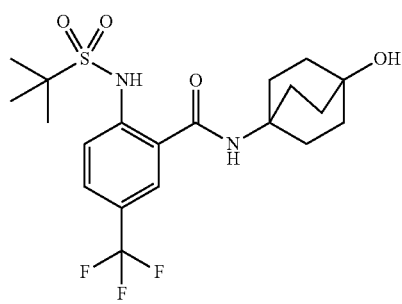 [SMILES: CC(C)(C)S(=O)(=O)Nc1ccc(C(F)(F)F)cc1C(=O)NC12CCC(O)(CC1)CC2]

Example 171: 2-((1,1-dimethylethyl)sulfonamido)-N-(4-hydroxybicyclo[2.2.2]octan-1-yl)-5-(trifluoromethyl)benzamide The titled compound was prepared from 2-((1,1-dimethylethyl)sulfonamido)-5-(trifluoromethyl)benzoic acid (0.14 g, 0.43 mmol) and 4-aminobicyclo[2.2.2]octan-1-ol hydrochloride (83 mg, 0.47 mmol) according to General Synthesis 10. $^1$H NMR (400 MHz, DMSO-$d_6$) δ 10.91 (s, 1H), 8.45 (s, 1H), 8.00 (d, J=2.0 Hz, 1H), 7.88 (d, J=8.8 Hz, 1H), 7.82

(dd, J=8.9, 2.0 Hz, 1H), 2.05 (m, 6H), 1.62 (m, 6H), 1.28 (s, 9H). LCMS-ESI⁻ (m/z): [M−H]⁻ calcd 447.16; found 447.29.

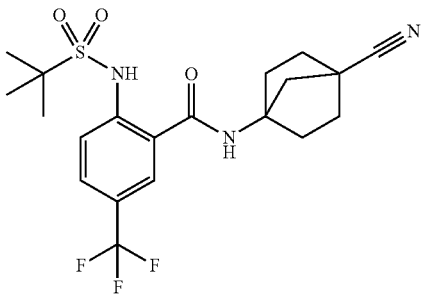 [SMILES: CC(C)(C)S(=O)(=O)Nc1ccc(C(F)(F)F)cc1C(=O)NC12CCC(C#N)(CC1)C2]

Example 172: N-(4-cyanobicyclo[2.2.1]heptan-1-yl)-2-((1,1-dimethylethyl)sulfonamido)-5-(trifluoromethyl)benzamide Step 1: Preparation of 4-((tert-butoxycarbonyl)amino)bicyclo[2.2.1]heptane-1-carboxylic acid To a stirred solution of 4-aminobicyclo[2.2.1]heptane-1-carboxylic acid hydrochloride (1.1 g, 5.6 mmol) in 1 N aqueous NaOH (17 mL, 17 mmol) was added a solution of di-tert-butyl dicarbonate (1.5 g, 6.7 mmol) in dioxane (8 mL). The reaction mixture was stirred at room temperature for 2 days. Water was added to the reaction mixture, which was then extracted once with hexane. The aqueous phase was acidified with 10% aqueous citric acid, giving a white precipitate, which was collected by filtration, washed with water, and dried to provide the desired intermediate. LCMS-ESI⁺ (m/z): [M-isobutylene+H]⁺ calcd 200.21; found 200.03.

Step 2: Preparation of tert-butyl (4-carbamoylbicyclo[2.2.1]heptan-1-yl)carbamate To a suspension of 4-((tert-butoxycarbonyl)amino)bicyclo[2.2.1]heptane-1-carboxylic acid (1.1 g, 4.4 mmol) in 2-methyltetrahydrofuran (10 mL) was added in a single portion 1,1'-carbonyldiimidazole (0.86 g, 5.3 mmol). After one hour of stirring, ammonium hydroxide solution (28-30% NH₃ basis, 6 mL) was added. An additional volume of 2-methyltetrahydrofuran (5 mL) was added, and the reaction mixture was stirred overnight. Filtration of the solid provided the desired intermediate. The filtrate was acidified by the addition of 10% citric acid solution and 10% aqueous hydrochloric acid. The acidic aqueous mixture was extracted three times with ethyl acetate. The combined organics were washed successively with water and saturated aqueous sodium chloride solution, dried over anhydrous magnesium sulfate, filtered, and concentrated under reduced pressure to provide an additional crop. LCMS-ESI⁺ (m/z): [M+H]⁺ calcd 255.16; found 255.09.

Step 3: Preparation of tert-butyl (4-cyanobicyclo[2.2.1]heptan-1-yl)carbamate

Phosphorus oxychloride (2.0 mL, 22 mmol) was added to a cooled (ice-water bath) solution of tert-butyl (4-carbamoylbicyclo[2.2.1]heptan-1-yl)carbamate (1.1 g, 4.3 mmol) in pyridine (17 mL) under magnetic stirring. The reaction mixture was stirred for 5 minutes in the bath and then for 60 minutes after the bath had been removed. The mixture was added to approximately 200 mL ice water. The resulting aqueous mixture was extracted three times with ethyl acetate. The combined extracts were washed once each with 10% hydrochloric acid and saturated aqueous sodium chloride solution, dried over anhydrous magnesium sulfate, filtered, and concentrated under reduced pressure to provide the desired intermediate. LCMS-ESI⁺ (m/z): [M+H]⁺ calcd 237.15; found 236.85.

Step 4: Preparation of 4-aminobicyclo[2.2.1]heptane-1-carbonitrile hydrochloride tert-Butyl (4-cyanobicyclo[2.2.1]heptan-1-yl)carbamate (1.1 g, 4.7 mmol) was taken up in dioxane (10 mL). A solution of hydrogen chloride in dioxane (4N, 50 mL, 200 mmol) was added. After stirring overnight at room temperature, the reaction mixture was concentrated under reduced pressure. The solid residue was taken up in ethyl acetate, collected by filtration, and dried to provide the desired intermediate. LCMS-ESI⁺ (m/z): [M+H]⁺ calcd 137.10; found 136.96.

Step 5: Preparation of N-(4-cyanobicyclo[2.2.1]heptan-1-yl)-2-((1,1-dimethylethyl)sulfonamido)-5-(trifluoromethyl)benzamide The titled compound was prepared from 2-((1,1-dimethylethyl)sulfonamido)-5-(trifluoromethyl)benzoic acid (0.10 g, 0.31 mmol) and 4-aminobicyclo[2.2.1]heptane-1-carbonitrile hydrochloride (56 mg, 0.32 mmol) according to General Synthesis 10. ¹H NMR (400 MHz, DMSO-d₆) δ 11.16 (s, 1H), 9.32 (s, 1H), 8.16 (d, J=2.0 Hz, 1H), 7.92 (d, J=8.8 Hz, 1H), 7.86 (dd, J=8.9, 2.0 Hz, 1H), 2.20 (s, 2H), 2.06 (m, 2H), 1.94 (m, 6H), 1.29 (s, 9H). LCMS-ESI⁻ (m/z): [M−H]⁻ calcd 442.15; found 442.27.

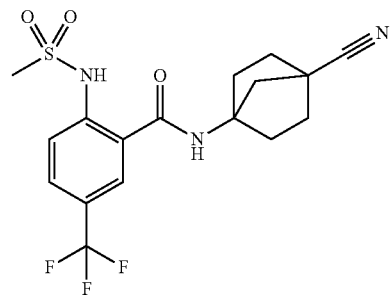 [SMILES: CS(=O)(=O)Nc1ccc(C(F)(F)F)cc1C(=O)NC12CCC(C#N)(CC1)C2]

Example 173: N-(4-cyanobicyclo[2.2.1]heptan-1-yl)-2-(methylsulfonamido)-5-(trifluoromethyl)benzamide The titled compound was prepared from 2-(methylsulfonamido)-5-(trifluoromethyl)benzoic acid (100 mg, 0.35 mmol) and 4-aminobicyclo[2.2.1]heptane-1-carbonitrile hydrochloride (64 mg, 0.37 mmol) according to General Synthesis 10. ¹H NMR (400 MHz, DMSO-d₆) δ 11.30 (s, 1H), 9.21 (s, 1H), 8.21 (d, J=2.0 Hz, 1H), 7.89 (dd, J=8.7, 2.1 Hz, 1H), 7.71 (d, J=8.7 Hz, 1H), 3.25 (s, 3H), 2.21 (s, 2H), 2.11-1.84 (m, 8H). LCMS-ESI⁺ (m/z): [M−H]⁻ calcd 400.10; found 400.17.

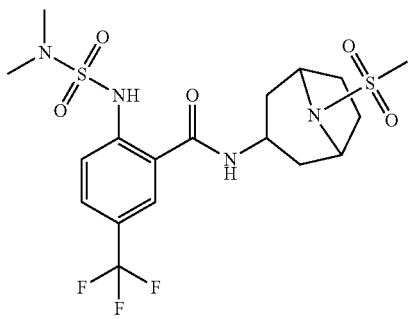

Example 174: 2-((N,N-dimethylsulfamoyl)amino)-N-(8-(methylsulfonyl)-8-azabicyclo[3.2.1]octan-3-yl)-5-(trifluoromethyl)benzamide Step 1: Preparation of 2-((N,N-dimethylsulfamoyl)amino)-5-(trifluoromethyl)benzoic acid The titled intermediate was made from 2-amino-5-(trifluoromethyl)benzoic acid (2.0 g, 9.7 mmol) in a manner analogous to the preparation of 2-((N,N-dimethylsulfamoyl)amino)-4-(trifluoromethyl)benzoic acid from 2-amino-4-(trifluoromethyl)benzoic acid LCMS-ESI⁻ (m/z): [M−H]⁻ calcd 311.04; found 311.04.

Step 2: Preparation of 2-((N,N-dimethylsulfamoyl)amino)-N-(8-(methylsulfonyl)-8-azabicyclo[3.2.1]octan-3-yl)-5-(trifluoromethyl)benzamide The titled compound as a mixture of diastereomers was prepared from 2-((N,N-dimethylsulfamoyl)amino)-5-(trifluoromethyl)benzoic acid (91 mg, 0.29 mmol) and 8-(methylsulfonyl)-8-azabicyclo[3.2.1]octan-3-amine (63 mg, 0.31 mmol) according to General Synthesis 10. ¹H NMR (400 MHz, DMSO-d₆) δ 11.69 (s, 1H, diastereomer 1), 11.11 (s, 1H, diasteromer 2), 8.97 (d, J=7.9 Hz, 1H, diasteromer 1), 8.71 (d, J=4.3 Hz, 1H, diastereromer 2), 8.22 (m, 1H, diastereomer 1), 7.98 (m, 1H, diasteromer 2), 7.89 (m, 2H, diastereomers 1 and 2), 7.70 (d, J=4.6 Hz, 1H, diasteromer 1), 7.67 (d, J=4.6 Hz, 1H, diastereomer 2), 4.34 (tt, J=11.8, 5.8 Hz, 1H, diastereomer 1), 4.20 (m, 2H, diasteromer 1), 4.15 (s, 2H, diastereomer 2), 4.06 (dtd, J=7.3, 4.8, 2.3 Hz, 1H, diastereomer 2), 2.96 (s, 3H, diastereomer 1), 2.96 (s, 3H, diastereomer 2), 2.76 (s, 6H, diastereomer 1), 2.75 (s, 6H, diastereomer 2), 2.18-2.08 (m, 2H), 2.08-1.96 (m, 8H), 1.93 (dd, J=5.9, 3.0 Hz, 1H, diastereomer 1), 1.90 (dd, J=6.1, 2.8 Hz, 1H, diastereomer 2), 1.85-1.68 (m, 4H). LCMS-ESI⁺ (m/z): [M+H]⁺ calcd 499.12; found 498.91.

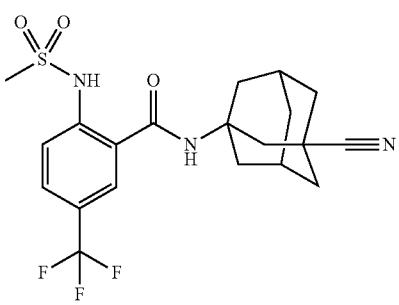 [SMILES: CS(=O)(=O)Nc1ccc(C(F)(F)F)cc1C(=O)NC12CC3CC(CC(C#N)(C3)C1)C2]

Example 175: N-((1R,5R)-3-cyanoadamantan-1-yl)-2-(methylsulfonamido)-5-(trifluoromethyl)benzamide Steps 1-3: Preparation of 3-aminoadamantane-1-carbonitrile hydrochloride The titled intermediate was prepared from 3-((tert-butoxycarbonyl)amino)adamantane-1-carboxylic acid (2.0 g, 6.7 mmol) according to the sequence that furnished 4-aminobicyclo[2.2.1]heptane-1-carbonitrile hydrochloride from 4-((tert-butoxycarbonyl)amino)bicyclo[2.2.1]heptane-1-carboxylic acid. LCMS-ESI⁺ (m/z): [M+H]⁺ calcd 177.13; found 176.96.

Step 4: Preparation of N-((1R,5R)-3-cyanoadamantan-1-yl)-2-(methylsulfonamido)-5-(trifluoromethyl)benzamide The titled compound was prepared from 2-(methylsulfonamido)-5-(trifluoromethyl)benzoic acid (104 mg, 0.37 mmol) and 3-aminoadamantane-1-carbonitrile hydrochloride (78 mg, 0.37 mmol) according to General Synthesis 10. ¹H NMR (400 MHz, DMSO-d₆) δ 10.90 (s, 1H), 8.46 (s, 1H), 8.10 (d, J=2.1 Hz, 1H), 7.87 (dd, J=8.8, 2.1 Hz, 1H), 7.69 (d, J=8.6 Hz, 1H), 3.23 (s, 3H), 2.40 (s, 2H), 2.20-2.07 (m, 4H), 2.02 (m, 2H), 1.96 (m, 4H), 1.64 (m, 2H). LCMS-ESI⁺ (m/z): [M+H]⁺ calcd 442.13; found 442.02.

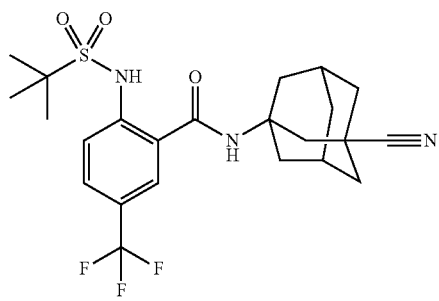 [SMILES: CC(C)(C)S(=O)(=O)Nc1ccc(C(F)(F)F)cc1C(=O)NC12CC3CC(CC(C#N)(C3)C1)C2]

Example 176: N-((1R,5R)-3-cyanoadamantan-1-yl)-2-((1,1-dimethylethyl)sulfonamido)-5-(trifluoromethyl)benzamide The titled compound was prepared from 2-((1,1-dimethylethyl)sulfonamido)-5-(trifluoromethyl)benzoic acid (121 mg, 0.37 mmol) and 3-aminoadamantane-1-carbonitrile hydrochloride (83 mg, 0.39 mmol) according to General Synthesis 10. ¹H NMR (400 MHz, DMSO-d₆) δ 10.78 (s, 1H), 8.59 (s, 1H), 8.06 (m, 1H), 7.90 (d, J=8.8 Hz, 1H), 7.84 (dd, J=8.9, 2.0 Hz, 1H), 2.39 (s, 2H), 2.21-2.08 (m, 4H), 2.06-1.99 (m, 2H), 1.96 (m, 4H), 1.64 (m, 2H), 1.30 (s, 9H). LCMS-ESI⁺ (m/z): [M+H]⁺ calcd 484.18; found 483.79.

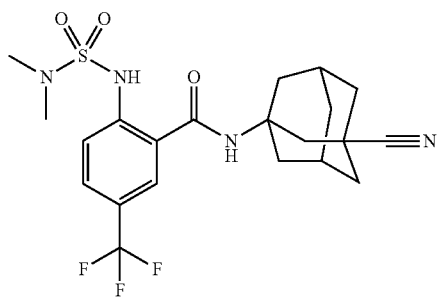 [SMILES: CN(C)S(=O)(=O)Nc1ccc(C(F)(F)F)cc1C(=O)NC12CC3CC(CC(C#N)(C3)C1)C2]

Example 177: N-((1R,5R)-3-cyanoadamantan-1-yl)-2-((N,N-dimethylsulfamoyl)amino)-5-(trifluoromethyl)benzamide The titled compound was prepared from 2-((N,N-dimethylsulfamoyl)amino)-5-(trifluoromethyl)benzoic acid (91 mg, 0.29 mmol) and 3-aminoadamantane-1-carbonitrile hydrochloride (65 mg, 0.31 mmol) according to General Synthesis 10. $^1$H NMR (400 MHz, DMSO-d$_6$) δ 10.98 (s, 1H), 8.52 (s, 1H), 8.10 (d, J=2.1 Hz, 1H), 7.87 (dd, J=8.8, 2.1 Hz, 1H), 7.68 (d, J=8.7 Hz, 1H), 2.75 (s, 6H), 2.40 (s, 2H), 2.22-2.08 (m, 4H), 2.08-1.98 (m, 2H), 1.98-1.91 (m, 4H), 1.65 (m, 2H). LCMS-ESI$^+$ (m/z): [M+H]$^+$ calcd 471.16; found 470.91.

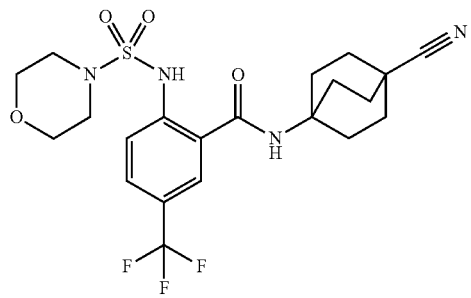 [SMILES: N#CC12CCC(NC(=O)c3cc(C(F)(F)F)ccc3NS(=O)(=O)N3CCOCC3)(CC1)CC2]

Example 178: N-(4-cyanobicyclo[2.2.2]octan-1-yl)-2-(morpholine-4-sulfonamido)-5-(trifluoromethyl)benzamide The titled compound was prepared from N-(4-cyanobicyclo[2.2.2]octan-1-yl)-2-iodo-5-(trifluoromethyl)benzamide (0.20 g, 0.45 mmol) and morpholine-4-sulfonamide (0.22 g, 1.3 mmol) according to General Synthesis 8. Purification was accomplished by flash chromatography (silica gel) instead of by reverse-phase HPLC. $^1$H NMR (400 MHz, DMSO-d$_6$) δ 11.08 (s, 1H), 8.51 (s, 1H), 8.07 (d, J=2.1 Hz, 1H), 7.87 (dd, J=8.8, 2.2 Hz, 1H), 7.71 (d, J=8.7 Hz, 1H), 3.55 (m, 4H), 3.08 (m, 4H), 2.01 (s, 12H). LCMS-ESI$^-$ (m/z): [M−H]$^-$ calcd 485.15; found 485.30.

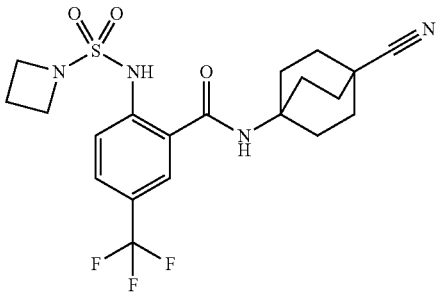 [SMILES: N#CC12CCC(NC(=O)c3cc(C(F)(F)F)ccc3NS(=O)(=O)N3CCC3)(CC1)CC2]

Example 179: 2-(azetidine-1-sulfonamido)-N-(4-cyanobicyclo[2.2.2]octan-1-yl)-5-(trifluoromethyl)benzamide The titled compound was prepared from N-(4-cyanobicyclo[2.2.2]octan-1-yl)-2-iodo-5-(trifluoromethyl)benzamide (0.20 g, 0.45 mmol) and azetidine-1-sulfonamide (0.18 g, 1.3 mmol) according to General Synthesis 8. Purification was accomplished by flash chromatography (silica gel) instead of by reverse-phase HPLC. $^1$H NMR (400 MHz, DMSO-d$_6$) δ 11.05 (s, 1H), 8.47 (s, 1H), 8.07 (d, J=2.1 Hz, 1H), 7.88 (dd, J=8.9, 2.1 Hz, 1H), 7.71 (d, J=8.7 Hz, 1H), 3.80 (t, J=7.7 Hz, 4H), 2.13 (p, J=7.7 Hz, 2H), 2.01 (s, 12H). LCMS-ESI$^-$ (m/z): [M−H]$^-$ calcd 455.14; found 455.29.

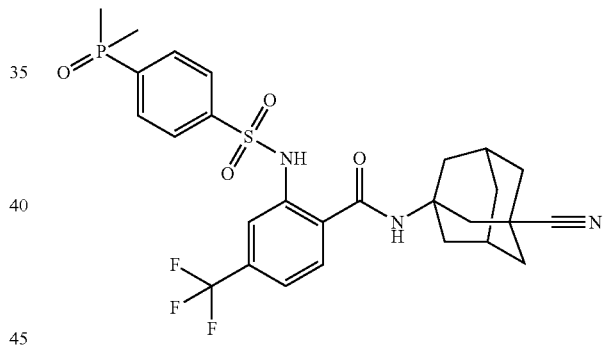

Example 180: 3-(cyanoadamantan-1-yl)-2-((4-(dimethylphosphoryl)phenyl)sulfonamido)-4-(trifluoromethyl)benzamide Step 1: Preparation of 2-((4-iodophenyl)sulfonamido)-4-(trifluoromethyl)benzoic acid A mixture of methyl 2-((4-iodophenyl)sulfonamido)-4-(trifluoromethyl)benzoate (previously described, 0.58 g, 1.2 mmol) in 2-methyltetrahydrofuran/methanol/water (2:2:1, 15 mL) was treated with sodium hydroxide (0.29 g, 7.2 mmol) and heated for two hours at 60° C. After cooling, the basic mixture was acidified with hydrochloric acid and then extracted three times with ethyl acetate. The combined extracts were washed once with saturated aqueous sodium chloride solution, dried over anhydrous magnesium sulfate, filtered, and concentrated under reduced pressure to provide the desired intermediate. LCMS-ESI$^-$ (m/z): [M−H]$^-$ calcd 469.92; found 470.01.

Step 2: Preparation of 3-cyanoadamantan-1-yl-2-((4-iodophenyl)sulfonamido)-4-(trifluoromethyl)benzamide The titled intermediate was prepared from 2-((4-iodophenyl)sulfonamido)-4-(trifluoromethyl)benzoic acid (0.45 g, 0.96 mmol) and 3-aminoadamantane-1-carbonitrile hydrochloride (0.20 g, 0.96 mmol) according to General Synthesis 7. Following aqueous work-up, the crude product was purified by flash chromatography (silica gel). LCMS-ESI⁻ (m/z): [M−H]⁻ calcd 628.05; found 628.29.

Step 3: Preparation of 3-(cyanoadamantan-1-yl)-2-((4-(dimethylphosphoryl)phenyl)sulfonamido)-4-(trifluoromethyl)benzamide A mixture of 3-cyanoadamantan-1-yl-2-((4-iodophenyl)sulfonamido)-4-(trifluoromethyl)benzamide (50 mg, 79 μmol), 4,5-bis(diphenylphosphino)-9,9-dimethylxanthene (XantPhos, 2.8 mg, 4.8 μmol) palladium(II) acetate (0.89 mg, 4.0 μmol), tribasic potassium phosphate (19 mg, 87 μmol), and dimethylphosphine oxide (6.8 mg, 87 μmol) in N,N-dimethylformamide (DMF, 0.5 mL) was heated in a microwave reactor at 150° C. for 20 minutes. The reaction mixture was purified by flash chromatography (silica gel) to provide the desired product. $^1$H NMR (400 MHz, DMSO-$d_6$) δ 10.87 (s, 1H), 8.26 (s, 1H), 7.96 (m, 2H), 7.83 (m, 3H), 7.60 (s, 1H), 7.57 (s, 1H), 2.30 (s, 2H), 2.17 (m, 2H), 2.03 (d, J=12.1 Hz, 2H), 1.95 (m, 4H), 1.91-1.81 (m, 2H), 1.69 (s, 3H), 1.65 (s, 3H), 1.66-1.60 (m, 2H). LCMS-ESI⁻ (m/z): [M−H]⁻ calcd 578.16; found 578.36.

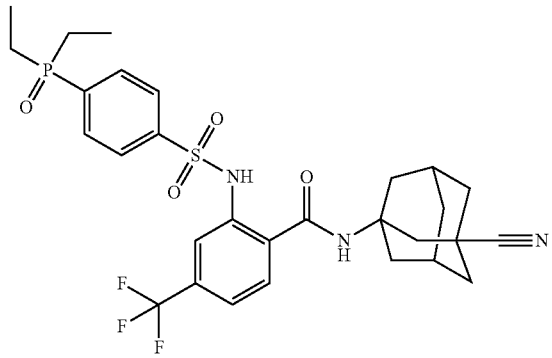 [SMILES: CCP(=O)(CC)c1ccc(S(=O)(=O)Nc2cc(C(F)(F)F)ccc2C(=O)NC23CC4CC(CC(C#N)(C4)C2)C3)cc1]

Example 181: Preparation of 3-(cyanoadamantan-1-yl)-2-((4-(diethylphosphoryl)phenyl)sulfonamido)-4-(trifluoromethyl)benzamide A mixture of 3-cyanoadamantan-1-yl-2-((4-iodophenyl)sulfonamido)-4-(trifluoromethyl)benzamide (55 mg, 87 μmol), 4,5-bis(diphenylphosphino)-9,9-dimethylxanthene (XantPhos, 3.0 mg, 5.2 μmol) palladium(II) acetate (0.98 mg, 4.4 μmol), tribasic potassium phosphate (20 mg, 96 μmol), and diethylphosphine oxide (10 mg, 96 μmol) in N,N-dimethylformamide (DMF, 0.5 mL) was heated in a microwave reactor at 150° C. for 40 minutes. The reaction mixture was purified by flash chromatography (silica gel) to provide the desired product. $^1$H NMR (400 MHz, DMSO-$d_6$) δ 10.85 (s, 1H), 8.22 (s, 1H), 7.91 (m, 2H), 7.87-7.78 (m, 3H), 7.59 (bs, 1H), 7.44 (d, J=1.8 Hz, 1H), 2.31 (s, 2H), 2.17 (m, 2H), 2.09-2.01 (m, 2H), 1.99-1.93 (m, 5H), 1.93-1.83 (m, 3H), 1.63 (m, 2H), 1.27-0.98 (m, 2H), 0.91 (t, J=7.8 Hz, 3H), 0.87 (t, J=8.1 Hz, 3H). LCMS-ESI⁻ (m/z): [M−H]⁻ calcd 606.19; found 606.40.

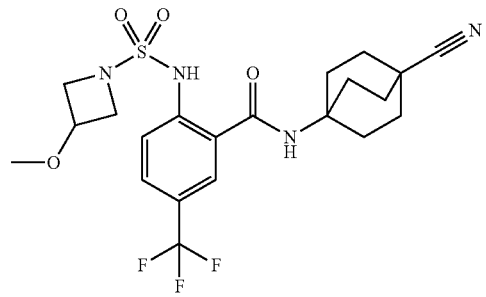 [SMILES: COC1CN(S(=O)(=O)Nc2ccc(C(F)(F)F)cc2C(=O)NC23CCC(C#N)(CC2)CC3)C1]

Example 182: N-(4-cyanobicyclo[2.2.2]octan-1-yl)-2-((3-methoxyazetidine)-1-sulfonamido)-5-(trifluoromethyl)benzamide The titled compound was prepared from N-(4-cyanobicyclo[2.2.2]octan-1-yl)-2-iodo-5-(trifluoromethyl)benzamide (0.20 g, 0.45 mmol) and 3-methoxyazetidine-1-sulfonamide (0.15 g, 0.89 mmol) according to General Synthesis 8. Purification was accomplished by flash chromatography (silica gel) instead of by reverse-phase HPLC. $^1$H NMR (400 MHz, DMSO-$d_6$) δ 11.21 (s, 1H), 8.46 (s, 1H), 8.09 (d, J=2.1 Hz, 1H), 7.88 (d, J=8.6 Hz, 1H), 7.71 (d, J=8.7 Hz, 1H), 4.12 (m, 1H), 3.98 (m, 2H), 3.66 (dd, J=8.8, 4.7 Hz, 2H), 3.15 (s, 3H), 2.01 (s, 12H). LCMS-ESI⁻ (m/z): [M−H]⁻ calcd 485.15; found 485.31.

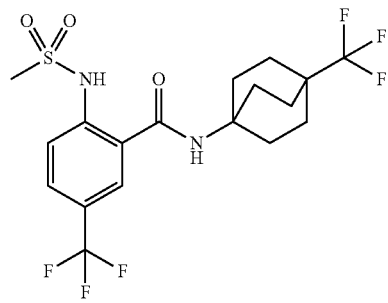 [SMILES: CS(=O)(=O)Nc1ccc(C(F)(F)F)cc1C(=O)NC12CCC(C(F)(F)F)(CC1)CC2]

Example 183: 2-(methylsulfonamido)-5-(trifluoromethyl)-N-(4-(trifluoromethyl)bicyclo[2.2.2]octan-1-yl)benzamide The titled compound was prepared from 2-(methylsulfonamido)-5-(trifluoromethyl)benzoic acid (100 mg, 0.35 mmol) and 4-(trifluoromethyl)bicyclo[2.2.2]octan-1-amine hydrochloride (85 mg, 0.37 mmol) according to General Synthesis 10. $^1$H NMR (400 MHz, DMSO-$d_6$) δ 10.98 (s, 1H), 8.45 (s, 1H), 8.09 (d, J=2.1 Hz, 1H), 7.86 (dd, J=8.8, 2.1 Hz, 1H), 7.68 (d, J=8.7 Hz, 1H), 3.23 (s, 3H), 2.03 (m, 6H), 1.75 (m, 6H). LCMS-ESI⁻ (m/z): [M−H]⁻ calcd 457.11; found 457.22.

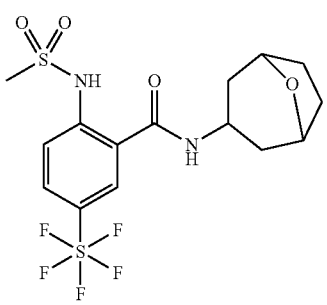 [SMILES: CS(=O)(=O)Nc1ccc(S(F)(F)(F)(F)F)cc1C(=O)NC1CC2CCC(C1)O2]

Example 184: N-(8-oxabicyclo[3.2.1]octan-3-yl)-2-(methylsulfonamido)-5-(pentafluoro-λ⁶-sulfanyl)benzamide The titled compound, as a mixture of diastereomers, was prepared from 2-(methylsulfonamido)-5-(pentafluoro-$\lambda^6$-sulfanyl)benzoic acid (180 mg, 0.53 mmol) and 8-oxabicyclo[3.2.1]octan-3-amine (74 mg, 0.58 mmol) according to General Synthesis 10. $^1$H NMR (400 MHz, DMSO-$d_6$) δ 10.85 (s, 1H), 8.76 (d, J=4.4 Hz, 1H), 8.08 (d, J=2.7 Hz, 0.5H), 8.05 (m, 1.5H), 7.70 (d, J=8.9 Hz, 1H), 4.29 (dt, J=6.0, 3.5 Hz, 2H), 4.01 (dp, J=9.3, 3.2, 2.5 Hz, 1H), 3.25 (s, 3H), 2.11-1.98 (m, 4H), 1.85 (m, 2H), 1.82-1.71 (m, 2H). LCMS-ESI⁻ (m/z): [M−H]⁻ calcd 449.07; found 449.23.

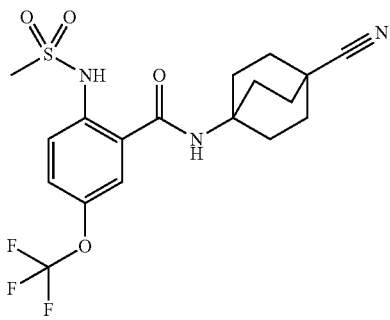 [SMILES: CS(=O)(=O)Nc1ccc(OC(F)(F)F)cc1C(=O)NC12CCC(C#N)(CC1)CC2]

Example 185: N-(4-cyanobicyclo[2.2.2]octan-1-yl)-2-(methylsulfonamido)-5-(trifluoromethoxy)benzamide Step 1: Preparation of 2-(methylsulfonamido)-5-(trifluoromethoxy)benzoic acid The titled intermediate was prepared from 2-bromo-5-(trifluoromethoxy)benzoic acid (1.0 g, 3.5 mmol) and methanesulfonamide (1.0 g, 11 mmol), according to General Synthesis 9. LCMS-ESI⁻ (m/z): [M−H]⁻ calcd 298.01; found 297.96.

Step 2: Preparation of N-(4-cyanobicyclo[2.2.2]octan-1-yl)-2-(methylsulfonamido)-5-(trifluoromethoxy)benzamide The titled compound was prepared from 2-(methylsulfonamido)-5-(trifluoromethoxy)benzoic acid (119 mg, 0.40 mmol) and 4-aminobicyclo[2.2.2]octan-1-carbonitrile hydrochloride (82 mg, 0.44 mmol) according to General Synthesis 10. $^1$H NMR (400 MHz, DMSO-$d_6$) δ 10.41 (s, 1H), 8.21 (s, 1H), 7.72 (d, J=2.2 Hz, 1H), 7.55 (m, 2H), 3.12 (s, 3H), 1.99 (s, 12H). LCMS-ESI⁻ (m/z): [M−H]⁻ calcd 430.11; found 430.20.

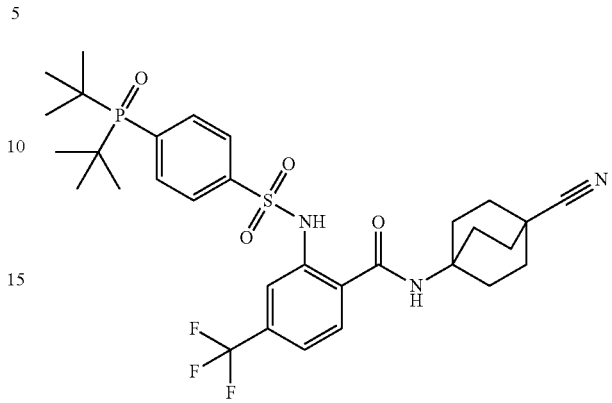

Example 186: N-(4-cyanobicyclo[2.2.2]octan-1-yl)-2-((4-(di-tert-butylphosphoryl)phenyl)sulfonamido)-4-(trifluoromethyl)benzamide Step 1: Preparation of 4-(di-tert-butylphosphoryl)benzenesulfonamide A mixture in N,N-dimethylformamide (DMF, 13 mL) of di-tert-butylphosphine oxide (0.61 g, 3.8 mmol), 4-iodobenzenesulfonamide (0.97 g, 3.4 mmol), 4,5-bis(diphenylphosphino)-9,9-dimethylxanthene (XantPhos, 0.12 g, 0.21 mmol) palladium(II) acetate (38 mg, 0.17 mol), and tribasic potassium phosphate (0.80 g, 3.8 mmol) was heated in a microwave reactor at 150° C. for 4 hours. Upon cooling, the mixture was filtered through a fritted pad of Celite diatomaceous earth. The filtrate was concentrated under reduced pressure, and the resulting residue was purified by reverse-phase high performance liquid chromatography (RP-HPLC, acetonitrile/water/0.1% trifluoroacetic acid) to provide the desired intermediate. LCMS-ESI⁺ (m/z): [M+H]⁺ calcd 318.12; found 318.10.

Step 2: Preparation of 2-bromo-N-(4-cyanobicyclo[2.2.2]octan-1-yl)-4-(trifluoromethyl)benzamide The titled intermediate was prepared from 2-bromo-4-(trifluoromethyl)benzoic acid (1.6 g, 5.9 mmol) and 4-aminobicyclo[2.2.2]octane-1-carbonitrile hydrochloride (1.2 g, 6.2 mmol) according to General Synthesis 7. LCMS-ESI⁻ (m/z): [M−H]⁻ calcd 399.04; found 399.27.

Step 3: Preparation of N-(4-cyanobicyclo[2.2.2]octan-1-yl)-2-((4-(di-tert-butylphosphoryl)phenyl)sulfonamido)-4-(trifluoromethyl)benzamide The titled compound was prepared from 2-bromo-N-(4-cyanobicyclo[2.2.2]octan-1-yl)-4-(trifluoromethyl)benzamide (0.11 g, 0.27 mmol) and 4-(di-tert-butylphosphoryl)benzenesulfonamide (0.17 g, 0.54 mmol) according to General Synthesis 8. Purification was accomplished by flash chromatography (silica gel) instead of by reverse-phase HPLC. $^1$H NMR (400 MHz, DMSO-$d_6$) δ 10.87 (s, 1H), 8.14 (s, 1H), 8.00 (m, 2H), 7.87-7.74 (m, 3H), 7.57 (d, J=8.1 Hz, 1H), 7.29 (d, J=1.7 Hz, 1H), 1.96 (tt, J=10.2, 5.7 Hz, 12H), 1.15 (s, 9H), 1.12 (s, 9H). LCMS-ESI⁻ (m/z): [M−H]⁻ calcd 636.24; found 636.42.

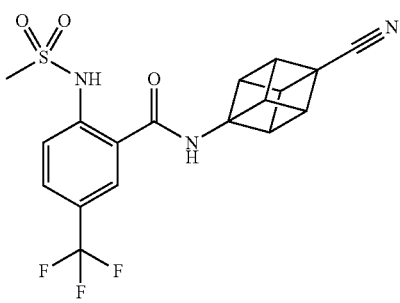 [SMILES: CS(=O)(=O)Nc1ccc(C(F)(F)F)cc1C(=O)NC12C3C4C1C1C2C3C41C#N]

Example 187: N-((2r,3R,4r,5S)-4-cyanocuban-1-yl)-2-(methylsulfonamido)-5-(trifluoromethyl)benzamide

Step 1: Preparation of methyl 4-((tert-butoxycarbonyl)amino)cubane-1-carboxylate To a stirred mixture of 4-(methoxycarbonyl)cubane-1-carboxylic acid (1.0 g, 4.8 mmol) in tert-butanol (20 mL) was added triethylamine (2.7 mL, 19 mmol) and then diphenyl phosphorylazide (1.6 mL, 7.3 mmol). The reaction mixture was heated at reflux overnight. Upon cooling, it was purified by flash chromatography (silica gel) to provide the desired intermediate.
LCMS-ESI⁺ (m/z): [M-Boc+H]⁺ calcd 178.08; found 178.00.

Step 2: Preparation of 4-((tert-butoxycarbonyl)amino)cubane-1-carboxylic acid Sodium hydroxide (0.29 g, 7.2 mmol) was added to a solution of methyl 4-((tert-butoxycarbonyl)amino)cubane-1-carboxylate (1.0 g, 3.6 mmol) in 2-methyltetrahydrofuran/methanol/water (2:2:1, 16 mL). The reaction mixture was sonicated for 10 minutes and then stirred overnight at room temperature. The mixture was diluted with 10% aqueous citric acid and extracted three times with ethyl acetate. The combined extracts were washed once each with water and saturated aqueous sodium chloride solution, dried over anhydrous magnesium sulfate, filtered, and concentrated to provide the desired intermediate. LCMS-ESI⁻ (m/z): [M-H]⁻ calcd 262.12; found 262.25.

Steps 3-5: Preparation of 4-aminocubane-1-carbonitrile hydrochloride

The titled intermediate was prepared from 4-((tert-butoxycarbonyl)amino)cubane-1-carboxylic acid (0.96 g, 3.6 mmol) according to the sequence that furnished 4-aminobicyclo[2.2.1]heptane-1-carbonitrile hydrochloride from 4-((tert-butoxycarbonyl)amino)bicyclo[2.2.1]heptane-1-carboxylic acid. LCMS-ESI⁺ (m/z): [M+H]⁺ calcd 145.07; found 144.93.

Step 6: Preparation of N-((2r,3R,4r,5S)-4-cyanocuban-1-yl)-2-(methylsulfonamido)-5-(trifluoromethyl)benzamide The titled compound was prepared from 2-(methylsulfonamido)-5-(trifluoromethyl)benzoic acid (80 mg, 0.28 mmol) and bicyclo[2.2.2]octan-1-amine hydrochloride (48 mg, 0.30 mmol) according to General Synthesis 10. ¹H NMR (400 MHz, DMSO-d₆) δ 11.62 (s, 1H), 9.88 (s, 1H), 8.28 (d, J=2.1 Hz, 1H), 7.91 (dd, J=8.8, 2.0 Hz, 1H), 7.74 (d, J=8.8 Hz, 1H), 4.30 (m, 6H), 3.26 (s, 3H). LCMS-ESI⁻ (m/z): [M-H]⁻ calcd 408.07; found 408.06.

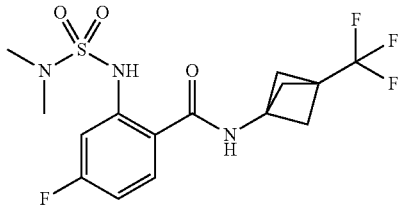 [SMILES: CN(C)S(=O)(=O)Nc1cc(F)ccc1C(=O)NC12CC(C(F)(F)F)(C1)C2]

Example 188: 2-((N,N-dimethylsulfamoyl)amino)-4-fluoro-N-(3-(trifluoromethyl)bicyclo[1.1.1]pentan-1-yl)benzamide

Step 1: Preparation of 2-((N,N-dimethylsulfamoyl)amino)-4-fluorobenzoic acid The titled intermediate was made from 2-amino-4-fluorobenzoic acid (3.1 g, 9.7 mmol) in a manner analogous to the preparation of 2-((N,N-dimethylsulfamoyl)amino)-4-(trifluoromethyl)benzoic acid from 2-amino-4-(trifluoromethyl)benzoic acid LCMS-ESI⁺ (m/z): [M+H]⁺ calcd 263.04; found 262.86.

Step 2: Preparation of 2-((N,N-dimethylsulfamoyl)amino)-4-fluoro-N-(3-(trifluoromethyl)bicyclo[1.1.1]pentan-1-yl)benzamide The titled compound was prepared from 2-((N,N-dimethylsulfamoyl)amino)-4-fluorobenzoic acid (119 mg, 0.40 mmol) and 3-(trifluoromethyl)bicyclo[1.1.1]pentan-1-amine hydrochloride (80 mg, 0.43 mmol) according to General Synthesis 4, step 3. ¹H NMR (400 MHz, DMSO-d₆) δ 11.48 (s, 1H), 9.60 (s, 1H), 7.91 (dd, J=9.0, 6.3 Hz, 1H), 7.23 (dd, J=11.2, 2.6 Hz, 1H), 7.03 (td, J=8.6, 2.6 Hz, 1H), 2.73 (s, 6H), 2.35 (s, 6H). LCMS-ESI⁻ (m/z): [M-H]⁻ calcd 394.09; found 394.28.

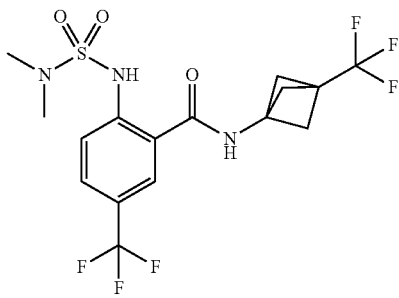 [SMILES: CN(C)S(=O)(=O)Nc1ccc(C(F)(F)F)cc1C(=O)NC12CC(C(F)(F)F)(C1)C2]

Example 189: 2-((N,N-dimethylsulfamoyl)amino)-5-(trifluoromethyl)-N-(3-(trifluoromethyl)bicyclo[1.1.1]pentan-1-yl)benzamide The titled compound was prepared from 2-((N,N-dimethylsulfamoyl)amino)-5-(trifluoromethyl)benzoic acid (82 mg, 0.26 mmol) and 3-(trifluoromethyl)bicyclo[1.1.1]pentan-1-amine hydrochloride (54 mg, 0.29 mmol) according to General Synthesis 10. $^1$H NMR (400 MHz, DMSO-d$_6$) δ 11.57 (s, 1H), 9.85 (s, 1H), 8.22 (d, J=1.0 Hz, 1H), 7.91 (dd, J=8.9, 2.0 Hz, 1H), 7.68 (d, J=8.7 Hz, 1H), 2.76 (s, 6H), 2.38 (s, 6H). LCMS-ESI⁻ (m/z): [M–H]⁻ calcd 444.09; found 444.14.

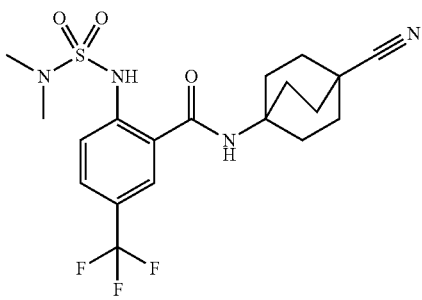 [SMILES: CN(C)S(=O)(=O)Nc1ccc(C(F)(F)F)cc1C(=O)NC12CCC(C#N)(CC1)CC2]

Example 190: N-(4-cyanobicyclo[2.2.2]octan-1-yl)-2-((N,N-dimethylsulfamoyl)amino)-5-(trifluoromethyl)benzamide The titled compound was prepared from 2-((N,N-dimethylsulfamoyl)amino)-5-(trifluoromethyl)benzoic acid (82 mg, 0.26 mmol) and 4-aminobicyclo[2.2.2]octane-1-carbonitrile hydrochloride (54 mg, 0.29 mmol) according to General Synthesis 10. $^1$H NMR (400 MHz, DMSO-d$_6$) δ 10.99 (s, 1H), 8.47 (s, 1H), 8.06 (d, J=1.4 Hz, 1H), 7.86 (dd, J=8.9, 2.1 Hz, 1H), 7.67 (d, J=8.7 Hz, 1H), 2.73 (s, 6H), 2.01 (s, 12H). LCMS-ESI⁻ (m/z): [M–H]⁻ calcd 443.14; found 443.27.

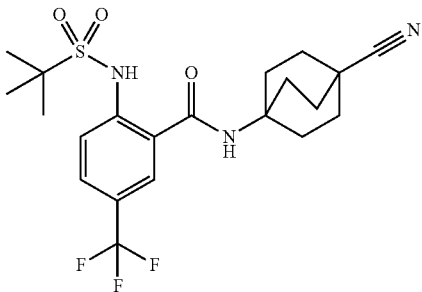 [SMILES: CC(C)(C)S(=O)(=O)Nc1ccc(C(F)(F)F)cc1C(=O)NC12CCC(C#N)(CC1)CC2]

Example 191: N-(4-cyanobicyclo[2.2.2]octan-1-yl)-2-((1,1-dimethylethyl)sulfonamido)-5-(trifluoromethyl)benzamide The titled compound was prepared from 2-((1,1-dimethylethyl)sulfonamido)-5-(trifluoromethyl)benzoic acid (0.15 g, 0.47 mmol) and 4-aminobicyclo[2.2.2]octane-1-carbonitrile hydrochloride (96 mg, 0.51 mmol) according to General Synthesis 10. $^1$H NMR (400 MHz, DMSO-d$_6$) δ 10.82 (s, 1H), 8.54 (s, 1H), 8.02 (d, J=2.1 Hz, 1H), 7.89 (d, J=8.8 Hz, 1H), 7.83 (dd, J=8.9, 2.1 Hz, 1H), 2.01 (s, 12H), 1.29 (s, 9H). LCMS-ESI⁻ (m/z): [M–H]⁻ calcd 456.16; found 456.27.

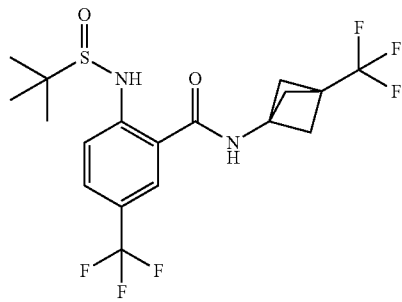 [SMILES: CC(C)(C)S(=O)Nc1ccc(C(F)(F)F)cc1C(=O)NC12CC(C(F)(F)F)(C1)C2]

Example 192: 2-((tert-butylsulfinyl)amino)-5-(trifluoromethyl)-N-(3-(trifluoromethyl)bicyclo[1.1.1]pentan-1-yl)benzamide Step 1: Preparation of 2-((tert-butylsulfinyl)amino)-5-(trifluoromethyl)benzoic acid The titled intermediate was prepared from 2-bromo-5-(trifluoromethyl)benzoic acid (0.63 g, 2.3 mmol) and 2-methylpropane-2-sulfinamide (0.29 g, 2.3 mmol) according to General Synthesis 9.

LCMS-ESI⁻ (m/z): [M–H]⁻ calcd 308.06; found 307.94.

Step 2: Preparation of 2-((tert-butylsulfinyl)amino)-5-(trifluoromethyl)benzoic acid The titled compound was prepared from 2-((tert-butylsulfinyl)amino)-5-(trifluoromethyl)benzoic acid (0.17 g, 0.54 mmol) and 3-(trifluoromethyl)bicyclo[1.1.1]pentan-1-amine hydrochloride (0.11 g, 0.60 mmol) according to General Synthesis 4, step 3. $^1$H NMR (400 MHz, DMSO-d$_6$) δ 10.69 (s, 1H), 9.72 (s, 1H), 8.16 (m, 1H), 7.81 (dd, J=8.8, 2.0 Hz, 1H), 7.53 (d, J=8.7 Hz, 1H), 2.37 (s, 6H), 1.26 (s, 9H). LCMS-ESI⁺ (m/z): [M+H]⁺ calcd 443.11; found 442.83.

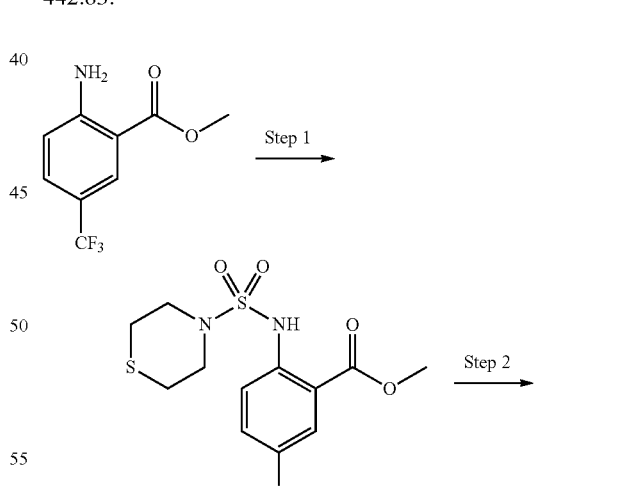

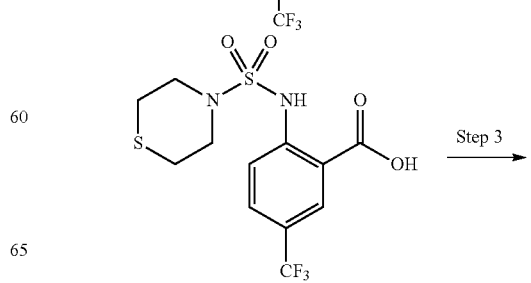

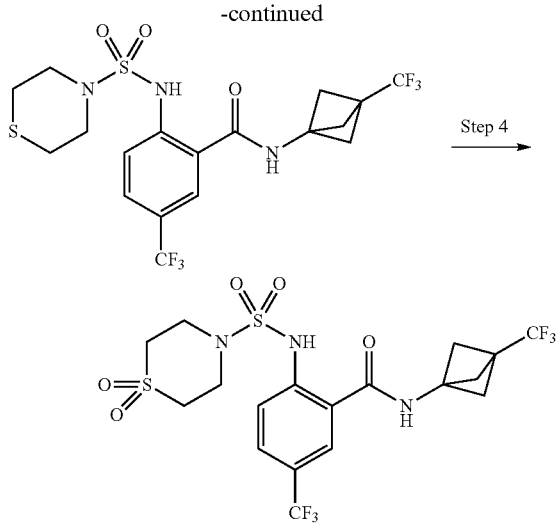

Example 193: 2-((1,1-dioxidothiomorpholine)-4-sulfonamido)-5-(trifluoromethyl)-N-(3-(trifluoromethyl)bicyclo[1.1.1]pentan-1-yl)benzamide Step 1: Preparation of methyl 2-(thiomorpholine-4-sulfonamido)-5-(trifluoromethyl)benzoate To a mixture of methyl 2-amino-5-(trifluoromethyl)benzoate (512 mg, 2.3 mmol) in dichloromethane (11 mL) of was added chlorosulfonic acid (170 μL, 2.6 mmol) followed by phosphorus pentoxide (535 mg, 2.6 mmol). The mixture was heated at 75° C. block overnight. After cooling, the reaction mixture was added to a solution of triethylamine (0.81 mL, 5.8 mmol) in dichloromethane (5 mL) that was cooled in an ice-water bath. A mixture of N,N-diisopropylethylamine (0.81 mL, 4.7 mmol) and thiomorpholine (244 μL, 2.6 mmol) in dichloromethane (5 mL) was added to the mixture, which was then stirred at 0° C. for 45 minutes. The cooling bath was removed, and the mixture was allowed to warm to room temperature. Ethyl acetate and saturated aqueous sodium chloride solution were added, and the layers were separated. The organic phase was washed once each with water and saturated aqueous sodium chloride solution, dried over anhydrous magnesium sulfate, filtered, and concentrated to a residue, which was then purified by flash chromatography (silica gel) to provide the desired intermediate. LCMS-ESI$^-$ (m/z): [M–H]$^-$ calcd 383.04; found 383.18.

Step 2: Preparation of 2-(thiomorpholine-4-sulfonamido)-5-(trifluoromethyl)benzoic acid A solution of methyl 2-(thiomorpholine-4-sulfonamido)-5-(trifluoromethyl)benzoate (0.15 g, 0.40 mmol) in tetrahydrofuran (4.5 mL) was treated with lithium hydroxide monohydrate (50 mg, 1.2 mmol) and water was added until the mixture became homogeneous (approximately 1 mL). The reaction mixture was stirred at room temperature overnight. After acidification of the mixture with 10% aqueous citric acid solution, it was extracted three times with ethyl acetate. The combined organic extracts were washed twice with saturated aqueous sodium chloride solution, dried over anhydrous magnesium sulfate, filtered, and concentrated under reduced pressure to provide the desired intermediate. LCMS-ESI$^-$ (m/z): [M–H]$^-$ calcd 369.03; found 369.05.

Step 3: Preparation of 2-(thiomorpholine-4-sulfonamido)-5-(trifluoromethyl)-N-(3-(trifluoromethyl)bicyclo[1.1.1]pentan-1-yl)benzamide The titled intermediate was prepared from 2-(thiomorpholine-4-sulfonamido)-5-(trifluoromethyl)benzoic acid (0.12 g, 0.32 mmol) and 3-(trifluoromethyl)bicyclo[1.1.1]pentan-1-amine hydrochloride (62 mg, 0.33 mmol) according to General Synthesis 4, step 3. LCMS-ESI$^-$ (m/z): [M–H]$^-$ calcd 502.08; found 502.16.

Step 4: Preparation of 2-((1,1-dioxidothiomorpholine)-4-sulfonamido)-5-(trifluoromethyl)-N-(3-(trifluoromethyl)bicyclo[1.1.1]pentan-1-yl)benzamide A mixture of 2-(thiomorpholine-4-sulfonamido)-5-(trifluoromethyl)-N-(3-(trifluoromethyl)bicyclo[1.1.1]pentan-1-yl)benzamide (0.16 g, 0.32 mmol) in 2-methyltetrahydrofuran (5 mL) was treated with 3-chloroperbenzoic acid (70-75%, 0.23 g, 0.95 mmol) in a single portion. After 30 minutes of stirring at room temperature, the reaction mixture was concentrated under reduced pressure and purified by reverse-phase high performance liquid chromatography (acetonitrile/water/0.1% trifluoroacetic aid) to provide the titled product. $^1$H NMR (400 MHz, DMSO-d$_6$) δ 11.70 (s, 1H), 9.88 (s, 1H), 8.22 (d, J=2.1 Hz, 1H), 7.91 (m, 1H), 7.65 (d, J=8.7 Hz, 1H), 3.67 (m, 4H), 3.22 (m, 4H), 2.38 (s, 6H). LCMS-ESI$^-$ (m/z): [M–H]$^-$ calcd 534.07; found 534.17.

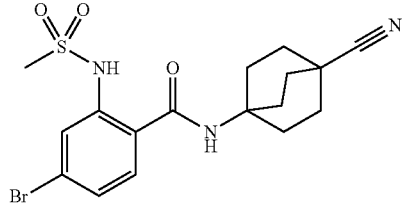 [SMILES: CS(=O)(=O)Nc1cc(Br)ccc1C(=O)NC12CCC(C#N)(CC1)CC2]

Example 194: Preparation of 4-bromo-N-(4-cyanobicyclo[2.2.2]octan-1-yl)-2-(methylsulfonamido)benzamide Following General Synthesis 1, using methyl 2-amino-4-bromobenzoate and 4-(methylsulfonyl)benzenesulfonyl chloride (2.0 equiv.) in Step 1 for 24 hours at room temperature, then 4-aminobicyclo[2.2.2]octane-1-carbonitrile hydrochloride in Step 3, 4-bromo-N-(4-cyanobicyclo[2.2.2]octan-1-yl)-2-(methylsulfonamido)benzamide was synthesized and purified by reverse phase chromatography. $^1$H NMR (400 MHz, DMSO-d$_6$) δ 10.66 (s, 1H), 8.16 (s, 1H), 7.68 (d, J=8.5 Hz, 1H), 7.62 (d, J=2.0 Hz, 1H), 7.40 (dd, J=8.4, 2.0 Hz, 1H), 3.15 (s, 3H), 1.99 (s, 12H). LCMS-ESI$^+$ (m/z): [M+H]$^+$ calcd 426.05; found 426.10.

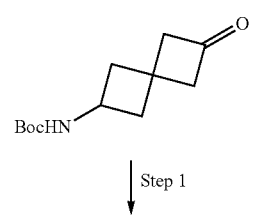

Step 1

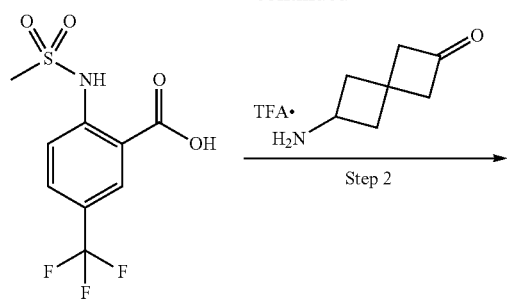

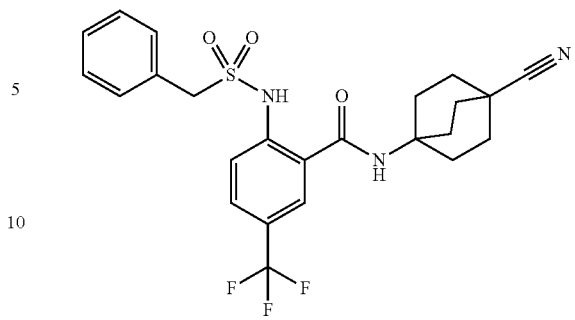

Example 196: Preparation of N-(4-cyanobicyclo[2.2.2]octan-1-yl)-2-((phenylmethyl)sulfonamido)-5-(trifluoromethyl)benzamide Following General Synthesis 2, using methyl 2-bromo-5-(trifluoromethyl)benzoate and phenylmethanesulfonamide in Step 1, then 4-aminobicyclo[2.2.2]octane-1-carbonitrile hydrochloride in Step 3, N-(4-cyanobicyclo[2.2.2]octan-1-yl)-2-((phenylmethyl)sulfonamido)-5-(trifluoromethyl)benzamide was synthesized and purified by crystallization. $^1$H NMR (400 MHz, DMSO-$d_6$) δ 11.00 (s, 1H), 8.39 (s, 1H), 8.07 (s, 1H), 7.78 (d, J=7.6 Hz, 1H), 7.61 (d, J=8.7 Hz, 1H), 7.35-7.28 (m, 3H), 7.26-7.20 (m, 2H), 4.72 (s, 2H), 1.98 (s, 12H). LCMS-ESI$^+$ (m/z): [M+H]$^+$ calcd 492.16; found 492.01.

Example 195: Preparation of 2-(methylsulfonamido)-N-(6-oxospiro[3.3]heptan-2-yl)-5-(trifluoromethyl)benzamide Step 1

To a solution of tert-butyl (6-oxospiro[3.3]heptan-2-yl)carbamate (100 mg, 0.444 mmol) in DCM (4.0 mL) was added trifluoroacetic acid (340 μL, 4.44 mmol). The solution was stirred at room temperature overnight and was concentrated to dryness to afford 6-aminospiro[3.3]heptan-2-one as the trifluoroacetic acid salt. The desired product was used in the next step without further purification.

Step 2: A mixture of 2-(methylsulfonamido)-5-(trifluoromethyl)benzoic acid (50.0 mg, 0.177 mmol), 6-aminospiro[3.3]heptan-2-one 2,2,2-trifluoroacetate (106 mg, 0.443 mmol), EDCI (41.1 mg, 0.265 mmol) and HOBT (35.8 mg, 0.265 mmol) in DMF (1.5 mL) was stirred for 5 minutes. N,N-Diisopropylethylamine (154 μL, 0.883 mmol) was added and the solution was stirred at room temperature for 18 hours. The solution was concentrated and the resulting residue was purified by reverse phase chromatography. $^1$H NMR (400 MHz, DMSO-$d_6$) δ 11.58 (s, 1H), 9.27 (d, J=6.9 Hz, 1H), 8.24 (s, 1H), 7.89 (d, J=8.4 Hz, 1H), 7.72 (d, J=8.8 Hz, 1H), 4.52-4.30 (m, 1H), 3.24 (s, 3H), 3.22-3.17 (m, 2H), 3.13-3.08 (m, 2H), 2.60-2.50 (m, 2H), 2.45-2.37 (m, 2H). LCMS-ESI$^+$ (m/z): [M+H]$^+$ calcd 391.09; found 391.03.

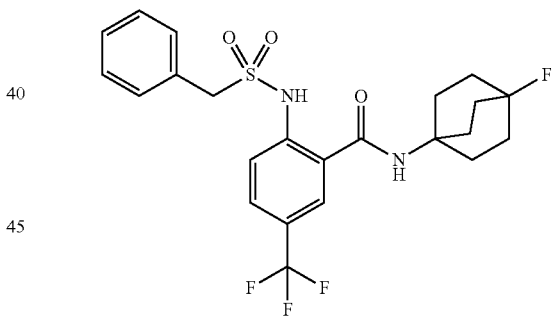

Example 197: Preparation of N-(4-fluorobicyclo[2.2.2]octan-1-yl)-2-((phenylmethyl)sulfonamido)-5-(trifluoromethyl)benzamide Following General Synthesis 2, using methyl 2-bromo-5-(trifluoromethyl)benzoate and phenylmethanesulfonamide in Step 1, then 4-fluorobicyclo[2.2.2]octan-1-amine hydrochloride in Step 3, N-(4-fluorobicyclo[2.2.2]octan-1-yl)-2-((phenylmethyl)sulfonamido)-5-(trifluoromethyl)benzamide was synthesized and purified by reverse phase chromatography. $^1$H NMR (400 MHz, DMSO-$d_6$) δ 11.05 (s, 1H), 8.37 (s, 1H), 8.07 (s, 1H), 7.78 (d, J=9.1 Hz, 1H), 7.61 (d, J=8.7 Hz, 1H), 7.35-7.28 (m, 3H), 7.25-7.20 (m, 2H), 4.72 (s, 2H), 2.16-2.08 (m, 6H), 1.90-1.81 (m, 6H). LCMS-ESI (m/z): [M+H]$^+$ calcd 485.15; found 484.98.

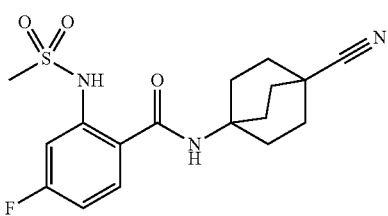 [SMILES: CS(=O)(=O)Nc1cc(F)ccc1C(=O)NC12CCC(C#N)(CC1)CC2]

Example 198: Preparation of N-(4-cyanobicyclo [2.2.2]octan-1-yl)-4-fluoro-2-(methylsulfonamido) benzamide Following General Synthesis 1, using 4-aminobicyclo [2.2.2]octane-1-carbonitrile hydrochloride in Step 3, N-(4-cyanobicyclo[2.2.2]octan-1-yl)-4-fluoro-2-(methylsulfonamido)benzamide was synthesized and purified by reverse phase chromatography. $^1$H NMR (400 MHz, DMSO-$d_6$) δ 10.98 (s, 1H), 8.11 (s, 1H), 7.84 (dd, J=8.9, 6.4 Hz, 1H), 7.26 (dd, J=11.1, 2.6 Hz, 1H), 7.02 (td, J=8.5, 2.5 Hz, 1H), 1.99 (s, 12H). LCMS-ESI$^+$ (m/z): [M+H]$^+$ calcd 366.13; found 366.14.

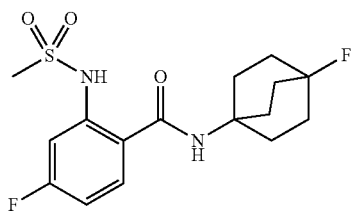 [SMILES: CS(=O)(=O)Nc1cc(F)ccc1C(=O)NC12CCC(F)(CC1)CC2]

Example 199: Preparation of 4-fluoro-N-(4-fluoro-bicyclo[2.2.2]octan-1-yl)-2-(methylsulfonamido) benzamide Following General Synthesis 1, using 4-fluorobicyclo [2.2.2]octan-1-amine hydrochloride in Step 3, 4-fluoro-N-(4-fluorobicyclo[2.2.2]octan-1-yl)-2-(methylsulfonamido) benzamide was synthesized and purified by reverse phase chromatography. $^1$H NMR (400 MHz, DMSO-$d_6$) δ 11.02 (s, 1H), 8.09 (s, 1H), 7.84 (dd, J=8.9, 6.4 Hz, 1H), 7.26 (dd, J=11.1, 2.6 Hz, 1H), 7.02 (td, J=8.5, 2.6 Hz, 1H), 3.18 (s, 3H), 2.19-2.09 (m, 6H), 1.92-1.81 (m, 6H). LCMS-ESI$^+$ (m/z): [M+H]$^+$ calcd 359.12; found 359.06.

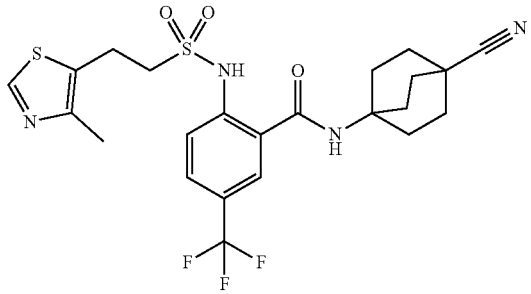 [SMILES: Cc1ncsc1CCS(=O)(=O)Nc1ccc(C(F)(F)F)cc1C(=O)NC12CCC(C#N)(CC1)CC2]

Example 200: Preparation of N-(4-cyanobicyclo [2.2.2]octan-1-yl)-2-((2-(4-methylthiazol-5-yl)ethyl) sulfonamido)-5-(trifluoromethyl)benzamide Following General Synthesis 2, using methyl 2-bromo-5-(trifluoromethyl)benzoate and 2-(4-methylthiazol-5-yl) ethane-1-sulfonamide in Step 1, then 4-aminobicyclo[2.2.2] octane-1-carbonitrile hydrochloride in Step 3, N-(4-cyanobicyclo[2.2.2]octan-1-yl)-2-((2-(4-methylthiazol-5-yl)ethyl)sulfonamido)-5-(trifluoromethyl)benzamide was synthesized and purified by reverse phase chromatography. $^1$H NMR (400 MHz, DMSO-$d_6$) δ 11.07 (s, 1H), 8.81 (s, 1H), 8.41 (s, 1H), 8.07 (s, 1H), 7.84 (dd, J=8.8, 2.1 Hz, 1H), 7.69 (d, J=8.7 Hz, 1H), 3.65-3.56 (m, 2H), 3.21-3.13 (m, 2H), 2.21 (s, 3H), 2.00 (s, 12H). LCMS-ESI$^+$ (m/z): [M+H]$^+$ calcd 527.14; found 527.25.

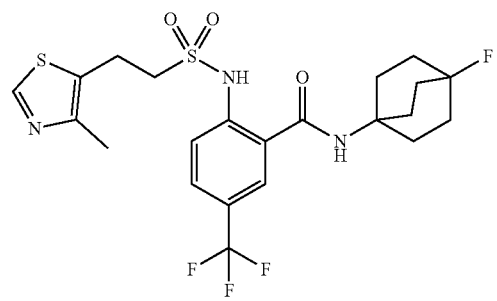 [SMILES: Cc1ncsc1CCS(=O)(=O)Nc1ccc(C(F)(F)F)cc1C(=O)NC12CCC(F)(CC1)CC2]

Example 201: Preparation of N-(4-fluorobicyclo [2.2.2]octan-1-yl)-2-((2-(4-methylthiazol-5-yl)ethyl) sulfonamido)-5-(trifluoromethyl)benzamide Following General Synthesis 2, using methyl 2-bromo-5-(trifluoromethyl)benzoate and 2-(4-methylthiazol-5-yl) ethane-1-sulfonamide in Step 1, then 4-fluorobicyclo[2.2.2] octan-1-amine hydrochloride in Step 3, N-(4-fluorobicyclo [2.2.2]octan-1-yl)-2-((2-(4-methylthiazol-5-yl)ethyl)sulfon-amido)-5-(trifluoromethyl)benzamide was synthesized and purified by reverse phase chromatography. $^1$H NMR (400 MHz, DMSO-$d_6$) δ 11.11 (s, 1H), 8.81 (s, 1H), 8.40 (s, 1H), 8.07 (s, 1H), 7.84 (dd, J=8.8, 2.1 Hz, 1H), 7.69 (d, J=8.7 Hz, 1H), 3.64-3.56 (m, 2H), 3.22-3.12 (m, 2H), 2.22 (s, 3H), 2.18-2.14 (m, 6H), 1.92 (m, 6H). LCMS-ESI$^+$ (m/z): [M+H]$^+$ calcd 520.14; found 520.23.

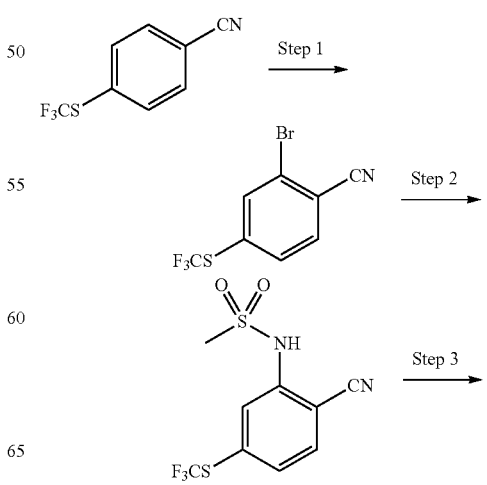

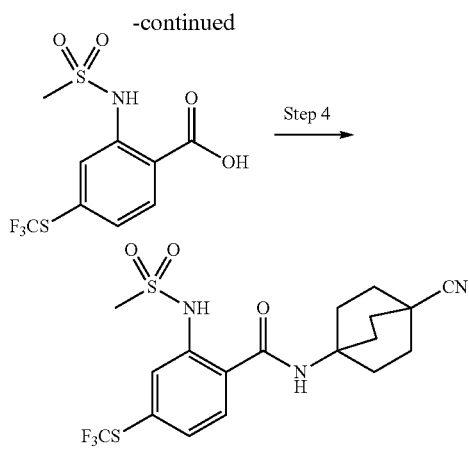

Example 202: Preparation of N-(4-cyanobicyclo[2.2.2]octan-1-yl)-2-(methylsulfonamido)-4-((trifluoromethyl)thio)benzamide

Step 1: Preparation of 2-bromo-4-((trifluoromethyl)thio)benzonitrile

A mixture of 4-(trifluoromethylthio)benzonitrile (5.0 g, 25 mmol), N-bromosuccinimide (4.8 g, 27 mmol), palladium(II) acetate (0.28 g, 1.2 mmol), and p-toluenesulfonic acid monohydrate (2.3 g, 12 mmol) in 1,2-dichloroethane (100 mL) was heated overnight at 80° C. The reaction mixture was purified by flash chromatography (silica gel) to provide the desired intermediate.

Step 2: Preparation of N-(2-cyano-5-((trifluoromethyl)thio)phenyl)methanesulfonamide Following Step 1 of General Synthesis 2, 2-bromo-4-((trifluoromethyl)thio)benzonitrile (0.64 g, 2.3 mmol) was coupled to methanesulfonamide (0.43 g, 4.5 mmol) to provide the desired intermediate. LCMS-ESI⁻ (m/z): [M–H]⁻ calcd 294.99; found 295.01.

Step 3: Preparation of 2-(methylsulfonamido)-4-((trifluoromethyl)thio)benzoic acid N-(2-cyano-5-((trifluoromethyl)thio)phenyl)methanesulfonamide (0.21 g, 0.71 mmol) was taken up in ethanol/water (5:2, 7 mL) and treated with sodium hydroxide (0.28 g, 7.1 mmol). The mixture was heated for four hours at 110° C. and then allowed to cool to room temperature. The reaction mixture was partitioned into ethyl acetate and 10% hydrochloric acid. The aqueous phase was extracted three times with ethyl acetate. The combined organic extracts were washed once with saturated aqueous sodium chloride solution, dried over anhydrous magnesium sulfate, filtered, and concentrated to dryness under reduced pressure to provide the desired intermediate. LCMS-ESI⁻ (m/z): [M–H]⁻ calcd 313.98; found 313.95.

Step 4: Preparation of N-(4-cyanobicyclo[2.2.2]octan-1-yl)-2-(methylsulfonamido)-4-((trifluoromethyl)thio)benzamide The titled compound was prepared from 2-(methylsulfonamido)-4-((trifluoromethyl)thio)benzoic acid (0.12 g, 0.37 mmol) and 4-aminobicyclo[2.2.2]octane-1-carbonitrile hydrochloride (73 mg, 0.39 mmol) according to General Synthesis 10. $^1$H NMR (400 MHz, DMSO-d$_6$) δ 10.35 (s, 1H), 8.28 (s, 1H), 7.78 (d, J=8.2 Hz, 1H), 7.74 (d, J=1.7 Hz, 1H), 7.53 (dd, J=8.2, 1.8 Hz, 1H), 3.13 (s, 3H), 1.99 (s, 12H). LCMS-ESI⁻ (m/z): [M–H]⁻ calcd 446.09; found 446.21.

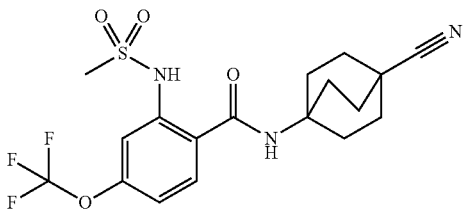 [SMILES: CS(=O)(=O)Nc1cc(OC(F)(F)F)ccc1C(=O)NC12CCC(C#N)(CC1)CC2]

Example 203: Preparation of N-(4-cyanobicyclo[2.2.2]octan-1-yl)-2-(methylsulfonamido)-4-(trifluoromethoxy)benzamide

Step 1: Preparation of 2-(methylsulfonamido)-4-(trifluoromethoxy)benzoic acid According to conditions of Step 1 of General Synthesis 9, 2-bromo-4-(trifluoromethyloxy)benzoic acid (1.0 g, 3.5 mmol) was coupled to methanesulfonamide (1.0 g, 11 mmol) to provide the desired intermediate. LCMS-ESI⁻ (m/z): [M–H]⁻ calcd 298.01; found 297.98.

Step 2: Preparation of N-(4-cyanobicyclo[2.2.2]octan-1-yl)-2-(methylsulfonamido)-4-(trifluoromethoxy)benzamide The titled compound was prepared from 2-(methylsulfonamido)-4-(trifluoromethoxy)benzoic acid (0.12 g, 0.41 mmol) and 4-aminobicyclo[2.2.2]octane-1-carbonitrile hydrochloride (81 mg, 0.44 mmol) according to General Synthesis 10. $^1$H NMR (400 MHz, DMSO-d$_6$) δ 10.69 (s, 1H), 8.21 (s, 1H), 7.84 (d, J=8.7 Hz, 1H), 7.39 (dd, J=2.3, 1.0 Hz, 1H), 7.19 (m, 1H), 3.16 (s, 3H), 1.99 (s, 12H). LCMS-ESI⁻ (m/z): [M–H]⁻ calcd 430.11; found 430.20.

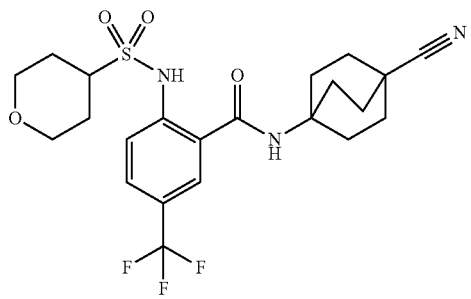 [SMILES: N#CC12CCC(NC(=O)c3cc(C(F)(F)F)ccc3NS(=O)(=O)C3CCOCC3)(CC1)CC2]

Example 204: Preparation of N-(4-cyanobicyclo[2.2.2]octan-1-yl)-2-((tetrahydro-2H-pyran)-4-sulfonamido)-5-(trifluoromethyl)benzamide The titled compound was prepared from N-(4-cyanobicyclo[2.2.2]octan-1-yl)-2-iodo-5-(trifluoromethyl)benzamide (0.20 g, 0.45 mmol) and tetrahydro-2H-pyran-4- sulfonamide (0.22 g, 1.3 mmol) according to General Synthesis 8. Purification was accomplished by flash chromatography (silica gel) instead of by reverse-phase HPLC. $^1$H NMR (400 MHz, DMSO-$d_6$) δ 11.00 (s, 1H), 8.49 (s, 1H), 8.07 (d, J=2.1 Hz, 1H), 7.86 (dd, J=9.0, 2.0 Hz, 1H), 7.77 (d, J=8.7 Hz, 1H), 3.89 (dd, J=11.5, 3.1 Hz, 1H), 3.59 (m, 1H), 3.29 (td, J=12.0, 2.2 Hz, 2H), 2.00 (s, 12H), 1.84 (ddd, J=12.3, 4.1, 1.8 Hz, 2H), 1.62 (qd, J=12.2, 4.7 Hz, 2H). LCMS-ESI⁻ (m/z): [M–H]⁻ calcd 484.16; found 484.30.

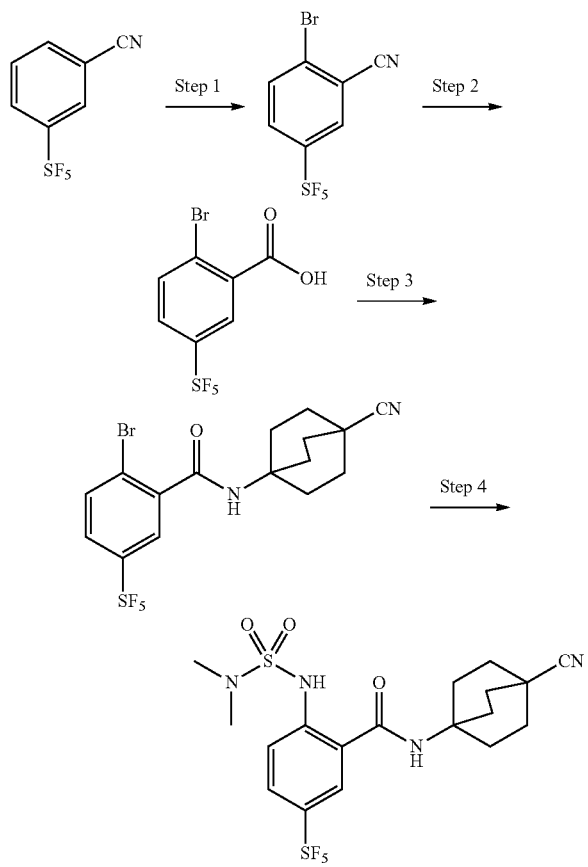

Example 205: Preparation of N-(4-cyanobicyclo [2.2.2]octan-1-yl)-2-((N,N-dimethylsulfamoyl) amino)-5-(pentafluoro-λ$^6$-sulfanyl)benzamide Step 1: Preparation of 2-bromo-5-(pentafluoro-λ$^6$-sulfanyl)benzonitrile A mixture of 3-(pentafluorosulfanyl)benzonitrile (5.0 g, 22 mmol), N-bromosuccinimide (4.3 g, 24 mmol), palladium(II) acetate (0.25 g, 1.1 mmol), and p-toluenesulfonic acid monohydrate (2.1 g, 11 mmol) in 1,2-dichloroethane (90 mL) was heated overnight at 80° C. The reaction mixture was purified by flash chromatography (silica gel) to provide the desired intermediate.

Step 2: Preparation of 2-bromo-5-(pentafluoro-λ$^6$-sulfanyl)benzoic acid

Water (12 mL) was added to a mixture of 2-bromo-5-(pentafluoro-λ$^6$-sulfanyl)benzonitrile (2.22 g, 7.2 mmol) in glacial acetic acid (12 mL). To the suspension was added sulfuric acid (12 mL), and the mixture was heated for 24 hours at 150° C. Upon cooling, the reaction mixture was diluted with water, and the solid was collected by filtration, washed with water, and dried overnight in a vacuum oven to provide the desired intermediate. LCMS-ESI⁻ (m/z): [M–H]⁻ calcd 324.90; found 324.88.

Step 3: Preparation of 2-bromo-N-(4-cyanobicyclo [2.2.2]octan-1-yl)-5-(pentafluoro-λ$^6$-sulfanyl)benzamide The titled intermediate was prepared from 2-bromo-5-(pentafluoro-λ$^6$-sulfanyl)benzoic acid (1.0 g, 3.1 mmol) and 4-aminobicyclo[2.2.2]octane-1-carbonitrile hydrochloride (0.60 g, 3.2 mmol) according to the conditions of General Synthesis 7. LCMS-ESI⁻ (m/z): [M–H]⁻ calcd 457.01; found 457.19.

Step 4: Preparation of N-(4-cyanobicyclo[2.2.2] octan-1-yl)-2-((N,N-dimethylsulfamoyl)amino)-5-(pentafluoro-λ$^6$-sulfanyl)benzamide The titled compound was prepared from 2-bromo-N-(4-cyanobicyclo[2.2.2]octan-1-yl)-5-(pentafluoro-λ$^6$-sulfanyl) benzamide (0.29 g, 0.63 mmol) and N,N-dimethylsulfamide (0.23 g, 1.9 mmol) according to General Synthesis 8. Purification was accomplished by flash chromatography (silica gel) instead of by reverse-phase HPLC. $^1$H NMR (400 MHz, DMSO-$d_6$) δ 10.90 (s, 1H), 8.54 (s, 1H), 8.15 (d, J=2.7 Hz, 1H), 8.04 (dd, J=9.2, 2.6 Hz, 1H), 7.65 (d, J=9.2 Hz, 1H), 2.74 (s, 6H), 2.01 (s, 12H). LCMS-ESI⁻ (m/z): [M–H]⁻ calcd 501.11; found 501.24.

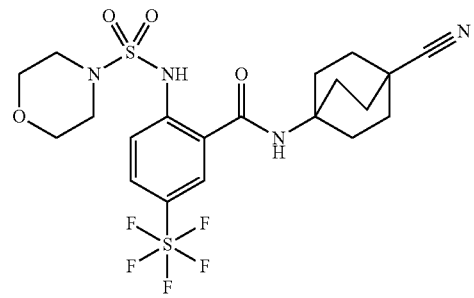 [SMILES: N#CC12CCC(NC(=O)c3cc(S(F)(F)(F)(F)F)ccc3NS(=O)(=O)N3CCOCC3)(CC1)CC2]

Example 206: Preparation of N-(4-cyanobicyclo [2.2.2]octan-1-yl)-2-(morpholine-4-sulfonamido)-5-(pentafluoro-λ$^6$-sulfanyl)benzamide The titled compound was prepared from 2-bromo-N-(4-cyanobicyclo[2.2.2]octan-1-yl)-5-(pentafluoro-λ$^6$-sulfanyl) benzamide (0.20 g, 0.44 mmol) and morpholine-4-sulfonamide (220 mg, 1.3 mmol) according to General Synthesis 8. Purification was accomplished by flash chromatography (silica gel) instead of by reverse-phase HPLC. $^1$H NMR (400 MHz, DMSO-$d_6$) δ 10.99 (s, 1H), 8.57 (s, 1H), 8.15 (d, J=2.7 Hz, 1H), 8.04 (d, J=8.0 Hz, 1H), 7.69 (d, J=9.2 Hz, 1H), 3.56 (m, 4H), 3.09 (t, J=4.7 Hz, 4H), 2.01 (s, 12H). LCMS-ESI⁻ (m/z): [M–H]⁻ calcd 543.12; found 543.29.

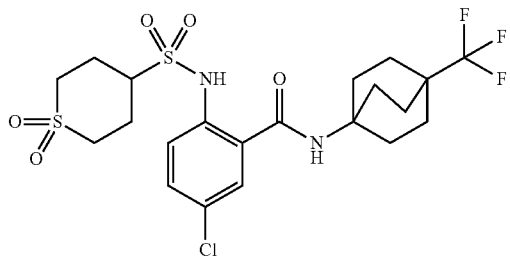 [SMILES: O=C(NC12CCC(C(F)(F)F)(CC1)CC2)c1cc(Cl)ccc1NS(=O)(=O)C1CCS(=O)(=O)CC1]

Example 207: Preparation of 5-chloro-2-((1,1-dioxidotetrahydro-2H-thiopyran)-4-sulfonamido)-N-(4-(trifluoromethyl)bicyclo[2.2.2]octan-1-yl)benzamide Step 1: Preparation of 2-bromo-5-chloro-N-(4-(trifluoromethyl)bicyclo[2.2.2]octan-1-yl)benzamide The titled intermediate was prepared from 2-bromo-5-chlorobenzoic acid (0.35 g, 1.5 mmol) and 4-(trifluoromethyl)bicyclo[2.2.2]octan-1-amine hydrochloride (0.36 g, 1.6 mmol) according to the conditions of General Synthesis 7. LCMS-ESI⁻ (m/z): [M−H]⁻ calcd 408.01; found 408.04.

Step 2: Preparation of 5-chloro-2-((1,1-dioxidotetrahydro-2H-thiopyran)-4-sulfonamido)-N-(4-(trifluoromethyl)bicyclo[2.2.2]octan-1-yl)benzamide The titled compound was prepared from 2-bromo-5-chloro-N-(4-(trifluoromethyl)bicyclo[2.2.2]octan-1-yl)benzamide (0.12 g, 0.29 mmol) and tetrahydro-2H-thiopyran-4-sulfonamide 1,1-dioxide (69 mg, 0.32 mmol) according to General Synthesis 8. ¹H NMR (400 MHz, DMSO-d₆) δ 10.78 (s, 1H), 8.31 (s, 1H), 7.83 (d, J=2.2 Hz, 1H), 7.59 (dd, J=9.0, 2.2 Hz, 1H), 7.55 (d, J=8.8 Hz, 1H), 3.63 (m, 1H), 3.19 (ddd, J=16.7, 12.4, 5.8 Hz, 4H), 2.39 (m, 2H), 2.07 (m, 2H), 2.01 (m, 6H), 1.75 (m, 6H). LCMS-ESI⁻ (m/z): [M−H]⁻ calcd 541.09; found 541.32.

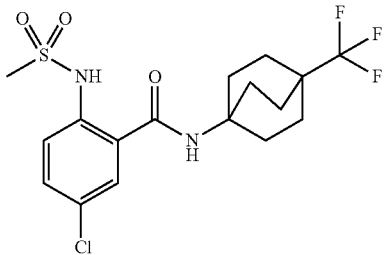 [SMILES: CS(=O)(=O)Nc1ccc(Cl)cc1C(=O)NC12CCC(C(F)(F)F)(CC1)CC2]

Example 208: Preparation of 5-chloro-2-(methylsulfonamido)-N-(4-(trifluoromethyl)bicyclo[2.2.2]octan-1-yl)benzamide The titled compound was prepared from 2-bromo-5-chloro-N-(4-(trifluoromethyl)bicyclo[2.2.2]octan-1-yl)benzamide (0.16 g, 0.40 mmol) and methanesulfonamide (0.11 g, 1.2 mmol) according to General Synthesis 8. ¹H NMR (400 MHz, DMSO-d₆) δ 10.41 (s, 1H), 8.27 (s, 1H), 7.80 (d, J=2.5 Hz, 1H), 7.64 (d, J=9.3 Hz, 1H), 7.57 (dd, J=8.8, 2.5 Hz, 1H), 3.10 (s, 3H), 1.98 (m, 6H), 1.74 (m, 6H). LCMS-ESI⁻ (m/z): [M−H]⁻ calcd 423.08; found 423.22.

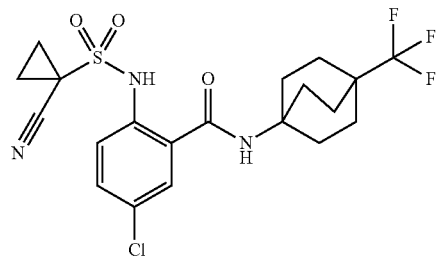 [SMILES: N#CC1(S(=O)(=O)Nc2ccc(Cl)cc2C(=O)NC23CCC(C(F)(F)F)(CC2)CC3)CC1]

Example 209: Preparation of 5-chloro-2-((1-cyanocyclopropane)-1-sulfonamido)-N-(4-(trifluoromethyl)bicyclo[2.2.2]octan-1-yl)benzamide Step 1: Preparation of 5-chloro-2-((1-cyanocyclopropane)-1-sulfonamido)benzoic acid The titled intermediate was prepared from 2-bromo-5-chlorobenzoic acid (0.28 g, 1.2 mmol) and 1-cyanocyclopropane-1-sulfonamide (0.17 g, 1.2 mmol) according to the conditions of Step 1 of General Synthesis 9. LCMS-ESI⁻ (m/z): [M−H]⁻ calcd 299.00; found 299.22.

Step 2: Preparation of 5-chloro-2-((1-cyanocyclopropane)-1-sulfonamido)-N-(4-(trifluoromethyl)bicyclo[2.2.2]octan-1-yl)benzamide The titled compound was prepared from 5-chloro-2-((1-cyanocyclopropane)-1-sulfonamido)benzoic acid (64 mg, 0.21 mmol) and 4-(trifluoromethyl)bicyclo[2.2.2]octan-1-amine hydrochloride (51 mg, 0.22 mmol) according to General Synthesis 10. ¹H NMR (400 MHz, DMSO-d₆) δ 11.30 (s, 1H), 8.35 (s, 1H), 7.83 (d, J=2.4 Hz, 1H), 7.60 (d, J=8.5 Hz, 1H), 7.54 (d, J=8.7 Hz, 1H), 2.02 (m, 6H), 1.84 (q, J=5.5, 5.0 Hz, 2H), 1.74 (m, 6H), 1.64 (q, J=5.4 Hz, 2H). LCMS-ESI⁻ (m/z): [M−H]⁻ calcd 474.09; found 474.31.

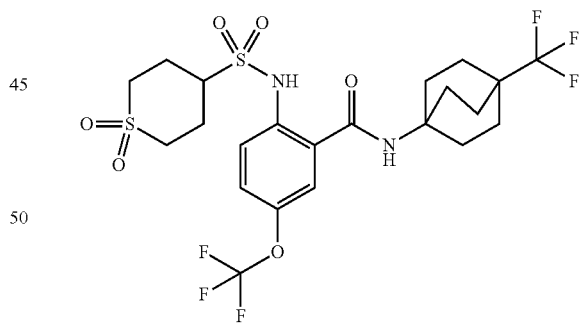

Example 210: Preparation of 2-((1,1-dioxidotetrahydro-2H-thiopyran)-4-sulfonamido)-5-(trifluoromethoxy)-N-(4-(trifluoromethyl)bicyclo[2.2.2]octan-1-yl)benzamide Step 1: Preparation of 2-((1,1-dioxidotetrahydro-2H-thiopyran)-4-sulfonamido)-5-(trifluoromethoxy)benzoic acid The titled intermediate was prepared from tetrahydro-2H-thiopyran-4-sulfonamide 1,1-dioxide (67 mg, 0.31 mmol)

and 2-bromo-5-(trifluoromethoxy)benzoic acid (90 mg, 0.31 mmol) according to the conditions of Step 1 of General Synthesis 9. LCMS-ESI⁻ (m/z): [M–H]⁻ calcd 416.02; found 416.09.

Step 2: Preparation of 2-((1,1-dioxidotetrahydro-2H-thiopyran)-4-sulfonamido)-5-(trifluoromethoxy)-N-(4-(trifluoromethyl)bicyclo[2.2.2]octan-1-yl)benzamide The titled compound was prepared from 2-((1,1-dioxidotetrahydro-2H-thiopyran)-4-sulfonamido)-5-(trifluoromethoxy)benzoic acid (0.13 g, 0.31 mmol) and 4-(trifluoromethyl)bicyclo[2.2.2]octan-1-amine hydrochloride (76 mg, 0.33 mmol) according to General Synthesis 10. ¹H NMR (400 MHz, DMSO-d₆) δ 10.85 (s, 1H), 8.31 (s, 1H), 7.77 (d, J=2.7 Hz, 1H), 7.63 (d, J=9.1 Hz, 1H), 7.56 (ddd, J=9.1, 2.7, 1.3 Hz, 1H), 3.65 (tt, J=11.9, 3.2 Hz, 1H), 3.22 (m, 4H), 2.40 (m, 2H), 2.14-1.92 (m, 8H), 1.75 (m, 6H). LCMS-ESI⁻ (m/z): [M–H]⁻ calcd 591.11; found 591.24.

Example 211: Preparation of 5-chloro-N-(4-cyanobicyclo[2.2.2]octan-1-yl)-2-((1-cyanocyclopropane)-1-sulfonamido)benzamide The titled compound was prepared from 5-chloro-2-((1-cyanocyclopropane)-1-sulfonamido)benzoic acid (74 mg, 0.25 mmol) and 4-aminobicyclo[2.2.2]octane-1-carbonitrile hydrochloride (48 mg, 0.26 mmol) according to General Synthesis 10. ¹H NMR (400 MHz, DMSO-d₆) δ 11.24 (s, 1H), 8.31 (s, 1H), 7.80 (d, J=2.4 Hz, 1H), 7.59 (m, 1H), 7.54 (d, J=8.7 Hz, 1H), 1.99 (s, 12H), 1.83 (q, J=5.4 Hz, 2H), 1.63 (q, J=5.4 Hz, 2H). LCMS-ESI⁻ (m/z): [M–H]⁻ calcd 431.10; found 431.27.

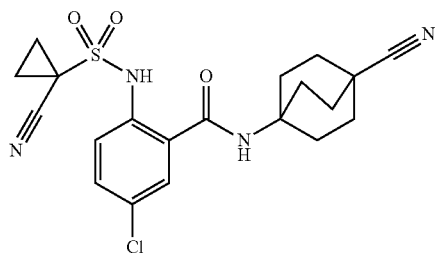 [SMILES: N#CC12CCC(NC(=O)c3cc(Cl)ccc3NS(=O)(=O)C3(C#N)CC3)(CC1)CC2]

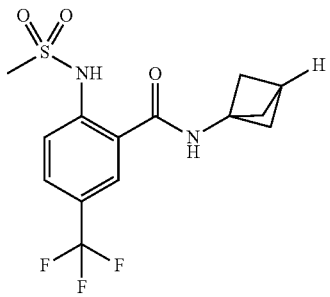 [SMILES: CS(=O)(=O)Nc1ccc(C(F)(F)F)cc1C(=O)NC12CC(C1)C2]

Example 212: Preparation of N-(bicyclo[1.1.1]pentan-1-yl)-2-(methylsulfonamido)-5-(trifluoromethyl)benzamide The titled compound was prepared from 2-(methylsulfonamido)-5-(trifluoromethyl)benzoic acid (100 mg, 0.35 mmol) and bicyclo[1.1.1]pentan-1-amine hydrochloride (44 mg, 0.37 mmol) according to General Synthesis 10. ¹H NMR (400 MHz, DMSO-d₆) δ 11.76 (s, 1H), 9.62 (s, 1H), 8.23 (m, 1H), 7.89 (dd, J=8.8, 2.0 Hz, 1H), 7.72 (d, J=8.7 Hz, 1H), 3.26 (s, 3H), 2.49 (s, 1H, partially obscured by DMSO), 2.13 (s, 6H). LCMS-ESI⁻ (m/z): [M–H]⁻ calcd 347.08; found 347.06.

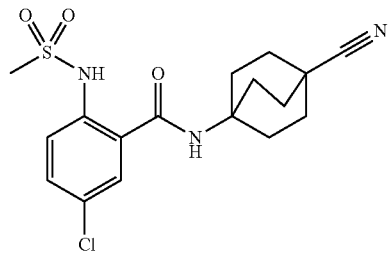 [SMILES: CS(=O)(=O)Nc1ccc(Cl)cc1C(=O)NC12CCC(C#N)(CC1)CC2]

Example 213: Preparation of 5-chloro-N-(4-cyanobicyclo[2.2.2]octan-1-yl)-2-(methylsulfonamido)benzamide The titled compound was prepared from 5-chloro-2-(methylsulfonamido)benzoic acid (85 mg, 0.34 mmol) and 4-aminobicyclo[2.2.2]octane-1-carbonitrile hydrochloride (67 mg, 0.36 mmol) according to General Synthesis 10. ¹H NMR (400 MHz, DMSO-d₆) δ 10.36 (s, 1H), 8.23 (s, 1H), 7.78 (d, J=2.5 Hz, 1H), 7.57 (dd, J=8.8, 2.5 Hz, 1H), 7.47 (d, J=8.8 Hz, 1H), 3.09 (s, 3H), 1.99 (s, 12H). LCMS-ESI⁻ (m/z): [M–H]⁻ calcd 380.09; found 380.20.

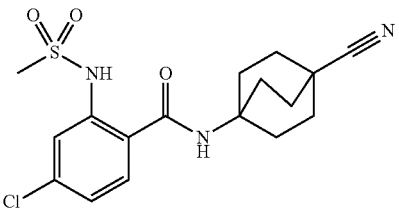 [SMILES: CS(=O)(=O)Nc1cc(Cl)ccc1C(=O)NC12CCC(C#N)(CC1)CC2]

Example 214: Preparation of 4-chloro-N-(4-cyanobicyclo[2.2.2]octan-1-yl)-2-(methylsulfonamido)benzamide The titled compound was prepared from 5-chloro-2-(methylsulfonamido)benzoic acid (85 mg, 0.34 mmol) and 4-aminobicyclo[2.2.2]octane-1-carbonitrile hydrochloride (67 mg, 0.36 mmol) according to General Synthesis 10. ¹H NMR (400 MHz, DMSO-d₆) δ 10.74 (s, 1H), 8.18 (s, 1H), 7.76 (d, J=8.5 Hz, 1H), 7.48 (d, J=2.1 Hz, 1H), 7.26 (dd, J=8.5, 2.1 Hz, 1H), 3.16 (s, 3H), 1.98 (s, 12H). LCMS-ESI⁻ (m/z): [M–H]⁻ calcd 380.09; found 380.22.

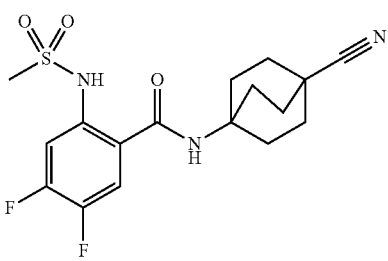 [SMILES: CS(=O)(=O)Nc1cc(F)c(F)cc1C(=O)NC12CCC(C#N)(CC1)CC2]

Example 215: Preparation of N-(4-cyanobicyclo[2.2.2]octan-1-yl)-4,5-difluoro-2-(methylsulfonamido)benzamide Step 1: Preparation of 4,5-difluoro-2-(methylsulfonamido)benzoic acid The titled intermediate was prepared from methanesulfonamide (0.92 g, 9.7 mmol) and 2-bromo-4,5-difluorobenzoic acid (1.2 g, 4.9 mmol) according to the conditions of Step 1 of General Synthesis 9. LCMS-ESI$^-$ (m/z): [M−H]$^-$ calcd 250.01; found 249.95.

Step 2: Preparation of N-(4-cyanobicyclo[2.2.2]octan-1-yl)-4,5-difluoro-2-(methylsulfonamido)benzamide The titled compound was prepared from 4,5-difluoro-2-(methylsulfonamido)benzoic acid (120 mg, 0.47 mmol) and 4-aminobicyclo[2.2.2]octane-1-carbonitrile hydrochloride (91 mg, 0.49 mmol) according to General Synthesis 10. $^1$H NMR (400 MHz, DMSO-d$_6$) δ 10.60 (s, 1H), 8.12 (s, 1H), 7.90 (dd, J=11.5, 8.8 Hz, 1H), 7.46 (dd, J=12.3, 7.3 Hz, 1H), 3.14 (s, 3H), 1.98 (s, 12H). LCMS-ESI$^-$ (m/z): [M−H]$^-$ calcd 382.11; found 382.18.

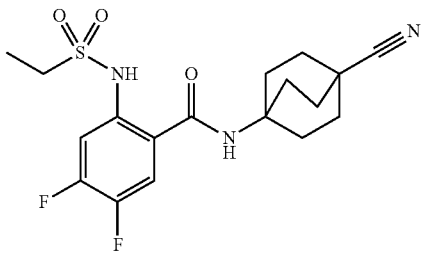 [SMILES: CCS(=O)(=O)Nc1cc(F)c(F)cc1C(=O)NC12CCC(C#N)(CC1)CC2]

Example 216: Preparation of N-(4-cyanobicyclo[2.2.2]octan-1-yl)-4,5-difluoro-2-(ethylsulfonamido)benzamide Step 1: Preparation of 2-(ethylsulfonamido)-4,5-difluorobenzoic acid The titled intermediate was prepared from ethanesulfonamide (0.78 g, 7.1 mmol) and 2-bromo-4,5-difluorobenzoic acid (1.1 g, 4.8 mmol) according to the conditions of Step 1 of General Synthesis 9. LCMS-ESI$^-$ (m/z): [M−H]$^-$ calcd 264.02; found 263.96.

Step 2: Preparation of N-(4-cyanobicyclo[2.2.2]octan-1-yl)-4,5-difluoro-2-(methylsulfonamido)benzamide The titled compound was prepared from 2-(ethylsulfonamido)-4,5-difluorobenzoic acid (130 mg, 0.50 mmol) and 4-aminobicyclo[2.2.2]octane-1-carbonitrile hydrochloride (99 mg, 0.53 mmol) according to General Synthesis 10. $^1$H NMR (400 MHz, DMSO-d$_6$) δ 10.73 (s, 1H), 8.17 (s, 1H), 7.93 (dd, J=11.5, 8.7 Hz, 1H), 7.48 (dd, J=12.4, 7.3 Hz, 1H), 3.25 (q, J=7.3 Hz, 2H), 1.98 (s, 12H), 1.15 (t, J=7.3 Hz, 3H). LCMS-ESI$^-$ (m/z): [M−H]$^-$ calcd 396.13; found 396.22.

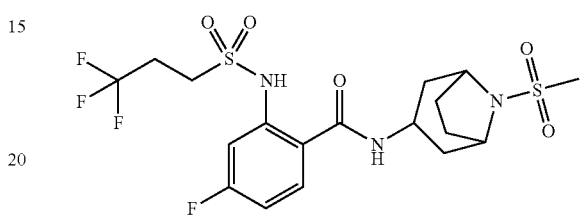

Example 217: Preparation of 4-fluoro-N-(8-(methylsulfonyl)-8-azabicyclo[3.2.1]octan-3-yl)-2-((3,3,3-trifluoropropyl)sulfonamido)benzamide 4-Fluoro-2-((3,3,3-trifluoropropyl)sulfonamido)benzoic acid was synthesized using General Synthesis 9, with the addition of sarcosine ligand (0.20 equiv.), and starting from 2-bromo-4-fluorobenzoic acid and 3,3,3-trifluoropropane-1-sulfonamide (1.2 equiv.). 4-Fluoro-2-((3,3,3-trifluoropropyl)sulfonamido)benzoic acid and 8-(methylsulfonyl)-8-azabicyclo[3.2.1]octan-3-amine (1.4 equiv.) were then subjected to General Synthesis 10 to afford 4-fluoro-N-(8-(methylsulfonyl)-8-azabicyclo[3.2.1]octan-3-yl)-2-((3,3,3-trifluoropropyl)sulfonamido)benzamide as a mixture of diastereomers. $^1$H NMR (400 MHz, DMSO-d$_6$) δ 11.67 (s, 1H, diastereomer 1), 11.11 (s, 1H, diastereomer 2), 8.72 (d, J=7.9 Hz, 1H, diastereomer 1), 8.54-8.44 (m, 1H, diastereomer 2), 7.97-7.85 (m, 1H, diastereomer 1), 7.81-7.70 (m, 1H, diastereomer 2), 7.40-7.27 (m, 2H, diastereomers 1 and 2), 7.21-7.01 (m, 2H, diastereomers 1 and 2), 4.38-4.23 (m, 1H, diastereomer 1), 4.18 (s, 2H, diastereomer 1), 4.13 (s, 2H, diastereomer 2), 4.06-3.98 (m, 1H, diastereomer 2), 3.67-3.55 (m, 4H, diastereomers 1 and 2), 2.96 (s, 3H, diastereomer 1), 2.95 (s, 3H, diastereomer 2), 2.82-2.64 (m, 4H, diastereomers 1 and 2), 2.15-1.94 (m, 10H, diastereomers 1 and 2), 1.94-1.83 (m, 2H, diastereomers 1 and 2), 1.82-1.68 (m, 4H, diastereomers 1 and 2). LCMS-ESI$^-$ (m/z): [M−H]$^-$ calcd 500.09; found 500.22.

Example 218: Preparation of 4-chloro-N-(8-(methylsulfonyl)-8-azabicyclo[3.2.1]octan-3-yl)-2-((3,3,3-trifluoropropyl)sulfonamido)benzamide 4-Chloro-2-((3,3,3-trifluoropropyl)sulfonamido)benzoic acid was synthesized using General Synthesis 9, with the addition of sarcosine ligand (0.20 equiv.), and starting from 2-bromo-4-chlorobenzoic acid and 3,3,3-trifluoropropane-1-sulfonamide (1.2 equiv.). 4-chloro-2-((3,3,3-trifluoropropyl)sulfonamido)benzoic acid and 8-(methylsulfonyl)-8-azabicyclo[3.2.1]octan-3-amine (1.4 equiv.) were then subjected to General Synthesis 10 to afford 4-chloro-N-(8-(methylsulfonyl)-8-azabicyclo[3.2.1]octan-3-yl)-2-((3,3,3-trifluoropropyl)sulfonamido)benzamide as a mixture of diastereomers. ¹H NMR (400 MHz, DMSO-d₆) δ 11.41 (s, 1H, diastereomer 1), 10.85 (s, 1H, diastereomer 2), 8.77 (d, J=7.8 Hz, 1H, diastereomer 1), 8.52 (d, J=3.3 Hz, 1H, diastereomer 2), 7.86-7.78 (m, 1H, diastereomer 1), 7.66 (d, J=8.5 Hz, 1H, diastereomer 2), 7.56 (d, J=2.1 Hz, 1H, diastereomer 1), 7.55 (d, J=2.1 Hz, 1H, diastereomer 2), 7.36 (dd, J=8.4, 2.0 Hz, 1H, diastereomer 1), 7.32 (dd, J=8.5, 2.0 Hz, 1H, diastereomer 2), 4.36-4.22 (m, 1H, diastereomer 1), 4.18 (s, 2H, diastereomer 1), 4.13 (s, 2H, diastereomer 2), 4.01 (d, J=4.5 Hz, 1H, diastereomer 2), 3.62-3.54 (m, 4H, diastereomers 1 and 2), 2.96 (s, 3H, diastereomer 1), 2.95 (s, 3H, diastereomer 2), 2.84-2.65 (m, 4H, diastereomers 1 and 2), 2.17-1.94 (m, 10H, diastereomers 1 and 2), 1.92-1.84 (m, 2H, diastereomers 1 and 2), 1.82-1.67 (m, 4H, diastereomers 1 and 2). LCMS-ESI⁻ (m/z): [M−H]⁻ calcd 516.06; found 516.25.

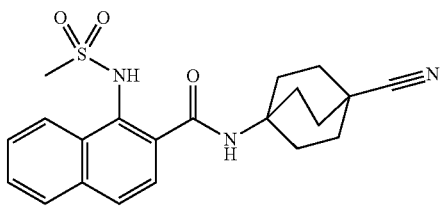 [SMILES: CS(=O)(=O)Nc1c(C(=O)NC23CCC(C#N)(CC2)CC3)ccc2ccccc12]

Example 219: Preparation of N-(4-cyanobicyclo[2.2.2]octan-1-yl)-1-(methylsulfonamido)-2-naphthamide 1-(Methylsulfonamido)-2-naphthoic acid was synthesized using General Synthesis 9, with the addition of N,N-dimethylglycine ligand (0.20 equiv.), and starting from 1-bromo-2-naphthoic acid and methanesulfonamide (1.2 equiv.). 1-(Methylsulfonamido)-2-naphthoic acid and 4-aminobicyclo[2.2.2]octane-1-carbonitrile hydrochloride (1.2 equiv.) were then subjected to General Synthesis 10 to afford N-(4-cyanobicyclo[2.2.2]octan-1-yl)-1-(methylsulfonamido)-2-naphthamide. H NMR (400 MHz, DMSO-d₆) δ 9.47 (s, 1H), 8.32 (d, J=8.0 Hz, 1H), 8.04-7.89 (m, 3H), 7.68-7.52 (m, 3H), 3.01 (s, 3H), 2.01 (s, 12H). LCMS-ESI⁻ (m/z): [M−H]⁻ calcd 396.14; found 396.23.

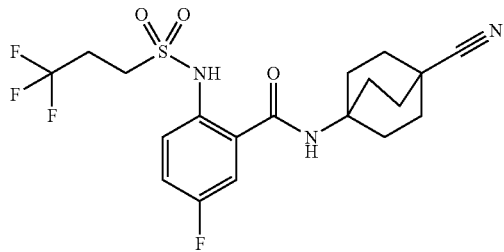 [SMILES: N#CC12CCC(NC(=O)c3cc(F)ccc3NS(=O)(=O)CCC(F)(F)F)(CC1)CC2]

Example 220: Preparation of N-(4-cyanobicyclo[2.2.2]octan-1-yl)-5-fluoro-2-((3,3,3-trifluoropropyl)sulfonamido)benzamide N-(4-cyanobicyclo[2.2.2]octan-1-yl)-5-fluoro-2-((3,3,3-trifluoropropyl)sulfonamido)benzamide was synthesized following the same procedure as Example 134, starting with 2-bromo-5-fluorobenzoic acid. ¹H NMR (400 MHz, DMSO-d₆) δ 10.30 (s, 1H), 8.15 (s, 1H), 7.53 (dd, J=9.3, 3.0 Hz, 1H), 7.49 (dd, J=9.0, 5.0 Hz, 1H), 7.38 (td, J=8.5, 3.0 Hz, 1H), 3.46-3.38 (m, 2H), 2.77-2.62 (m, 2H), 1.98 (s, 12H). LCMS-ESI⁻ (m/z): [M−H]⁻ calcd 446.12; found 446.18.

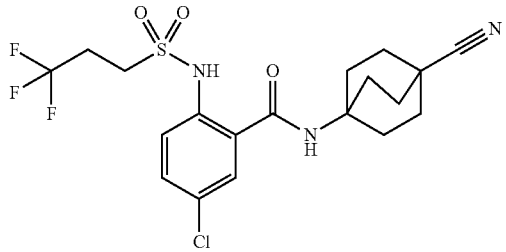

Example 221: Preparation of 5-chloro-N-(4-cyanobicyclo[2.2.2]octan-1-yl)-2-((3,3,3-trifluoropropyl)sulfonamido)benzamide 5-Chloro-N-(4-cyanobicyclo[2.2.2]octan-1-yl)-2-((3,3,3-trifluoropropyl)sulfonamido)benzamide was synthesized following the same procedure as Example 134, starting with 2-bromo-5-chlorobenzoic acid. ¹H NMR (400 MHz, DMSO-d₆) δ 10.55 (s, 1H), 8.25 (s, 1H), 7.75 (d, J=2.4 Hz, 1H), 7.57 (dd, J=8.8, 2.4 Hz, 1H), 7.50 (d, J=8.8 Hz, 1H), 3.53-3.43 (m, 2H), 2.78-2.64 (m, 2H), 1.99 (s, 12H). LCMS-ESI⁻ (m/z): [M−H]⁻ calcd 462.09; found 462.23.

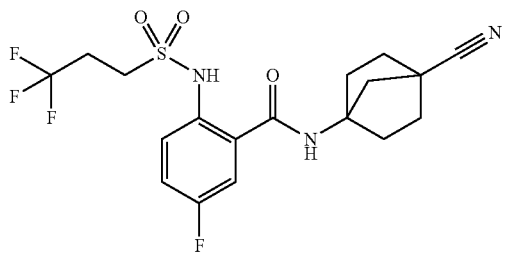 [SMILES: N#CC12CCC(NC(=O)c3cc(F)ccc3NS(=O)(=O)CCC(F)(F)F)(CC1)C2]

Example 222: Preparation of N-(4-cyanobicyclo[2.2.1]heptan-1-yl)-5-fluoro-2-((3,3,3-trifluoropropyl)sulfonamido)benzamide N-(4-cyanobicyclo[2.2.1]heptan-1-yl)-5-fluoro-2-((3,3,3-trifluoropropyl)sulfonamido)benzamide was synthesized following the same procedure as Example 134, starting with 2-bromo-5-fluorobenzoic acid, and using 4-aminobicyclo[2.2.1]heptane-1-carbonitrile hydrochloride in General Synthesis 10. ¹H NMR (400 MHz, DMSO-d₆) δ 10.56 (s, 1H), 8.93 (s, 1H), 7.64 (dd, J=9.5, 3.1 Hz, 1H), 7.53 (dd, J=9.1, 4.9 Hz, 1H), 7.41 (td, J=8.4, 2.8 Hz, 1H), 3.50-3.40 (m, 2H), 2.80-2.62 (m, 2H), 2.17 (s, 2H), 2.12-1.78 (m, 8H). LCMS-ESI⁻ (m/z): [M−H]⁻ calcd 432.10; found 432.20.

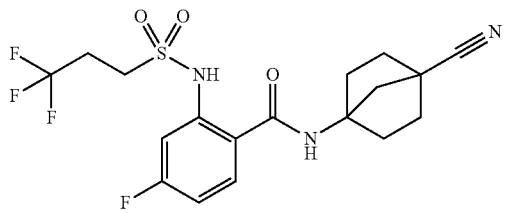 [SMILES: N#CC12CCC(NC(=O)c3ccc(F)cc3NS(=O)(=O)CCC(F)(F)F)(CC1)C2]

Example 223: Preparation of N-(4-cyanobicyclo [2.2.1]heptan-1-yl)-4-fluoro-2-((3,3,3-trifluoropropyl)sulfonamido)benzamide N-(4-cyanobicyclo[2.2.1]heptan-1-yl)-4-fluoro-2-((3,3,3-trifluoropropyl)sulfonamido)benzamide was synthesized following the same procedure as Example 134, using 4-aminobicyclo[2.2.1]heptane-1-carbonitrile hydrochloride in General Synthesis 10. $^1$H NMR (400 MHz, DMSO-$d_6$) δ 11.43 (s, 1H), 8.96 (s, 1H), 7.93 (dd, J=8.9, 6.4 Hz, 1H), 7.39-7.27 (m, 1H), 7.09 (td, J=8.5, 2.5 Hz, 1H), 3.66-3.51 (m, 2H), 2.81-2.64 (m, 2H), 2.18 (s, 2H), 2.11-1.78 (m, 8H). LCMS-ESI$^-$ (m/z): [M–H]$^-$ calcd 432.10; found 432.19.

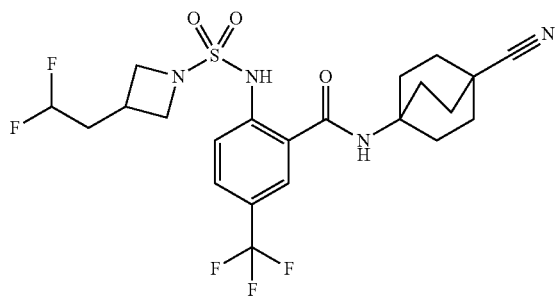 [SMILES: N#CC12CCC(NC(=O)c3cc(C(F)(F)F)ccc3NS(=O)(=O)N3CC(CC(F)F)C3)(CC1)CC2]

Example 224: Preparation of N-(4-cyanobicyclo [2.2.2]octan-1-yl)-2-((3-(difluoromethoxy)azetidine)-1-sulfonamido)-5-(trifluoromethyl)benzamide

Step 1: Preparation of benzyl 3-hydroxyazetidine-1-carboxylate

Azetidin-3-ol (0.40 g, 5.5 mmol), potassium carbonate (2.1 g, 15 mmol), and N-(benzyloxycarbonyloxy)succinimide (1.4 g, 5.6 mmol) were treated with dioxane (8.0 mL) and water (8.0 mL). The mixture was stirred at room temperature overnight, and then partitioned between ethyl acetate and 0.5 M aqueous hydrochloric acid. The aqueous phase was extracted with ethyl acetate. The combined organic extracts were washed with sat. aq. sodium chloride solution, dried over anhydrous magnesium sulfate, filtered, and concentrated to a residue under reduced atmosphere. The residue was purified by silica flash chromatography to afford benzyl 3-hydroxyazetidine-1-carboxylate. LCMS-ESI$^+$ (m/z): [M+H]$^+$ calcd 208.10; found 207.76.

Step 2: Preparation of benzyl 3-(difluoromethoxy)azetidine-1-carboxylate

Benzyl 3-hydroxyazetidine-1-carboxylate (250 mg, 1.2 mmol) was taken up in acetonitrile (2.2 mL) and treated with copper iodide (47 mg, 0.24 mmol). The mixture was heated to 50° C. with stirring. 2,2-Difluoro-2-(fluorosulfonyl)acetic acid (330 mg, 1.8 mmol) in acetonitrile (0.6 mL) was then added dropwise over a period of 45 minutes, at 50° C. The mixture was stirred for an additional 30 minutes at 50° C., at which point the reaction mixture was cooled to room temperature and concentrated to a residue. The residue was taken up in ethyl acetate and the solids were removed by filtration. The filtrate was concentrated to a residue, which was purified by silica flash chromatography to afford benzyl 3-(difluoromethoxy)azetidine-1-carboxylate. LCMS-ESI$^+$ (m/z): [M+H]$^+$ calcd 258.09; found 257.79.

Step 3: Preparation of 3-(difluoromethoxy)azetidine hydrochloride

Benzyl 3-(difluoromethoxy)azetidine-1-carboxylate (220 mg, 0.84 mmol) was taken up in ethanol (5.0 mL), then treated with concentrated hydrochloric acid (59 mg, 1.6 mmol) and 10% palladium on carbon (43 mg, 0.041 mmol). The reaction vessel was evacuated and backfilled with hydrogen gas at 40 psi. The mixture was shaken under pressure for 2 hours, then filtered through Celite, and concentrated to a residue. Product used without further purification.

Step 4: Preparation of 3-(difluoromethoxy)azetidine-1-sulfonamide

Title compound prepared according to General Synthesis 12, using 3-(difluoromethoxy)azetidine hydrochloride (130 mg, 1.0 equiv.), (tert-butoxycarbonyl)((4-(dimethyliminio) pyridin-1(4H)-yl)sulfonyl)amide (1.2 equiv.), triethylamine (1.2 equiv.), and dichloromethane (3.0 mL).

Step 5: Preparation of N-(4-cyanobicyclo[2.2.2] octan-1-yl)-2-((3-(difluoromethoxy)azetidine)-1-sulfonamido)-5-(trifluoromethyl)benzamide 2-Bromo-N-(4-cyanobicyclo[2.2.2]octan-1-yl)-5-(trifluoromethyl)benzamide was prepared according to General Synthesis 7, using 2-bromo-5-(trifluoromethyl)benzoic acid (1.0 equiv.) and 4-aminobicyclo[2.2.2]octane-1-carbonitrile hydrochloride (1.3 equiv.). 2-Bromo-N-(4-cyanobicyclo [2.2.2]octan-1-yl)-5-(trifluoromethyl)benzamide (42 mg, 0.10 mmol) and 3-(difluoromethoxy)azetidine-1-sulfonamide (20 mg, 0.10 mmol) were treated with tris(dibenzylideneacetone)dipalladium(0) (9.1 mg, 0.010 mmol), 4,5-bis (diphenylphosphino)-9,9-dimethylxanthene (8.6 mg, 0.015 mmol), tribasic potassium phosphate (42 mg, 0.20 mmol), and toluene (0.5 mL), then heated at 100° C. for 2 hours. The mixture was then partitioned between ethyl acetate and 0.5 M aqueous hydrochloric acid. The aqueous phase was extracted with ethyl acetate. The combined organic extracts were washed with sat. aq. sodium chloride solution, dried over anhydrous magnesium sulfate, filtered, and concentrated to a residue under reduced atmosphere. The residue was purified by reverse phase preparative HPLC to afford the title compound. $^1$H NMR (400 MHz, DMSO-$d_6$) δ 11.26 (s, 1H), 8.45 (s, 1H), 8.09 (s, 1H), 7.88 (d, J=8.6 Hz, 1H), 7.70 (d, J=8.6 Hz, 1H), 6.70 (t, J=74.3 Hz, 1H), 4.99-4.85 (m, 1H), 4.15-4.11 (m, 2H), 3.83-3.80 (m, 2H), 2.01 (s, 12H). LCMS-ESI$^-$ (m/z): [M–H]$^-$ calcd 521.13; found 521.24.

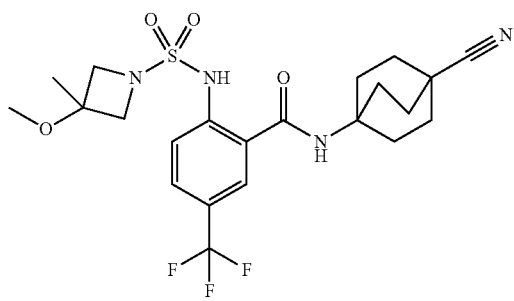 [SMILES: COC1(C)CN(S(=O)(=O)Nc2ccc(C(F)(F)F)cc2C(=O)NC23CCC(C#N)(CC2)CC3)C1]

Example 225: Preparation of N-(4-cyanobicyclo[2.2.2]octan-1-yl)-2-((3-methoxy-3-methylazetidine)-1-sulfonamido)-5-(trifluoromethyl)benzamide

Step 1: Preparation of benzyl 3-hydroxy-3-methylazetidine-1-carboxylate

Title compound prepared as described in Example 224, Step 1, using 3-methylazetidin-3-ol (1.0 equiv.). LCMS-ESI⁺ (m/z): [M+H]⁺ calcd 222.11; found 221.79.

Step 2: Preparation of benzyl 3-methoxy-3-methylazetidine-1-carboxylate

Benzyl 3-hydroxy-3-methylazetidine-1-carboxylate (0.584 g, 2.64 mmol) was dissolved in tetrahydrofuran (1.0 mL), and then added dropwise to a suspension of 60% sodium hydride in mineral oil (423 mg, 10.6 mmol) in tetrahydrofuran (3.0 mL) at 0° C. The reaction mixture was then allowed to warm to room temperature, with stirring, for 30 minutes. The mixture was then cooled to 0° C. and treated with iodomethane (2.25 g, 15.8 mmol) in tetrahydrofuran (2.0 mL). After warming to room temperature and stirring overnight, the reaction was quenched with sat. aq. ammonium chloride. The aqueous phase was extracted with ethyl acetate. The combined organic extracts were washed with sat. aq. sodium chloride solution, dried over anhydrous sodium sulfate, filtered, and concentrated to a residue under reduced atmosphere. Residue purified by silica flash chromatography to afford benzyl 3-methoxy-3-methylazetidine-1-carboxylate. LCMS-ESI⁺ (m/z): [M+H]⁺ calcd 236.13; found 235.77.

Step 3: Preparation of 3-methoxy-3-methylazetidine hydrochloride

Title compound prepared as described in Example 224, Step 3, starting from benzyl 3-methoxy-3-methylazetidine-1-carboxylate and carried out with hydrogen gas at atmospheric pressure.

Step 4: Preparation of benzyl ((3-methoxy-3-methylazetidin-1-yl)sulfonyl)carbamate A solution of benzyl alcohol (522 mg, 4.83 mmol) in acetonitrile (13 mL) was cooled to 0° C. with stirring. Chlorosulfonyl isocyanate (683 mg, 4.83 mmol) was then added dropwise and the mixture was stirred at 0° C. for 2 hours. Pyridine (954 mg, 12.1 mmol) was then added and the mixture was stirred at 0° C. for 2 hours. 3-methoxy-3-methylazetidine hydrochloride in acetonitrile (2.0 mL) was then added dropwise. The mixture was stirred at 0° C. for 30 minutes, then allowed to warm to room temperature and stirred overnight. The mixture was concentrated and partitioned between ethyl acetate and 0.5 M aq. citric acid. The aqueous phase was extracted with ethyl acetate. The combined organic extracts were washed with sat. aq. sodium chloride solution, dried over anhydrous magnesium sulfate, filtered, and concentrated to a residue under reduced atmosphere. Residue purified by silica flash chromatography to afford benzyl ((3-methoxy-3-methylazetidin-1-yl)sulfonyl)carbamate. LCMS-ESI⁺ (m/z): [M+H]⁺ calcd 315.10; found 314.77.

Step 4: Preparation of 3-methoxy-3-methylazetidine-1-sulfonamide

Title compound prepared as described in Example 224, Step 3, starting from benzyl ((3-methoxy-3-methylazetidin-1-yl)sulfonyl)carbamate, omitting the hydrochloric acid, and carried out with hydrogen gas at atmospheric pressure.

Step 5: Preparation of N-(4-cyanobicyclo[2.2.2]octan-1-yl)-2-((3-methoxy-3-methylazetidine)-1-sulfonamido)-5-(trifluoromethyl)benzamide 2-Bromo-N-(4-cyanobicyclo[2.2.2]octan-1-yl)-5-(trifluoromethyl)benzamide was prepared according to General Synthesis 7, using 2-bromo-5-(trifluoromethyl)benzoic acid (1.0 equiv.) and 4-aminobicyclo[2.2.2]octane-1-carbonitrile hydrochloride (1.3 equiv.). 2-Bromo-N-(4-cyanobicyclo[2.2.2]octan-1-yl)-5-(trifluoromethyl)benzamide (1 equiv.) and 3-methoxy-3-methylazetidine-1-sulfonamide (1 equiv.) were subjected to the conditions described in General Synthesis 8 to afford N-(4-cyanobicyclo[2.2.2]octan-1-yl)-2-((3-methoxy-3-methylazetidine)-1-sulfonamido)-5-(trifluoromethyl)benzamide. ¹H NMR (400 MHz, DMSO-d₆) δ 11.26 (s, 1H), 8.47 (s, 1H), 8.10 (s, 1H), 7.88 (d, J=8.9 Hz, 1H), 7.74 (d, J=8.7 Hz, 1H), 3.78 (d, J=8.4 Hz, 2H), 3.61 (d, J=8.5 Hz, 2H), 3.08 (s, 3H), 2.01 (s, 12H), 1.34 (s, 3H). LCMS-ESI⁻ (m/z): [M−H]⁻ calcd 521.13; found 521.24.

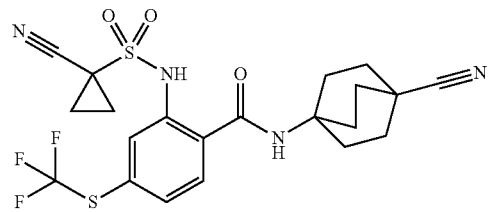 [SMILES: N#CC12CCC(NC(=O)c3ccc(SC(F)(F)F)cc3NS(=O)(=O)C3(C#N)CC3)(CC1)CC2]

Example 226: Preparation of N-(4-cyanobicyclo[2.2.2]octan-1-yl)-2-((1-cyanocyclopropane)-1-sulfonamido)-4-((trifluoromethyl)thio)benzamide

Step 1: Preparation of 2-((1-cyanocyclopropane)-1-sulfonamido)-4-((trifluoromethyl)thio)benzoic acid Title compound prepared as described in General Synthesis 9, starting from 2-bromo-4-((trifluoromethyl)thio)benzoic acid (1 equiv.) and 1-cyanocyclopropane-1-sulfonamide (1.1 equiv.) and with the addition of sarcosine (0.2 equiv.). LCMS-ESI⁻ (m/z): [M−H]⁻ calcd 364.99; found 365.02.

Step 2: Preparation of N-(4-cyanobicyclo[2.2.2]octan-1-yl)-2-((1-cyanocyclopropane)-1-sulfonamido)-4-((trifluoromethyl)thio)benzamide Title compound prepared as described in General Synthesis 10, starting from 2-((1-cyanocyclopropane)-1-sulfonamido)-4-((trifluoromethyl)thio)benzoic acid (1 equiv.) and 4-aminobicyclo[2.2.2]octane-1-carbonitrile hydrochloride (1.2 equiv.). ¹H NMR (400 MHz, DMSO-d₆) δ 11.22 (s, 1H), 8.37 (s, 1H), 7.87-7.77 (m, 2H), 7.62 (s, 1H), 1.99 (s, 12H), 1.80 (s, 2H), 1.59 (m, 2H). LCMS-ESI⁻ (m/z): [M−H]-calcd 497.09; found 497.24.

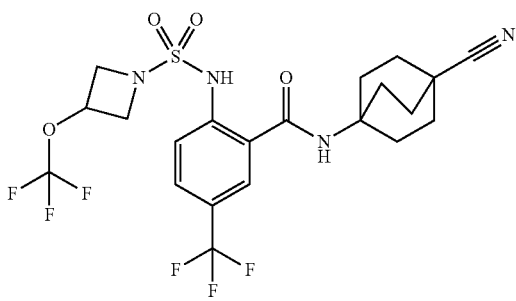 [SMILES: N#CC12CCC(NC(=O)c3cc(C(F)(F)F)ccc3NS(=O)(=O)N3CC(OC(F)(F)F)C3)(CC1)CC2]

Example 227: Preparation of N-(4-cyanobicyclo[2.2.2]octan-1-yl)-2-((3-(trifluoromethoxy)azetidine)-1-sulfonamido)-5-(trifluoromethyl)benzamide Step 1: Preparation of benzyl 3-(((methylthio)carbonothioyl)oxy)azetidine-1-carboxylate Benzyl 3-hydroxyazetidine-1-carboxylate (200 mg, 0.96 mmol), prepared as described in Example 224, Step 1, was dissolved in tetrahydrofuran (1.0 mL). This solution was dispensed dropwise into a suspension of 60% sodium hydride in mineral oil (153 mg, 3.90 mmol) in tetrahydrofuran (3.0 mL) at 0° C. The mixture was then warmed to room temperature and allowed to stir for 30 minutes. Carbon disulfide (220 mg, 2.88 mmol) was then added and stirred for 90 minutes. The mixture was then cooled to 0° C. and iodomethane (818 mg, 5.76 mmol) was added dropwise. After stirring at room temperature for 2 hours, the reaction was quenched with sat. aq. ammonium chloride. The aqueous phase was extracted with ethyl acetate. Combined organic extracts were washed with sat. aq. sodium chloride solution, dried over anhydrous sodium sulfate, filtered, and concentrated to a residue under reduced atmosphere. Residue purified by silica flash chromatography to afford benzyl 3-(((methylthio)carbonothioyl)oxy)azetidine-1-carboxylate. LCMS-ESI+ (m/z): [M+H]+ calcd 298.06; found 297.73.

Step 2: Preparation of benzyl 3-(trifluoromethoxy)azetidine-1-carboxylate

70% Hydrofluoric acid in pyridine (1.98 g, 69.2 mmol) was added dropwise to a solution of 1,3-dibromo-5,5-dimethylhydantoin (779 mg, 2.72 mmol) in dichloromethane (5.0 mL) at −78° C., with stirring. Benzyl 3-(((methylthio)carbonothioyl)oxy)azetidine-1-carboxylate (270 mg, 0.91 mmol) in dichloromethane (2.0 mL) was then added dropwise at −78° C. The mixture was allowed to warm to room temperature, with stirring, overnight. Reaction quenched with sat. aq. sodium bicarbonate. The aqueous phase was extracted with dichloromethane. Combined organic extracts were washed with sat. aq. sodium chloride solution, dried over anhydrous sodium sulfate, filtered, and concentrated to a residue under reduced atmosphere. Residue purified by silica flash chromatography to afford benzyl 3-(trifluoromethoxy)azetidine-1-carboxylate. LCMS-ESI+ (m/z): [M+H]+ calcd 276.08; found 275.77.

Step 3: Preparation of 3-(trifluoromethoxy)azetidine hydrochloride

Title compound prepared as described in Example 224, Step 3, starting from benzyl 3-(trifluoromethoxy)azetidine-1-carboxylate, and carried out with hydrogen gas at atmospheric pressure.

Step 4: Preparation of 3-(trifluoromethoxy)azetidine-1-sulfonamide

Title compound prepared according to General Synthesis 12, using 3-(difluoromethoxy)azetidine hydrochloride (86 mg, 1.0 equiv.), (tert-butoxycarbonyl)((4-(dimethyliminio)pyridin-1(4H)-yl)sulfonyl)amide (1.1 equiv.), triethylamine (3.0 equiv.), and dichloromethane (1.6 mL).

Step 5: Preparation of N-(4-cyanobicyclo[2.2.2]octan-1-yl)-2-((3-(trifluoromethoxy)azetidine)-1-sulfonamido)-5-(trifluoromethyl)benzamide N-(4-cyanobicyclo[2.2.2]octan-1-yl)-2-iodo-5-(trifluoromethyl)benzamide was prepared according to General Synthesis 7, using 2-iodo-5-(trifluoromethyl)benzoic acid (1.0 equiv.) and 4-aminobicyclo[2.2.2]octane-1-carbonitrile hydrochloride (1.3 equiv.). N-(4-cyanobicyclo[2.2.2]octan-1-yl)-2-iodo-5-(trifluoromethyl)benzamide (50 mg, 0.11 mmol) and 3-(trifluoromethoxy)azetidine-1-sulfonamide (37 mg, 0.17 mmol) were treated with copper(I) iodide (2.1 mg, 0.011 mmol), ethyl 2-oxocyclohexane-1-carboxylate (5.63 mg, 0.033 mmol), cesium carbonate (73 mg, 0.22 mmol), and dimethylformamide (0.30 mL). The mixture was stirred at 80° C. overnight, then partitioned between ethyl acetate and 0.5 M aq. hydrochloric acid. The aqueous phase was extracted with ethyl acetate. Combined organic extracts were washed with sat. aq. sodium chloride solution, dried over anhydrous magnesium sulfate, filtered, and concentrated to a residue under reduced atmosphere. Residue purified by reverse phase preparative HPLC to afford N-(4-cyanobicyclo[2.2.2]octan-1-yl)-2-((3-(trifluoromethoxy)azetidine)-1-sulfonamido)-5-(trifluoromethyl)benzamide.
$^1$H NMR (400 MHz, DMSO-$d_6$) δ 11.31 (s, 1H), 8.44 (s, 1H), 8.10 (s, 1H), 7.88 (d, J=8.5 Hz, 1H), 7.70 (d, J=8.6 Hz, 1H), 5.17 (p, J=6.3 Hz, 1H), 4.31-4.15 (m, 2H), 3.95-3.92 (m, 2H), 2.01 (s, 12H). LCMS-ESI− (m/z): [M−H]− calcd 539.12; found 539.26.

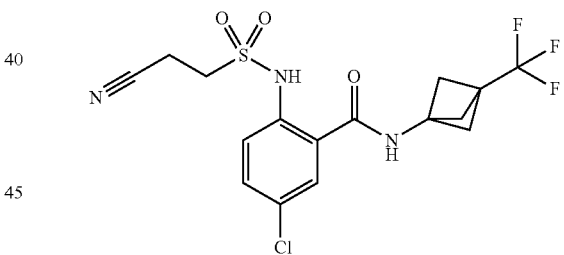

Example 228: Preparation of 5-chloro-2-((2-cyanoethyl)sulfonamido)-N-(3-(trifluoromethyl)bicyclo[1.1.1]pentan-1-yl)benzamide Step 1: Preparation of 5-chloro-2-((2-cyanoethyl)sulfonamido)benzoic acid According to conditions of Step 1 of General Synthesis 9, 2-bromo-5-chlorobenzoic acid (0.27 g, 1.2 mmol) was coupled to 2-cyanoethanesulfonamide (0.16 g, 1.2 mmol) to provide the desired intermediate. LCMS-ESI− (m/z): [M−H]− calcd 287.00; found 287.03.

Step 2: Preparation of 5-chloro-2-((2-cyanoethyl)sulfonamido)-N-(3-(trifluoromethyl)bicyclo[1.1.1]pentan-1-yl)benzamide The titled compound was prepared from 5-chloro-2-((2-cyanoethyl)sulfonamido)benzoic acid (0.11 g, 0.37 mmol)

and 3-(trifluoromethyl)bicyclo[1.1.1]pentan-1-amine hydrochloride (77 mg, 0.41 mmol), according to General Synthesis 10. $^1$H NMR (400 MHz, DMSO-d$_6$) δ 11.12 (s, 1H), 9.62 (s, 1H), 7.88 (d, J=2.5 Hz, 1H), 7.61 (dd, J=8.8, 2.4 Hz, 1H), 7.52 (d, J=8.9 Hz, 1H), 3.66 (t, J=6.8 Hz, 2H), 2.95 (t, J=6.8 Hz, 2H), 2.35 (s, 6H). LCMS-ESI− (m/z): [M−H]− calcd 420.05; found 420.10.

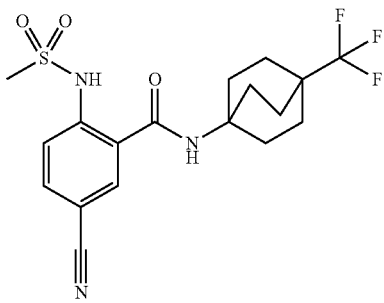 [SMILES: CS(=O)(=O)Nc1ccc(C#N)cc1C(=O)NC12CCC(C(F)(F)F)(CC1)CC2]

Example 229: Preparation of 5-cyano-2-(methylsulfonamido)-N-(4-(trifluoromethyl)bicyclo[2.2.2]octan-1-yl)benzamide Step 1: Preparation of 2-bromo-5-cyano-N-[4-(trifluoromethyl)-1-bicyclo[2.2.2]octanyl]benzamide The titled intermediate was prepared from 2-bromo-5-cyanobenzoic acid (0.40 g, 1.8 mmol) and 4-(trifluoromethyl)bicyclo[2.2.2]octan-1-amine hydrochloride (0.41 g, 1.8 mmol) according to the conditions of General Synthesis 7. LCMS-ESI+ (m/z): [M+H]+ calcd 401.04; found 401.17.

Step 2: Preparation of 5-cyano-2-(methylsulfonamido)-N-(4-(trifluoromethyl)bicyclo[2.2.2]octan-1-yl)benzamide The titled compound was prepared 2-bromo-5-cyano-N-[4-(trifluoromethyl)-1-bicyclo[2.2.2]octanyl]benzamide (0.26 g, 0.65 mmol) and methanesulfonamide (0.19 g, 1.9 mmol) according to General Synthesis 8. Purification was accomplished by flash chromatography (silica gel) instead of by reverse-phase HPLC. $^1$H NMR (400 MHz, DMSO-d$_6$) δ 11.19 (s, 1H), 8.32 (s, 1H), 8.29 (d, J=2.0 Hz, 1H), 7.95 (dd, J=8.7, 1.9 Hz, 1H), 7.63 (d, J=8.7 Hz, 1H), 3.27 (s, 3H), 2.02 (m, 6H), 1.76 (m, 6H). LCMS-ESI− (m/z): [M−H]− calcd 414.12; found 414.23.

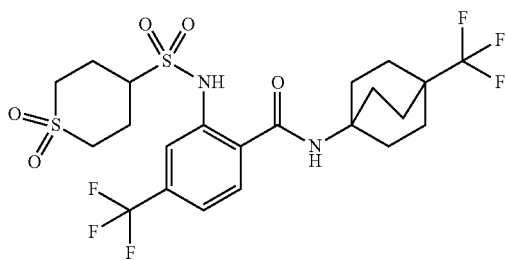 [SMILES: O=C(NC12CCC(C(F)(F)F)(CC1)CC2)c1ccc(C(F)(F)F)cc1NS(=O)(=O)C1CCS(=O)(=O)CC1]

Example 230: Preparation of 2-((1,1-dioxidotetrahydro-2H-thiopyran)-4-sulfonamido)-4-(trifluoromethyl)-N-(4-(trifluoromethyl)bicyclo[2.2.2]octan-1-yl)benzamide Step 1: Preparation of 2-((1,1-dioxidotetrahydro-2H-thiopyran)-4-sulfonamido)-4-(trifluoromethyl) benzoic acid According to conditions of Step 1 of General Synthesis 9, 2-bromo-4-(trifluoromethyl)benzoic acid (0.13 g, 0.47 mmol) was coupled to tetrahydro-2H-thiopyran-4-sulfonamide 1,1-dioxide (0.11 g, 0.52 mmol) to provide the desired intermediate. LCMS-ESI− (m/z): [M−H]− calcd 400.02; found 400.11.

Step 2: Preparation of 2-((1,1-dioxidotetrahydro-2H-thiopyran)-4-sulfonamido)-4-(trifluoromethyl)-N-(4-(trifluoromethyl)bicyclo[2.2.2]octan-1-yl)benzamide The titled compound was prepared from crude 2-((1,1-dioxidotetrahydro-2H-thiopyran)-4-sulfonamido)-4-(trifluoromethyl)benzoic acid (0.47 mmol assumed) and 4-(trifluoromethyl)bicyclo[2.2.2]octan-1-amine hydrochloride (0.11 g, 0.47 mmol), according to General Synthesis 10. $^1$H NMR (400 MHz, DMSO-d$_6$) δ 10.79 (s, 1H), 8.41 (s, 1H), 7.90 (d, J=8.1 Hz, 1H), 7.79 (d, J=1.7 Hz, 1H), 7.60 (dd, J=8.3, 1.7 Hz, 1H), 3.66 (tt, J=11.9, 3.2 Hz, 1H), 3.23 (m, 4H), 2.05 (m, 2H), 2.01 (m, 6H), 1.76 (m, 6H). LCMS-ESI− (m/z): [M−H]− calcd 575.12; found 575.32.

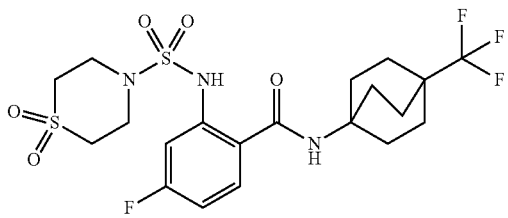

Example 231: Preparation of 2-((1,1-dioxidothiomorpholine)-4-sulfonamido)-4-fluoro-N-(4-(trifluoromethyl)bicyclo[2.2.2]octan-1-yl)benzamide Step 1 (General Synthesis 11): Preparation of benzyl (thiomorpholinosulfonyl)carbamate To a cooled (ice-water bath), stirring solution of benzyl alcohol (2.9 mL, 28 mmol) in acetonitrile (200 mL) was added chlorosulfonyl isocyanate (2.9 mL, 33 mmol). After 30 minutes, pyridine (6.7 mL, 83 mmol) was added. After an additional 30 minutes of stirring, the reaction mixture was transferred to the 4° C. refrigerator for overnight storage. After removal from the refrigerator, the reaction mixture was stirred in an ice-water bath while thiomorpholine (11 mL, 110 mmol) was added. After stirring in the bath for 10 minutes, the bath was removed, and stirring was continued at room temperature for 5 hours. Water was added to this reaction mixture, and the mixture was extracted three times with ethyl acetate. The combined organic extracts were washed with saturated aqueous sodium chloride solution, dried over anhydrous magnesium sulfate, filtered, and concentrated under reduced pressure to provide a crude residue containing the titled intermediate, which was carried forward without further purification. LCMS-ESI⁻ (m/z): [M−H]⁻ calcd 315.06; found 315.10.

Step 2: Preparation of benzyl ((1,1-dioxidothiomorpholino)sulfonyl)carbamate

To a solution of crude benzyl (thiomorpholinosulfonyl)carbamate (7.5 g, 23 mmol) in acetonitrile (100 mL) was added 32% by weight peracetic acid solution (12 mL, 60 mmol). The resulting mixture was stirred overnight at room temperature, after which the precipitated solid was collected by filtration to give the first crop of titled intermediate. The filtrate was concentrated carefully under reduced pressure (not to dryness) to give a slurry, which was diluted with cold water. An additional crop of titled intermediate was collected by filtration, washed with water, and dried in a vacuum oven. LCMS-ESI⁻ (m/z): [M−H]⁻ calcd 347.04; found 347.11.

Step 3: Preparation of thiomorpholine-4-sulfonamide 1,1-dioxide

A suspension of benzyl ((1,1-dioxidothiomorpholino)sulfonyl)carbamate (1.4 g, 4.0 mmol) in ethanol/2-methyltetrahydrofuran (1:1, 100 mL) was degassed and was then treated with 10% palladium on carbon (ca. 55% water, 260 mg). The stirred suspension was evacuated and filled with hydrogen (balloon), an atmosphere under which the mixture was stirred for 3.5 hours before filtration through a pad of Celite diatomaceous and concentration of the filtrate to give the titled intermediate. LCMS-ESI⁻ (m/z): [M−H]⁻ calcd 213.01; found 212.98.

Step 4: Preparation of 2-((1,1-dioxidothiomorpholine)-4-sulfonamido)-4-fluorobenzoic acid According to conditions of Step 1 of General Synthesis 9, 2-bromo-4-fluorobenzoic acid (0.20 g, 0.91 mmol) was coupled to thiomorpholine-4-sulfonamide 1,1-dioxide (0.22 g, 1.0 mmol) to provide the desired intermediate. LCMS-ESI⁻ (m/z): [M−H]⁻ calcd 351.02; found 351.03.

Step 5: Preparation of 2-((1,1-dioxidothiomorpholine)-4-sulfonamido)-4-fluoro-N-(4-(trifluoromethyl)bicyclo[2.2.2]octan-1-yl)benzamide The titled compound was prepared 2-((1,1-dioxidothiomorpholine)-4-sulfonamido)-4-fluorobenzoic acid (0.15 g, 0.41 mmol) and 4-(trifluoromethyl)bicyclo[2.2.2]octan-1-amine hydrochloride (0.10 g, 0.43 mmol), according to General Synthesis 10. ¹H NMR (400 MHz, DMSO-d₆) δ 11.36 (s, 1H), 8.29 (s, 1H), 7.88 (dd, J=8.9, 6.3 Hz, 1H), 7.22 (dd, J=10.8, 2.6 Hz, 1H), 7.08 (td, J=8.5, 2.6 Hz, 1H), 3.62 (m, 4H), 3.19 (m, 4H), 2.01 (m, 6H), 1.75 (m, 6H). LCMS-ESI⁻ (m/z): [M−H]⁻ calcd 526.12; found 526.30.

Example 232: Preparation of 2-((6-cyano-2-azaspiro[3.3]heptane)-2-sulfonamido)-4,5-difluoro-N-(3-(trifluoromethyl)bicyclo[1.1.1]pentan-1-yl)benzamide Step 1: Preparation of tert-butyl 6-(tosyloxy)-2-azaspiro[3.3]heptane-2-carboxylate A magnetically-stirred solution of tert-butyl 6-hydroxy-2-azaspiro[3.3]heptane-2-carboxylate (5.0 g, 23 mmol) in dichloromethane (46 mL) was successively treated with triethylamine (6.5 mL, 47 mmol), 4-toluenesulfonyl chloride (4.9 g, 26 mmol), and 4-dimethylaminopyridine (0.58 g, 4.7 mmol). The reaction mixture was stirred at room temperature overnight and was then filtered through a fritted pad of Celite diatomaceous earth. After concentration of the filtrate under reduced pressure, the residue was taken up in ethyl acetate and was successively washed with saturated aqueous solutions of ammonium chloride and sodium chloride. The organic phase was dried over anhydrous magnesium sulfate, filtered, and concentrated under reduced pressure. The residue was triturated with diethyl ether and collected by filtration to provide the titled intermediate. LCMS-ESI⁺ (m/z): [M−isobutylene+H]⁺ calcd 312.08; found 311.81.

Step 2: Preparation of tert-butyl 6-cyano-2-azaspiro[3.3]heptane-2-carboxylate

A mixture of tert-butyl 6-(p-tolylsulfonyloxy)-2-azaspiro[3.3]heptane-2-carboxylate (4.5 g, 12 mmol) and potassium cyanide (1.6 g, 24 mmol) in DMSO (60 mL) was heated at 100° C. overnight. After allowing the mixture to cool and the partitioning thereof between water and ethyl acetate, the aqueous phase was extracted three times with ethyl acetate. The combined organics were washed once with saturated aqueous sodium chloride solution, dried over anhydrous magnesium sulfate, filtered, and concentrated under reduced pressure. Analysis of the residue by LCMS-ESI⁺ confirmed the consumption of the starting material, hence the crude material was carried forward without further characterization.

Step 3: Preparation of 2-azaspiro[3.3]heptane-6-carbonitrile 2,2,2-trifluoroacetate A solution of tert-butyl 6-cyano-2-azaspiro[3.3]heptane-2-carboxylate (1.0 g, 4.5 mmol) in dichloromethane (15 mL) was treated dropwise with trifluoroacetic acid (TFA, 3.4 mL, 45 mmol) and was stirred for an hour at room temperature. A second portion of TFA (3.4 mL, 45 mmol) was added. The mixture was concentrated under reduced pressure after an additional hour of stirring at room temperature. The residue was co-evaporated twice with diethyl ether, and carried forward without further purification.

Step 4: Preparation of (tert-butoxycarbonyl)((4-(dimethyliminio)pyridin-1(4H)-yl)sulfonyl)amide To a 0° C. (ice-water bath) solution of tert-butanol (11 mL, 115 mol) in dichloromethane (55 mL) was added dropwise chlorosulfonyl isocyanate (6.5 mL, 75 mmol). After 15 minutes of stirring, 4-dimethylaminopyridine (19 g, 150 mmol) was added. The bath then was removed, and the reaction mixture stirred for one hour at room temperature. The mixture was diluted with dichloromethane (130 mL) and was washed four times with water and once with

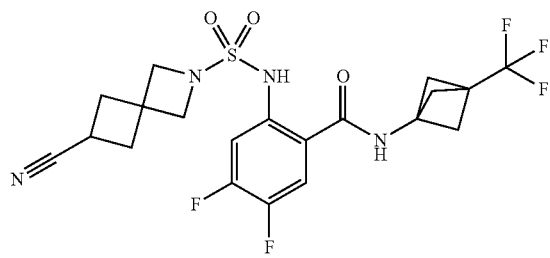 [SMILES: N#CC1CC2(C1)CN(S(=O)(=O)Nc1cc(F)c(F)cc1C(=O)NC13CC(C(F)(F)F)(C1)C3)C2]

saturated aqueous sodium chloride solution. After drying over anhydrous sodium sulfate and decanting, the organic layer was concentrated under reduced pressure to provide the titled intermediate. LCMS-ESI⁺ (m/z): [M+H]⁺ calcd 302.11; found 301.79.

Step 5 (General Synthesis 12, step 1): Preparation of tert-butyl ((6-cyano-2-azaspiro[3.3]heptan-2-yl)sulfonyl)carbamate (tert-Butoxycarbonyl)((4-(dimethyliminio)pyridin-1(4H)-yl)sulfonyl)amide (0.51 g, 1.7 mmol) was added to a solution of 2-azaspiro[3.3]heptane-6-carbonitrile 2,2,2-trifluoroacetate salt (0.40 g, 1.7 mmol) in acetonitrile (15 mL). The suspension was treated with triethylamine (0.94 mL, 6.7 mmol) and was sonicated for 20 minutes before the mixture was concentrated under reduced pressure. The residue was purified by flash chromatography (silica gel) to provide the titled intermediate. LCMS-ESI⁻ (m/z): [M−H]⁻ calcd 300.11; found 300.15.

Step 6 (General Synthesis 12, step 2): Preparation of 6-cyano-2-azaspiro[3.3]heptane-2-sulfonamide A solution of tert-butyl ((6-cyano-2-azaspiro[3.3]heptan-2-yl)sulfonyl)carbamate (0.12 g, 0.41 mmol) in dichloromethane (2 mL) was treated with trifluoroacetic acid (0.38 mL, 4.9 mmol) and was stirred overnight at room temperature. Concentration of the reaction mixture provided the titled intermediate, which was carried forward without further purification. LCMS-ESI⁺ (m/z): [M+H]⁺ calcd 202.06; found 201.97.

Step 7: Preparation of 2-bromo-4,5-difluoro-N-[3-(trifluoromethyl)-1-bicyclo[1.1.1]pentanyl]benzamide The titled intermediate was prepared from 2-bromo-4,5-difluorobenzoic acid (1.5 g, 6.3 mmol) and 3-(trifluoromethyl)bicyclo[1.1.1]pentan-1-amine hydrochloride (1.2 g, 6.6 mmol) according to the conditions of General Synthesis 7. LCMS-ESI⁺ (m/z): [M+H]⁺ calcd 369.98; found 370.06.

Step 8: Preparation of 2-((6-cyano-2-azaspiro[3.3]heptane)-2-sulfonamido)-4,5-difluoro-N-(3-(trifluoromethyl)bicyclo[1.1.1]pentan-1-yl)benzamide The titled compound was prepared from 2-bromo-4,5-difluoro-N-[3-(trifluoromethyl)-1-bicyclo[1.1.1]pentanyl]benzamide (0.13 g, 0.34 mmol) and 6-cyano-2-azaspiro[3.3]heptane-2-sulfonamide (0.08 g, 0.38 mmol) according to General Synthesis 8. Purification was accomplished by flash chromatography (silica gel) instead of by RP-HPLC. ¹H NMR (400 MHz, DMSO-d₆) δ 11.28 (s, 1H), 9.62 (s, 1H), 7.98 (dd, J=11.7, 8.6 Hz, 1H), 7.47 (dd, J=12.5, 7.3 Hz, 1H), 3.82 (d, J=14.9 Hz, 4H), 3.22 (p, J=8.6 Hz, 1H), 2.48-2.44 (partially obscured by DMSO, m, 4H), 2.37 (s, 6H). LCMS-ESI⁻ (m/z): [M−H]⁻ calcd 489.11; found 489.26.

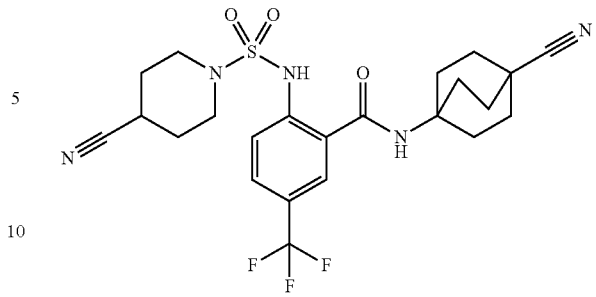

Example 233: Preparation of N-(4-cyanobicyclo[2.2.2]octan-1-yl)-2-((4-cyanopiperidine)-1-sulfonamido)-5-(trifluoromethyl)benzamide

Step 1: Preparation of tert-butyl ((4-cyanopiperidin-1-yl)sulfonyl)carbamate The titled intermediate was prepared from piperidine-4-carbonitrile (10 g, 92 mmol) according to the method of General Synthesis 11, substituting tert-butanol (2.2 mL, 23 mmol) for benzyl alcohol. Following the aqueous work-up, the crude residue was purified by flash chromatography (silica gel). LCMS-ESI⁻ (m/z): [M−H]⁻ calcd 288.11; found 288.11.

Step 2: Preparation of 4-cyanopiperidine-1-sulfonamide

The titled intermediate was prepared from tert-butyl ((4-cyanopiperidin-1-yl)sulfonyl)carbamate according to the method of General Synthesis 12, step 2. LCMS-ESI⁻ (m/z): [M−H]⁻ calcd 188.06; found 188.02.

Step 3: Preparation of N-(4-cyanobicyclo[2.2.2]octan-1-yl)-2-iodo-5-(trifluoromethyl)benzamide The titled intermediate was prepared from 2-iodo-5-(trifluoromethyl)benzoic acid (9.0 g, 28 mmol) and 4-aminobicyclo[2.2.2]octane-1-carbonitrile hydrochloride (6.4 g, 34 mmol) according to the conditions of General Synthesis 7. LCMS-ESI⁻ (m/z): [M−H]⁻ calcd 447.03; found 447.15.

Step 4: Preparation of N-(4-cyanobicyclo[2.2.2]octan-1-yl)-2-((4-cyanopiperidine)-1-sulfonamido)-5-(trifluoromethyl)benzamide The titled compound was prepared from N-(4-cyanobicyclo[2.2.2]octan-1-yl)-2-iodo-5-(trifluoromethyl)benzamide (0.20 g, 0.45 mmol) and 4-cyanopiperidine-1-sulfonamide (0.23 g, 1.2 mmol) according to General Synthesis 8. ¹H NMR (400 MHz, DMSO-d₆) δ 11.13 (s, 1H), 8.47 (s, 1H), 8.09 (s, 1H), 7.86 (d, J=8.7 Hz, 1H), 7.66 (d, J=8.7 Hz, 1H), 3.20 (m, 1H), 3.02 (dddd, J=24.2, 19.6, 11.9, 6.7 Hz, 4H), 2.01 (s, 12H), 1.89 (m, 2H), 1.70 (m, 2H). LCMS-ESI⁻ (m/z): [M−H]⁻ calcd 508.17; found 508.32.

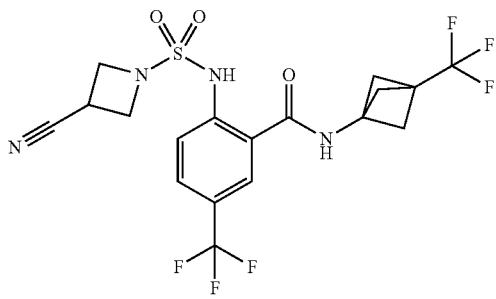 [SMILES: N#CC1CN(S(=O)(=O)Nc2ccc(C(F)(F)F)cc2C(=O)NC23CC(C(F)(F)F)(C2)C3)C1]

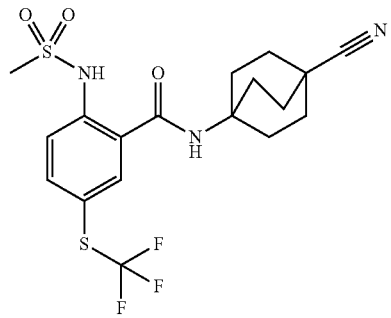 [SMILES: CS(=O)(=O)Nc1ccc(SC(F)(F)F)cc1C(=O)NC12CCC(C#N)(CC1)CC2]

Example 234: Preparation of 2-((3-cyanoazetidine)-1-sulfonamido)-5-(trifluoromethyl)-N-(3-(trifluoromethyl)bicyclo[1.1.1]pentan-1-yl)benzamide Step 1: Preparation of 2-iodo-5-(trifluoromethyl)-N-(3-(trifluoromethyl)bicyclo[1.1.1]pentan-1-yl)benzamide The titled intermediate was prepared from 2-iodo-5-(trifluoromethyl)benzoic acid (0.79 g, 2.5 mmol) and 3-(trifluoromethyl)bicyclo[1.1.1]pentan-1-amine hydrochloride (0.52 g, 2.8 mmol) according to the conditions of General Synthesis 7. LCMS-ESI$^+$ (m/z): [M+H]$^+$ calcd 447.97; found 448.03.

Step 2: Preparation of tert-butyl ((3-cyanoazetidin-1-yl)sulfonyl)carbamate

The titled intermediate was prepared from azetidine-3-carbonitrile hydrochloride (10 g, 85 mmol) according to the method of General Synthesis 11, substituting tert-butanol (2.0 mL, 21 mmol) for benzyl alcohol. LCMS-ESI$^-$ (m/z): [M–H]$^-$ calcd 260.08; found 260.07.

Step 3: Preparation of 3-cyanoazetidine-1-sulfonamide

The titled intermediate was prepared from tert-butyl ((3-cyanoazetidin-1-yl)sulfonyl)carbamate according to the method of General Synthesis 12, step 2. LCMS-ESI$^-$ (m/z): [M–H]$^-$ calcd 160.03; found 159.96.

Step 4: Preparation of 2-((3-cyanoazetidine)-1-sulfonamido)-5-(trifluoromethyl)-N-(3-(trifluoromethyl)bicyclo[1.1.1]pentan-1-yl)benzamide The titled compound was prepared from 2-iodo-5-(trifluoromethyl)-N-[3-(trifluoromethyl)-1-bicyclo[1.1.1]pentanyl]benzamide (0.20 g, 0.45 mmol) and 3-cyanoazetidine-1-sulfonamide (0.43 g, 2.7 mmol) according to General Synthesis 8. $^1$H NMR (400 MHz, DMSO-d$_6$) δ 11.78 (s, 1H), 9.86 (s, 1H), 8.23 (d, J=2.1 Hz, 1H), 7.94 (d, J=8.9 Hz, 1H), 7.70 (d, J=8.7 Hz, 1H), 4.14 (t, J=8.5 Hz, 2H), 4.02 (t, J=7.1 Hz, 2H), 3.79 (m, 1H), 2.38 (s, 6H). LCMS-ESI$^-$ (m/z): [M–H]$^-$ calcd 481.08; found 481.17.

Example 235: Preparation of N-(4-cyanobicyclo[2.2.2]octan-1-yl)-2-(methylsulfonamido)-5-((trifluoromethyl)thio)benzamide Step 1: Preparation of 2-iodo-4-((trifluoromethyl)thio)aniline 4-aminophenyl trifluoromethyl sulfide (7.7 g, 40 mmol) was added via pipette to a magnetically stirred mixture of iodine (10 g, 40 mmol) and silver sulfate (12 g, 40 mmol) in ethanol (400 mL). The reaction flask was covered in aluminum foil and left to stir overnight at room temperature. On the following day, the mixture was filtered, and the filter cake was washed with ethyl acetate. The filtrate was concentrated under reduced pressure. The residue was taken up in isopropyl acetate and was washed successively with 5% aqueous sodium hydroxide (100 mL), water (100 mL), and saturated aqueous sodium chloride solution (100 mL). The organics were dried over anhydrous magnesium sulfate, filtered and concentrated to dryness under reduced pressure to provide the titled intermediate. LCMS-ESI$^+$ (m/z): [M+H]$^+$ calcd 319.91; found 319.95.

Step 2: Preparation of N-(2-iodo-4-((trifluoromethyl)thio)phenyl)methanesulfonamide A solution of 2-iodo-4-((trifluoromethyl)thio)aniline (3.1 g, 9.7 mmol) in dichloromethane (50 mL) was treated successively with pyridine (7.8 mL, 97 mmol) and methanesulfonyl chloride (7.6 mL, 97 mmol), and the mixture was stirred at 50° C. over three nights. Upon cooling, the reaction mixture was treated with 10% aqueous hydrochloric acid (approximately 30 mL) and was stirred for 15 minutes. After dilution with ethyl acetate, the aqueous phase was extracted twice with ethyl acetate. The combined organic phases were washed once with saturated sodium chloride solution, dried over anhydrous magnesium sulfate, filtered, and concentrated under reduced pressure. The residue was purified by flash chromatography (silica gel) to provide a mixture of the titled intermediate and N-(2-iodo-4-((trifluoromethyl)thio)phenyl)-N-(methylsulfonyl)methanesulfonamide. This chromatographed residue was taken up in 1:12-methyltetrahydofuran/water (50 mL) and treated with 1N aqueous potassium hydroxide solution (10 mL). After being stirred briefly, the mixture was acidified with 10% aqueous hydrochloric acid solution and extracted three times with ethyl acetate. The combined extracts were washed once with saturated aqueous sodium chloride solution, dried over anhydrous magnesium sulfate, filtered, and concentrated to dryness under reduced pressure to provide the titled intermediate. LCMS-ESI$^-$ (m/z): [M–H]$^-$ calcd 395.89; found 395.99.

Step 3: Preparation of N-(2-cyano-4-((trifluoromethyl)thio)phenyl)methanesulfonamide A mixture of N-(2-iodo-4-((trifluoromethyl)thio)phenyl)methanesulfonamide (3.1 g, 7.8 mmol) and cuprous cyanide (1.4 g, 16 mmol) in N,N-dimethylformamide (40 mL) was heated overnight at 100° C. and then was concentrated under reduced pressure. The residue was taken up in ethyl acetate (~150 mL), treated with 10% aqueous hydrochloric acid, and filtered through a pad of Celite diatomaceous earth. The aqueous phase was extracted three times with ethyl acetate. The combined organic layers were washed once with saturated aqueous sodium chloride solution, dried over anhydrous magnesium sulfate, filtered, and concentrated under reduced pressure to provide the desired intermediate. LCMS-ESI⁻ (m/z): [M–H]⁻ calcd 294.99; found 295.01.

Step 4: Preparation of 2-(methylsulfonamido)-5-((trifluoromethyl)thio)benzoic acid A mixture of N-(2-cyano-4-((trifluoromethyl)thio)phenyl)methanesulfonamide (7.8 mmol assumed) in EtOH (70 mL) and water (12 mL) was treated with sodium hydroxide pellets (4.7 g, 120 mmol). The flask was equipped with reflux condenser and the mixture was heated to reflux overnight. After cooling, the mixture was acidified with concentrated hydrochloric acid. The acidified mixture was then extracted three times with ethyl acetate. The combined extracts were washed once with saturated aqueous sodium chloride solution, dried over anhydrous magnesium sulfate, filtered, and concentrated under reduced pressure to provide the desired intermediate. LCMS-ESI⁻ (m/z): [M–H]⁻ calcd 313.98; found 313.98.

Step 5: Preparation of N-(4-cyanobicyclo[2.2.2]octan-1-yl)-2-(methylsulfonamido)-5-((trifluoromethyl)thio)benzamide The titled compound was prepared from 2-(methylsulfonamido)-5-((trifluoromethyl)thio)benzoic acid (0.13 g, 0.42 mmol) and 4-aminobicyclo[2.2.2]octane-1-carbonitrile hydrochloride (83 mg, 0.44 mmol), according to General Synthesis 10. ¹H NMR (400 MHz, DMSO-d₆) δ 10.95 (s, 1H), 8.31 (s, 1H), 8.12 (d, J=2.2 Hz, 1H), 7.84 (dd, J=8.9, 2.0 Hz, 1H), 7.61 (d, J=8.7 Hz, 1H), 3.22 (s, 3H), 2.00 (s, 12H). LCMS-ESI⁻ (m/z): [M–H]⁻ calcd 446.09; found 446.20.

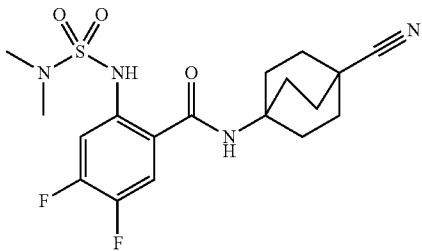 [SMILES: CN(C)S(=O)(=O)Nc1cc(F)c(F)cc1C(=O)NC12CCC(C#N)(CC1)CC2]

Example 236: Preparation of N-(4-cyanobicyclo[2.2.2]octan-1-yl)-2-((N,N-dimethylsulfamoyl)amino)-4,5-difluorobenzamide

Step 1: Preparation of 2-((N,N-dimethylsulfamoyl)amino)-4,5-difluorobenzoic acid According to conditions of Step 1 of General Synthesis 9, 2-bromo-4,5-difluorobenzoic acid (1.0 g, 4.2 mmol) was coupled to N,N-dimethylsulfamide (0.79 g, 6.3 mmol) to provide, after flash chromatography (silica gel), the desired intermediate. LCMS-ESI⁻ (m/z): [M–H]⁻ calcd 279.03; found 279.02.

Step 2: Preparation of N-(4-cyanobicyclo[2.2.2]octan-1-yl)-2-((N,N-dimethylsulfamoyl)amino)-4,5-difluorobenzamide The titled compound was prepared from 2-((N,N-dimethylsulfamoyl)amino)-4,5-difluorobenzoic acid (0.15 g, 0.54 mmol) and 4-aminobicyclo[2.2.2]octane-1-carbonitrile hydrochloride (0.11 g, 0.56 mmol), according to General Synthesis 10. ¹H NMR (400 MHz, DMSO-d₆) δ 10.77 (s, 1H), 8.20 (s, 1H), 7.92 (dd, J=11.5, 8.7 Hz, 1H), 7.42 (dd, J=12.4, 7.3 Hz, 1H), 2.70 (s, 6H), 1.99 (s, 12H). LCMS-ESI– (m/z): [M–H]⁻ calcd 411.14; found 411.25.

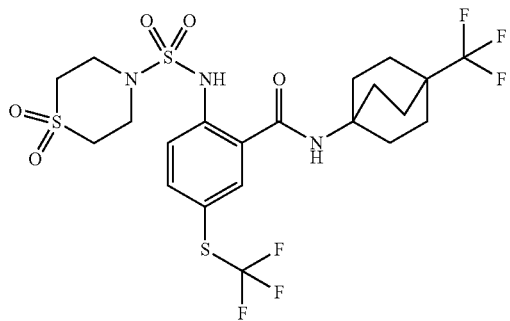 [SMILES: O=C(NC12CCC(C(F)(F)F)(CC1)CC2)c1cc(SC(F)(F)F)ccc1NS(=O)(=O)N1CCS(=O)(=O)CC1]

Example 237: Preparation of 2-((1,1-dioxidothiomorpholine)-4-sulfonamido)-N-(4-(trifluoromethyl)bicyclo[2.2.2]octan-1-yl)-5-((trifluoromethyl)thio)benzamide

Step 1: Preparation of 2-bromo-5-((trifluoromethyl)thio)benzonitrile

A mixture of 3-(trifluoromethylthio)benzonitrile (5.0 g, 25 mmol), N-bromosuccinimide (4.8 g, 27 mmol), palladium(II) acetate (0.28 g, 1.2 mmol, 5 mol %), and p-toluenesulfonic acid monohydrate (2.3 g, 12 mmol) in 1,2-dichloroethane (100 mL) was heated for two days at 70° C. LC/MS analysis indicated the consumption of the starting material. Following concentration of the reaction mixture under reduced pressure, it was purified by flash chromatography (silica gel) to provide the desired intermediate, which was carried forward to the next step.

Step 2: Preparation of 2-bromo-5-((trifluoromethyl)thio)benzoic acid

Water (15 mL) was added to a mixture of 2-bromo-5-((trifluoromethyl)thio)benzonitrile (2.7 g, 9.6 mmol) in glacial acetic acid (15 mL). Sulfuric acid (15 mL) was then added, and the mixture was heated overnight at 140° C. Upon cooling, the reaction mixture was diluted with water. The precipitated solid was collected by filtration, washed with water, and dried overnight in a vacuum oven to provide the desired intermediate. LCMS-ESI– (m/z): [M–H]⁻ calcd 298.91; found 298.86.

Step 3: Preparation of 2-((1,1-dioxidothiomorpho-line)-4-sulfonamido)-5-((trifluoromethyl)thio)benzoic acid According to conditions of Step 1 of General Synthesis 9, 2-bromo-5-((trifluoromethyl)thio)benzoic acid (0.33 g, 1.1 mmol) was coupled to thiomorpholine-4-sulfonamide 1,1-dioxide (0.23 g, 1.1 mmol) to provide the desired intermediate. LCMS-ESI⁻ (m/z): [M–H]⁻ calcd 432.99; found 433.01.

Step 4: Preparation of 2-((1,1-dioxidothiomorpho-line)-4-sulfonamido)-N-(4-(trifluoromethyl)bicyclo[2.2.2]octan-1-yl)-5-((trifluoromethyl)thio)benzamide The titled compound was prepared from 2-((1,1-dioxidothiomorpholine)-4-sulfonamido)-5-((trifluoromethyl)thio) benzoic acid (0.15 g, 0.35 mmol) and 4-(trifluoromethyl)bicyclo[2.2.2]octan-1-amine hydrochloride (79 mg, 0.35 mmol), according to General Synthesis 10. ¹H NMR (400 MHz, DMSO-d₆) δ 11.31 (s, 1H), 8.43 (s, 1H), 8.16 (d, J=2.2 Hz, 1H), 7.85 (d, J=8.7 Hz, 1H), 7.59 (d, J=8.6 Hz, 1H), 3.65 (m, 4H), 3.21 (t, J=5.2 Hz, 4H), 2.03 (m, 6H), 1.76 (m, 6H). LCMS-ESI– (m/z): [M–H]⁻ calcd 608.08; found 608.23.

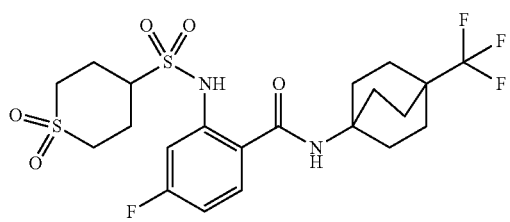 [SMILES: O=C(NC12CCC(C(F)(F)F)(CC1)CC2)c1ccc(F)cc1NS(=O)(=O)C1CCS(=O)(=O)CC1]

Example 238: Preparation of 2-((1,1-dioxidotetrahydro-2H-thiopyran)-4-sulfonamido)-4-fluoro-N-(4-(trifluoromethyl)bicyclo[2.2.2]octan-1-yl)benzamide Step 1: Preparation of tetrahydro-2H-thiopyran-4-sulfonamide 1,1-dioxide A solution of 1,1-dioxo-1λ⁶-thiane-4-sulfonyl chloride (0.24 g, 1.9 mmol) in dioxane (4 mL), stirred in an ice-water bath, was treated with ammonium hydroxide (2.5 mL, 19 mmol). The cooling bath was removed and mixture was allowed to stir overnight. The mixture was concentrated to a suspension, filtered, and the filter cake dried in a vacuum oven overnight to give the titled intermediate. LCMS-ESI– (m/z): [M–H]⁻ calcd 212.01; found 212.01.

Step 2: Preparation of 2-((1,1-dioxidotetrahydro-2H-thiopyran)-4-sulfonamido)-4-fluorobenzoic acid According to conditions of Step 1 of General Synthesis 9, 2-bromo-4-fluorobenzoic acid (0.12 g, 0.56 mmol) was coupled to tetrahydro-2H-thiopyran-4-sulfonamide 1,1-dioxide (0.13 g, 0.59 mmol) to provide the desired intermediate. LCMS-ESI– (m/z): [M–H]⁻ calcd 350.02; found 350.11.

Step 3: Preparation of 2-((1,1-dioxidotetrahydro-2H-thiopyran)-4-sulfonamido)-4-fluoro-N-(4-(trifluoromethyl)bicyclo[2.2.2]octan-1-yl)benzamide The titled compound was prepared from 2-((1,1-dioxidotetrahydro-2H-thiopyran)-4-sulfonamido)-4-fluorobenzoic acid (0.20 g, 0.56 mmol) and 4-(trifluoromethyl)bicyclo[2.2.2]octan-1-amine hydrochloride (0.13 g, 0.56 mmol), according to General Synthesis 10. ¹H NMR (400 MHz, DMSO-d₆) δ 11.39 (s, 1H), 8.25 (s, 1H), 7.89 (dd, J=8.9, 6.4 Hz, 1H), 7.31 (dd, J=11.0, 2.6 Hz, 1H), 7.06 (td, J=8.5, 2.6 Hz, 1H), 3.74 (tt, J=11.9, 3.2 Hz, 1H), 3.20 (m, 4H), 2.39 (m, 2H), 2.14-1.92 (m, 8H), 1.75 (m, 6H). LCMS-ESI– (m/z): [M–H]⁻ calcd 525.12; found 525.30.

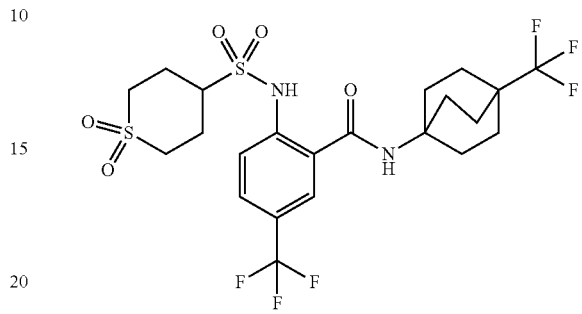

Example 239: Preparation of 2-((1,1-dioxidotetrahydro-2H-thiopyran)-4-sulfonamido)-5-(trifluoromethyl)-N-(4-(trifluoromethyl)bicyclo[2.2.2]octan-1-yl)benzamide Step 1: Preparation of 2-((1,1-dioxidotetrahydro-2H-thiopyran)-4-sulfonamido)-5-(trifluoromethyl)benzoic acid According to conditions of Step 1 of General Synthesis 9, 2-bromo-5-(trifluoromethyl)benzoic acid (0.16 g, 0.60 mmol) was coupled to tetrahydro-2H-thiopyran-4-sulfonamide 1,1-dioxide (0.14 g, 0.64 mmol) to provide the desired intermediate. LCMS-ESI⁻ (m/z): [M–H]⁻ calcd 400.02; found 400.11.

Step 2: Preparation of 2-((1,1-dioxidotetrahydro-2H-thiopyran)-4-sulfonamido)-5-(trifluoromethyl)-N-(4-(trifluoromethyl)bicyclo[2.2.2]octan-1-yl)benzamide The titled compound was prepared from 2-((1,1-dioxidotetrahydro-2H-thiopyran)-4-sulfonamido)-5-(trifluoromethyl)benzoic acid (0.24 g, 0.60 mmol) and 4-(trifluoromethyl)bicyclo[2.2.2]octan-1-amine hydrochloride (0.14 g, 0.60 mmol), according to General Synthesis 10. ¹H NMR (400 MHz, DMSO-d₆) δ 11.29 (s, 1H), 8.53 (s, 1H), 8.12 (d, J=2.1 Hz, 1H), 7.89 (dd, J=8.8, 2.1 Hz, 1H), 7.75 (d, J=8.7 Hz, 1H), 3.73 (tt, J=11.8, 3.2 Hz, 1H), 3.33-3.12 (m, 4H), 2.40 (m, 2H), 2.16-1.95 (m, 8H), 1.76 (m, 6H). LCMS-ESI– (m/z): [M–H]⁻ calcd 575.12; found 575.32.

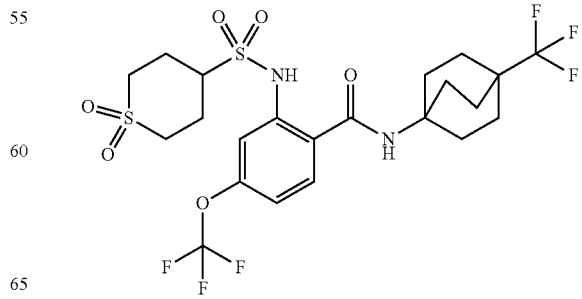

Example 240: Preparation of 2-((1,1-dioxidotetrahydro-2H-thiopyran)-4-sulfonamido)-4-(trifluoromethoxy)-N-(4-(trifluoromethyl)bicyclo[2.2.2]octan-1-yl)benzamide

Step 1: Preparation 2-((1,1-dioxidotetrahydro-2H-thiopyran)-4-sulfonamido)-4-(trifluoromethoxy)benzoic acid According to conditions of Step 1 of General Synthesis 9, 2-bromo-4-(trifluoromethoxy)benzoic acid (0.13 g, 0.44 mmol) was coupled to tetrahydro-2H-thiopyran-4-sulfonamide 1,1-dioxide (98 mg, 0.46 mmol) to provide the desired intermediate. LCMS-ESI– (m/z): [M–H]⁻ calcd 416.02; found 416.12.

Step 2: Preparation of 2-((1,1-dioxidotetrahydro-2H-thiopyran)-4-sulfonamido)-4-(trifluoromethoxy)-N-(4-(trifluoromethyl)bicyclo[2.2.2]octan-1-yl)benzamide The titled compound was prepared from 2-((1,1-dioxidotetrahydro-2H-thiopyran)-4-sulfonamido)-4-(trifluoromethoxy)benzoic acid (0.18 g, 0.44 mmol) and 4-(trifluoromethyl)bicyclo[2.2.2]octan-1-amine hydrochloride (0.10 g, 0.44 mmol), according to General Synthesis 10. $^1$H NMR (400 MHz, DMSO-d$_6$) δ 11.10 (s, 1H), 8.32 (s, 1H), 7.89 (d, J=8.8 Hz, 1H), 7.46 (d, J=2.3 Hz, 1H), 7.29-7.14 (m, 1H), 3.70 (m, 1H), 3.21 (m, J=12.4, 5.9 Hz, 4H), 2.41 (d, J=13.7 Hz, 2H), 2.12-1.94 (m, 8H), 1.75 (m, 6H). LCMS-ESI– (m/z): [M–H]⁻ calcd 591.11; found 591.32.

Example 241: Preparation of 4-chloro-2-((1,1-dioxidotetrahydro-2H-thiopyran)-4-sulfonamido)-N-(4-(trifluoromethyl)bicyclo[2.2.2]octan-1-yl)benzamide

Step 1: Preparation 4-chloro-2-((1,1-dioxidotetrahydro-2H-thiopyran)-4-sulfonamido)benzoic acid According to conditions of Step 1 of General Synthesis 9, 2-bromo-4-chlorobenzoic acid (0.13 g, 0.53 mmol) was coupled to tetrahydro-2H-thiopyran-4-sulfonamide 1,1-dioxide (0.12 g, 0.56 mmol) to provide the desired intermediate. LCMS-ESI– (m/z): [M–H]⁻ calcd 366.02; found 366.12.

Step 2: Preparation of 4-chloro-2-((1,1-dioxidotetrahydro-2H-thiopyran)-4-sulfonamido)-N-(4-(trifluoromethyl)bicyclo[2.2.2]octan-1-yl)benzamide The titled compound was prepared from 4-chloro-2-((1,1-dioxidotetrahydro-2H-thiopyran)-4-sulfonamido)benzoic acid (0.20 g, 0.53 mmol) and 4-(trifluoromethyl)bicyclo[2.2.2]octan-1-amine hydrochloride (0.13 g, 0.56 mmol), according to General Synthesis 10. $^1$H NMR (400 MHz, DMSO-d$_6$) δ 11.16 (s, 1H), 8.28 (s, 1H), 7.81 (d, J=8.6 Hz, 1H), 7.54 (d, J=2.1 Hz, 1H), 7.29 (dd, J=8.5, 2.1 Hz, 1H), 3.71 (tt, J=11.8, 3.2 Hz, 1H), 3.21 (m, 4H), 2.40 (m, 2H), 2.13-2.04 (partially overlapping with m @ δ 2.00, m, 2H), 2.00 (m, 6H), 1.75 (m, 6H). LCMS-ESI– (m/z): [M–H]⁻ calcd 541.09; found 541.33.

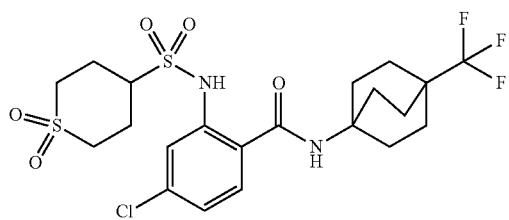 [SMILES: O=C(NC12CCC(C(F)(F)F)(CC1)CC2)c1ccc(Cl)cc1NS(=O)(=O)C1CCS(=O)(=O)CC1]

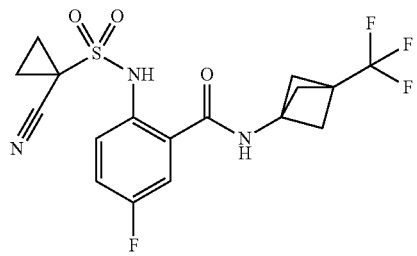 [SMILES: N#CC1(S(=O)(=O)Nc2ccc(F)cc2C(=O)NC23CC(C(F)(F)F)(C2)C3)CC1]

Example 242: Preparation of 2-((1-cyanocyclopropane)-1-sulfonamido)-5-fluoro-N-(3-(trifluoromethyl)bicyclo[1.1.1]pentan-1-yl)benzamide

Step 1: Preparation 2-((1-cyanocyclopropane)-1-sulfonamido)-5-fluorobenzoic acid According to conditions of Step 1 of General Synthesis 9, 2-bromo-5-fluorobenzoic acid (0.27 g, 1.2 mmol) was coupled to 1-cyanocyclopropane-1-sulfonamide (0.19 g, 1.3 mmol) to provide, after flash chromatography (silica gel), the desired intermediate. LCMS-ESI– (m/z): [M–H]⁻ calcd 283.03; found 283.05.

Step 2: Preparation of 2-((1-cyanocyclopropane)-1-sulfonamido)-5-fluoro-N-(3-(trifluoromethyl)bicyclo[1.1.1]pentan-1-yl)benzamide The titled compound was prepared from 2-[(1-cyanocyclopropyl)sulfonylamino]-5-fluorobenzoic acid (98 mg, 0.35 mmol) and 3-(trifluoromethyl)bicyclo[1.1.1]pentan-1-amine hydrochloride (71 mg, 0.38 mmol), according to General Synthesis 10. $^1$H NMR (400 MHz, DMSO-d$_6$) δ 11.17 (s, 1H), 9.63 (s, 1H), 7.65 (dd, J=9.4, 3.0 Hz, 1H), 7.57 (dd, J=9.0, 5.0 Hz, 1H), 7.46 (m, 1H), 2.36 (s, 6H), 1.80 (q, J=5.4 Hz, 2H), 1.60 (q, J=5.3 Hz, 2H). LCMS-ESI– (m/z): [M–H]⁻ calcd 416.08; found 416.24.

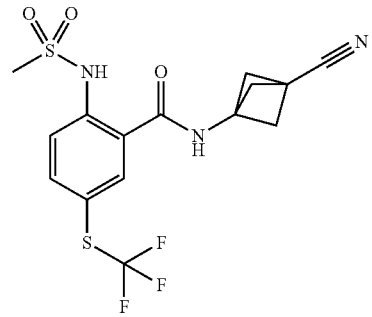 [SMILES: CS(=O)(=O)Nc1ccc(SC(F)(F)F)cc1C(=O)NC12CC(C#N)(C1)C2]

Example 243: Preparation of N-(3-cyanobicyclo[1.1.1]pentan-1-yl)-2-(methylsulfonamido)-5-((trifluoromethyl)thio)benzamide The titled compound was prepared from 2-(methylsulfonamido)-5-((trifluoromethyl)thio)benzoic acid (0.15 g, 0.48 mmol) and 3-aminobicyclo[1.1.1]pentane-1-carbonitrile hydrochloride (72 mg, 0.50 mmol), according to General Synthesis 10. $^1$H NMR (400 MHz, DMSO-d$_6$) δ 11.48 (s, 1H), 9.73 (s, 1H), 8.21 (d, J=2.1 Hz, 1H), 7.88 (dd, J=8.7, 2.0 Hz, 1H), 7.67 (d, J=8.7 Hz, 1H), 3.27 (s, 3H), 2.61 (s, 6H). LCMS-ESI– (m/z): [M–H]$^-$ calcd 404.04; found 404.13.

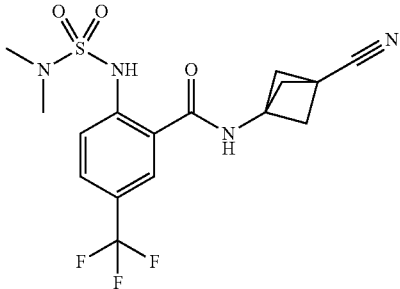 [SMILES: CN(C)S(=O)(=O)Nc1ccc(C(F)(F)F)cc1C(=O)NC12CC(C#N)(C1)C2]

Example 244: Preparation of N-(3-cyanobicyclo[1.1.1]pentan-1-yl)-2-((N,N-dimethylsulfamoyl)amino)-5-(trifluoromethyl)benzamide Step 1: Preparation of 2-bromo-N-(3-cyanobicyclo[1.1.1]pentan-1-yl)-5-(trifluoromethyl)benzamide The titled intermediate was prepared from 2-bromo-5-(trifluoromethyl)benzoic acid (1.5 g, 5.6 mmol) and 3-aminobicyclo[1.1.1]pentane-1-carbonitrile hydrochloride (0.83 g, 5.7 mmol) according to the conditions of General Synthesis 7. LCMS-ESI$^+$ (m/z): [M+H]$^+$ calcd 358.99; found 359.03.

Step 2: Preparation of N-(3-cyanobicyclo[1.1.1]pentan-1-yl)-2-((N,N-dimethylsulfamoyl)amino)-5-(trifluoromethyl)benzamide The titled compound was prepared from 2-bromo-N-(3-cyanobicyclo[1.1.1]pentan-1-yl)-5-(trifluoromethyl)benzamide (0.26 g, 0.71 mmol) and N,N-dimethylsulfamide (0.27 g, 2.1 mmol) according to General Synthesis 8. Purification was accomplished by flash chromatography (silica gel) instead of by RP-HPLC. $^1$H NMR (400 MHz, DMSO-d$_6$) δ 11.50 (s, 1H), 9.81 (s, 1H), 8.17 (d, J=2.1 Hz, 1H), 7.90 (dd, J=8.9, 2.0 Hz, 1H), 7.67 (d, J=8.8 Hz, 1H), 2.76 (s, 6H), 2.62 (s, 6H). LCMS-ESI– (m/z): [M–H]$^-$ calcd 401.10; found 401.16.

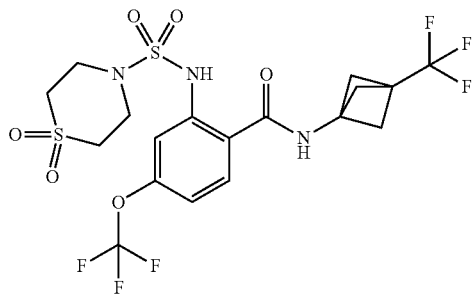 [SMILES: O=C(NC12CC(C(F)(F)F)(C1)C2)c1ccc(OC(F)(F)F)cc1NS(=O)(=O)N1CCS(=O)(=O)CC1]

Example 245: Preparation of 2-((1,1-dioxidothiomorpholine)-4-sulfonamido)-4-(trifluoromethoxy)-N-(3-(trifluoromethyl)bicyclo[1.1.1]pentan-1-yl)benzamide Step 1: Preparation of 2-((1,1-dioxidothiomorpholine)-4-sulfonamido)-4-(trifluoromethoxy)benzoic acid According to conditions of Step 1 of General Synthesis 9, 2-bromo-4-(trifluoromethoxy)benzoic acid (0.52 g, 1.8 mmol) was coupled to thiomorpholine-4-sulfonamide 1,1-dioxide (0.43 g, 2.0 mmol) to provide the desired intermediate. LCMS-ESI– (m/z): [M–H]$^-$ calcd 417.01; found 417.07.

Step 2: Preparation of 2-((1,1-dioxidothiomorpholine)-4-sulfonamido)-4-(trifluoromethoxy)-N-(3-(trifluoromethyl)bicyclo[1.1.1]pentan-1-yl)benzamide The titled compound was prepared from 2-((1,1-dioxidothiomorpholine)-4-sulfonamido)-4-(trifluoromethoxy)benzoic acid (0.15 g, 0.36 mmol) and 3-(trifluoromethyl)bicyclo[1.1.1]pentan-1-amine hydrochloride (74 mg, 0.39 mmol), according to General Synthesis 10. $^1$H NMR (400 MHz, DMSO-d$_6$) δ 11.42 (s, 1H), 9.73 (s, 1H), 7.95 (d, J=8.8 Hz, 1H), 7.35 (d, J=1.3 Hz, 1H), 7.26 (d, J=8.7 Hz, 1H), 3.62 (m, 4H), 3.19 (t, J=5.3 Hz, 4H), 2.37 (s, 6H). LCMS-ESI– (m/z): [M–H]$^-$ calcd 550.06; found 550.22.

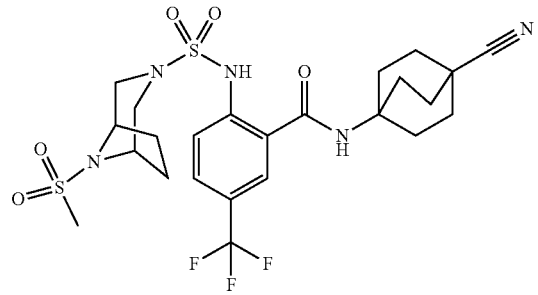 [SMILES: CS(=O)(=O)N1C2CCC1CN(S(=O)(=O)Nc1ccc(C(F)(F)F)cc1C(=O)NC13CCC(C#N)(CC1)CC3)C2]

Example 246: Preparation of N-(4-cyanobicyclo[2.2.2]octan-1-yl)-2-(((1R,5S)-8-(methylsulfonyl)-3,8-diazabicyclo[3.2.1]octane)-3-sulfonamido)-5-(trifluoromethyl)benzamide Step 1: Preparation of tert-butyl 3-(N-((benzyloxy)carbonyl)sulfamoyl)-3,8-diazabicyclo[3.2.1]octane-8-carboxylate The titled intermediate was prepared from tert-butyl 3,8-diazabicyclo[3.2.1]octane-8-carboxylate (7.1 g, 34 mmol) and benzyl alcohol (1.6 mL, 15 mmol) according to the method of General Synthesis 11. Following the aqueous work-up, the crude residue was purified by flash chromatography (silica gel). LCMS-ESI– (m/z): [M–H]$^-$ calcd 424.16; found 424.25.

Step 2: Preparation of benzyl (3,8-diazabicyclo[3.2.1]octan-3-yl)sulfonyl)carbamate hydrochloride To a stirred solution of tert-butyl 3-(N-((benzyloxy)carbonyl)sulfamoyl)-3,8-diazabicyclo[3.2.1]octane-8-carboxylate (1.4 g, 3.3 mmol) in dichloromethane (20 mL) was added hydrogen chloride solution (4N in dioxane, 20 mL, 80 mmol), and the reaction mixture was stirred overnight at room temperature before concentration under reduced pressure. The residue was co-evaporated once from diethyl ether to provide the titled intermediate. LCMS-ESI⁻ (m/z): [M−H]⁻ calcd 324.11; found 324.15.

Step 3: Preparation of benzyl (8-(methylsulfonyl)-3,8-diazabicyclo[3.2.1]octan-3-yl)sulfonyl)carbamate A stirred mixture of benzyl 3,8-diazabicyclo[3.2.1]octan-3-yl)sulfonyl)carbamate hydrochloride (1.2 g, 3.3 mmol) and pyridine (2.1 mL, 26 mmol) in acetonitrile (15 mL) at room temperature was treated with methanesulfonyl chloride (0.38 mL, 4.9 mmol). After being sonicated for 10 minutes, the mixture was heated at 45° C. for 3 hours before being concentrated under reduced pressure. The residue was partitioned between ethyl acetate and 10% aqueous hydrochloric acid. The aqueous phase was extracted three times with ethyl acetate. The combined extracts were washed three times with 10% ammonium hydroxide solution. The combined ammoniacal extracts were acidified with hydrochloric acid and extracted three times with ethyl acetate. The combined extracts were washed once with saturated aqueous sodium chloride solution, dried over anhydrous magnesium sulfate, filtered, and concentrated to provide the titled intermediate. LCMS-ESI⁻ (m/z): [M−H]⁻ calcd 402.09; found 402.14.

Step 4: Preparation of 8-(methylsulfonyl)-3,8-diazabicyclo[3.2.1]octane-3-sulfonamide A solution of benzyl (8-(methylsulfonyl)-3,8-diazabicyclo[3.2.1]octan-3-yl)sulfonyl)carbamate (1.69 g, 4.2 mmol) in ethanol was degassed before the introduction of 10% palladium on charcoal (350 mg). The stirred suspension was subjected to three cycles of evacuation under vacuum/purge with hydrogen (1 atm) before being left to stir overnight under an atmosphere of hydrogen. The suspension was filtered through a pad of Celite diatomaceous earth, washing the filter cake successively with ethanol, ethyl acetate, tetrahydrofuran, and acetonitrile. The filtrate was concentrated to a solid that was then triturated with diethyl ether and collected by vacuum filtration to provide the titled intermediate. LCMS-ESI⁻ (m/z): [M−H]⁻ calcd 268.05; found 268.08.

Step 5: Preparation of N-(4-cyanobicyclo[2.2.2]octan-1-yl)-2-(((1R,5S)-8-(methylsulfonyl)-3,8-diazabicyclo[3.2.1]octane)-3-sulfonamido)-5-(trifluoromethyl)benzamide The titled compound was prepared N-(4-cyanobicyclo[2.2.2]octan-1-yl)-2-iodo-5-(trifluoromethyl)benzamide (0.20 g, 0.45 mmol) and 8-(methylsulfonyl)-3,8-diazabicyclo[3.2.1]octane-3-sulfonamide (0.36 g, 1.3 mmol) according to General Synthesis 8. Purification was accomplished by flash chromatography (silica gel) instead of by reverse-phase HPLC. ¹H NMR (400 MHz, DMSO-d₆) δ 11.16 (s, 1H), 8.50 (s, 1H), 8.09 (d, J=2.1 Hz, 1H), 7.89 (dd, J=8.6, 2.0 Hz, 1H), 7.67 (d, J=8.7 Hz, 1H), 4.21 (dd, J=4.7, 2.4 Hz, 2H), 3.40 (dd, J=11.5, 2.6 Hz, 2H), 2.98 (s, 3H), 2.91 (d, J=11.0 Hz, 2H), 2.01 (m, 12H), 1.82 (m, 2H), 1.45 (t, J=7.0 Hz, 2H). LCMS-ESI⁻ (m/z): [M−H]⁻ calcd 588.16; found 588.36.

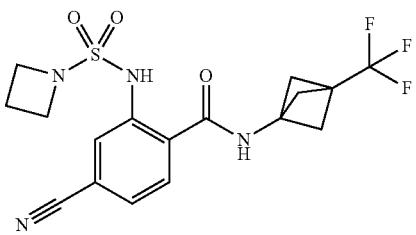 [SMILES: N#Cc1ccc(C(=O)NC23CC(C(F)(F)F)(C2)C3)c(NS(=O)(=O)N2CCC2)c1]

Example 247: Preparation of 2-(azetidine-1-sulfonamido)-4-cyano-N-(3-(trifluoromethyl)bicyclo[1.1.1]pentan-1-yl)benzamide Following Step 1 of General Synthesis 9, using 2-bromo-4-cyanobenzoic acid (1.0 eq), azetidine-1-sulfonamide (2.0 eq) and sarcosine (0.2 eq), then Step 3 of General Synthesis 1 using 3-(trifluoromethyl)bicyclo[1.1.1]pentan-1-amine hydrochloride (1.2 eq), 2-(azetidine-1-sulfonamido)-4-cyano-N-(3-(trifluoromethyl)bicyclo[1.1.1]pentan-1-yl)benzamide was synthesized and purified by reverse phase chromatography. ¹H NMR (400 MHz, DMSO-d₆) δ 11.06 (s, 1H), 9.80 (s, 1H), 7.95 (d, J=8.2 Hz, 1H), 7.81 (d, J=1.6 Hz, 1H), 7.68 (d, J=8.2 Hz, 1H), 3.83 (t, J=7.7 Hz, 4H), 2.37 (s, 6H), 2.15 (p, J=7.7 Hz, 2H). LCMS-ESI⁺ (m/z): [M+H]⁺ calcd 415.11; found 415.07.

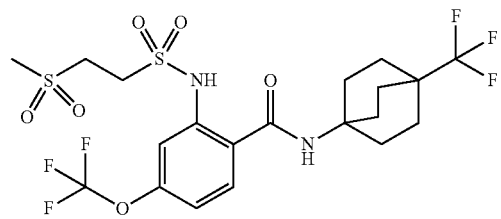 [SMILES: CS(=O)(=O)CCS(=O)(=O)Nc1cc(OC(F)(F)F)ccc1C(=O)NC12CCC(C(F)(F)F)(CC1)CC2]

Example 248: Preparation of 2-((2-(methylsulfonyl)ethyl)sulfonamido)-4-(trifluoromethoxy)-N-(4-(trifluoromethyl)bicyclo[2.2.2]octan-1-yl)benzamide Following Step 1 of General Synthesis 9, using 2-bromo-4-(trifluoromethoxy)benzoic acid (1.0 eq), 2-(methylsulfonyl)ethane-1-sulfonamide (2.0 eq) and sarcosine (0.2 eq), then Step 3 of General Synthesis 1 using 4-(trifluoromethyl)bicyclo[2.2.2]octan-1-amine hydrochloride (1.2 eq), 2-((2-(methylsulfonyl)ethyl)sulfonamido)-4-(trifluoromethoxy)-N-(4-(trifluoromethyl)bicyclo[2.2.2]octan-1-yl)benzamide was synthesized and purified by reverse phase chromatography. ¹H NMR (400 MHz, DMSO-d₆) δ 10.93 (s, 1H), 8.27 (s, 1H), 7.84 (d, J=8.7 Hz, 1H), 7.42 (d, J=2.3 Hz, 1H), 7.24 (d, J=8.8 Hz, 1H), 3.72-3.61 (m, 2H), 3.57-3.49 (m, 2H), 3.08 (s, 3H), 2.07-1.94 (m, 6H), 1.82-1.65 (m, 6H). LCMS-ESI⁺ (m/z): [M+H]⁺ calcd 567.11; found 567.15.

Biological Assays

PC-3 Oxygen Rate Consumption (OCR) Assay Procedure:

One day before the assay, PC-3 cells were seeded at $2.5 \times 10^4$ cells/160 µL/well in a 96-well XFe96 cell plate, part of a FlexPak containing a cell plate and a cartridge (Agilent, Sunnyvale, Calif.). The cells were incubated overnight at 37° C. in a 5% CO₂ and 90% humidity incubator with F12K culture medium (ThermoFisher Scientific/Invitrogen, Grand Island, N.Y.) containing 10% FBS and 1% penicillin/streptomycin. On the day of the assay, the cells were washed twice with 300 μL/well Medium A [XF assay medium (Agilent) supplemented 10 mM glucose, 1 mM pyruvate, and 2% fetal bovine serum (FBS)], and incubated with 175 μL/well Media A for 1 hr in a 37° C., non-$CO_2$ incubator prior to the measurement of cellular respiration. Compounds of interests were prepared in 1:2 serial dilutions with 100% DMSO and then further diluted into 8× working stock with Media A prior to being loaded to Injection Port A on a XFe96 Analyzer (Agilent). Six replicates were used for each treatment. The cartridge was calibrated in the XFe96 Analyzer 30 minute prior to the measurement of cellular respiration. Basal levels of OCR were measured three times, each using a "3-minute mixing/3-minute measurement" program. The compound effect was measured immediately after compound injection from Injection Port A, and OCR was monitored continuously 10 times, each time using a "1-minute mixing/2-minute measurement" program for a total of 30 minutes post compound injection. The level of OCR at 3-min post-injection was normalized to % increase over DMSO-treated cells. The concentration of compound required to reach the half-maximal OCR increase was defined as $EC_{50}$. Table 2 contains PC3 OCR $EC_{50}$ values for the compounds disclosed.

TABLE 1

| Example No. | EC50-PC3-OCR-FBS-3min (units = nM) |
|---|---|
| 1 | 13053.8 |
| 2 | 3646.27 |
| 3 | 784.552 |
| 4 | 618.973 |
| 5 | 5801.08 |
| 6 | 267.133 |
| 7 | 812.953 |
| 8 | 4098.27 |
| 9 | 5562.77 |
| 10 | 1217.4 |
| 11 | 1920.41 |
| 12 | 6877.06 |
| 13 | 5718.13 |
| 14 | ≥20000 |
| 15 | 10918 |
| 16 | 5548.27 |
| 17 | 5831.37 |
| 18 | 113624 |
| 19 | 6412.18 |
| 20 | 14315.3 |
| 21 | 38947.2 |
| 22 | 9974.49 |
| 23 | 12019.5 |
| 24 | 3320.49 |
| 25 | ≥50000 |
| 26 | 6939.13 |
| 27 | 4501.9 |
| 28 | 2760.15 |
| 29 | 8797.05 |
| 30 | 1110.58 |
| 31 | 594.988 |
| 32 | 1521.47 |
| 33 | 1926.32 |
| 34 | 2714.22 |
| 35 | 1213.91 |
| 36 | ≥20000 |
| 37 | 2099.85 |
| 38 | 478.401 |
| 39 | 7336.2 |
| 40 | 6580.36 |
| 41 | 2163.55 |
| 42 | 27514.4 |
| 43 | 2992.25 |
| 44 | 1158.27 |
| 45 | 5453.84 |
| 46 | 3483.61 |

TABLE 1-continued

| Example No. | EC50-PC3-OCR-FBS-3min (units = nM) |
|---|---|
| 47 | 17329.6 |
| 48 | 5807.16 |
| 49 | 4991.91 |
| 50 | ≥100000 |
| 51 | 28813.6 |
| 52 | 200000 |
| 53 | 46141.2 |
| 54 | 1224.02 |
| 55 | 6321.08 |
| 56 | 824.53 |
| 57 | 8086.05 |
| 58 | 63358.5 |
| 59 | 1840.99 |
| 60 | 6222.54 |
| 61 | ≥100000 |
| 62 | 1525.01 |
| 63 | 936.711 |
| 64 | 5217.6 |
| 65 | 21791.6 |
| 66 | 8346.4 |
| 67 | 5915.57 |
| 68 | 5127.24 |
| 69 | 518.498 |
| 70 | 590.595 |
| 71 | 6669.86 |
| 72 | 4009.96 |
| 73 | 2623.94 |
| 74 | 6172.35 |
| 75 | 25934.3 |
| 76 | 9194.32 |
| 77 | 8645.11 |
| 78 | 39844 |
| 79 | 21192.8 |
| 80 | 2536.98 |
| 81 | 2391.89 |
| 82 | 6324.04 |
| 83 | 5427.08 |
| 84 | 1038.36 |
| 85 | 12506.8 |
| 86 | 8274.84 |
| 87 | 3280.77 |
| 88 | 26269.6 |
| 89 | 26673.1 |
| 90 | 2668.43 |
| 91 | 2969.36 |
| 92 | 8093.9 |
| 93 | 2635.16 |
| 94 | 6160.88 |
| 95 | 1123.48 |
| 96 | 1282.17 |
| 97 | 1431.89 |
| 98 | 1982.69 |
| 99 | 1184.65 |
| 100 | 14205.9 |
| 101 | 1182.98 |
| 102 | 2417.98 |
| 103 | 1883.46 |
| 104 | 37495.5 |
| 105 | 22857.1 |
| 106 | 18750.1 |
| 107 | 30643.1 |
| 108 | 8441.19 |
| 109 | 379.68 |
| 110 | 445.483 |
| 111 | 811.278 |
| 112 | 1291.93 |
| 113 | 696.528 |
| 114 | 3479.61 |
| 115 | 12596.7 |
| 116 | 1576.96 |
| 117 | 4023.81 |
| 118 | 49238.8 |
| 119 | 1257.64 |
| 120 | 8014.7 |
| 121 | 2262.67 |
| 122 | 1523.5 |
| 123 | 4836.49 |

TABLE 1-continued

| Example No. | EC50-PC3-OCR-FBS-3min (units = nM) |
|---|---|
| 124 | 79387.4 |
| 125 | 12352.9 |
| 126 | 5117.46 |
| 127 | 2408.15 |
| 128 | 15352.7 |
| 129 | 24288.9 |
| 130 | 4681.79 |
| 131 | 19520.6 |
| 132 | 50866.4 |
| 133 | 14721.3 |
| 134 | 2678.21 |
| 135 | 1618.45 |
| 136 | ≥100000 |
| 137 | ≥100000 |
| 138 | ≥100000 |
| 139 | 23735 |
| 140 | 36109 |
| 141 | 1180.15 |
| 142 | ≥100000 |
| 143 | 10208.8 |
| 144 | 18551.7 |
| 145 | ≥100000 |
| 146 | 676.891 |
| 147 | 1575.52 |
| 148 | 17695.6 |
| 149 | ≥20000 |
| 150 | ≥20000 |
| 151 | 9393.93 |
| 152 | 1126.07 |
| 153 | 10699.6 |
| 154 | 8016.66 |
| 155 | 5867.13 |
| 156 | ≥200000 |
| 157 | 352.217 |
| 158 | 1425.45 |
| 159 | ≥200000 |
| 160 | 631.681 |
| 161 | 1089.45 |
| 162 | 34086.2 |
| 163 | 3774.9 |
| 164 | 1737.99 |
| 165 | 20784.3 |
| 166 | 1068.12 |
| 167 | 5879.72 |
| 168 | 15021.2 |
| 169 | 11419.7 |
| 170 | 44769.8 |
| 171 | 112301 |
| 172 | 1664.47 |
| 173 | 26391.60 |
| 174 | 107530 |
| 175 | 5983.63 |
| 176 | 1699.79 |
| 177 | 1860.59 |
| 178 | 5928.69 |
| 179 | 8836.25 |
| 180 | ≥200000 |
| 181 | 113903 |
| 182 | 13016.9 |
| 183 | 823.864 |
| 184 | 48125 |
| 185 | 31961.2 |
| 186 | 12553.3 |
| 187 | 11484.7 |
| 188 | 3291.98 |
| 189 | 511.355 |
| 190 | 4146.84 |
| 191 | 1764.95 |
| 192 | 14662.7 |
| 193 | 9952.73 |
| 194 | ≥50000 |
| 195 | 67517.2 |
| 196 | 1376.36 |
| 197 | 892.588 |
| 198 | ≥200000 |
| 199 | ≥100000 |
| 200 | 5092.99 |

TABLE 1-continued

| Example No. | EC50-PC3-OCR-FBS-3min (units = nM) |
|---|---|
| 201 | 1289.76 |
| 202 | 9318.56 |
| 203 | 22989 |
| 204 | 15677.2 |
| 205 | 1212.33 |
| 206 | 2709.42 |
| 207 | 8124.56 |
| 208 | 10603.3 |
| 209 | 647.862 |
| 210 | 4354.14 |
| 211 | 15421.1 |
| 212 | 8624.97 |
| 213 | 81897.3 |
| 214 | 26328.3 |
| 215 | 21372.6 |
| 216 | 16926.3 |
| 217 | 111857.0 |
| 218 | 53350.4 |
| 219 | ≥200000 |
| 220 | 5091 |
| 221 | 1085.41 |
| 222 | 5697.24 |
| 223 | 4426.25 |
| 224 | 2423.22 |
| 225 | 6737.18 |
| 226 | 7097.46 |
| 227 | 1447.39 |
| 228 | 3371.84 |
| 229 | 4417.17 |
| 230 | 5587.82 |
| 231 | 4689.50 |
| 232 | 5583.69 |
| 233 | 4792.42 |
| 234 | 3861.76 |
| 235 | 4525.11 |
| 236 | 25198.20 |
| 237 | 7729.28 |
| 238 | 29682.10 |
| 239 | 7729.28 |
| 240 | 3013.63 |
| 241 | 6383.30 |
| 242 | 4344.62 |
| 243 | 6143.15 |
| 244 | 7646.28 |
| 245 | 3838.62 |
| 246 | 14474.4 |
| 247 | 4793.87 |
| 248 | 5702.28 |

What is claimed:

1. A compound of Formula II:

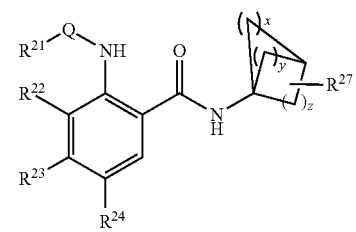

or a pharmaceutically acceptable salt, stereoisomer, mixture of stereoisomers, tautomer, or deuterated analogs thereof, wherein:

x, y, and z are independently 1, 2, 3, or 4,

Q is $S(O)_2$;

$R^{21}$ is selected from the group consisting of: $C_{1-6}$ alkyl, $C_{2-6}$ alkenyl, $C_{2-6}$ alkynyl, $-NR^{33}R^{33}$, 6-10 membered aryl, 5-10 membered heteroaryl, $C_{3-12}$ cycloalkyl, and 4-12 membered heterocyclyl, wherein each $C_{1-6}$ alkyl, $C_{2-6}$ alkenyl, $C_{2-6}$ alkynyl, 6-10 membered aryl, 5-10 membered heteroaryl, $C_{3-12}$ cycloalkyl, and 4-12 membered heterocyclyl are optionally further substituted with one or more $R^{31}$ groups;

$R^{31}$ is selected from the group consisting of: hydroxyl, oxo, halo, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —P(O)$R^{34}R^{34}$, —S(O)(NH)$R^{34}$, —S(O)(N$R^{28}$)$R^{34}$, —S(O)(NH)N$R^{33}R^{33}$, —S(O)(N$R^{28}$)N$R^{33}R^{33}$, —SH, —S(O)$_{0-2}R^{34}$, —S(O)$_{1-2}$N$R^{33}R^{33}$, —SF$_5$, —NO$_2$, —N$R^{33}R^{33}$, —N$R^{33}$SO$_2R^{34}$, —OS(O)$_2R^{34}$, —C(O)O$R^{34}$, —C(O)$R^{34}$, —N$R^{33}$C(O)O$R^{34}$, —N$R^{33}$C(O)N$R^{33}R^{33}$, —N$R^{33}$S(O)$_2$N$R^{33}R^{33}$, and —C(O)N$R^{33}R^{33}$, wherein each of the $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl are optionally substituted with one or more $R^{29}$ groups;

each $R^{29}$ is independently selected from the group consisting of: —H, oxo, —OH, —CN, halo, $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —N$R^{33}R^{33}$, —N$R^{33}$C(O)O$R^{34}$, —OS(O)$_2R^{34}$—C(O)O$R^{34}$, —S(O)(NH)$R^{34}$, —S(O)(NR)$R^{34}$, —S(O)(NH)N$R^{33}R^{33}$, —S(O)(N$R^{28}$)N$R^{33}R^{33}$, —S(O)$_{0-2}R^{34}$, —S(O)$_{1-2}$N$R^{33}R^{33}$, —C(O)N$R^{33}R^{33}$, —N$R^{33}$SO$_2R^{34}$, —C(O)$R^{34}$, —N$R^{33}$C(O)N$R^{33}R^{33}$, —N$R^{33}$S(O)$_2$N$R^{33}R^{33}$, —SF$_5$, and —NO$_2$, wherein each of the $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl is optionally substituted with one or more $R^{36}$;

each $R^{33}$ is independently selected from the group consisting of —H, $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{35}$ groups;

each $R^{34}$ is independently selected from the group consisting of: $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl are optionally substituted with one or more $R^{35}$ groups;

each $R^{35}$ is independently selected from the group consisting of: —H, halo, —CN, —OH, oxo, —NO$_2$, —SF$_5$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —S(O)(NH)$R^{36}$, —S(O)(N$R^{28}$)$R^{36}$, —S(O)(NH)N$R^{36}R^{36}$, —S(O)(N$R^{28}$)N$R^{36}R^{36}$, —S(O)$_{0-2}R^{36}$, —S(O)$_2$NH$_2$, —NH$_2$, —S(O)$_2$N$R^{36}R^{36}$, C(O)$R^{36}$, —C(O)N$R^{36}R^{36}$ and C(O)O$R^{36}$, wherein said 3-12 membered cycloalkyl, 4-12 membered heterocyclyl, 6-10 membered aryl, and 5-10 membered heteroaryl is optionally substituted with one or more $R^{36}$ groups;

each $R^{36}$ is independently selected from halo, —CN, —OH, —NH$_2$, oxo, —NO$_2$, —SF$_5$, $C_{1-3}$ alkyl, $C_{1-3}$ haloalkyl, $C_{1-6}$ alkoxy, $C_{1-6}$ haloalkoxy, $C_{1-6}$ hydroxyalkyl, thiohaloalkyl, sulfonylalkyl, sulfonylhaloalkyl, sulfonylcycloalkyl, 3-6 membered cycloalkyl, —C(O)NH$_2$ and —S(O)$_2$NH$_2$;

$R^{22}$ is selected from the group consisting of: —H, —CN, —F, —Cl, $C_{1-3}$ alkyl, $C_{1-3}$ haloalkyl, $C_{1-3}$ heteroalkyl, $C_{1-3}$ alkoxy and $C_{1-3}$ haloalkoxy;

each $R^{23}$ and $R^{24}$ is independently selected from the group consisting of: —H, halo, —OH, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —SF$_5$, —S(O)$_{0-2}R^{34}$, —S(O)(NH)$R^{34}$, —S(O)(N$R^{28}$)$R^{34}$, —S(O)(NH)N$R^{33}R^{33}$, —S(O)(N$R^{28}$)N$R^{33}R^{33}$, —SH, —N$R^{33}R^{33}$, —N$R^{33}$SO$_2R^{34}$, —N$R^{33}$S(O)$_2$N$R^{33}R^{33}$, —N$R^{33}$C(O)N$R^{33}R^{33}$, —N$R^{33}$C(O)O$R^{34}$, tri-$C_{1-4}$ alkylsilyl, —C(O)$R^{34}$, —C(O)O$R^{34}$, —C(O)N$R^{33}R^{33}$, and —NO$_2$, wherein said $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl are optionally further substituted with one or more $R^{29}$ groups;

wherein $R^{22}$ and $R^{23}$, or $R^{23}$ and $R^{24}$ can optionally join, together with the atoms to which they are attached, to form a 5-6 membered cycloalkyl, a 5-6 membered heterocyclyl, phenyl, or a 5-6 membered heteroaryl, each such cyclic groups respectively fused to the phenyl to which they are attached, and each optionally substituted with one or more $R^{29}$ groups;

$R^{27}$ is selected from the group consisting of: —H, halo, —CN, oxo, —OH, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, 3-12 membered cycloalkyl, —S(O)$_{0-2}R^{34}$, —S(O)(NH)$R^{34}$, —S(O)(N$R^{28}$)$R^{34}$, —S(O)(NH)N$R^{33}R^{33}$, —S(O)(N$R^{28}$)N$R^{33}R^{33}$, —N$R^{33}R^{33}$, —P(O)$R^{34}R^{34}$, —C(O)OH, —C(O)O$R^{34}$, —C(O)N$R^{33}R^{33}$, —S(O)$_2$N$R^{33}R^{33}$, —C(O)$R^{34}$, 6-10 membered aryl, 5-10 membered heteroaryl, and 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, and 3-12 membered cycloalkyl is optionally substituted with one or more $R^{35}$;

$R^{28}$ is selected from the group consisting of: $C_{1-6}$ alkyl, —C(O)$R^{34}$, 3-12 membered cycloalkyl, $C_{1-6}$ heteroalkyl, 6-10 membered aryl, 5-10 membered heteroaryl, 4-12 membered heterocyclyl, —C(O)O$R^{34}$—C(O)N$R^{33}R^{33}$, and —SO$_2R^{34}$, wherein each of the $C_{1-6}$ alkyl, 3-12 membered cycloalkyl, $C_{1-6}$ heteroalkyl, 6-10 membered aryl, 5-10 membered heteroaryl, 4-12 membered heterocyclyl is optionally substituted with halo, —CN, oxo, hydroxyl, $C_{1-6}$ alkyl, $C_{1-6}$ alkoxy, —S(O)$_{1-2}R^{34}$, —S(O)$_2$N$R^{33}R^{33}$, —NO$_2$, —SF$_5$, $C_{1-6}$ haloalkyl, $C_{1-6}$ haloalkoxy, $C_{1-6}$ hydroxyalkyl, —N$R^{33}R^{33}$, —C(O)O$R^{34}$, $C_{1-6}$ heteroalkyl, 3-6 membered cycloalkyl optionally substituted with one or more $R^{36}$, 4-12 membered heterocyclyl optionally substituted with one or more $R^{36}$, 6-10 membered aryl optionally substituted with one or more $R^{36}$, or 5-10 membered heteroaryl optionally substituted with one or more $R^{36}$;

subject to the provisos that:
(i) when x+y+z is 6 to 10, and both $R^{23}$ and $R^{27}$ are H, then $R^{24}$ is selected from the group consisting of: $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl, 7-12 membered monocyclic heterocyclyl, —$SF_5$, —$NR^{33}R^{33}$, —$NR^{33}C(O)OR^{34}$, —$NR^{33}SO_2R^{34}$, —$NR^{33}S(O)_2NR^{33}R^{33}$, —$NR^{33}C(O)NR^{33}R^{33}$, tri-$C_{1-4}$ alkylsilyl, —$C(O)R^{34}$, —$C(O)OR^{34}$, —$C(O)NR^{33}R^{33}$, —$S(O)_{0-2}R^{34}$, —$S(O)(NH)R^{34}$, —$S(O)(NR^{28})R^{34}$, —$S(O)(NH)NR^{33}R^{33}$, —$S(O)(NR^{28})NR^{33}R^{33}$, —SH and —$NO_2$, wherein each of the $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl and 7-12 membered monocyclic heterocyclyl is optionally substituted with one or more $R^{29}$; 5-6 membered heterocyclyl is optionally substituted with $R^{37}$; and 8-10 membered bicyclic heterocyclyl is optionally substituted with one or more $R^{38}$; and (ii) when x+y+z is 4 or 5, and $R^{27}$ is —H or methyl, $R^{23}$ is selected from the group consisting of: halo, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$SF_5$, —$S(O)_{0-2}R^{34}$, —$S(O)(NH)R^{34}$, —$S(O)(NR^{28})R^{34}$, —$S(O)(NH)NR^{33}R^{33}$, —$S(O)(NR^{28})NR^{33}R^{33}$, —SH, —$NR^{33}R^{33}$, —$NR^{33}SO_2R^{34}$, —$NR^{33}S(O)_2NR^{33}R^{33}$, —$NR^{33}C(O)NR^{33}R^{33}$, —$NR^{33}C(O)OR^{34}$, tri-$C_{1-4}$ alkylsilyl, —$C(O)R^{34}$, —$C(O)OR^{34}$, —$C(O)NR^{33}R^{33}$, and —$NO_2$, wherein each of the $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl is optionally further substituted with one or more $R^{29}$ groups;

wherein $R^{37}$ is selected from the group consisting of —OH, oxo, —CN, $C_{2-6}$ alkenyl, $C_{2-6}$ alkynyl, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$S(O)_{0-2}R^{34}$, —$NR^{33}SO_2R^{34}$, —$NR^{33}S(O)_2NR^{33}R^{33}$, —$NR^{33}C(O)NR^{33}R^{33}$, —$NR^{33}C(O)OR^{34}$, —$C(O)R^{34}$, —$C(O)OR^{34}$ and —$C(O)NR^{33}R^{33}$;

and wherein $R^{38}$ is selected from the group consisting of $C_{2-6}$ alkenyl, $C_{2-6}$ alkynyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$S(O)_{0-2}R^{34}$—$NR^{33}R^{33}$, —$NR^{33}SO_2R^{34}$, —$NR^{33}S(O)_2NR^{33}R^{33}$, —$NR^{33}C(O)NR^{33}R^{33}$, —$NR^{33}C(O)OR^{34}$, —$C(O)R^{34}$, —$C(O)OR^{34}$ and —$C(O)NR^{33}R^{33}$.

2. The compound of claim 1, wherein $R^{21}$ is selected from the group consisting of: $C_{1-6}$ alkyl, —$NR^{33}R^{33}$, 6-10 membered aryl, 5-10 membered heteroaryl, $C_{3-12}$ cycloalkyl, and 4-12 membered heterocyclyl, wherein each $C_{1-6}$ alkyl, 6-10 membered aryl, 5-10 membered heteroaryl, $C_{3-12}$ cycloalkyl, and 4-12 membered heterocyclyl is further substituted with one or more $R^{31}$ groups.

3. The compound of claim 1, wherein $R^{22}$ is selected from the group consisting of: —H, —CN, —F, methyl, $C_1$haloalkyl, $C_{1-3}$ heteroalkyl, methoxy and $C_1$ haloalkoxy.

4. The compound of claim 3, wherein $R^{22}$ is selected from the group consisting of: —H, —CN, —F, and methyl.

5. The compound of claim 1, wherein $R^{24}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, —$SF_5$, —$S(O)_{0-2}R^{34}$, —$S(O)(NH)R^{34}$, —$S(O)(NR^{28})R^{34}$, —$S(O)(NH)NR^{33}R^{33}$, —$S(O)(NR^{28})NR^{33}R^{33}$, —$NR^{33}R^{33}$, —$NR^{33}SO_2R^{34}$, —$NR^{33}S(O)_2NR^{33}R^{33}$, —$NR^{33}C(O)NR^{33}R^{33}$, —$NR^{33}C(O)OR^{34}$, —$C(O)R^{34}$, —$C(O)OR^{34}$, —$C(O)NR^{33}R^{33}$, and —$NO_2$, wherein each of the $C_{1-6}$ alkyl, $C_{1-6}$ alkoxy, $C_{1-6}$ hydroxyalkyl, and $C_{1-6}$ heteroalkyl, is further substituted with one or more $R^{29}$ groups.

6. The compound of claim 5, wherein $R^{24}$ is selected from the group consisting of: —H, —F, —Cl, —OH, —CN, $S(O)_{0-2}R^{34}$, —$C(O)R^{34}$, —$NO_2$, —$SF_5$, $C_{1-6}$ alkyl, and $C_{1-6}$ alkoxy, and wherein said $C_{1-6}$ alkyl or $C_{1-6}$ alkoxy is optionally substituted with one or more F, and $R^{34}$ is selected from the group consisting of $C_{1-6}$ alkyl, $C_{3-6}$ cycloalkyl, $C_{1-6}$ hydroxyalkyl, and $C_{1-6}$ heteroalkyl, wherein the $C_{1-6}$ alkyl, $C_{3-6}$ cycloalkyl, $C_{1-6}$ hydroxyalkyl, and $C_{1-6}$ heteroalkyl, is optionally substituted with one or more $R^{35}$ groups, and $R^{35}$ is independently selected from the group consisting of halo, —CN and OH.

7. The compound of claim 6, wherein $R^{24}$ is selected from the group consisting of: —H, —F, —Cl, —OH, —CN, —$SF_5$, $C_{1-6}$ alkyl, and $C_{1-6}$ alkoxy, and wherein said $C_{1-6}$ alkyl or $C_{1-6}$ alkoxy is optionally substituted with one or more —F, and $R^{34}$ is a $C_{1-3}$ haloalkyl.

8. A compound of Formula III:

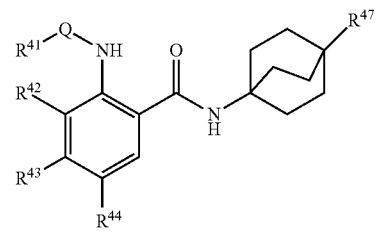

III or a pharmaceutically acceptable salt, stereoisomer, mixture of stereoisomers, tautomer, or deuterated analogs thereof, wherein:

Q is —$S(O)_2$—, $R^{41}$ is selected from the group consisting of: $C_{1-6}$ alkyl, $C_{2-6}$ alkenyl, $C_{2-6}$ alkynyl, —$NR^{53}R^{53}$, 6-10 membered aryl, 5-10 membered heteroaryl, $C_{3-12}$ cycloalkyl, and 4-12 membered heterocyclyl, wherein each $C_{1-6}$ alkyl, $C_{2-6}$ alkenyl, $C_{2-6}$ alkynyl, 6-10 membered aryl, 5-10 membered heteroaryl, $C_{3-12}$ cycloalkyl, and 4-12 membered heterocyclyl is optionally further substituted with one or more $R^{51}$ groups;

$R^{51}$ is selected from the group consisting of: hydroxyl, oxo, halo, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$P(O)R^{54}R^{54}$, —$S(O)(NH)R^{54}$, —$S(O)(NR^{48})R^{54}$, —$S(O)(NH)NR^{53}R^{53}$, —$S(O)(NR^{48})NR^{53}R^{53}$, —$S(O)_{0-2}R^{54}$, —$S(O)_{1-2}NR^{53}R^{53}$, —$SF_5$, —$NO_2$, —$NR^{53}R^{53}$, —$NR^{53}SO_2R^{54}$, —$OS(O)_2R^{54}$, —$C(O)OR^{54}$, —$C(O)R^{54}$, —$NR^{53}C(O)OR^{54}$, —$NR^{53}C(O)NR^{53}R^{53}$, —$NR^{53}S(O)_2NR^{53}R^{53}$, and —$C(O)NR^{53}R^{53}$, wherein each $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl is optionally substituted with one or more $R^{49}$ groups;

each $R^{49}$ is independently selected from the group consisting of: —H, oxo, —OH, —CN, halo, $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —NR$^{53}$R$^{53}$, —NR$^{53}$C(O)OR$^{54}$, —OS(O)$_2$R$^{54}$—C(O)OR$^{54}$, —S(O)(NH)R$^{54}$, —S(O)(NR$^{48}$)R$^{54}$, —S(O)(NH)NR$^{53}$R$^{53}$, —S(O)(NR$^{48}$)NR$^{53}$R$^{53}$, —S(O)$_{0-2}$R$^{54}$, —S(O)$_{1-2}$NR$^{53}$R$^{53}$, —C(O)NR$^{53}$R$^{53}$, —NR$^{53}$SO$_2$R$^{54}$, —C(O)R$^{54}$, —NR$^{53}$C(O)NR$^{53}$R$^{53}$, —NR$^{53}$S(O)$_2$NR$^{53}$R$^{53}$, —SF$_5$, and —NO$_2$, wherein each of the $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl is optionally substituted with $R^{56}$;

each $R^{53}$ is independently selected from the group consisting of —H, $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl is optionally substituted with one or more $R^{55}$ groups;

each $R^{54}$ is independently selected from the group consisting of: $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl is optionally substituted with one or more $R^{55}$ groups;

each $R^{55}$ is independently selected from —H, halo, —CN, —OH, oxo, —NO$_2$, —SF$_5$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —S(O)(NH)R$^{56}$, —S(O)(NR$^{48}$)R$^{56}$, —S(O)(NH)NR$^{56}$R$^{56}$, —S(O)(NR$^{48}$)NR$^{56}$R$^{56}$, —S(O)$_{0-2}$R$^{56}$, —S(O)$_2$NH$_2$, —NH$_2$, —S(O)$_2$NR$^{56}$R$^{56}$, C(O)R$^{56}$, —C(O)NR$^{56}$R$^{56}$ and C(O)OR$^{56}$, wherein said 3-12 membered cycloalkyl, 4-12 membered heterocyclyl, 6-10 membered aryl, and 5-10 membered heteroaryl is optionally substituted with one or more $R^{56}$ groups;

each $R^{56}$ is independently selected from the group consisting of: halo, —CN, —OH, —NH$_2$, oxo, —NO$_2$, —SF$_5$, $C_{1-3}$ alkyl, $C_{1-3}$ haloalkyl, $C_{1-6}$ alkoxy, $C_{1-6}$ haloalkoxy, $C_{1-6}$ hydroxyalkyl, thiohaloalkyl, sulfonylalkyl, sulfonylhaloalkyl, sulfonylcycloalkyl, 3-6 membered cycloalkyl, —C(O)NH$_2$ and —S(O)$_2$NH$_2$;

$R^{42}$ is selected from the group consisting of: —H, —CN, —F, —Cl, $C_{1-3}$ alkyl, $C_{1-3}$ haloalkyl, $C_{1-3}$ heteroalkyl, $C_{1-3}$ alkoxy and $C_{1-3}$ haloalkoxy;

each $R^{43}$ and $R^{44}$ is independently selected from the group consisting of: —H, halo, —OH, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —SF$_5$, —S(O)$_{0-2}$R$^{54}$, —S(O)(NH)R$^{54}$, —S(O)(NR$^{48}$)R$^{54}$, —S(O)(NH)NR$^{53}$R$^{53}$, —S(O)(NR$^{48}$)NR$^{53}$R$^{53}$, —SH, —S(O)$_{1-2}$NR$^{53}$R$^{53}$, —NR$^{53}$R$^{53}$, —NR$^{53}$SO$_2$R$^{54}$, —NR$^{53}$S(O)$_2$NR$^{53}$R$^{53}$, —NR$^{53}$C(O)NR$^{53}$R$^{53}$, —NR$^{53}$C(O)OR$^{54}$, tri-$C_{1-4}$ alkylsilyl, —C(O)R$^{54}$, —C(O)OR$^{54}$, —C(O)NR$^{53}$R$^{53}$, and —NO$_2$, wherein said $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl is optionally further substituted with one or more $R^{49}$ groups;

wherein $R^{42}$ and $R^{43}$, or $R^{43}$ and $R^{44}$ optionally join, together with the atoms to which they are attached, to form a 5-6 membered cycloalkyl, a 5-6 membered heterocyclyl, phenyl, or a 5-6 membered heteroaryl, each such cyclic groups respectively fused to the phenyl to which they are attached, and each optionally substituted with one or more $R^{49}$ groups;

$R^{47}$ is selected from the group consisting of: —H, halo, —CN, —OH, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, 3-12 membered cycloalkyl, —S(O)$_{0-2}$R$^{54}$, —S(O)(NH)R$^{54}$, —S(O)(NR$^{48}$)R$^{54}$, —S(O)(NH)NR$^{53}$R$^{53}$, —S(O)(NR$^{48}$)NR$^{53}$R$^{53}$, —SH, —NR$^{53}$R$^{53}$, —P(O)R$^{54}$R$^{54}$, —C(O)OH, —C(O)OR$^{54}$, —C(O)NR$^{53}$R$^{53}$, —S(O)$_2$NR$^{53}$R$^{53}$, —C(O)R$^{54}$, 6-10 membered aryl, 5-10 membered heteroaryl, and 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, and 3-12 membered cycloalkyl is optionally substituted with one or more $R^{55}$;

$R^{48}$ is selected from the group consisting of: $C_{1-6}$ alkyl, —C(O)R$^{54}$, 3-12 membered cycloalkyl, $C_{1-6}$ heteroalkyl, 6-10 membered aryl, 5-10 membered heteroaryl, 4-12 membered heterocyclyl, C(O)OR$^{54}$, C(O)NR$^{53}$R$^{53}$, and SO$_2$R$^{54}$, wherein each of the $C_{1-6}$ alkyl, 3-12 membered cycloalkyl, $C_{1-6}$ heteroalkyl, 6-10 membered aryl, 5-10 membered heteroaryl, and 4-12 membered heterocyclyl is optionally substituted with halo, —CN, oxo, hydroxyl, $C_{1-6}$ alkyl, $C_{1-6}$ alkoxy, —S(O)$_{1-2}$R$^{54}$, —S(O)$_2$NR$^{53}$R$^{53}$, —NO$_2$, —SF$_5$, $C_{1-6}$ haloalkyl, $C_{1-6}$ haloalkoxy, $C_{1-6}$ hydroxyalkyl, —NR$^{53}$R$^{53}$, —C(O)OR$^{54}$, $C_{1-6}$ heteroalkyl, 3-6 membered cycloalkyl optionally substituted with $R^{56}$, 4-12 membered heterocyclyl optionally substituted with one or more $R^{56}$, 6-10 membered aryl optionally substituted with one or more $R^{56}$, or 5-10 membered heteroaryl optionally substituted with one or more $R^{56}$;

subject to the proviso that:
when both $R^{43}$ and $R^{47}$ are H, then $R^{44}$ is selected from the group consisting of: $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl, 7-12 membered monocyclic heterocyclyl, —SF$_5$, —NR$^{53}$R$^{53}$, —NR$^{53}$C(O)OR$^{54}$, —NR$^{53}$SO$_2$R$^{54}$, —NR$^{53}$S(O)$_2$NR$^{53}$R$^{53}$, —NR$^{53}$C(O)NR$^{53}$R$^{53}$, tri-$C_{1-4}$ alkylsilyl, —C(O)R$^{54}$, —C(O)OR$^{54}$, —C(O)NR$^{53}$R$^{53}$, —S(O)$_{0-2}$R$^{54}$, —S(O)(NH)R$^{54}$, —S(O)(NR$^{48}$)R$^{54}$, —S(O)(NH)NR$^{53}$R$^{53}$, —S(O)(NR$^{48}$)NR$^{53}$R$^{53}$, —SH and —NO$_2$, wherein each of the $C_{7-12}$ cycloalkyl, $C_{2-6}$ alkenyl, $C_{2-6}$ alkynyl, $C_{1-6}$ hydroxyalkyl, $C_{1-6}$ heteroalkyl, 4-membered heterocyclyl, 7-membered heterocyclyl and 7-12 membered monocyclic heterocyclyl are optionally substituted with one or more $R^{49}$; 5-6 membered heterocyclyl is optionally substituted with $R^{57}$; and 8-10 membered bicyclic heterocyclyl is optionally substituted with one or more $R^{58}$;

wherein $R^{57}$ is selected from the group consisting of: —OH, oxo, —CN, $C_{2-6}$ alkenyl, $C_{2-6}$ alkynyl, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —S(O)$_{0-2}$R$^{54}$, —NR$^{53}$SO$_2$R$^{54}$, —NR$^{53}$S(O)$_2$NR$^{53}$R$^{53}$, —NR$^{53}$C(O)NR$^{53}$R$^{53}$, —NR$^{53}$C(O)OR$^{54}$, —C(O)R$^{54}$, —C(O)OR$^{54}$ and —C(O)NR$^{53}$R$^{53}$;

and wherein $R^{58}$ is selected from the group consisting of: $C_{2-6}$ alkenyl, $C_{2-6}$ alkynyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —S(O)$_{0-2}$R$^{54}$, —NR$^{53}$R$^{53}$, —NR$^{53}$SO$_2$R$^{54}$, —NR$^{53}$S(O)$_2$NR$^{53}$R$^{53}$, —NR$^{53}$C(O)NR$^{53}$R$^{53}$, —NR$^{53}$C(O)OR$^{54}$, —C(O)R$^{54}$, —C(O)OR$^{54}$ and —C(O)NR$^{53}$R$^{53}$.

9. The compound of claim 8, wherein $R^{47}$ is selected from the group consisting of —H, halo, —CN, —OH, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, —S(O)$_{0-2}$R$^{54}$, —S(O)(NH)R$^{54}$, —S(O)(NR$^{48}$)R$^{54}$, —S(O)(NH)NR$^{53}$R$^{53}$, —S(O)(NR$^{48}$)NR$^{53}$R$^{53}$, —NR$^{53}$R$^{53}$, —C(O)OH, —C(O)OR$^{54}$, —C(O)NR$^{53}$R$^{53}$, —S(O)$_2$NR$^{53}$R$^{53}$, —C(O)R$^{54}$, 6-10 membered aryl, 5-10 membered heteroaryl, and 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, and 3-12 membered cycloalkyl is optionally substituted with one or more $R^{55}$.

10. The compound of claim 8, wherein $R^{47}$ is selected from the group consisting of —H, halo, —CN, —OH, $C_{1-6}$ alkyl, $C_{2-6}$ alkynyl, $C_{1-6}$ alkoxy, $C_{1-6}$ hydroxyalkyl, $C_{1-6}$ heteroalkyl, 3-6 membered cycloalkyl, —S(O)$_{0-2}$R$^{54}$, —C(O)OH, —C(O)OR$^{54}$, —C(O)NR$^{53}$R$^{53}$, —S(O)$_2$NR$^{53}$R$^{53}$, —C(O)R$^{54}$, 6-10 membered aryl, 5-10 membered heteroaryl, and 4-12 membered heterocyclyl; wherein each of said 4-12 membered heterocyclyl, 6-10 membered aryl, 5-10 membered heteroaryl, $C_{1-6}$ alkyl, $C_{2-6}$ alkynyl, $C_{1-6}$ alkoxy, $C_{1-6}$ hydroxyalkyl, $C_{1-6}$ heteroalkyl, and 3-6 membered cycloalkyl is optionally substituted with one or more $R^{55}$.

11. The compound of claim 8, wherein $R^{47}$ is selected from the group consisting of —H, halo, —CN, —OH, $C_{1-3}$ alkyl, $C_{1-3}$ alkoxy, $C_{1-3}$ hydroxyalkyl, $C_{1-6}$ heteroalkyl, and 6-10 membered aryl, wherein each of said 6-10 membered aryl, $C_{1-3}$ alkyl, $C_{1-3}$ alkoxy, $C_{1-3}$ hydroxyalkyl, and $C_{1-6}$ heteroalkyl is optionally substituted with one or more $R^{55}$, wherein $R^{55}$ is selected from the group consisting of: halo, —CN, —NO$_2$, —SF$_5$, $C_{1-3}$ alkyl, $C_{1-3}$ haloalkyl, $C_{1-6}$ alkoxy, and $C_{1-6}$ haloalkoxy.

12. The compound of claim 8, wherein $R^{41}$ is selected from the group consisting of: $C_{1-6}$ alkyl, —NR$^{53}$R$^{53}$, 6-10 membered aryl, 5-10 membered heteroaryl, $C_{3-12}$ cycloalkyl, and 4-12 membered heterocyclyl, wherein each $C_{1-6}$ alkyl, 6-10 membered aryl, 5-10 membered heteroaryl, $C_{3-12}$ cycloalkyl, and 4-12 membered heterocyclyl is further optionally substituted with one or more $R^{51}$ groups.

13. The compound of claim 8, wherein $R^{51}$ is selected from the group consisting of: hydroxyl, oxo, halo, —CN, $C_{1-6}$ alkyl, $C_{1-6}$ alkoxy, $C_{1-6}$ hydroxyalkyl, $C_{1-6}$ heteroalkyl, 3-6 membered cycloalkyl, 4-12 membered heterocyclyl, 6-10 membered aryl, 5-10 membered heteroaryl, —S(O)(NH)R$^{54}$, —S(O)(NR$^{48}$)R$^{54}$, —S(O)(NH)NR$^{53}$R$^{53}$, —S(O)(NR$^{48}$)NR$^{53}$R$^{53}$, —S(O)$_{0-2}$R$^{54}$, —S(O)$_{1-2}$NR$^{53}$R$^{53}$, —SF$_5$, —NO$_2$, —NR$^{53}$R$^{53}$, —NR$^{53}$SO$_2$R$^{54}$, —C(O)OR$^{54}$, —C(O)R$^{54}$, —NR$^{53}$C(O)OR$^{54}$, and —C(O)NR$^{53}$R$^{53}$, wherein each $C_{1-6}$ alkyl, $C_{1-6}$ alkoxy, $C_{1-6}$ hydroxyalkyl, $C_{1-6}$ heteroalkyl, 3-6 membered cycloalkyl, 4-12 membered heterocyclyl, 6-10 membered aryl, and 5-10 membered heteroaryl is optionally substituted with one or more $R^{49}$ groups.

14. The compound of claim 8, wherein each $R^{49}$ is independently selected from the group consisting of: —H, oxo, —OH, —CN, halo, $C_{1-3}$ alkyl, $C_{1-3}$ alkoxy, $C_{1-6}$ hydroxyalkyl, $C_{1-6}$ heteroalkyl, 3-6 membered cycloalkyl, —NR$^{53}$R$^{53}$, —C(O)OR$^{54}$, —S(O)$_{0-2}$R$^{54}$, —S(O)$_{1-2}$NR$^{53}$R$^{53}$, —C(O)NR$^{53}$R$^{53}$, —NR$^{53}$SO$_2$R$^{54}$, —C(O)R$^{54}$, —SF$_5$, and —NO$_2$, wherein each of the $C_{1-3}$ alkyl, $C_{1-3}$ alkoxy, 3-6 membered cycloalkyl, is optionally substituted with —CN, or one or more halo.

15. The compound of claim 8, wherein $R^{42}$ is selected from the group consisting of: —H, —CN, —F, methyl, $C_1$ haloalkyl, $C_{1-3}$ heteroalkyl, methoxy and $C_1$ haloalkoxy.

16. The compound of claim 8, wherein $R^{42}$ is selected from the group consisting of: —H and —F.

17. The compound of claim 8 wherein $R^{44}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, —SF$_5$, —S(O)$_{0-2}$R$^{54}$, —S(O)(NH)R$^{54}$, —S(O)(NR$^{48}$)R$^{54}$, —S(O)(NH)NR$^{53}$R$^{53}$, —S(O)(NR$^{48}$)NR$^{53}$R$^{53}$, —NR$^{53}$R$^{53}$, —NR$^{53}$SO$_2$R$^{54}$, —NR$^{53}$S(O)$_2$NR$^{53}$R$^{53}$, —NR$^{53}$C(O)NR$^{53}$R$^{53}$, —NR$^{53}$C(O)OR$^{54}$, —C(O)R$^{54}$, —C(O)OR$^{54}$, —C(O)NR$^{53}$R$^{53}$, and —NO$_2$, wherein each $C_{1-6}$ alkyl, $C_{1-6}$ alkoxy, $C_{1-6}$ hydroxyalkyl, and $C_{1-6}$ heteroalkyl is further substituted with one or more $R^{49}$ groups.

18. The compound of claim 8, wherein $R^{44}$ is selected from the group consisting of: —H, —F, —Cl, —OH, —CN, —S(O)$_{0-2}$R$^{54}$, —NO$_2$, —SF$_5$, $C_{1-6}$ alkyl, and $C_{1-6}$ alkoxy, and wherein said $C_{1-6}$ alkyl or $C_{1-6}$ alkoxy is optionally substituted with one or more —F, and $R^{54}$ is selected from the group consisting of $C_{1-6}$ alkyl, $C_{1-6}$ hydroxyalkyl, and $C_{1-6}$ heteroalkyl, wherein the $C_{1-6}$ alkyl, $C_{1-6}$ hydroxyalkyl, and $C_{1-6}$ heteroalkyl, is optionally substituted with one or more $R^{55}$ groups, and $R^{55}$ is independently selected from halo, —CN, —OH, and oxo.

19. The compound of claim 8, wherein $R^{44}$ is selected from the group consisting of: —H, —F, —Cl, —OH, —CN, —SR$^{54}$, —SF$_5$, $C_{1-6}$ alkyl, and $C_{1-6}$ alkoxy, and wherein said $C_{1-6}$ alkyl or $C_{1-6}$ alkoxy is optionally substituted with one or more —F, and $R^{54}$ is $C_{1-3}$ haloalkyl.

20. The compound of claim 8, wherein $R^{43}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, $C_{3-12}$ cycloalkyl, 4-12 membered heterocyclyl, 6-10 membered aryl, 5-10 membered heteroaryl, —SF$_5$, —S(O)$_{0-2}$R$^{54}$, —S(O)(NH)R$^{54}$, —S(O)(NR$^{48}$)R$^{54}$, —S(O)(NH)NR$^{53}$R$^{53}$, —S(O)(NR$^{48}$)NR$^{53}$R$^{53}$, —NR$^{53}$R$^{53}$, —NR$^{53}$SO$_2$R$^{54}$, —NR$^{53}$S(O)$_2$NR$^{53}$R$^{53}$, —NR$^{53}$C(O)NR$^{53}$R$^{53}$, —NR$^{53}$C(O)OR$^{54}$, —C(O)R$^{54}$, —C(O)OR$^{54}$, —C(O)NR$^{53}$R$^{53}$, and —NO$_2$, wherein said $C_{1-6}$ alkyl, $C_{1-6}$ alkoxy, $C_{1-6}$ hydroxyalkyl, $C_{1-6}$ heteroalkyl, $C_{3-12}$ cycloalkyl, 4-12 membered heterocyclyl, 6-10 membered aryl, and 5-10 membered heteroaryl is further substituted with one or more $R^{49}$ groups.

21. The compound of claim 8, wherein $R^{49}$ is selected from the group consisting of: —H, oxo, —OH, —CN, halo, $C_{1-3}$ alkyl, $C_{1-3}$ alkoxy, $C_{1-6}$ hydroxyalkyl, $C_{1-6}$ heteroalkyl, 3-6 membered cycloalkyl, —NR$^{53}$R$^{53}$, —C(O)OR$^{54}$, —S(O)$_{0-2}$R$^{54}$, —S(O)$_{1-2}$NR$^{53}$R$^{53}$, —C(O)NR$^{53}$R$^{53}$, and —C(O)R$^{54}$, wherein each of the $C_{1-3}$ alkyl, $C_{1-3}$ alkoxy, $C_{1-6}$ hydroxyalkyl, $C_{1-6}$ heteroalkyl, and 3-6 membered cycloalkyl is optionally substituted with —CN or one or more halo.

22. The compound of claim 8, wherein $R^{49}$ is selected from the group consisting of: —H, oxo, —OH, —CN, halo, $C_{1-3}$ alkyl, $C_{1-3}$ alkoxy, $C_{1-6}$ hydroxyalkyl, $C_{1-6}$ heteroalkyl, 3-6 membered cycloalkyl, —$NR^{53}R^{53}$, —$C(O)OR^{54}$, —$S(O)_{0-2}R^{54}$, —$S(O)_{1-2}NR^{53}R^{53}$, —$C(O)NR^{53}R^{53}$, and —$C(O)R^{54}$, wherein each of the $C_{1-3}$ alkyl, $C_{1-3}$ alkoxy, $C_{1-6}$ hydroxyalkyl, $C_{1-6}$ heteroalkyl, and 3-6 membered cycloalkyl is optionally substituted with —CN or one or more halo.

23. The compound of claim 22, wherein $R^{49}$ is selected from the group consisting of: —H, oxo, —OH, —CN, halo, $C_{1-3}$ alkyl, $C_{1-3}$ alkoxy, $C_{1-3}$ hydroxyalkyl, $C_{1-6}$ heteroalkyl, 3-6 membered cycloalkyl, —$C(O)OR^{54}$, —$S(O)_{0-2}R^{54}$, —$S(O)_{1-2}NR^{53}R^{53}$, and —$C(O)R^{54}$, wherein each of the $C_{1-3}$ alkyl, $C_{1-3}$ alkoxy, $C_{1-3}$ hydroxyalkyl, $C_{1-6}$ heteroalkyl, and 3-6 membered cycloalkyl is optionally substituted with —CN or one or more halo.

24. A compound of Formula IV:

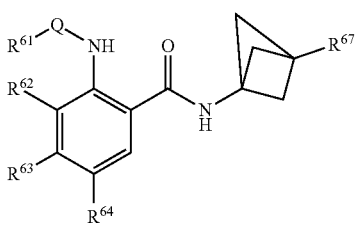

IV or a pharmaceutically acceptable salt, stereoisomer, mixture of stereoisomers, tautomer, or deuterated analogs thereof, wherein:

Q is —$S(O)_2$—, $R^{61}$ is selected from the group consisting of: $C_{1-6}$ alkyl, $C_{2-6}$ alkenyl, $C_{2-6}$ alkynyl, —$NR^{73}R^{73}$, 6-10 membered aryl, 5-10 membered heteroaryl, $C_{3-12}$ cycloalkyl, and 4-12 membered heterocyclyl, wherein each of the $C_{1-6}$ alkyl, $C_{2-6}$ alkenyl, $C_{2-6}$ alkynyl, 6-10 membered aryl, 5-10 membered heteroaryl, $C_{3-12}$ cycloalkyl, and 4-12 membered heterocyclyl is optionally further substituted with one or more $R^{71}$ groups;

$R^{71}$ is selected from the group consisting of: hydroxyl, oxo, halo, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$P(O)R^{74}R^{74}$, —$S(O)(NH)R^{74}$, —$S(O)(NR^{68})R^{74}$, —$S(O)(NH)NR^{73}R^{73}$, —$S(O)(,NR^{68})NR^{73}R^{73}$, —SH, —$S(O)_{0-2}R^{74}$, —$S(O)_{1-2}NR^{73}R^{73}$, —$SF_5$, —$NO_2$, —$NR^{73}R^{73}$, —$NR^{73}SO_2R^{74}$, —$OS(O)_2R^{74}$, —$C(O)OR^{74}$, —$C(O)R^{74}$, —$NR^{73}C(O)OR^{74}$, —$NR^{73}C(O)NR^{73}R^{73}$, —$NR^{73}S(O)_2NR^{73}R^{73}$, and —$C(O)NR^{73}R^{73}$, wherein each of the $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl is optionally substituted with one or more $R^{69}$ groups;

each $R^{69}$ is independently selected from the group consisting of: —H, oxo, —OH, —CN, halo, $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$NR^{73}R^{73}$, —$NR^{73}C(O)OR^{74}$, —$OS(O)_2R^{74}$, —$C(O)OR^{74}$, —$S(O)(NH)R^{74}$, —$S(O)(NR^{68})R^{74}$, —$S(O)(NH)NR^{73}R^{73}$, $S(O)(NR^{68})NR^{73}R^{73}$, —SH, —$S(O)_{0-2}R^{74}$, —$S(O)_{1-2}NR^{73}R^{73}$, —$C(O)NR^{73}R^{73}$, —$NR^{73}SO_2R^{74}$, —$C(O)R^{74}$, —$NR^{73}C(O)NR^{73}R^{73}$, —$NR^{73}S(O)_2NR^{73}R^{73}$, —$SF_5$, and —$NO_2$, wherein each of the $C_{1-6}$ alkyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl is optionally substituted with one or more $R^{76}$ groups;

each $R^{73}$ is independently selected from the group consisting of —H, $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl is optionally substituted with one or more $R^{75}$ groups;

each $R^{74}$ is independently selected from the group consisting of: $C_{1-6}$ alkyl, $C_{1-6}$ hydroxyalkyl, $C_{1-6}$ heteroalkyl, $C_{3-6}$ cycloalkyl, 6-10 membered aryl, 4-12 membered heterocyclyl and 5-10 membered heteroaryl, wherein the $C_{1-6}$ alkyl, $C_{1-6}$ hydroxyalkyl, $C_{1-6}$ heteroalkyl, 3-6 membered cycloalkyl, 4-12 membered heterocyclyl, 6-10 membered aryl and 5-10 membered heteroaryl is optionally substituted with one or more $R^{75}$ groups;

each $R^{75}$ is independently selected from —H, halo, —CN, —OH, oxo, —$NO_2$, —$SF_5$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$S(O)(NH)R^{66}$, —$S(O)(NR^{68})R^{66}$, —$S(O)(NH)NR^{66}R^{66}$, —$S(O)(NR^{68})NR^{66}R^{66}$, —SH, —$S(O)_{0-2}R^{66}$, —$S(O)_2NH_2$, —$NH_2$, —$S(O)_2NR^{66}R^{66}$, —$C(O)NR^{66}R^{66}$, and —$C(O)OR^{66}$, wherein each of the 3-12 membered cycloalkyl, 4-12 membered heterocyclyl, 6-10 membered aryl, and 5-10 membered heteroaryl is optionally substituted with one or more $R^{76}$ groups;

each $R^{76}$ is independently selected from halo, —CN, —OH, —$NH_2$, oxo, —$NO_2$, —$SF_5$, $C_{1-3}$ alkyl, $C_{1-3}$ haloalkyl, $C_{1-6}$ alkoxy, $C_{1-6}$ haloalkoxy, $C_{1-6}$ hydroxyalkyl, thioalkyl, thiohaloalkyl, thiocycloalkyl, sulfonylalkyl, sulfonylhaloalkyl, sulfonylcycloalkyl, 3-6 membered cycloalkyl, —$C(O)NH_2$ and —$S(O)_2NH_2$;

$R^{62}$ is selected from the group consisting of: —H, —CN, —F, —Cl, $C_{1-3}$ alkyl, $C_{1-3}$ haloalkyl, $C_{1-3}$ heteroalkyl, $C_{1-3}$ alkoxy and $C_{1-3}$ haloalkoxy;

each $R^{63}$ and $R^{64}$ is independently selected from the group consisting of: —H, halo, —OH, —CN, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, 5-10 membered heteroaryl, —$SF_5$, —$S(O)_{0-2}R^{74}$, —$S(O)(NH)R^{74}$, —$S(O)(NR^{68})R^{74}$, —$S(O)(NH)NR^{73}R^{73}$, —$S(O)(NR^{68})NR^{73}R^{73}$, —SH, —$NR^{73}R^{73}$, —$NR^{73}SO_2R^{74}$, —$NR^{73}S(O)_2NR^{73}R^{73}$, —$NR^{73}C(O)NR^{73}R^{73}$, —$NR^{73}C(O)OR^{74}$, tri-$C_{1-4}$ alkylsilyl, —$C(O)R^{74}$, —$C(O)OR^{74}$, —$C(O)NR^{73}R^{73}$ and —$NO_2$, wherein said $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ heteroalkyl, 3-12 membered cycloalkyl, 4-12 membered heterocyclyl, 6-10 membered aryl, and 5-10 membered heteroaryl is optionally further substituted with one or more $R^{69}$ groups;

wherein $R^{62}$ and $R^{63}$, or $R^{63}$ and $R^{64}$ can optionally join, together with the atoms to which they are attached, to form a 5-6 membered cycloalkyl, a 5-6 membered heterocyclyl, phenyl, or a 5-6 membered heteroaryl, each such cyclic groups respectively fused to the phenyl to which they are attached, and each optionally substituted with one or more $R^{69}$ groups;

$R^{67}$ is selected from the group consisting of: —H, halo, —CN, —OH, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, 3-12 membered cycloalkyl, —S(O)$_{0-2}R^{74}$, —S(O)(NH)$R^{74}$, —S(O)(NR$^{68}$)$R^{74}$, —S(O)(NH)NR$^{73}R^{73}$, —S(O)(NR$^{68}$)NR$^{73}R^{73}$, —SH, —NR$^{73}R^{73}$, —P(O)$R^{74}R^{74}$, —C(O)OH, —C(O)OR$^{74}$, —C(O)NR$^{73}R^{73}$, —S(O)$_2$NR$^{73}R^{73}$, —C(O)$R^{74}$, 6-10 membered aryl, 5-10 membered heteroaryl and 4-12 membered heterocyclyl; wherein each of said 4-12 membered heterocyclyl, 6-10 membered aryl, 5-10 membered heteroaryl, $C_{1-6}$ alkyl, $C_{2-6}$ alkenyl, $C_{2-6}$ alkynyl, tri-$C_{1-4}$ alkylsilyl, $C_{1-6}$ alkoxy, $C_{1-6}$ hydroxyalkyl, $C_{1-6}$ heteroalkyl, and 3-12 membered cycloalkyl is optionally substituted with one or more $R^{75}$;

$R^{68}$ is selected from the group consisting of: $C_{1-6}$ alkyl, —C(O)$R^{74}$, 3-12 membered cycloalkyl, $C_{1-6}$ heteroalkyl, 6-10 membered aryl, 5-10 membered heteroaryl, 4-12 membered heterocyclyl, —C(O)OR$^{74}$, —C(O)NR$^{73}R^{73}$, and —SO$_2R^{74}$, wherein each of the $C_{1-6}$ alkyl, 3-12 membered cycloalkyl, $C_{1-6}$ heteroalkyl, 6-10 membered aryl, 5-10 membered heteroaryl, and 4-12 membered heterocyclyl is optionally substituted with halo, —CN, oxo, hydroxyl, $C_{1-6}$ alkyl, $C_{1-6}$ alkoxy, —S(O)$_{1-2}R^{74}$, —S(O)$_2$NR$^{73}R^{73}$, —NO$_2$, —SF$_5$, $C_{1-6}$ haloalkyl, $C_{1-6}$ haloalkoxy, $C_{1-6}$ hydroxyalkyl, —NR$^{73}R^{73}$, —C(O)OR$^{74}$, $C_{1-6}$ heteroalkyl, 3-6 membered cycloalkyl optionally substituted with $R^{76}$, 4-12 membered heterocyclyl optionally substituted with one or more $R^{76}$, 6-10 membered aryl optionally substituted with one or more $R^{76}$, or 5-10 membered heteroaryl optionally substituted with one or more $R^{76}$.

25. The compound of claim 24, wherein $R^{61}$ is selected from the group consisting of: $C_{1-6}$ alkyl, —NR$^{73}R^{73}$, 6-10 membered aryl, 5-10 membered heteroaryl, $C_{3-12}$ cycloalkyl, and 4-12 membered heterocyclyl, wherein each of the $C_{1-6}$ alkyl, 6-10 membered aryl, 5-10 membered heteroaryl, $C_{3-12}$ cycloalkyl, and 4-12 membered heterocyclyl is further substituted with one or more $R^{71}$ groups.

26. The compound of claim 24, wherein $R^{62}$ is selected from the group consisting of: —H, —CN, —F, methyl, $C_1$ haloalkyl, $C_{1-3}$ heteroalkyl, methoxy and $C_1$ haloalkoxy.

27. The compound of claim 26, wherein $R^{62}$ is selected from the group consisting of: —H and —F.

28. The compound of claim 24, wherein $R^{64}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, —SF$_5$, —S(O)$_{0-2}R^{74}$, —S(O)(NH)$R^{74}$, —S(O)(NR$^{68}$)$R^{74}$, —S(O)(NH)NR$^{73}R^{73}$, —S(O)(NR$^{68}$)NR$^{73}R^{73}$, —NR$^{73}R^{73}$, —NR$^{73}$ SO$_2R^{74}$, —NR$^{73}$ S(O)$_2$NR$^{73}R^{73}$, —NR$^{73}$C(O) NR$^{73}R^{73}$, —NR$^{73}$C(O)OR$^{74}$, —C(O)$R^{74}$, —C(O)OR$^{74}$, —C(O)NR$^{73}R^{73}$, and —NO$_2$, wherein said $C_{1-6}$ alkyl, $C_{1-6}$ alkoxy, $C_{1-6}$ hydroxyalkyl, and $C_{1-6}$ heteroalkyl is further substituted with one or more $R^{69}$ groups.

29. The compound of claim 28, wherein $R^{64}$ is selected from the group consisting of: —H, —F, —Cl, —OH, —CN, —S(O)$_{0-2}R^{74}$, —SF$_5$, —NO$_2$, $C_{1-6}$ alkyl, and $C_{1-6}$ alkoxy, and wherein said $C_{1-6}$ alkyl or $C_{1-6}$ alkoxy is optionally substituted with one or more —F and $R^{74}$ is selected from the group consisting of $C_{1-6}$ alkyl, $C_{1-6}$ hydroxyalkyl, and $C_{1-6}$ heteroalkyl, wherein the $C_{1-6}$ alkyl, $C_{1-6}$ hydroxyalkyl, and $C_{1-6}$ heteroalkyl, is optionally substituted with one or more $R^{75}$ groups, and $R^{75}$ is independently selected from the group consisting of: halo, —CN, —OH, and oxo.

30. The compound of claim 29, wherein $R^{64}$ is selected from the group consisting of: —H, —F, —Cl, —OH, —CN, SR$^{74}$, —SF$_5$, $C_{1-6}$ alkyl, and $C_{1-6}$ alkoxy, and wherein said $C_{1-6}$ alkyl or $C_{1-6}$ alkoxy is optionally substituted with one or more —F, and $R^{74}$ is $C_{1-3}$ haloalkyl.

31. The compound of claim 24, wherein $R^{63}$ is selected from the group consisting of: —H, halo, —OH, —CN, $C_{1-6}$ alkyl, $C_{1-6}$ alkoxy, $C_{1-6}$ hydroxyalkyl, $C_{1-6}$ heteroalkyl, $C_{3-12}$ cycloalkyl, 4-12 membered heterocyclyl, 6-10 membered aryl, 5-10 membered heteroaryl, —SF$_5$, —S(O)$_{0-2}R^{74}$, —S(O)(NH)$R^{74}$, —S(O)(NR$^{68}$)$R^{74}$, —S(O)(NH)NR$^{73}R^{73}$, —S(O)(NR$^{68}$)NR$^{73}R^{73}$, —NR$^{73}R^{73}$, —NR$^{73}$SO$_2R^{74}$, —NR$^{73}$S(O)$_2$NR$^{73}R^{73}$, —NR$^{73}$C(O)NR$^{73}R^{73}$, —NR$^{73}$C(O)OR$^{74}$, —C(O)$R^{74}$, —C(O)OR$^{74}$, —C(O)NR$^{73}R^{73}$, and —NO$_2$, wherein said $C_{1-6}$ alkyl, $C_{1-6}$ alkoxy, $C_{1-6}$ hydroxyalkyl, $C_{1-6}$ heteroalkyl, $C_{3-12}$ cycloalkyl, 4-12 membered heterocyclyl, 6-10 membered aryl, and 5-10 membered heteroaryl is further substituted with one or more $R^{69}$ groups.

32. The compound of claim 24, wherein $R^{69}$ is selected from the group consisting of: —H, oxo, —OH, —CN, halo, $C_{1-3}$ alkyl, $C_{1-3}$ alkoxy, $C_{1-6}$ hydroxyalkyl, $C_{1-6}$ heteroalkyl, 3-6 membered cycloalkyl, —NR$^{73}R^{73}$, —C(O)OR$^{74}$, —S(O)$_{0-2}R^{74}$, —S(O)$_{1-2}$NR$^{73}R^{73}$, —C(O)NR$^{73}R^{73}$, and —C(O)$R^{74}$, wherein each of the $C_{1-3}$ alkyl, $C_{1-3}$ alkoxy, $C_{1-6}$ hydroxyalkyl, $C_{1-6}$ heteroalkyl, and 3-6 membered cycloalkyl is optionally substituted with —CN or one or more halo.

33. The compound of claim 31, wherein $R^{63}$ is selected from the group consisting of: —H, halo, —CN, $C_{1-3}$ alkyl, $C_{1-3}$ alkoxy, $C_{1-3}$ hydroxyalkyl, $C_{1-6}$ heteroalkyl, $C_{3-6}$ cycloalkyl, 4-6 membered heterocyclyl, 5-10 membered heteroaryl, —SF$_5$, —S(O)$_{0-2}R^{74}$, and —NO$_2$, wherein said $C_{1-3}$ alkyl, $C_{1-3}$ alkoxy, $C_{1-3}$ hydroxyalkyl, $C_{1-6}$ heteroalkyl, $C_{3-6}$ cycloalkyl, 4-6 membered heterocyclyl, and 5-10 membered heteroaryl is further substituted with one or more $R^{69}$ groups.

34. The compound of claim 32, wherein $R^{69}$ is selected from the group consisting of: —H, oxo, —OH, —CN, halo, $C_{1-3}$ alkyl, $C_{1-3}$ alkoxy, $C_{1-3}$ hydroxyalkyl, $C_{1-6}$ heteroalkyl, 3-6 membered cycloalkyl, —C(O)OR$^{74}$, —S(O)$_{0-2}R^{74}$, —S(O)$_{1-2}$NR$^{73}R^{73}$, and —C(O)$R^{74}$, wherein each of the $C_{1-3}$ alkyl, $C_{1-3}$ alkoxy, $C_{1-3}$ hydroxyalkyl, $C_{1-6}$ heteroalkyl, and 3-6 membered cycloalkyl is optionally substituted with —CN or one or more halo.

35. A compound selected from the group consisting of:

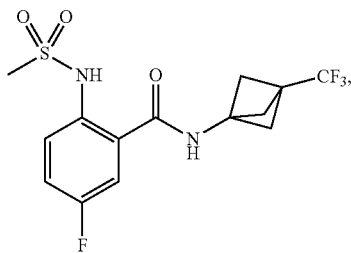

-continued
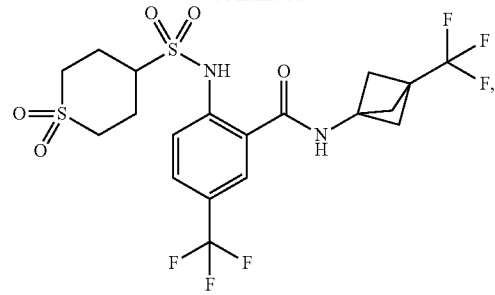
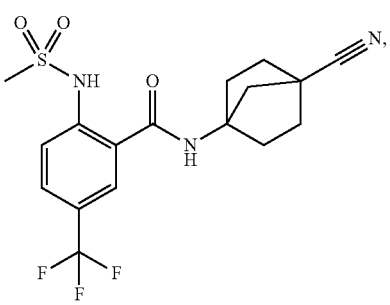
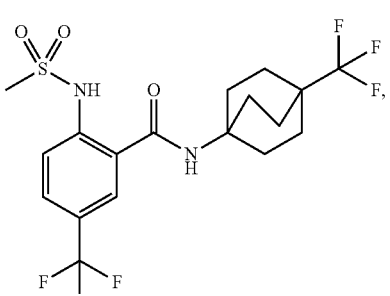
, and
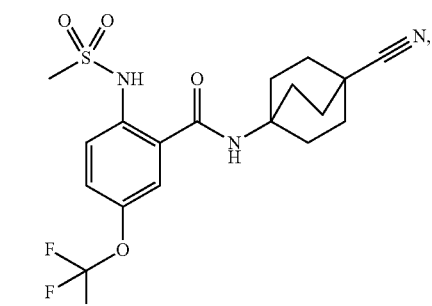
36. A compound selected from the group consisting of:
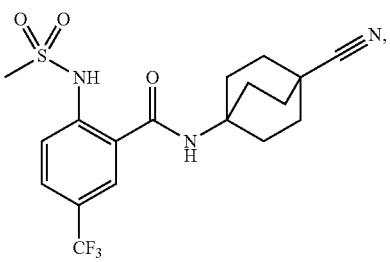
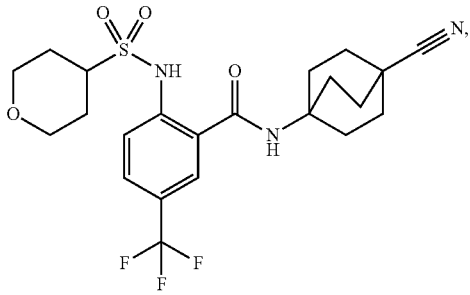

215
-continued

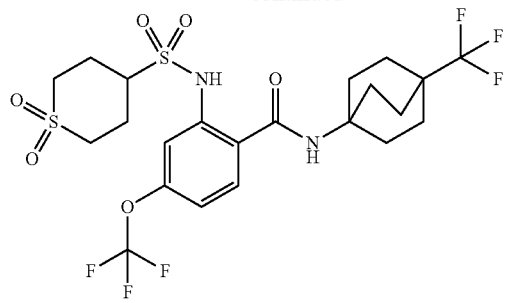

, and

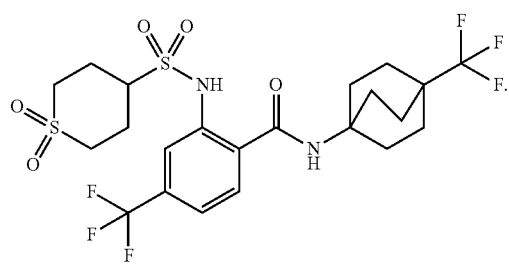 [SMILES: O=C(NC12CCC(C(F)(F)F)(CC1)CC2)c1ccc(C(F)(F)F)cc1NS(=O)(=O)C1CCS(=O)(=O)CC1]

37. A pharmaceutical composition comprising a compound of claim 1, or a pharmaceutically acceptable salt, stereoisomer, mixture of stereoisomers, tautomer, or deuterated analogs thereof, together with a pharmaceutically acceptable excipient.

38. A pharmaceutical composition comprising a compound of claim 8, or a pharmaceutically acceptable salt, stereoisomer, mixture of stereoisomers, tautomer, or deuterated analogs thereof, together with a pharmaceutically acceptable excipient.

39. A pharmaceutical composition comprising a compound of claim 24, or a pharmaceutically acceptable salt, stereoisomer, mixture of stereoisomers, tautomer, or deuterated analogs thereof, together with a pharmaceutically acceptable excipient.

40. A pharmaceutical composition comprising a compound of claim 35, or a pharmaceutically acceptable salt, stereoisomer, mixture of stereoisomers, tautomer, or deuterated analogs thereof, together with a pharmaceutically acceptable excipient.

41. A pharmaceutical composition comprising a compound of claim 36, or a pharmaceutically acceptable salt, stereoisomer, mixture of stereoisomers, tautomer, or deuterated analogs thereof, together with a pharmaceutically acceptable excipient.

42. A compound selected from the group consisting of:

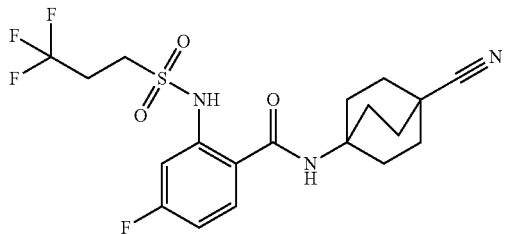

and

216
-continued

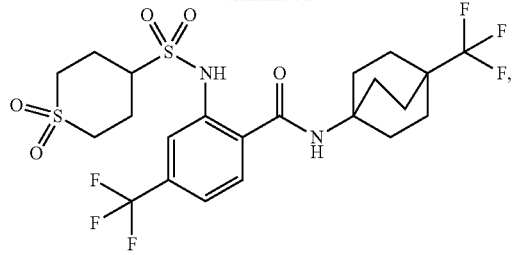

or a pharmaceutically acceptable salt, stereoisomer, mixture of stereoisomers, tautomer, or deuterated analog thereof.

43. A compound selected from the group consisting of:

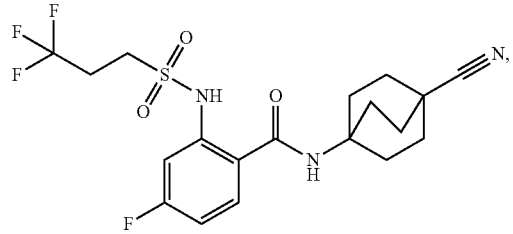

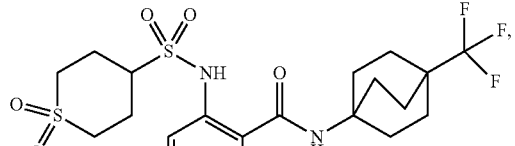

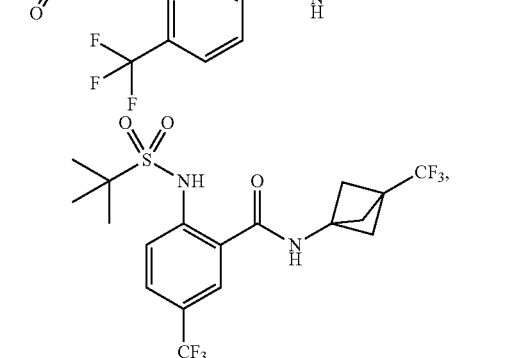

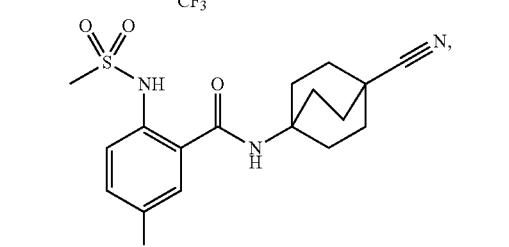

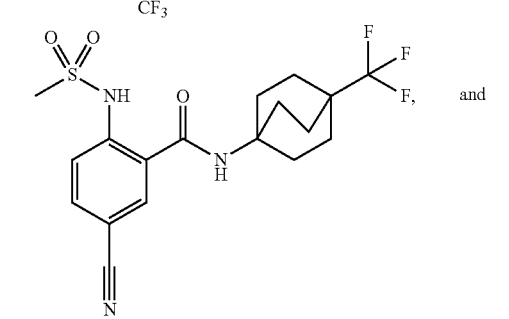

and

-continued
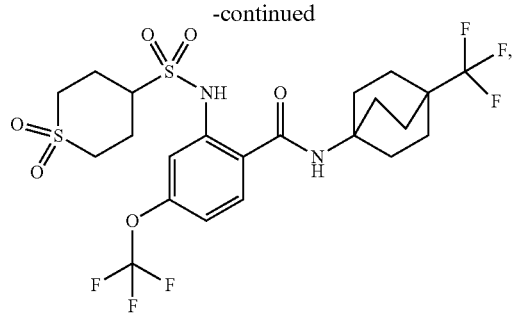
or a pharmaceutically acceptable salt, stereoisomer, mixture of stereoisomers, tautomer, or deuterated analog thereof.
* * * * *